United States Patent
Crooke et al.

(10) Patent No.: US 12,030,910 B2
(45) Date of Patent: *Jul. 9, 2024

(54) COMPOUNDS AND METHODS FOR THE MODULATION OF PROTEINS

(71) Applicant: Ionis Pharmaceuticals, Inc., Carlsbad, CA (US)

(72) Inventors: Stanley T. Crooke, Carlsbad, CA (US); Xue-hai Liang, Del Mar, CA (US); Wen Shen, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 179 days.

This patent is subject to a terminal disclaimer.

(21) Appl. No.: 17/021,510

(22) Filed: Sep. 15, 2020

(65) Prior Publication Data
US 2021/0269472 A1    Sep. 2, 2021

Related U.S. Application Data

(62) Division of application No. 15/525,232, filed as application No. PCT/US2015/060938 on Nov. 16, 2015, now Pat. No. 10,822,369.

(60) Provisional application No. 62/233,183, filed on Sep. 25, 2015, provisional application No. 62/156,812, filed on May 4, 2015, provisional application No. 62/156,139, filed on May 1, 2015, provisional application No. 62/139,626, filed on Mar. 27, 2015, provisional application No. 62/080,223, filed on Nov. 14, 2014.

(51) Int. Cl.
*C07H 21/04* (2006.01)
*A61K 31/7088* (2006.01)
*C07H 21/00* (2006.01)
*C12N 15/113* (2010.01)
*C12N 15/67* (2006.01)
*C12P 19/34* (2006.01)

(52) U.S. Cl.
CPC ......... *C07H 21/04* (2013.01); *A61K 31/7088* (2013.01); *C07H 21/00* (2013.01); *C12N 15/113* (2013.01); *C12N 15/1137* (2013.01); *C12N 15/1138* (2013.01); *C12N 15/67* (2013.01); *C12P 19/34* (2013.01); *C12N 2310/11* (2013.01); *C12N 2310/315* (2013.01); *C12N 2310/3341* (2013.01); *C12N 2310/346* (2013.01); *C12Y 301/26004* (2013.01)

(58) Field of Classification Search
None
See application file for complete search history.

(56) References Cited

U.S. PATENT DOCUMENTS

| | | |
|---|---|---|
| 7,718,625 B2 | 5/2010 | Eichler et al. |
| 2002/0160976 A1 | 10/2002 | Miles et al. |
| 2004/0110144 A1 | 6/2004 | Bennett et al. |
| 2005/0048549 A1 | 3/2005 | Cao et al. |
| 2006/0166922 A1 | 7/2006 | Eichler et al. |

FOREIGN PATENT DOCUMENTS

| | | |
|---|---|---|
| WO | WO 1992/013070 | 8/1992 |
| WO | WO 2014/097226 | 6/2014 |
| WO | WO 2014/172698 | 10/2014 |
| WO | WO 2015/023937 | 2/2015 |
| WO | WO 2015/023938 | 2/2015 |
| WO | WO 2015/023939 | 2/2015 |
| WO | WO 2015/023941 | 2/2015 |
| WO | WO 2015/023975 | 2/2015 |

OTHER PUBLICATIONS

Araujo, Patricia R., et al. "Before it gets started: regulating translation at the 5' UTR." Comparative and functional genomics 2012 (2012).*
Babendure et al., "Control of mammalian translation by mRNA structure near caps" RNA (2006) 12: 851-861.
Bandyopadhyay et al., "Alzheimer's disease therapeutics targeted to the control of amyloid precursor protein translation: Maintenance of brain iron homeostasis" Biochem. Pharm. (2014) 88: 486-494.
Barbosa et al., "Gene Expression Regulation by Upstream Open Reading Frames and Human Disease" PLOS (2013) 9(8): 1-12.
Brenet et al., "Identification of secondary structure in the 5'-untranslated region of the human adrenomedullin mRNA with implications for the regulation of mRNA translation" Oncogene (2006) 25: 6510-6519.
Calvo et al., "Upstream open reading frames cause widespread reduction of protein expression and are polymorphic among humans" PNAS (2009) 106(18): 7507-7512.
Caron et al., "Dual-acting riboswitch control of translation initiation and mRNA decay" Proc. Natl. Acad. Sci. USA (2012) 109(50): 3444-3453.
Cazzola et al., "Hereditary Hyperferritinemia-Cataract Syndrome: Relationship Between Phenotypes and Specific Mutations in the Iron-Responsive Element of Ferritin Light-Chain mRNA" Blood (1997) 90(2): 814-821.
Cheng et al., "Functional activiation of the cystic fibrosis trafficking mutant ΔF508-CFTR by overexpression" Am. Physiol. Soc. (1995): L615-L624.
Dvir et al., "Deciphering the rules by which 5'-UTR sequences affect protein expression in yeast" Proc Natl Acad Sci USA (2013) 110(30): E2792-E2801.

(Continued)

*Primary Examiner* — Kimberly Chong
(74) *Attorney, Agent, or Firm* — McNeill Baur LLC

(57) ABSTRACT

In certain embodiments, the present disclosure provides compounds and methods of increasing the amount or activity of a target protein in a cell. In certain embodiments, the compounds comprise a translation suppression element inhibitor. In certain embodiments, the translation suppression element inhibitor is a uORF inhibitor. In certain embodiments, the uORF inhibitor is an antisense compound.

18 Claims, No Drawings

Specification includes a Sequence Listing.

(56) References Cited

OTHER PUBLICATIONS

Extended EP Search Report for 15859580.1 dated Jun. 19, 2018.
Gillen et al., "microRNA regulation of expression of the cystic fibrosis transmembrane conductance regulator gene" Biochem. J. (2011) 438(1): 25-32.
Giordano et al., "Molecular and Functional Analysis of the Large 5'Promoter Region of CFTR Gene Revealed Pathogenic Mutations in CF and CFTR-Related Disorders" J. Mol. Diagn. (2013) 15(3): 331-340.
Hinnebusch et al., "Translational control by 5'-untranslated regions of eukaryotic mRNAs" Science (2016) 352(6292): 1413-1416.
International Search Report for PCT/US15/60938 dated Feb. 4, 2016.
Jenkins et al., "A Conserved Stem Loop Motif in the 5'Untranslated Region Regulates Transforming Growth Factor-β1 Translation" PLOS One (2010) 5(8): 1-12.
Lamping et al., "Small, synthetic, GC-rich mRNA stem-loop modules 5' proximal to the AUG start-codon predictably tune gene expression in yeast" Microb. Cell Fact. (2013) 12: 1-19.
Li et al., "MicroRNA-122 antagonism against hepatitis C virus genotypes 1-6 and reduced efficacy by host RNA insertion or mutations in the HCV 5' UTR" Proc Natl Acad Sci USA (2011) 108(12): 4991-4996.
Liang et al., "Translation efficiency of mRNAs is increased by antisense oligonucleotides targeting upstream open reading frames" Nat Biotechnol (2016) 34(8): 875-880.
Liang et al., "Antisense oligonucleotides targeting translation inhibitory elements in 5' UTRs can selectively increase protein levels" Nucleic Acids Res (2017) 45(16): 9528-9546.
Lukowski et al., "CFTR mRNA expression is regulated by an upstream open reading frame and RNA secondary structure in its 5' untranslated region" Hum. Mol. Gen. (2014) 1-14.
Majdalani et al., "Regulation of RpoS by a novel small RNA: the characterization of RprA" Molecular Microbiology (2001) 39(5): 1382-1394.
Matsuda et al., "Determinants of initiation codon selection during translation in mammalian cells" PLOS One (2010) 5(11): 1-13.
Morris et al., "Upstream open reading frames as regulators of mRNA translation" Mol Cell Biol (2000) 20(23): 8635-8642.
Orom et al., "MicroRNA-10a binds the 5'UTR of ribosomal protein mRNAs and enhances their translation" Mol. Cell (2008) 30(4): 460-471.
Pendleton et al., "Regulation of Endothelial Argininosuccinate Synthase Expression and NO Production by an Upstream Open Reading Frame" J. Biol. Chem. (2005) 280(25): 24252-24260.
Rogers et al., "Differential utilization of upstream AUGs in the β-secretase mRNA suggests that a shunting mechanism regulates translation" PNAS (2004) 101(9): 2794-2799.
Schwanhausser et al., "Global quantification of mammalian gene expression control" Nature (2011) 473: 337-342.
Shabman et al., "An upstream open reading frame modulates ebola virus polymerase translation and virus replication" PLOS Pathog (2013) 9(1): 1-18.
Spitale et al., "Structural imprints in vivo decode RNA regulatory mechanisms" Nature (2015) 519: 486-503.
Swiatkowska et al., "The Role of Structural Elements of the 5'-Terminal Region of p53 mRNA in Translation under Stress Conditions Assayed by the Antisense Oligonucleotide Approach" PLOS One (2015): 1-20.
Wang "The Principles of MiRNA-Masking Antisense Oligonucleotides Technology" Chapter 3, Methods in Molecular Biology (2011) 676: 43-49.
Wethmar "The regulatory potential of upstream open reading frames in eukaryotic gene expression" Wiley Interdiscip Rev RNA (2014) 5(6): 765-778.
Xiao et al., "Novel Approaches for Gene-Specific Interference Via Manipulating Actions of MicroRNAs: Examination on the Pacemaker Channel Genes HCN2 and HCN4" J. Cell. Physiol. (2007): 285-292.
Xue et al., "RNA regulons in Hox 5' UTRs confer ribosome specificity to gene regulation" Nature (2015) 517: 33-38.
Zammarchi et al., "5' UTR Control of Native ERG and of Tmprss2:ERG Variants Activity in Prostate Cancer" PLOS One (2013) 8(3): 1-14.
Zhang et al., "The 5'-untranslated region of multidrug resistance associated protein 2 (MRP2; ABCC2) regulates downstream open reading frame expression through translational regulation" Mol Pharmacol (2010) 77(2): 237-246.

\* cited by examiner

COMPOUNDS AND METHODS FOR THE MODULATION OF PROTEINS

SEQUENCE LISTING

The present application is being filed along with a Sequence Listing in electronic format. The Sequence Listing is provided as a file entitled CORE0132USASEQ_ST25.txt, created May 8, 2017, which is 72 Kb in size. The information in the electronic format of the sequence listing is incorporated herein by reference in its entirety.

BACKGROUND

Translation of a polypeptide or protein encoded by an mRNA typically begins at the start codon of the primary open reading frame (pORF) of the mRNA. Some mRNA transcripts also comprise one or more additional start codons. Such additional start codons may be upstream of the pORF start codon. Such an additional start codon that is upstream of a pORF is referred to as an upstream open reading frame (uORF) start site. The potential role of additional start sites in regulating translation of pORF protein products has been discussed previously (see Barbosa et al. PLOS Genetics. 9, e1003529 (2013)) which is hereby incorporated by reference in its entirety. Mutations that introduce or eliminate an additional start codon (a uORF start codon) in a transcript can disrupt regulation of its translation and can lead to disease (see Calvo et al. Proc. Natl. Acad. Sci. 106, 7507 (2009)) which is hereby incorporated by reference in its entirety.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics or affinity for a target nucleic acid. In 1998, the antisense compound, Vitravene® (fomivirsen; developed by Isis Pharmaceuticals Inc., Carlsbad, CA) was the first antisense drug to achieve marketing clearance from the U.S. Food and Drug Administration (FDA), and is currently a treatment of cytomegalovirus (CMV)-induced retinitis in AIDS patients. For another example, an antisense compound targeting ApoB, KYNAMRO™, has been approved by the U.S. Food and Drug Administration (FDA) as an adjunct treatment to lipid-lowering medications and diet to reduce low density lipoprotein-cholesterol (LDL-C), ApoB, total cholesterol (TC), and non-high density lipoprotein-cholesterol (non HDL-C) in patients with homozygous familial hypercholesterolemia (HoFH).

SUMMARY

The present disclosure provides compounds that interact with the 5'-UTR of a target transcript to increase translation of a target protein. It was discovered that certain compounds that interact with the 5'-UTR can increase translation of a given target transcript. For example, in certain embodiments, the present disclosure provides antisense compounds targeted to one or more regions of the 5'-UTR. These regions of the 5'-UTR may include a translation suppression element, such as a stem-loop structure or a uORF. When the antisense compounds interact with the translation suppression element in the 5'-UTR, the antisense compounds increase translation of the target transcript. One aspect of the invention is the increase in expression through contacting a cell with an agent targets a translation suppression element in the 5'-UTR. In certain embodiments, antisense compounds targeted to the 5'-UTR increase expression of a given target protein by disrupting a translation suppression element within the 5'-UTR.

Antisense oligonucleotide technology has been used most often to reduce the amount an mRNA via antisense induced RNase H cleavage or to alter splicing of a pre-mRNA transcript in a cell. In certain embodiments, the present disclosure provides antisense compounds that increase expression of a target protein in a cell. In this manner, antisense oligonucleotides may be used to increase the expression of a desired protein in a cell. In certain embodiments, an increase in the expression of a target protein in a cell is achieved by having the antisense compound reduce ribosomal recognition of one or more upstream open reading frames. In certain embodiments, recognition of an upstream open reading frame reduces expression of a target protein in a cell. Therefore, in certain embodiments, targeting the upstream open reading frame, or the nucleobase sequence upstream or downstream of the upstream open reading frame, reduces ribosomal recognition of the upstream open reading frame and thereby increases expression of one or more target proteins. Therefore, in certain embodiments, targeting the upstream open reading frame, or the nucleobase sequence upstream or downstream of the upstream open reading frame, reduces ribosomal recognition of the upstream open reading frame and thereby increases ribosomal recognition of a start codon in the primary open reading frame.

In certain embodiments, the present invention uses antisense compounds to increase expression of a target protein. In certain instances, a transcript encoding a protein of interest includes a pORF and one or more additional start sites, such as uORF start sites. In certain embodiments, the present disclosure provides modified oligonucleotides that are complementary to the target transcript at or near such uORF start sites. Antisense compounds designed to reduce the amount of a target protein typically induce cleavage of the target transcript (e.g., through recruitment of RNase H). In contrast, in certain embodiments of the present invention, modified oligonucleotides are not designed to elicit cleavage. Rather, in certain such embodiments, the modified oligonucleotides of the present invention mask a uORF start site in favor of increased translation at a pORF start site. In certain embodiments, the modified oligonucleotides of the present invention disrupt initiation of translation at a uORF start site and, in certain embodiments, thereby increase translation of the target protein. In certain embodiments, modified oligonucleotides of the present invention disrupt the regulatory function of the 5'-UTR. In certain such embodiments, translation of the desired protein is increased. In certain embodiments, modified oligonucleotides of the present invention recruit proteins to the transcript that interfere with initiation of translation at the uORF start site. In certain embodiments, antisense compounds of the invention result in decreased translation of a uORF polypeptide.

The present disclosure provides methods of increasing translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing translation of the target protein in the cell.

The present disclosure provides methods of decreasing suppression of translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby decreasing suppression of translation of the target protein in the cell.

The present disclosure provides methods of increasing the amount or activity of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing the amount or activity of the target protein in the cell.

The present disclosure provides methods of increasing the amount a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing expression of the target protein in the cell.

The present disclosure provides the following non-limiting numbered embodiments:

Embodiment 1: A method of increasing the amount or activity of a target protein in a cell, comprising contacting the cell with a uORF inhibitor, wherein the target protein is encoded by a target transcript comprising at least one uORF start site; and thereby increasing the amount or activity of the target protein in the cell.

Embodiment 2: A method of increasing expression of a target protein in a cell, comprising contacting the cell with a uORF inhibitor, wherein the target protein is encoded by a target transcript comprising at least one uORF start site; and thereby increasing expression of the target protein in the cell.

Embodiment 3: A method of increasing translation a target protein in a cell, comprising contacting the cell with a uORF inhibitor, wherein the target protein is encoded by a target transcript comprising at least one uORF start site; and thereby increasing translation of the target protein in the cell.

Embodiment 4: A method of decreasing suppression of translation a target protein in a cell, comprising contacting the cell with a uORF inhibitor, wherein the target protein is encoded by a target transcript comprising at least one uORF start site; and thereby decreasing suppression of translation of the target protein in the cell.

Embodiment 5: A method of decreasing translation of a uORF polypeptide in a cell, comprising contacting the cell with a uORF inhibitor; and thereby decreasing translation of the uORF polypeptide in the cell.

Embodiment 6: The method of any of embodiments 1-5, wherein the uORF inhibitor is a small molecule.

Embodiment 7: The method of any of embodiments 1-5, wherein the uORF inhibitor is an antibody.

Embodiment 8: The method of any of embodiments 1-5, wherein the uORF inhibitor is a peptide.

Embodiment 9: The method of any of embodiments 1-5, wherein the uORF inhibitor is a nucleic acid.

Embodiment 10: The method of any of embodiments 1-5, wherein the uORF inhibitor is an siRNA.

Embodiment 11: The method of any of embodiments 1-5, wherein the uORF inhibitor is an antisense compound.

Embodiment 12: The method of embodiment 11, wherein the antisense compound is a modified oligonucleotide.

Embodiment 13: A method of increasing the amount or activity of a target protein in a cell, comprising contacting the cell with an antisense compound comprising a modified oligonucleotide, wherein the target protein is encoded by a target transcript comprising at least one uORF start site and wherein the modified oligonucleotide is complementary to a target site within a uORF start site region of the target transcript; and thereby increasing the amount or activity of the target protein in the cell.

Embodiment 14: A method of increasing expression of a target protein in a cell, comprising contacting the cell with an antisense compound comprising a modified oligonucleotide, wherein the target protein is encoded by a target transcript comprising at least one uORF start site and wherein the modified oligonucleotide is complementary to target site within a uORF start site region of the target transcript; and thereby increasing expression of the target protein in the cell.

Embodiment 15: A method of increasing translation a target protein in a cell, comprising contacting the cell with an antisense compound comprising a modified oligonucleotide, wherein the target protein is encoded by a target transcript comprising at least one uORF start site and wherein the modified oligonucleotide is complementary to a target site within a uORF start site region of the target transcript; and thereby increasing translation of the target protein in the cell.

Embodiment 16: A method of decreasing suppression of translation a target protein in a cell, comprising contacting the cell with an antisense compound comprising a modified oligonucleotide, wherein the target protein is encoded by a target transcript comprising at least one uORF start site and wherein the modified oligonucleotide is complementary to a target site within a uORF start site region of the target transcript; and thereby decreasing suppression of translation of the target protein in the cell.

Embodiment 17: A method of decreasing translation of a uORF polypeptide in a cell, comprising contacting the cell with an antisense compound comprising a modified oligonucleotide complementary to a target site within a uORF region of the target transcript; and thereby decreasing translation of the uORF polypeptide in the cell.

Embodiment 18: The method of any of embodiments 1-17, wherein the uORF start site region is the 5' untranslated region.

Embodiment 19: The method of any of embodiments 13-18, wherein the target site comprises the uORF start site.

Embodiment 20: The method of any of embodiments 13-19, wherein the target site region consists of the uORF start site and the 100 nucleosides upstream and the 100 nucleosides downstream of the uORF start site.

Embodiment 21: The method of any of embodiments 13-19, wherein the target site region consists of the uORF start site and the 75 nucleosides upstream and the 75 nucleosides downstream of the uORF start site.

Embodiment 22: The method of any of embodiments 13-19, wherein the target site region consists of the uORF start site and the 50 nucleosides upstream and the 50 nucleosides downstream of the uORF start site.

Embodiment 23: The method of any of embodiments 13-19, wherein the target site region consists of the uORF start site and the 30 nucleosides upstream and the 30 nucleosides downstream of the uORF start site.

Embodiment 24: The method of any of embodiments 13-19, wherein the target site region consists of the uORF start site and the 20 nucleosides upstream and the 20 nucleosides downstream of the uORF start site.

Embodiment 25: The method of any of embodiments 13-19, wherein the target site region consists of the uORF start site and the 15 nucleosides upstream and the 15 nucleosides downstream of the uORF start site.

Embodiment 26: The method of any of embodiments 13-25, wherein the uORF start site is a wild-type uORF start site.

Embodiment 27: The method of any of embodiments 13-25, wherein the uORF start site is a mutant uORF start site.

Embodiment 28: The method of any of embodiments 13-27, wherein the target transcript comprises more than one uORF region.

Embodiment 29: The method of any of embodiments 13-27, wherein the target transcript comprises two uORF regions.

Embodiment 30: The method of any of embodiments 13-29, wherein the uORF start site comprises a weak Kozak sequence.

Embodiment 31: The method of any of embodiments 13-29, wherein the uORF start site comprises a strong Kozak sequence.

Embodiment 32: The method of any of embodiments 13-31, wherein the uORF start site has a non-canonical start codon.

Embodiment 33: The method of embodiment 32, wherein the non-canonical start codon is AUU.

Embodiment 34: The method of any of embodiments 13-33, wherein the target transcript encodes RNase H1.

Embodiment 35: The method of any of embodiments 13-34, wherein the target transcript is encoded by a gene selected from the genes in Table 1 or Table 2.

Embodiment 36: The method of any of embodiments 12-35, wherein the modified oligonucleotide has a nucleobase sequence comprising the nucleobases CAT.

Embodiment 37: The method of any of embodiments 12-35, wherein the modified oligonucleotide has a nucleobase sequence wherein the first three of the 5'-most nucleobases are CAT.

Embodiment 38: The method of any of embodiments 12-35, wherein the modified oligonucleotide has a nucleobase sequence wherein the $2^{nd}$, $3^{rd}$ and $4^{th}$ nucleobases from the 5'-most terminal nucleobase are CAT.

Embodiment 39: The method of any of embodiments 12-35, wherein the modified oligonucleotide has a nucleobase sequence wherein the $3^{rd}$ $4^{th}$ and $5^{th}$ nucleobases from the 5'-most terminal nucleobase are CAT.

Embodiment 40: The method of any of embodiments 12-35, wherein the modified oligonucleotide has a nucleobase sequence wherein the $4^{th}$, $5^{th}$ and $6^{th}$ nucleobases from the 5'-most terminal nucleobase are CAT.

Embodiment 41: The method of any of embodiments 12-35, wherein the modified oligonucleotide has a nucleobase sequence wherein the $5^{th}$ $6^{th}$ and $7^{th}$ nucleobases from the 5'-most terminal nucleobase are CAT.

Embodiment 42: The method of any of embodiments 12-35, wherein the modified oligonucleotide has a nucleobase sequence wherein the $6^{th}$ $7^{th}$ and $8^{th}$ nucleobases from the 5'-most terminal nucleobase are CAT.

Embodiment 43: The method of any of embodiments 12-35, wherein the modified oligonucleotide has a nucleobase sequence wherein the $7^{th}$ $8^{th}$ and $9^{th}$ nucleobases from the 5'-most terminal nucleobase are CAT.

Embodiment 44: The method of any of embodiments 12-35, wherein the modified oligonucleotide has a nucleobase sequence wherein the first three of the 3'-most nucleobases are CAT.

Embodiment 45: The method of any of embodiments 12-35, wherein the modified oligonucleotide has a nucleobase sequence wherein the $2^{nd}$, $3^{rd}$ and $4^{th}$ nucleobases from the 3'-most terminal nucleobase are CAT.

Embodiment 46: The method of any of embodiments 12-35, wherein the modified oligonucleotide has a nucleobase sequence wherein the $3^{rd}$ $4^{th}$ and $5^{th}$ nucleobases from the 3'-most terminal nucleobase are CAT.

Embodiment 47: The method of any of embodiments 12-35, wherein the modified oligonucleotide has a nucleobase sequence wherein the $4^{th}$, $5^{th}$ and $6^{th}$ nucleobases from the 3'-most terminal nucleobase are CAT.

Embodiment 48: The method of any of embodiments 12-35, wherein the modified oligonucleotide has a nucleobase sequence wherein the $5^{th}$ $6^{th}$ and $7^{th}$ nucleobases from the 3'-most terminal nucleobase are CAT.

Embodiment 49: The method of any of embodiments 12-35, wherein the modified oligonucleotide comprises a nucleobase sequence complementary to a Kozak sequence.

Embodiment 50: The method of any of embodiments 12-35, wherein the modified oligonucleotide has a nucleobase sequence comprising at least 8 contiguous nucleobases complementary to the uORF region of SEQ ID NOs: 1 or 2.

Embodiment 51: The method of any of embodiments 12-35, wherein the modified oligonucleotide has a nucleobase sequence comprising at least 8 contiguous nucleobases of any of the nucleobase sequences of SEQ ID NOs: 3, 4, 5, 6, 7, 8, 9, 10, 11, 12, 13, 14, 15, 16, 17 or 18.

Embodiment 52: The method of any of embodiments 12-35, wherein the modified oligonucleotide has a nucleobase sequence comprising at least 10 contiguous nucleobases of any of the nucleobase sequences of SEQ ID NOs: 3, 4, 5, 6, 7, 8, 9, 10, 11, 12, 13, 14, 15, 16, 17 or 18.

Embodiment 53: The method of any of embodiments 12-35, wherein the modified oligonucleotide has a nucleobase sequence comprising at least 12 contiguous nucleobases of any of the nucleobase sequences of SEQ ID NOs: 3, 4, 5, 6, 7, 8, 9, 10, 11, 12, 13, 14, 15, 16, 17 or 18.

Embodiment 54: The method of any of embodiments 12-35, wherein the modified oligonucleotide has a nucleobase sequence comprising at least 14 contiguous nucleobases of any of the nucleobase sequences of SEQ ID NOs: 3, 4, 5, 6, 7, 8, 9, 10, 11, 12, 13, 14, 15, 16, 17 or 18.

Embodiment 55: The method of any of embodiments 12-35, wherein the modified oligonucleotide has a nucleobase sequence consisting of the nucleobase sequence of any of SEQ ID NOs: 3, 4, 5, 6, 7, 8, 9, 10, 11, 12, 13, 14, 15, 16, 17 or 18.

Embodiment 56: The method of any of embodiments 12-55, wherein the modified oligonucleotide consists of 10 to 40 linked nucleosides.

Embodiment 57: The method of any of embodiments 12-55, wherein the modified oligonucleotide consists of 12 to 22 linked nucleosides.

Embodiment 58: The method of any of embodiments 12-55, wherein the modified oligonucleotide consists of 15 to 22 linked nucleosides.

Embodiment 59: The method of any of embodiments 12-55, wherein the modified oligonucleotide consists of 18 to 20 linked nucleosides.

Embodiment 60: The method of any of embodiments 12-59, wherein the modified oligonucleotide comprises at least one modified nucleoside.

Embodiment 61: The method of embodiment 60, wherein at least one modified nucleoside comprises a modified sugar moiety.

Embodiment 62: The method of embodiment 61, wherein at least one modified sugar moiety is a 2'-substituted sugar moiety.

Embodiment 63: The method of embodiment 62, wherein the 2'-substituent of at least one 2'-substituted sugar moiety is selected from among: 2'-OMe, 2'-F, and 2'-MOE.

Embodiment 64: The method of any of embodiments 60-63, wherein the 2'-substituent of at least one 2'-substituted sugar moiety is a 2'-MOE.

Embodiment 65: The method of any of embodiments 60-61, wherein at least one modified sugar moiety is a bicyclic sugar moiety.

Embodiment 66: The method of embodiment 65, wherein at least one bicyclic sugar moiety is LNA or cEt.

Embodiment 67: The method of any of embodiments 61-66, wherein at least one sugar moiety is a sugar surrogate.

Embodiment 68: The method of embodiment 67, wherein at least one sugar surrogate is a morpholino.

Embodiment 69: The method of embodiment 67, wherein at least one sugar surrogate is a modified morpholino.

Embodiment 70: The method of embodiment 67, wherein at least one sugar surrogate is a peptide nucleic acid.

Embodiment 71: The method of any of embodiment 60-70, wherein the modified oligonucleotide comprises at least 5 modified nucleosides, each independently comprising a modified sugar moiety.

Embodiment 72: The method of any of embodiment 60-70, wherein the modified oligonucleotide comprises at least 6 modified nucleosides, each independently comprising a modified sugar moiety.

Embodiment 73: The method of any of embodiment 60-70, wherein the modified oligonucleotide comprises at least 7 modified nucleosides, each independently comprising a modified sugar moiety.

Embodiment 74: The method of any of embodiment 60-70, wherein the modified oligonucleotide comprises at least 8 modified nucleosides, each independently comprising a modified sugar moiety.

Embodiment 75: The method of any of embodiment 60-70, wherein the modified oligonucleotide comprises at least 9 modified nucleosides, each independently comprising a modified sugar moiety.

Embodiment 76: The method of embodiment 60-70, wherein the modified oligonucleotide comprises at least 10 modified nucleosides, each independently comprising a modified sugar moiety.

Embodiment 77: The method of any of embodiments 60-76, wherein each nucleoside of the modified oligonucleotide is a modified nucleoside or an unmodified nucleoside.

Embodiment 78: The method of embodiment 77, wherein each unmodified nucleoside is a 2'-deoxy nucleoside.

Embodiment 79: The method of any of embodiments 77-78, wherein the modified oligonucleotide comprises at least 6 2'-deoxy nucleosides.

Embodiment 80: The method of any of embodiments 77-78, wherein the modified oligonucleotide comprises at least 7 2'-deoxy nucleosides.

Embodiment 81: The method of any of embodiments 77-78, wherein the modified oligonucleotide comprises at least 8 2'-deoxy nucleosides.

Embodiment 82: The method of any of embodiments 77-78, wherein the modified oligonucleotide comprises at least 9 2'-deoxy nucleosides.

Embodiment 83: The method of any of embodiments 77-78, wherein the modified oligonucleotide comprises at least 10 2'-deoxy nucleosides.

Embodiment 84: The method of any of embodiments 79-83, wherein the modified oligonucleotide contains no more than 4 contiguous 2'-deoxy nucleosides.

Embodiment 85: The method of any of embodiments 77-78, wherein the modified oligonucleotide comprises at least 15 modified nucleosides, each independently comprising a modified sugar moiety.

Embodiment 86: The method of embodiment 85, wherein each nucleoside of the modified oligonucleotide is a modified nucleoside, each independently comprising a modified sugar moiety.

Embodiment 87: The method of any of embodiments 60-86, wherein the modified oligonucleotide comprises at least two modified nucleosides comprising modified sugar moieties that are the same as one another.

Embodiment 88: The method of any of embodiments 60-86, wherein the modified oligonucleotide comprises at least two modified nucleosides comprising modified sugar moieties that are different from one another.

Embodiment 89: The method of any of embodiments 60-86, wherein the modified oligonucleotide comprises a modified region of at least 5 contiguous modified nucleosides.

Embodiment 90: The method of embodiment 89, wherein the modified oligonucleotide comprises a modified region of at least 10 contiguous modified nucleosides.

Embodiment 91: The method of embodiment 89, wherein the modified oligonucleotide comprises a modified region of at least 15 contiguous modified nucleosides.

Embodiment 92: The method of embodiment 89, wherein the modified oligonucleotide comprises a modified region of at least 18 contiguous modified nucleosides.

Embodiment 93: The method of embodiment 89, wherein the modified oligonucleotide comprises a modified region of at least 20 contiguous modified nucleosides.

Embodiment 94: The method of any of embodiments 90-93, wherein each modified nucleoside of the modified region has a modified sugar moiety independently selected from among: 2'-F, 2'-OMe, 2'-MOE, cEt, LNA, morpholino, modified morpholino, and peptide nucleic acid.

Embodiment 95: The method of any of embodiments 90-94, wherein the modified nucleosides of the modified region each comprise the same modification as one another.

Embodiment 96: The method of embodiment 95, wherein the modified nucleosides of the modified region each comprise the same 2'-substituted sugar moiety.

Embodiment 97: The method of embodiment 95, wherein the 2'-substituted sugar moiety of the modified nucleosides of the region of modified nucleosides is selected from 2'-F, 2'-OMe, and 2'-MOE.

Embodiment 98: The method of embodiment 96, wherein the 2'-substituted sugar moiety of the modified nucleosides of the region of modified nucleosides is 2'-MOE.

Embodiment 99: The method of embodiment 95, wherein the modified nucleosides of the region of modified nucleosides each comprise the same bicyclic sugar moiety.

Embodiment 100: The method of embodiment 99, wherein the bicyclic sugar moiety of the modified nucleosides of the region of modified nucleosides is selected from LNA and cEt.

Embodiment 101: The method of embodiment 95, wherein the modified nucleosides of the region of modified nucleosides each comprises a sugar surrogate.

Embodiment 102: The method of embodiment 101, wherein the sugar surrogate of the modified nucleosides of the region of modified nucleosides is a morpholino.

Embodiment 103: The method of embodiment 101, wherein the sugar surrogate of the modified nucleosides of the region of modified nucleosides is a modified morpholino.

Embodiment 104: The method of embodiment 101, wherein the sugar surrogate of the modified nucleosides of the region of modified nucleosides is a peptide nucleic acid.

Embodiment 105: The method of any of embodiments 60-104, wherein the modified nucleotide comprises no more than 4 contiguous naturally occurring nucleosides.

Embodiment 106: The method of any of embodiments 60-107, wherein each nucleoside of the modified oligonucleotide is a modified nucleoside.

Embodiment 107: The method of embodiment 106 wherein each modified nucleoside comprises a modified sugar moiety.

Embodiment 108: The method of embodiment 107, wherein the modified nucleosides of the modified oligonucleotide comprise the same modification as one another.

Embodiment 109: The method of embodiment 108, wherein the modified nucleosides of the modified oligonucleotide each comprise the same 2'-substituted sugar moiety.

Embodiment 110: The method of embodiment 109, wherein the 2'-substituted sugar moiety of the modified oligonucleotide is selected from 2'-F, 2'-OMe, and 2'-MOE.

Embodiment 111: The method of embodiment 110, wherein the 2'-substituted sugar moiety of the modified oligonucleotide is 2'-MOE.

Embodiment 112: The method of embodiment 110, wherein the 2'-substituted sugar moiety of the modified oligonucleotide is 2'-OMe.

Embodiment 113: The method of embodiment 108, wherein the modified nucleosides of the modified oligonucleotide each comprise the same bicyclic sugar moiety.

Embodiment 114: The method of embodiment 113, wherein the bicyclic sugar moiety of the modified oligonucleotide is selected from LNA and cEt.

Embodiment 115: The method of embodiment 98, wherein the modified nucleosides of the modified oligonucleotide each comprises a sugar surrogate.

Embodiment 116: The method of embodiment 115, wherein the sugar surrogate of the modified oligonucleotide is a morpholino.

Embodiment 117: The method of embodiment 115, wherein the sugar surrogate of the modified oligonucleotide is a modified morpholino.

Embodiment 118: The method of embodiment 115, wherein the sugar surrogate of the modified oligonucleotide is a peptide nucleic acid.

Embodiment 119: The method of any of embodiments 60-118, wherein the modified oligonucleotide comprises at least one modified internucleoside linkage.

Embodiment 120: The method of embodiment 119, wherein the modified internucleoside linkage is a phosphorothioate internucleoside linkage.

Embodiment 121: The method of embodiment 119 or 120, wherein each internucleoside linkage is either a phosphodiester internucleoside linkage or a phosphorothioate internucleoside linkage.

Embodiment 122: The method of embodiment 119, wherein each internucleoside linkage is a modified internucleoside linkage.

Embodiment 123: The method of embodiment 119 or 120, comprising at least one phosphorothioate internucleoside linkage.

Embodiment 124: The method of embodiment 119, wherein each internucleoside linkage is a modified internucleoside linkage and wherein each internucleoside linkage comprises the same modification.

Embodiment 125: The method of embodiment 122, wherein each internucleoside linkage is a phosphorothioate internucleoside linkage.

Embodiment 126: The method of any of embodiments 60-125, wherein the antisense compound comprises at least one conjugate group.

Embodiment 127: The method of embodiment 126, wherein the conjugate group comprises Gal-NAc.

Embodiment 128: The method of any of embodiments 60-126, wherein the antisense compound consists of the modified oligonucleotide.

Embodiment 129: The method of any of embodiments 13-128, wherein the expression, translation, or amount or activity of the target protein is increased by at least 10%.

Embodiment 130: The method of any of embodiments 13-128, wherein the expression, translation, or amount or activity of the target protein is increased by at least 20%.

Embodiment 131: The method of any of embodiments 13-128, wherein the expression, translation, or amount or activity of the target protein is increased by at least 30%.

Embodiment 132: The method of any of embodiments 13-128, wherein the expression, translation, or amount or activity of the target protein is increased by at least 50%.

Embodiment 133: The method of any of embodiments 13-128, wherein the expression, translation, or amount or activity of the target protein is increased by at least 100%.

Embodiment 134: The method of any of embodiments 13-128, wherein the expression, translation, or amount or activity of the target protein is increased by at least 120%.

Embodiment 135: The method of any of embodiments 13-128, wherein the expression, translation, or amount or activity of the target protein is increased by at least 150%.

Embodiment 136: The method of any of embodiments 1-135, wherein the cell is in vitro.

Embodiment 137: The method of any of embodiments 1-135, wherein the cell is in a subject.

Embodiment 138: The method of embodiment 137, wherein the subject has a disease or condition and wherein at least one symptom of the disease or condition is ameliorated.

Embodiment 139: The method of embodiment 137 or 138, wherein the cell is in an animal.

Embodiment 140: The method of embodiment 139, wherein the animal is a human.

Embodiment 141: An antisense compound comprising a modified oligonucleotide consisting of 10-30 linked nucleosides having a nucleobase sequence complementary to a target site within a uORF start site region of a target transcript and wherein the modified oligonucleotide does not have more than four contiguous unmodified 2'-deoxy nucleosides.

Embodiment 142: The antisense compound of embodiments 141, wherein the uORF start site region is the 5' untranslated region.

Embodiment 143: The antisense compound of any of embodiments 141-142, wherein the target site comprises the uORF start site.

Embodiment 144: The antisense compound of any of embodiments 141-143, wherein the target site is within 50 nucleosides upstream or downstream of the uORF start site.

Embodiment 145: The antisense compound of any of embodiments 141-143, wherein the target site is within 40 nucleosides upstream or downstream of the uORF start site.

Embodiment 146: The antisense compound of any of embodiments 141-143, wherein the target site is within 30 nucleosides upstream or downstream of the uORF start site.

Embodiment 147: The antisense compound of any of embodiments 141-143, wherein the target site is within 20 nucleosides upstream or downstream of the uORF start site.

Embodiment 148: The antisense compound of any of embodiments 141-143, wherein the target site is within 10 nucleosides upstream or downstream of the uORF start site.

Embodiment 149: The antisense compound of any of embodiments 141-143, wherein the target site is within 5 nucleosides upstream or downstream of the uORF start site.

Embodiment 150: The antisense compound of any of embodiments 141-143, wherein the target site comprises a wild-type uORF region.

Embodiment 151: The antisense compound of any of embodiments 141-143, wherein the target site comprises a uORF region that arises from a mutation.

Embodiment 152: The antisense compound of any of embodiments 141-143, wherein the target transcript comprises more than one uORF region.

Embodiment 153: The antisense compound of any of embodiments 141-143, wherein the target transcript comprises two uORF regions.

Embodiment 154: The antisense compound of any of embodiments 141-143, wherein the uORF start site region comprises a weak Kozak sequence.

Embodiment 155: The antisense compound of any of embodiments 141-143, wherein the uORF start site region comprises a strong Kozak sequence.

Embodiment 156: The antisense compound of any of embodiments 141-143, wherein the uORF start site has a non-canonical start codon.

Embodiment 157: The antisense compound of embodiment 156, wherein the non-canonical start codon is AUU.

Embodiment 158: The antisense compound of any of embodiments 141-157, wherein the target transcript encodes RNase H1.

Embodiment 159: The antisense compound of any of embodiments 141-157, wherein the target transcript encodes a protein translated from a gene selected from the genes in Table 1 or Table 2.

Embodiment 160: The antisense compound of any of embodiments 141-159, wherein the modified oligonucleotide has a nucleobase sequence comprising the nucleobases CAT.

Embodiment 161: The antisense compound of any of embodiments 141-159, wherein the modified oligonucleotide has a nucleobase sequence wherein the first three of the 5'-most nucleobases are CAT.

Embodiment 162: The antisense compound of any of embodiments 141-159, wherein the modified oligonucleotide has a nucleobase sequence wherein the $2^{nd}$, $3^{rd}$ and $4^{th}$ nucleobases from the 5'-most terminal nucleobase are CAT.

Embodiment 163: The antisense compound of any of embodiments 141-159, wherein the modified oligonucleotide has a nucleobase sequence wherein the $3^{rd}$ $4^{th}$ and $5^{th}$ nucleobases from the 5'-most terminal nucleobase are CAT.

Embodiment 164: The antisense compound of any of embodiments 141-159, wherein the modified oligonucleotide has a nucleobase sequence wherein the $4^{th}$, $5^{th}$ and $6^{th}$ nucleobases from the 5'-most terminal nucleobase are CAT.

Embodiment 165: The antisense compound of any of embodiments 141-159, wherein the modified oligonucleotide has a nucleobase sequence wherein the $5^{th}$ $6^{th}$ and $7^{th}$ nucleobases from the 5'-most terminal nucleobase are CAT.

Embodiment 166: The antisense compound of any of embodiments 141-159, wherein the modified oligonucleotide has a nucleobase sequence wherein the $6^{th}$ $7^{th}$ and $8^{th}$ nucleobases from the 5'-most terminal nucleobase are CAT.

Embodiment 167: The antisense compound of any of embodiments 141-159, wherein the modified oligonucleotide has a nucleobase sequence wherein the $7^{th}$ $8^{th}$ and $9^{th}$ nucleobases from the 5'-most terminal nucleobase are CAT.

Embodiment 168: The antisense compound of any of embodiments 141-167, wherein the modified oligonucleotide has a nucleobase sequence complementary to a Kozak sequence.

Embodiment 169: The antisense compound of any of embodiments 141-168, wherein the modified oligonucleotide has a nucleobase sequence comprising at least 8 contiguous nucleobases complementary to the uORF region of SEQ ID NOs: 1 or 2.

Embodiment 170: The antisense compound of any of embodiments 141-168, wherein the modified oligonucleotide has a nucleobase sequence comprising at least 8 contiguous nucleobases of any of the nucleobase sequences of SEQ ID NOs: 3, 4, 5, 6, 7, 8, 9, 10, 11, 12, 13, 14, 15, 16, 17 or 18.

Embodiment 171: The antisense compound of any of embodiments 141-168, wherein the modified oligonucleotide has a nucleobase sequence comprising at least 10 contiguous nucleobases of any of the nucleobase sequences of SEQ ID NOs: 3, 4, 5, 6, 7, 8, 9, 10, 11, 12, 13, 14, 15, 16, 17 or 18.

Embodiment 172: The antisense compound of any of embodiments 141-168, wherein the modified oligonucleotide has a nucleobase sequence comprising at least 12 contiguous nucleobases of any of the nucleobase sequences of SEQ ID NOs: 3, 4, 5, 6, 7, 8, 9, 10, 11, 12, 13, 14, 15, 16, 17 or 18.

Embodiment 173: The antisense compound of any of embodiments 141-168, wherein the modified oligonucleotide has a nucleobase sequence comprising at least 14 contiguous nucleobases of any of the nucleobase sequences of SEQ ID NOs: 3, 4, 5, 6, 7, 8, 9, 10, 11, 12, 13, 14, 15, 16, 17 or 18.

Embodiment 174: The antisense compound of any of embodiments 141-168, wherein the modified oligonucleotide has a nucleobase sequence consisting of the nucleobase sequence of any of SEQ ID NOs: 3, 4, 5, 6, 7, 8, 9, 10, 11, 12, 13, 14, 15, 16, 17 or 18.

Embodiment 175: The antisense compound of any of embodiments 141-174, wherein the modified oligonucleotide consists of 10 to 40 linked nucleosides.

Embodiment 176: The antisense compound of any of embodiments 141-174, wherein the modified oligonucleotide consists of 12 to 22 linked nucleosides.

Embodiment 177: The antisense compound of any of embodiments 141-174, wherein the modified oligonucleotide consists of 15 to 22 linked nucleosides.

Embodiment 178: The antisense compound of any of embodiments 141-174, wherein the modified oligonucleotide consists of 18 to 20 linked nucleosides.

Embodiment 179: The antisense compound of any of embodiments 141-174, wherein the modified oligonucleotide comprises at least one modified nucleoside.

Embodiment 180: The antisense compound of any of embodiments 175-179, wherein at least one modified nucleoside comprises a modified sugar moiety.

Embodiment 181: The antisense compound of embodiment 180, wherein at least one modified sugar moiety is a 2'-substituted sugar moiety.

Embodiment 182: The antisense compound of embodiment 181, wherein the 2'-substituent of at least one 2'-substituted sugar moiety is selected from among: 2'-OMe, 2'-F, and 2'-MOE.

Embodiment 183: The antisense compound of any of embodiments 179-182, wherein the 2'-substituent of at least one 2'-substituted sugar moiety is a 2'-MOE.

Embodiment 184: The antisense compound of any of embodiments 179-180, wherein at least one modified sugar moiety is a bicyclic sugar moiety.

Embodiment 185: The antisense compound of embodiment 184, wherein at least one bicyclic sugar moiety is LNA or cEt.

Embodiment 186: The antisense compound of any of embodiments 179-185, wherein at least one sugar moiety is a sugar surrogate.

Embodiment 187: The antisense compound of embodiment 186, wherein at least one sugar surrogate is a morpholino.

Embodiment 188: The antisense compound of embodiment 186, wherein at least one sugar surrogate is a modified morpholino.

Embodiment 189: The antisense compound of embodiment 186, wherein at least one sugar surrogate is a peptide nucleic acid.

Embodiment 190: The antisense compound of any of embodiment 179-189, wherein the modified oligonucleotide comprises at least 5 modified nucleosides, each independently comprising a modified sugar moiety.

Embodiment 191: The antisense compound of any of embodiment 179-189, wherein the modified oligonucleotide comprises at least 6 modified nucleosides, each independently comprising a modified sugar moiety.

Embodiment 192: The antisense compound of any of embodiment 179-189, wherein the modified oligonucleotide comprises at least 7 modified nucleosides, each independently comprising a modified sugar moiety.

Embodiment 193: The antisense compound of any of embodiment 179-189, wherein the modified oligonucleotide comprises at least 8 modified nucleosides, each independently comprising a modified sugar moiety.

Embodiment 194: The antisense compound of any of embodiment 179-189, wherein the modified oligonucleotide comprises at least 9 modified nucleosides, each independently comprising a modified sugar moiety.

Embodiment 195: The antisense compound of embodiment 179-189, wherein the modified oligonucleotide comprises at least 10 modified nucleosides, each independently comprising a modified sugar moiety.

Embodiment 196: The antisense compound of any of embodiments 179-195, wherein each nucleoside of the modified oligonucleotide is a modified nucleoside or an unmodified nucleoside.

Embodiment 197: The antisense compound of embodiment 196, wherein each unmodified nucleoside is a 2'-deoxy nucleoside.

Embodiment 198: The antisense compound of any of embodiments 196-197, wherein the modified oligonucleotide comprises at least 6 2'-deoxy nucleosides.

Embodiment 199: The antisense compound of any of embodiments 196-197, wherein the modified oligonucleotide comprises at least 7 2'-deoxy nucleosides.

Embodiment 200: The antisense compound of any of embodiments 196-197, wherein the modified oligonucleotide comprises at least 8 2'-deoxy nucleosides.

Embodiment 201: The antisense compound of any of embodiments 196-197, wherein the modified oligonucleotide comprises at least 9 2'-deoxy nucleosides.

Embodiment 202: The antisense compound of any of embodiments 196-197, wherein the modified oligonucleotide comprises at least 10 2'-deoxy nucleosides.

Embodiment 203: The antisense compound of any of embodiments 198-1202, wherein the modified oligonucleotide contains no more than 4 contiguous 2'-deoxy nucleosides.

Embodiment 204: The antisense compound of any of embodiments 196-197, wherein the modified oligonucleotide comprises at least 15 modified nucleosides, each independently comprising a modified sugar moiety.

Embodiment 205: The antisense compound of embodiment 204, wherein each nucleoside of the modified oligonucleotide is a modified nucleoside, each independently comprising a modified sugar moiety.

Embodiment 206: The antisense compound of any of embodiments 141-205, wherein the modified oligonucleotide comprises at least two modified nucleosides comprising modified sugar moieties that are the same as one another.

Embodiment 207: The antisense compound of any of embodiments 141-205, wherein the modified oligonucleotide comprises at least two modified nucleosides comprising modified sugar moieties that are different from one another.

Embodiment 208: The antisense compound of any of embodiments 141-204, wherein the modified oligonucleotide comprises a modified region of at least 5 contiguous modified nucleosides.

Embodiment 209: The antisense compound of embodiment 208, wherein the modified oligonucleotide comprises a modified region of at least 10 contiguous modified nucleosides.

Embodiment 210: The antisense compound of embodiment 208, wherein the modified oligonucleotide comprises a modified region of at least 15 contiguous modified nucleosides.

Embodiment 211: The antisense compound of embodiment 208, wherein the modified oligonucleotide comprises a modified region of at least 18 contiguous modified nucleosides.

Embodiment 212: The antisense compound of embodiment 208, wherein the modified oligonucleotide comprises a modified region of at least 20 contiguous modified nucleosides.

Embodiment 213: The antisense compound of any of embodiments 209-212, wherein each modified nucleoside of the modified region has a modified sugar moiety independently selected from among: 2'-F, 2'-OMe, 2'-MOE, cEt, LNA, morpholino, modified morpholino, and peptide nucleic acid.

Embodiment 214: The antisense compound of any of embodiments 209-213, wherein the modified nucleosides of the modified region each comprise the same modification as one another.

Embodiment 215: The antisense compound of embodiment 214, wherein the modified nucleosides of the modified region each comprise the same 2'-substituted sugar moiety.

Embodiment 216: The antisense compound of embodiment 214, wherein the 2'-substituted sugar moiety of the modified nucleosides of the region of modified nucleosides is selected from 2'-F, 2'-OMe, and 2'-MOE.

Embodiment 217: The antisense compound of embodiment 215, wherein the 2'-substituted sugar moiety of the modified nucleosides of the region of modified nucleosides is 2'-MOE.

Embodiment 218: The antisense compound of embodiment 214, wherein the modified nucleosides of the region of modified nucleosides each comprise the same bicyclic sugar moiety.

Embodiment 219: The antisense compound of embodiment 218, wherein the bicyclic sugar moiety of the modified nucleosides of the region of modified nucleosides is selected from LNA and cEt.

Embodiment 220: The antisense compound of embodiment 214, wherein the modified nucleosides of the region of modified nucleosides each comprises a sugar surrogate.

Embodiment 221: The antisense compound of embodiment 220, wherein the sugar surrogate of the modified nucleosides of the region of modified nucleosides is a morpholino.

Embodiment 222: The antisense compound of embodiment 220, wherein the sugar surrogate of the modified nucleosides of the region of modified nucleosides is a modified morpholino.

Embodiment 223: The antisense compound of embodiment 220, wherein the sugar surrogate of the modified nucleosides of the region of modified nucleosides is a peptide nucleic acid.

Embodiment 224: The antisense compound of any of embodiments 141-204, or 206 to 223, wherein the modified nucleotide comprises no more than 4 contiguous naturally occurring nucleosides.

Embodiment 225: The antisense compound of any of embodiments 141-196, wherein each nucleoside of the modified oligonucleotide is a modified nucleoside.

Embodiment 226: The antisense compound of embodiment 225 wherein each modified nucleoside comprises a modified sugar moiety.

Embodiment 227: The antisense compound of embodiment 226, wherein the modified nucleosides of the modified oligonucleotide comprise the same modification as one another.

Embodiment 228: The antisense compound of embodiment 227, wherein the modified nucleosides of the modified oligonucleotide each comprise the same 2'-substituted sugar moiety.

Embodiment 229: The antisense compound of embodiment 228, wherein the 2'-substituted sugar moiety of the modified oligonucleotide is selected from 2'-F, 2'-OMe, and 2'-MOE.

Embodiment 230: The antisense compound of embodiment 229, wherein the 2'-substituted sugar moiety of the modified oligonucleotide is 2'-MOE.

Embodiment 231: The antisense compound of embodiment 229, wherein the 2'-substituted sugar moiety of the modified oligonucleotide is 2'-OMe.

Embodiment 232: The antisense compound of embodiment 227, wherein the modified nucleosides of the modified oligonucleotide each comprise the same bicyclic sugar moiety.

Embodiment 233: The antisense compound of embodiment 232, wherein the bicyclic sugar moiety of the modified oligonucleotide is selected from LNA and cEt.

Embodiment 234: The antisense compound of embodiment 227, wherein the modified nucleosides of the modified oligonucleotide each comprises a sugar surrogate.

Embodiment 235: The antisense compound of embodiment 234, wherein the sugar surrogate of the modified oligonucleotide is a morpholino.

Embodiment 236: The antisense compound of embodiment 234, wherein the sugar surrogate of the modified oligonucleotide is a modified morpholino.

Embodiment 237: The antisense compound of embodiment 234, wherein the sugar surrogate of the modified oligonucleotide is a peptide nucleic acid.

Embodiment 238: The antisense compound of any of embodiments 141-237, wherein the modified oligonucleotide comprises at least one modified internucleoside linkage.

Embodiment 239: The antisense compound of embodiment 238, wherein each internucleoside linkage is a modified internucleoside linkage.

Embodiment 240: The antisense compound of embodiment 238 or 239, comprising at least one phosphorothioate internucleoside linkage.

Embodiment 241: The antisense compound of embodiment 238 or 239, wherein each internucleoside linkage is a phosphorothioate linkage or a phosphodiester internucleoside linkage.

Embodiment 242: The antisense compound of embodiment 238, wherein each internucleoside linkage is a modified internucleoside linkage and wherein each internucleoside linkage comprises the same modification.

Embodiment 243: The antisense compound of embodiment 242, wherein each internucleoside linkage is a phosphorothioate internucleoside linkage.

Embodiment 244: The antisense compound of any of embodiments 141-243, comprising at least one conjugate group.

Embodiment 245: The antisense compound of embodiment 244, wherein the conjugate group comprises Gal-NAc.

Embodiment 246: The antisense compound of any of embodiments 141-243, consisting of the modified oligonucleotide.

Embodiment 247: The antisense compound of any of embodiments 141-246, wherein the antisense compound increases translation of the target protein.

Embodiment 248: The antisense compound of any of embodiments 141-247, wherein the antisense compound does not relieve suppression of transcription.

Embodiment 249: The antisense compound of any of embodiments 141-248, wherein the antisense compound does not modulate splicing of the target transcript.

Embodiment 250: A pharmaceutical composition comprising the antisense compound of any of embodiments 141-249 and at least one pharmaceutically acceptable carrier or diluent.

Embodiment 251: A method of increasing the amount or activity of a target protein in a cell, comprising contacting the cell with the antisense compound or composition of any of embodiments 141-250.

Embodiment 252: A method of increasing expression of a target protein in a cell, comprising contacting the cell with the antisense compound or composition of any of embodiments 141-250.

Embodiment 253: A method of increasing translation a target protein in a cell, comprising contacting the cell with the antisense compound or composition of any of embodiments 141-250.

Embodiment 254: A method of decreasing suppression of translation a target protein in a cell, comprising contacting the cell with the antisense compound or composition of any of embodiments 141-250.

Embodiment 255: A method of decreasing translation of a uORF polypeptide in a cell, comprising contacting the cell with an antisense compound or composition of any of embodiments 141-250.

Embodiment 256: The method of any of embodiments 251-255, wherein the cell is in vitro.

Embodiment 257: The method of any of embodiments 251-255, wherein the cell is in an animal.

Embodiment 258: The method of embodiment 257, wherein the animal is a human.

Embodiment 259: A method of administering the antisense compound or composition of any of embodiments 141-250 to a subject in need thereof.

Embodiment 260: A method of treating a disease or condition, comprising administering the antisense compound or composition of any of embodiments 141-250 to a subject in need thereof.

Embodiment 261: The method of embodiment 260, wherein administering the antisense compound or composition of any of claims 141-250 to a subject in need thereof ameliorates one or more symptoms of the disease or condition Embodiment 262: The method of any of embodiments 259-261, wherein the subject is a human.

Embodiment 263: Use of the antisense compound or composition of any of embodiments 141-250 for the treatment of a disease or condition.

Embodiment 264: Use of the antisense compound or composition of any of embodiments 141-250 for the preparation of a medicament for the treatment of a disease or condition.

Embodiment 265: A method of increasing translation of a target protein in a cell, comprising contacting the cell with a translation suppression element inhibitor, wherein the target protein is encoded by a target transcript comprising at least one translation suppression element; and thereby increasing translation of the target protein in a cell.

Embodiment 266: A method of decreasing suppression of translation a target protein in a cell, comprising contacting the cell with a translation suppression element inhibitor, wherein the target protein is encoded by a target transcript comprising at least one translation suppression element; and thereby decreasing suppression of translation of the target protein in a cell.

Embodiment 267: A method of increasing the amount or activity of a target protein in a cell, comprising contacting the cell with a translation suppression element inhibitor, wherein the target protein is encoded by a target transcript comprising at least one translation suppression element; and thereby increasing the amount or activity of the target protein in the cell.

Embodiment 268: A method of increasing expression of a target protein in a cell, comprising contacting the cell with a translation suppression element inhibitor, wherein the target protein is encoded by a target transcript comprising at least one translation suppression element; and thereby increasing the expression of the target protein in a cell.

Embodiment 269: The method of any of embodiments 265-268, wherein the translation suppression element inhibitor is a small molecule.

Embodiment 270: The method of any of embodiments 265-268, wherein the translation suppression element inhibitor is an antibody.

Embodiment 271: The method of any of embodiments 265-268, wherein the translation suppression element inhibitor is a peptide.

Embodiment 272: The method of any of embodiments 265-268, wherein the translation suppression element inhibitor is a nucleic acid.

Embodiment 273: The method of any of embodiments 265-268, wherein the translation suppression element inhibitor is an siRNA.

Embodiment 274: The method of any of embodiments 265-268, wherein the translation suppression element inhibitor is an antisense compound.

Embodiment 275: The method of embodiment 274, wherein the antisense compound is a modified oligonucleotide.

Embodiment 276: A method of increasing translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing translation of the target protein in the cell.

Embodiment 277: A method of decreasing suppression of translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby decreasing suppression of translation of the target protein in the cell.

Embodiment 278: A method of increasing the amount or activity of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing the amount or activity of the target protein in the cell.

Embodiment 279: A method of increasing expression of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing expression of the target protein in the cell.

Embodiment 280: The method of any of embodiments 276-279, wherein the translation suppression element region is the 5' untranslated region.

Embodiment 281: The method of any of embodiments 276-280, wherein the target transcript encodes RNase H1.

Embodiment 282: The method of any of embodiments 276-280, wherein the target transcript does not encode RNase H1.

Embodiment 283: The method of any of embodiments 276-281, wherein the modified oligonucleotide has a nucleobase sequence comprising at least 8 contiguous nucleobases of any of the nucleobase sequences of SEQ ID NOs: 8, 9, 11, or 12.

Embodiment 284: The method of any of embodiments 276-281, wherein the modified oligonucleotide has a nucleobase sequence comprising at least 10 contiguous nucleobases of any of the nucleobase sequences of SEQ ID NOs: 8, 9, 11, or 12.

Embodiment 285: The method of any of embodiments 276-281, wherein the modified oligonucleotide has a nucleobase sequence comprising at least 12 contiguous nucleobases of any of the nucleobase sequences of SEQ ID NOs: 8, 9, 11, or 12.

Embodiment 286: The method of any of embodiments 276-281, wherein the modified oligonucleotide has a nucleobase sequence comprising at least 14 contiguous nucleobases of any of the nucleobase sequences of SEQ ID NOs: 8, 9, 11, or 12.

Embodiment 287: The method of any of embodiments 276-281, wherein the modified oligonucleotide has a nucleobase sequence consisting of the nucleobase sequence of any of SEQ ID NOs: 8, 9, 11, or 12.

Embodiment 288: The method of any of embodiments 276-282, wherein the modified oligonucleotide has a nucleobase sequence wherein at least 35% all the nucleobases are G or C nucleobases.

Embodiment 289: The method of any of embodiments 276-282, wherein the modified oligonucleotide has a nucleobase sequence wherein at least 40% all the nucleobases are G or C nucleobases.

Embodiment 290: The method of any of embodiments 276-282, wherein the modified oligonucleotide has a nucleobase sequence wherein at least 45% all the nucleobases are G or C nucleobases.

Embodiment 291: The method of any of embodiments 276-282, wherein the modified oligonucleotide has a nucleobase sequence wherein at least 50% all the nucleobases are G or C nucleobases.

Embodiment 292: The method of any of embodiments 276-282, wherein the modified oligonucleotide has a nucleobase sequence wherein at least 55% all the nucleobases are G or C nucleobases.

Embodiment 293: The method of any of embodiments 276-282, wherein the modified oligonucleotide has a nucleobase sequence wherein at least 60% all the nucleobases are G or C nucleobases.

Embodiment 294: The method of any of embodiments 276-282, wherein the modified oligonucleotide has a nucleobase sequence wherein at least 65% all the nucleobases are G or C nucleobases.

Embodiment 295: The method of any of embodiments 276-282, wherein the modified oligonucleotide has a nucleobase sequence wherein at least 70% all the nucleobases are G or C nucleobases.

Embodiment 296: The method of any of embodiments 276-282, wherein at least a portion of the nucleobase sequence of the modified oligonucleotide is complementary to a G-quartet.

Embodiment 297: The method of any of embodiments 276-295, wherein the modified oligonucleotide has a nucleobase sequence that is not complementary to a G-quartet.

Embodiment 298: The method of any of embodiments 276-297, wherein the modified oligonucleotide consists of 10 to 40 linked nucleosides.

Embodiment 299: The method of any of embodiments 276-297, wherein the modified oligonucleotide consists of 12 to 22 linked nucleosides.

Embodiment 300: The method of any of embodiments 276-297, wherein the modified oligonucleotide consists of 15 to 22 linked nucleosides.

Embodiment 301: The method of any of embodiments 276-297, wherein the modified oligonucleotide consists of 18 to 20 linked nucleosides.

Embodiment 302: The method of any of embodiments 276-297, wherein the modified oligonucleotide comprises at least one modified nucleoside.

Embodiment 303: The method of embodiment 302, wherein at least one modified nucleoside comprises a modified sugar moiety.

Embodiment 304: The method of embodiment 303, wherein at least one modified sugar moiety is a 2'-substituted sugar moiety.

Embodiment 305: The method of embodiment 304, wherein the 2'-substituent of at least one 2'-substituted sugar moiety is selected from among: 2'-OMe, 2'-F, and 2'-MOE.

Embodiment 306: The method of any of embodiments 302-305, wherein the 2'-substituent of at least one 2'-substituted sugar moiety is a 2'-MOE.

Embodiment 307: The method of any of embodiments 302-305, wherein the 2'-substituent of at least one 2'-substituted sugar moiety is not 2'OMe.

Embodiment 308: The method of any of embodiments 302-303, wherein at least one modified sugar moiety is a bicyclic sugar moiety.

Embodiment 309: The method of embodiment 308, wherein at least one bicyclic sugar moiety is LNA or cEt.

Embodiment 310: The method of any of embodiments 301-308, wherein at least one sugar moiety is a sugar surrogate.

Embodiment 311: The method of embodiment 303, wherein at least one sugar surrogate is a morpholino.

Embodiment 312: The method of embodiment 310, wherein at least one sugar surrogate is a modified morpholino.

Embodiment 313: The method of embodiment 310, wherein at least one sugar surrogate is a peptide nucleic acid.

Embodiment 314: The method of any of embodiment 302-313, wherein the modified oligonucleotide comprises at least 5 modified nucleosides, each independently comprising a modified sugar moiety.

Embodiment 315: The method of any of embodiment 302-313, wherein the modified oligonucleotide comprises at least 6 modified nucleosides, each independently comprising a modified sugar moiety.

Embodiment 316: The method of any of embodiment 302-313, wherein the modified oligonucleotide comprises at least 7 modified nucleosides, each independently comprising a modified sugar moiety.

Embodiment 317: The method of any of embodiment 302-313, wherein the modified oligonucleotide comprises at least 8 modified nucleosides, each independently comprising a modified sugar moiety.

Embodiment 318: The method of any of embodiment 302-313, wherein the modified oligonucleotide comprises at least 9 modified nucleosides, each independently comprising a modified sugar moiety.

Embodiment 319: The method of embodiment 302-313, wherein the modified oligonucleotide comprises at least 10 modified nucleosides, each independently comprising a modified sugar moiety.

Embodiment 320: The method of any of embodiments 302-319, wherein each nucleoside of the modified oligonucleotide is a modified nucleoside or an unmodified nucleoside.

Embodiment 321: The method of embodiment 320, wherein each unmodified nucleoside is a 2'-deoxy nucleoside.

Embodiment 322: The method of any of embodiments 320-321, wherein the modified oligonucleotide comprises at least 6 2'-deoxy nucleosides.

Embodiment 323: The method of any of embodiments 320-321, wherein the modified oligonucleotide comprises at least 7 2'-deoxy nucleosides.

Embodiment 324: The method of any of embodiments 320-321, wherein the modified oligonucleotide comprises at least 8 2'-deoxy nucleosides.

Embodiment 325: The method of any of embodiments 320-321, wherein the modified oligonucleotide comprises at least 9 2'-deoxy nucleosides.

Embodiment 326: The method of any of embodiments 320-321, wherein the modified oligonucleotide comprises at least 10 2'-deoxy nucleosides.

Embodiment 327: The method of any of embodiments 322-326, wherein the modified oligonucleotide contains no more than 4 contiguous 2'-deoxy nucleosides.

Embodiment 328: The method of any of embodiments 322-326, wherein the modified oligonucleotide comprises at least 15 modified nucleosides, each independently comprising a modified sugar moiety.

Embodiment 329: The method of embodiment 320, wherein each nucleoside of the modified oligonucleotide is a modified nucleoside, each independently comprising a modified sugar moiety.

Embodiment 330: The method of any of embodiments 303-329, wherein the modified oligonucleotide comprises at least two modified nucleosides comprising modified sugar moieties that are the same as one another.

Embodiment 331: The method of any of embodiments 303-329, wherein the modified oligonucleotide comprises at least two modified nucleosides comprising modified sugar moieties that are different from one another.

Embodiment 332: The method of any of embodiments 303-329, wherein the modified oligonucleotide comprises a modified region of at least 5 contiguous modified nucleosides.

Embodiment 333: The method of embodiment 332, wherein the modified oligonucleotide comprises a modified region of at least 10 contiguous modified nucleosides.

Embodiment 334: The method of embodiment 332, wherein the modified oligonucleotide comprises a modified region of at least 15 contiguous modified nucleosides.

Embodiment 335: The method of embodiment 332, wherein the modified oligonucleotide comprises a modified region of at least 18 contiguous modified nucleosides.

Embodiment 336: The method of embodiment 332, wherein the modified oligonucleotide comprises a modified region of at least 20 contiguous modified nucleosides.

Embodiment 337: The method of any of embodiments 332-336, wherein each modified nucleoside of the modified region has a modified sugar moiety independently selected from among: 2'-F, 2'-OMe, 2'-MOE, cEt, LNA, morpholino, modified morpholino, and peptide nucleic acid.

Embodiment 338: The method of any of embodiments 332-337, wherein the modified nucleosides of the modified region each comprise the same modification as one another.

Embodiment 339: The method of embodiment 338, wherein the modified nucleosides of the modified region each comprise the same 2'-substituted sugar moiety.

Embodiment 340: The method of embodiment 338, wherein the 2'-substituted sugar moiety of the modified nucleosides of the region of modified nucleosides is selected from 2'-F, 2'-OMe, and 2'-MOE.

Embodiment 341: The method of embodiment 339, wherein the 2'-substituted sugar moiety of the modified nucleosides of the region of modified nucleosides is 2'-MOE.

Embodiment 342: The method of embodiment 338, wherein the modified nucleosides of the region of modified nucleosides each comprise the same bicyclic sugar moiety.

Embodiment 343: The method of embodiment 342, wherein the bicyclic sugar moiety of the modified nucleosides of the region of modified nucleosides is selected from LNA and cEt.

Embodiment 344: The method of embodiment 338, wherein the modified nucleosides of the region of modified nucleosides each comprises a sugar surrogate.

Embodiment 345: The method of embodiment 344, wherein the sugar surrogate of the modified nucleosides of the region of modified nucleosides is a morpholino.

Embodiment 346: The method of embodiment 344, wherein the sugar surrogate of the modified nucleosides of the region of modified nucleosides is a modified morpholino.

Embodiment 347: The method of embodiment 344, wherein the sugar surrogate of the modified nucleosides of the region of modified nucleosides is a peptide nucleic acid.

Embodiment 348: The method of any of embodiments 338-347, wherein the modified nucleotide comprises no more than 4 contiguous naturally occurring nucleosides.

Embodiment 349: The method of any of embodiments 338-347, wherein each nucleoside of the modified oligonucleotide is a modified nucleoside.

Embodiment 350: The method of embodiment 349 wherein each modified nucleoside comprises a modified sugar moiety.

Embodiment 351: The method of embodiment 350, wherein the modified nucleosides of the modified oligonucleotide comprise the same modification as one another.

Embodiment 352: The method of embodiment 351, wherein the modified nucleosides of the modified oligonucleotide each comprise the same 2'-substituted sugar moiety.

Embodiment 353: The method of embodiment 352, wherein the 2'-substituted sugar moiety of the modified oligonucleotide is selected from 2'-F, 2'-OMe, and 2'-MOE.

Embodiment 354: The method of embodiment 353, wherein the 2'-substituted sugar moiety of the modified oligonucleotide is 2'-MOE.

Embodiment 355: The method of embodiment 353, wherein the 2'-substituted sugar moiety of the modified oligonucleotide is 2'-OMe.

Embodiment 356: The method of embodiment 351, wherein the modified nucleosides of the modified oligonucleotide each comprise the same bicyclic sugar moiety.

Embodiment 357: The method of embodiment 356, wherein the bicyclic sugar moiety of the modified oligonucleotide is selected from LNA and cEt.

Embodiment 358: The method of embodiment 349-350, wherein the modified nucleosides of the modified oligonucleotide each comprises a sugar surrogate.

Embodiment 359: The method of embodiment 358, wherein the sugar surrogate of the modified oligonucleotide is a morpholino.

Embodiment 360: The method of embodiment 358, wherein the sugar surrogate of the modified oligonucleotide is a modified morpholino.

Embodiment 361: The method of embodiment 358, wherein the sugar surrogate of the modified oligonucleotide is a peptide nucleic acid.

Embodiment 362: The method of any of embodiments 276-361, wherein the modified oligonucleotide comprises at least one modified internucleoside linkage.

Embodiment 363: The method of embodiment 361, wherein the modified internucleoside linkage is a phosphorothioate internucleoside linkage.

Embodiment 364: The method of embodiment 362 or 363, wherein each internucleoside linkage is either a phosphodiester internucleoside linkage or a phosphorothioate internucleoside linkage.

Embodiment 365: The method of embodiment 362, wherein each internucleoside linkage is a modified internucleoside linkage.

Embodiment 366: The method of embodiment 362 or 363, comprising at least one phosphorothioate internucleoside linkage.

Embodiment 367: The method of embodiment 362, wherein each internucleoside linkage is a modified internucleoside linkage and wherein each internucleoside linkage comprises the same modification.

Embodiment 368: The method of embodiment 363, wherein each internucleoside linkage is a phosphorothioate internucleoside linkage.

Embodiment 369: The method of any of embodiments 276-368, wherein the antisense compound comprises at least one conjugate group.

Embodiment 370: The method of embodiment 369, wherein the conjugate group comprises Gal-NAc.

Embodiment 371: The method of any of embodiments 276-368, wherein the antisense compound consists of the modified oligonucleotide.

Embodiment 372: The method of any of embodiments 276-371, wherein the expression, translation, or amount or activity of the target protein is increased by at least 10%.

Embodiment 373: The method of any of embodiments 276-371, wherein the expression, translation, or amount or activity of the target protein is increased by at least 20%.

Embodiment 374: The method of any of embodiments 276-371, wherein the expression, translation, or amount or activity of the target protein is increased by at least 30%.

Embodiment 375: The method of any of embodiments 276-371, wherein the expression, translation, or amount or activity of the target protein is increased by at least 50%.

Embodiment 376: The method of any of embodiments 276-371, wherein the expression, translation, or amount or activity of the target protein is increased by at least 100%.

Embodiment 377: The method of any of embodiments 276-371, wherein the expression, translation, or amount or activity of the target protein is increased by at least 120%.

Embodiment 378: The method of any of embodiments 276-371, wherein the expression, translation, or amount or activity of the target protein is increased by at least 150%.

Embodiment 379: The method of any of embodiments 265-378, wherein the cell is in vitro.

Embodiment 380: The method of any of embodiments 265-378, wherein the cell is in a subject.

Embodiment 381: The method of embodiment 380, wherein the subject has a disease or condition and wherein at least one symptom of the disease or condition is ameliorated.

Embodiment 382: The method of embodiment 380 or 381, wherein the cell is in an animal.

Embodiment 383: The method of embodiment 382, wherein the animal is a human.

Embodiment 384: An antisense compound comprising a modified oligonucleotide consisting of 10-30 linked nucleosides having a nucleobase sequence complementary to a target site within a translation suppression element region of a target transcript and wherein the modified oligonucleotide does not have more than four contiguous unmodified 2'-deoxy nucleosides.

Embodiment 385: The antisense compound of embodiments 384, wherein the translation suppression element region is the 5' untranslated region.

Embodiment 386: A method of increasing the amount or activity of a target protein in a cell, comprising contacting the cell with a uORF inhibitor, wherein the target protein is encoded by a target transcript comprising at least one uORF start site; and thereby increasing the amount or activity of the target protein in the cell.

Embodiment 387: A method of increasing expression of a target protein in a cell, comprising contacting the cell with a uORF inhibitor, wherein the target protein is encoded by a target transcript comprising at least one uORF start site; and thereby increasing expression of the target protein in the cell.

Embodiment 388: A method of increasing translation of a target protein in a cell, comprising contacting the cell with a uORF inhibitor, wherein the target protein is encoded by a target transcript comprising at least one uORF start site; and thereby increasing translation of the target protein in the cell.

Embodiment 389: A method of decreasing suppression of translation a target protein in a cell, comprising contacting the cell with a uORF inhibitor, wherein the target protein is encoded by a target transcript comprising at least one uORF start site; and thereby decreasing suppression of translation of the target protein in the cell.

Embodiment 390: A method of decreasing translation of a uORF polypeptide in a cell, comprising contacting the cell with a uORF inhibitor; and thereby decreasing translation of the uORF polypeptide in the cell.

Embodiment 391: The method of any of embodiments 386-390, wherein the uORF inhibitor is a small molecule.

Embodiment 392: The method of any of embodiments 386-390, wherein the uORF inhibitor is an antibody.

Embodiment 393: The method of any of embodiments 386-390, wherein the uORF inhibitor is a peptide.

Embodiment 394: The method of any of embodiments 386-390, wherein the uORF inhibitor is a nucleic acid.

Embodiment 395: The method of any of embodiments 386-390, wherein the uORF inhibitor is an siRNA.

Embodiment 396: The method of any of embodiments 386-390, wherein the uORF inhibitor is an antisense compound.

Embodiment 397: The method of embodiment 396, wherein the antisense compound is a modified oligonucleotide.

Embodiment 398: A method of increasing the amount or activity of a target protein in a cell, comprising contacting the cell with an antisense compound comprising a modified oligonucleotide, wherein the target protein is encoded by a target transcript comprising at least one uORF start site and wherein the modified oligonucleotide is complementary to a target site within a uORF start site region of the target transcript; and thereby increasing the amount or activity of the target protein in the cell.

Embodiment 399: A method of increasing expression of a target protein in a cell, comprising contacting the cell with an antisense compound comprising a modified oligonucleotide, wherein the target protein is encoded by a target transcript comprising at least one uORF start site and wherein the modified oligonucleotide is complementary to target site within a uORF start site region of the target transcript; and thereby increasing expression of the target protein in the cell.

Embodiment 400: A method of increasing translation of a target protein in a cell, comprising contacting the cell with an antisense compound comprising a modified oligonucleotide, wherein the target protein is encoded by a target transcript comprising at least one uORF start site and wherein the modified oligonucleotide is complementary to a target site within a uORF start site region of the target transcript; and thereby increasing translation of the target protein in the cell.

Embodiment 401: A method of decreasing suppression of translation of a target protein in a cell, comprising contacting the cell with an antisense compound comprising a modified oligonucleotide, wherein the target protein is encoded by a target transcript comprising at least one uORF start site and wherein the modified oligonucleotide is complementary to a target site within a uORF start site region of the target transcript; and thereby decreasing suppression of translation of the target protein in the cell.

Embodiment 402: A method of decreasing translation of a uORF polypeptide in a cell, comprising contacting the cell with an antisense compound comprising a modified oligonucleotide complementary to a target site within a uORF region of the target transcript; and thereby decreasing translation of the uORF polypeptide in the cell.

Embodiment 403: The method of any of embodiments 386-402, wherein the uORF start site region is the 5' untranslated region.

Embodiment 404: The method of any of embodiments 398-403, wherein the target site comprises the uORF start site.

Embodiment 405: The method of any of embodiments 398-404, wherein the target site region consists of the uORF start site and the 100 nucleosides upstream and the 100 nucleosides downstream of the uORF start site.

Embodiment 406: The method of any of embodiments 398-404, wherein the target site region consists of the uORF start site and the 75 nucleosides upstream and the 75 nucleosides downstream of the uORF start site.

Embodiment 407: The method of any of embodiments 398-404, wherein the target site region consists of the uORF start site and the 50 nucleosides upstream and the 50 nucleosides downstream of the uORF start site.

Embodiment 408: The method of any of embodiments 398-404, wherein the target site region consists of the uORF start site and the 30 nucleosides upstream and the 30 nucleosides downstream of the uORF start site.

Embodiment 409: The method of any of embodiments 398-404, wherein the target site region consists of the uORF start site and the 20 nucleosides upstream and the 20 nucleosides downstream of the uORF start site.

Embodiment 410: The method of any of embodiments 398-404, wherein the target site region consists of the uORF start site and the 15 nucleosides upstream and the 15 nucleosides downstream of the uORF start site.

Embodiment 411: The method of any of embodiments 398-404, wherein the target site region is downstream of the uORF start site.

Embodiment 412: The method of any of embodiments 398-404, wherein the target site region is 6 to 65 nucleobases downstream of the uORF start site.

Embodiment 413: The method of any of embodiments 398-404, wherein the target site region is 6 to 23 nucleobases downstream of the uORF start site.

Embodiment 414: The method of any of embodiments 398-404, wherein the target site region is 47 to 64 nucleobases downstream of the uORF start site.

Embodiment 415: The method of any of embodiments 398-414, wherein the uORF start site is a wild-type uORF start site.

Embodiment 416: The method of any of embodiments 398-414, wherein the uORF start site is a mutant uORF start site.

Embodiment 417: The method of any of embodiments 398-416, wherein the target transcript comprises more than one uORF region.

Embodiment 418: The method of any of embodiments 398-417, wherein the target transcript comprises two uORF regions.

Embodiment 419: The method of any of embodiments 398-418, wherein the uORF start site comprises a weak Kozak sequence.

Embodiment 420: The method of any of embodiments 398-418, wherein the uORF start site comprises a strong Kozak sequence.

Embodiment 421: The method of any of embodiments 398-420, wherein the uORF start site has a non-canonical start codon.

Embodiment 422: The method of embodiment 421, wherein the non-canonical start codon is AUU.

Embodiment 423: The method of any of embodiments 398-422, wherein the target transcript encodes RNase H1.

Embodiment 424: The method of any of embodiments 398-422, wherein the target transcript encodes LRP-PRC.

Embodiment 425: The method of any of embodiments 398-422, wherein the target transcript encodes SFXN3.

Embodiment 426: The method of any of embodiments 398-422, wherein the target transcript encodes MRPL11.

Embodiment 427: The method of any of embodiments 398-422, wherein the target transcript encodes THPO.

Embodiment 428: The method of any of embodiments 398-422, wherein the target transcript encodes CFTR.

Embodiment 429: The method of any of embodiments 398-422, wherein the target transcript encodes a protein selected from the group consisting of La/SSB, NPM1, TCP1-alpha, TCP1-epsilon, TCP1-beta, HSP90-AA1, hsp90-AB, HSPA1L, RAN, IMP9, Annexin A2, FTCD/58K, PC4/SUB1, VARS, and DHX36.

Embodiment 430: The method of any of embodiments 398-422, wherein the target transcript is encoded by a gene selected from the genes in Table 1 or Table 2.

Embodiment 431: The method of any of embodiments 397-430, wherein the modified oligonucleotide has a nucleobase sequence 80% complementary to the target transcript.

Embodiment 432: The method of any of embodiments 397-430, wherein the modified oligonucleotide has a nucleobase sequence 85% complementary to the target transcript.

Embodiment 433: The method of any of embodiments 397-430, wherein the modified oligonucleotide has a nucleobase sequence 90% complementary to the target transcript.

Embodiment 434: The method of any of embodiments 397-430, wherein the modified oligonucleotide has a nucleobase sequence 95% complementary to the target transcript.

Embodiment 435: The method of any of embodiments 397-430, wherein the modified oligonucleotide has a nucleobase sequence 100% complementary to the target transcript.

Embodiment 436: The method of any of embodiments 397-430, wherein the modified oligonucleotide has a nucleobase having at least 1 mismatch relative to the target transcript.

Embodiment 437: The method of any of embodiments 397-430, wherein the modified oligonucleotide has a nucleobase having at least 2 mismatches relative to the target transcript.

Embodiment 438: The method of any of embodiments 397-430, wherein the modified oligonucleotide has a nucleobase having at least 3 mismatches relative to the target transcript.

Embodiment 439: The method of any of embodiments 397-430, wherein the modified oligonucleotide has a nucleobase sequence comprising the nucleobases CAT.

Embodiment 440: The method of any of embodiments 397-430, wherein the modified oligonucleotide has a nucleobase sequence wherein the first three of the 5'-most nucleobases are CAT.

Embodiment 441: The method of any of embodiments 397-430, wherein the modified oligonucleotide has a nucleobase sequence wherein the $2^{nd}$, $3^{rd}$ and $4^{th}$ nucleobases from the 5'-most terminal nucleobase are CAT.

Embodiment 442: The method of any of embodiments 397-430, wherein the modified oligonucleotide has a nucleobase sequence wherein the $3^{rd}$ $4^{th}$ and $5^{th}$ nucleobases from the 5'-most terminal nucleobase are CAT.

Embodiment 443: The method of any of embodiments 397-430, wherein the modified oligonucleotide has a nucleobase sequence wherein the $4^{th}$, $5^{th}$ and $6^{th}$ nucleobases from the 5'-most terminal nucleobase are CAT.

Embodiment 444: The method of any of embodiments 397-430, wherein the modified oligonucleotide has a nucleobase sequence wherein the 5$^{th}$ 6$^{th}$ and 7$^{th}$ nucleobases from the 5'-most terminal nucleobase are CAT.

Embodiment 445: The method of any of embodiments 397-430, wherein the modified oligonucleotide has a nucleobase sequence wherein the 6$^{th}$ 7$^{th}$ and 8$^{th}$ nucleobases from the 5'-most terminal nucleobase are CAT.

Embodiment 446: The method of any of embodiments 397-430, wherein the modified oligonucleotide has a nucleobase sequence wherein the 7$^{th}$, 8$^{th}$ and 9$^{th}$ nucleobases from the 5'-most terminal nucleobase are CAT.

Embodiment 447: The method of any of embodiments 397-430, wherein the modified oligonucleotide has a nucleobase sequence wherein the first three of the 3'-most nucleobases are CAT.

Embodiment 448: The method of any of embodiments 397-430, wherein the modified oligonucleotide has a nucleobase sequence wherein the 2$^{nd}$, 3$^{rd}$ and 4$^{th}$ nucleobases from the 3'-most terminal nucleobase are CAT.

Embodiment 449: The method of any of embodiments 397-430, wherein the modified oligonucleotide has a nucleobase sequence wherein the 3$^{rd}$ 4$^{th}$ and 5$^{th}$ nucleobases from the 3'-most terminal nucleobase are CAT.

Embodiment 450: The method of any of embodiments 397-430, wherein the modified oligonucleotide has a nucleobase sequence wherein the 4$^{th}$, 5$^{th}$ and 6$^{th}$ nucleobases from the 3'-most terminal nucleobase are CAT.

Embodiment 451: The method of any of embodiments 397-430, wherein the modified oligonucleotide has a nucleobase sequence wherein the 5$^{th}$ 6$^{th}$ and 7$^{th}$ nucleobases from the 3'-most terminal nucleobase are CAT.

Embodiment 452: The method of any of embodiments 397-430, wherein the modified oligonucleotide comprises a nucleobase sequence complementary to a Kozak sequence.

Embodiment 453: The method of any of embodiments 397-430, wherein the modified oligonucleotide has a nucleobase sequence comprising at least 8 contiguous nucleobases complementary to the uORF region of SEQ ID NOs: 1 or 2.

Embodiment 454: The method of any of embodiments 397-430, wherein the modified oligonucleotide has a nucleobase sequence comprising at least 8 contiguous nucleobases of any of the nucleobase sequences of SEQ ID NOs: 3, 4, 5, 6, 7, 8, 9, 10, 11, 12, 13, 14, 15, 16, 17, 18, 21, 23, 25, 26, 27, 28, 29, 30, 31, 32, 33, 34, 35, 36, 37, 38, 39, 40, 41, 42, 44, 45, 52, 53, 54, 55, 56, 57, 58, 59, 60, 61, 62, 63, 64, 65, 66, 67, 68, 69, 70, 71, 72, 73, 74, 75, 76, 77, 82, or 83.

Embodiment 455: The method of any of embodiments 397-430, wherein the modified oligonucleotide has a nucleobase sequence comprising at least 10 contiguous nucleobases of any of the nucleobase sequences of SEQ ID NOs: 3, 4, 5, 6, 7, 8, 9, 10, 11, 12, 13, 14, 15, 16, 17, 18, 21, 23, 25, 26, 27, 28, 29, 30, 31, 32, 33, 34, 35, 36, 37, 38, 39, 40, 41, 42, 44, 45, 52, 53, 54, 55, 56, 57, 58, 59, 60, 61, 62, 63, 64, 65, 66, 67, 68, 69, 70, 71, 72, 73, 74, 75, 76, 77, 82, or 83.

Embodiment 456: The method of any of embodiments 397-430, wherein the modified oligonucleotide has a nucleobase sequence comprising at least 12 contiguous nucleobases of any of the nucleobase sequences of SEQ ID NOs: 3, 4, 5, 6, 7, 8, 9, 10, 11, 12, 13, 14, 15, 16, 17, 18, 21, 23, 25, 26, 27, 28, 29, 30, 31, 32, 33, 34, 35, 36, 37, 38, 39, 40, 41, 42, 44, 45, 52, 53, 54, 55, 56, 57, 58, 59, 60, 61, 62, 63, 64, 65, 66, 67, 68, 69, 70, 71, 72, 73, 74, 75, 76, 77, 82, or 83.

Embodiment 457: The method of any of embodiments 397-430, wherein the modified oligonucleotide has a nucleobase sequence comprising at least 14 contiguous nucleobases of any of the nucleobase sequences of SEQ ID NOs: 3, 4, 5, 6, 7, 8, 9, 10, 11, 12, 13, 14, 15, 16, 17, 18, 21, 23, 25, 26, 27, 28, 29, 30, 31, 32, 33, 34, 35, 36, 37, 38, 39, 40, 41, 42, 44, 45, 52, 53, 54, 55, 56, 57, 58, 59, 60, 61, 62, 63, 64, 65, 66, 67, 68, 69, 70, 71, 72, 73, 74, 75, 76, 77, 82, or 83.

Embodiment 458: The method of any of embodiments 397-430, wherein the modified oligonucleotide has a nucleobase sequence consisting of the nucleobase sequence of any of SEQ ID NOs: 3, 4, 5, 6, 7, 8, 9, 10, 11, 12, 13, 14, 15, 16, 17, 18, 21, 23, 25, 26, 27, 28, 29, 30, 31, 32, 33, 34, 35, 36, 37, 38, 39, 40, 41, 42, 44, 45, 52, 53, 54, 55, 56, 57, 58, 59, 60, 61, 62, 63, 64, 65, 66, 67, 68, 69, 70, 71, 72, 73, 74, 75, 76, 77, 82, or 83.

Embodiment 459: The method of any of embodiments 397-458, wherein the modified oligonucleotide consists of 10 to 40 linked nucleosides.

Embodiment 460: The method of any of embodiments 397-458, wherein the modified oligonucleotide consists of 12 to 22 linked nucleosides.

Embodiment 461: The method of any of embodiments 397-458, wherein the modified oligonucleotide consists of 15 to 22 linked nucleosides.

Embodiment 462: The method of any of embodiments 397-458, wherein the modified oligonucleotide consists of 18 to 20 linked nucleosides.

Embodiment 463: The method of any of embodiments 397-462, wherein the modified oligonucleotide comprises at least one modified nucleoside.

Embodiment 464: The method of embodiment 463, wherein at least one modified nucleoside comprises a modified sugar moiety.

Embodiment 465: The method of embodiment 464, wherein at least one modified sugar moiety is a 2'-substituted sugar moiety.

Embodiment 466: The method of embodiment 465, wherein the 2'-substituent of at least one 2'-substituted sugar moiety is selected from among: 2'-OMe, 2'-F, and 2'-MOE.

Embodiment 467: The method of any of embodiments 463-466, wherein the 2'-substituent of at least one 2'-substituted sugar moiety is a 2'-MOE.

Embodiment 468: The method of any of embodiments 463-464, wherein at least one modified sugar moiety is a bicyclic sugar moiety.

Embodiment 469: The method of embodiment 468, wherein at least one bicyclic sugar moiety is LNA or cEt.

Embodiment 470: The method of any of embodiments 464-469, wherein at least one sugar moiety is a sugar surrogate.

Embodiment 471: The method of embodiment 470, wherein at least one sugar surrogate is a morpholino.

Embodiment 472: The method of embodiment 470, wherein at least one sugar surrogate is a modified morpholino.

Embodiment 473: The method of embodiment 470, wherein at least one sugar surrogate is a peptide nucleic acid.

Embodiment 474: The method of any of embodiment 463-473, wherein the modified oligonucleotide com- Embodiment 475: The method of any of embodiment 463-473, wherein the modified oligonucleotide comprises at least 6 modified nucleosides, each independently comprising a modified sugar moiety.

Embodiment 476: The method of any of embodiment 463-473, wherein the modified oligonucleotide comprises at least 7 modified nucleosides, each independently comprising a modified sugar moiety.

Embodiment 477: The method of any of embodiment 463-473, wherein the modified oligonucleotide comprises at least 8 modified nucleosides, each independently comprising a modified sugar moiety.

Embodiment 478: The method of any of embodiment 463-473, wherein the modified oligonucleotide comprises at least 9 modified nucleosides, each independently comprising a modified sugar moiety.

Embodiment 479: The method of embodiment 463-473, wherein the modified oligonucleotide comprises at least 10 modified nucleosides, each independently comprising a modified sugar moiety.

Embodiment 480: The method of any of embodiments 463-479, wherein each nucleoside of the modified oligonucleotide is a modified nucleoside or an unmodified nucleoside.

Embodiment 481: The method of embodiment 480, wherein each unmodified nucleoside is a 2'-deoxy nucleoside.

Embodiment 482: The method of any of embodiments 480-481, wherein the modified oligonucleotide comprises at least 6 2'-deoxy nucleosides.

Embodiment 483: The method of any of embodiments 480-481, wherein the modified oligonucleotide comprises at least 7 2'-deoxy nucleosides.

Embodiment 484: The method of any of embodiments 480-481, wherein the modified oligonucleotide comprises at least 8 2'-deoxy nucleosides.

Embodiment 485: The method of any of embodiments 480-481, wherein the modified oligonucleotide comprises at least 9 2'-deoxy nucleosides.

Embodiment 486: The method of any of embodiments 480-481, wherein the modified oligonucleotide comprises at least 10 2'-deoxy nucleosides.

Embodiment 487: The method of any of embodiments 482-486, wherein the modified oligonucleotide contains no more than 4 contiguous 2'-deoxy nucleosides.

Embodiment 488: The method of any of embodiments 480-481, wherein the modified oligonucleotide comprises at least 15 modified nucleosides, each independently comprising a modified sugar moiety.

Embodiment 489: The method of embodiment 488, wherein each nucleoside of the modified oligonucleotide is a modified nucleoside, each independently comprising a modified sugar moiety.

Embodiment 490: The method of any of embodiments 463-489, wherein the modified oligonucleotide comprises at least two modified nucleosides comprising modified sugar moieties that are the same as one another.

Embodiment 491: The method of any of embodiments 463-489, wherein the modified oligonucleotide comprises at least two modified nucleosides comprising modified sugar moieties that are different from one another.

Embodiment 492: The method of any of embodiments 463-489, wherein the modified oligonucleotide comprises a modified region of at least 5 contiguous modified nucleosides.

Embodiment 493: The method of embodiment 492, wherein the modified oligonucleotide comprises a modified region of at least 10 contiguous modified nucleosides.

Embodiment 494: The method of embodiment 492, wherein the modified oligonucleotide comprises a modified region of at least 15 contiguous modified nucleosides.

Embodiment 495: The method of embodiment 492, wherein the modified oligonucleotide comprises a modified region of at least 18 contiguous modified nucleosides.

Embodiment 496: The method of embodiment 4 88, wherein the modified oligonucleotide comprises a modified region of at least 20 contiguous modified nucleosides.

Embodiment 497: The method of any of embodiments 493-496, wherein each modified nucleoside of the modified region has a modified sugar moiety independently selected from among: 2'-F, 2'-OMe, 2'-MOE, cEt, LNA, morpholino, modified morpholino, and peptide nucleic acid.

Embodiment 498: The method of any of embodiments 493-497, wherein the modified nucleosides of the modified region each comprise the same modification as one another.

Embodiment 499: The method of embodiment 498, wherein the modified nucleosides of the modified region each comprise the same 2'-substituted sugar moiety.

Embodiment 500: The method of embodiment 498, wherein the 2'-substituted sugar moiety of the modified nucleosides of the region of modified nucleosides is selected from 2'-F, 2'-OMe, and 2'-MOE.

Embodiment 501: The method of embodiment 500, wherein the 2'-substituted sugar moiety of the modified nucleosides of the region of modified nucleosides is 2'-MOE.

Embodiment 502: The method of embodiment 499, wherein the modified nucleosides of the region of modified nucleosides each comprise the same bicyclic sugar moiety.

Embodiment 503: The method of embodiment 502, wherein the bicyclic sugar moiety of the modified nucleosides of the region of modified nucleosides is selected from LNA and cEt.

Embodiment 504: The method of embodiment 498, wherein the modified nucleosides of the region of modified nucleosides each comprises a sugar surrogate.

Embodiment 505: The method of embodiment 504, wherein the sugar surrogate of the modified nucleosides of the region of modified nucleosides is a morpholino.

Embodiment 506: The method of embodiment 504, wherein the sugar surrogate of the modified nucleosides of the region of modified nucleosides is a modified morpholino.

Embodiment 507: The method of embodiment 504, wherein the sugar surrogate of the modified nucleosides of the region of modified nucleosides is a peptide nucleic acid.

Embodiment 508: The method of any of embodiments 463-507, wherein the modified nucleotide comprises no more than 4 contiguous naturally occurring nucleosides.

Embodiment 509: The method of any of embodiments 463-507, wherein each nucleoside of the modified oligonucleotide is a modified nucleoside.

Embodiment 510: The method of embodiment 509 wherein each modified nucleoside comprises a modified sugar moiety.

Embodiment 511: The method of embodiment 510 wherein each modified nucleoside comprises a modified sugar moiety, and wherein $1^{st}$ and $2^{nd}$ nucleosides from the 3'-most terminal nucleoside are bicyclic sugar moieties.

Embodiment 512: The method of embodiment 510 wherein each modified nucleoside comprises a modified sugar moiety, and wherein $1^{st}$, $2^{nd}$ and $3^{rd}$ nucleosides from the 3'-most terminal nucleoside are bicyclic sugar moieties.

Embodiment 513: The method of embodiment 510 wherein each modified nucleoside comprises a modified sugar moiety, and wherein $1^{st}$, $2^{nd}$, $3^{rd}$ and $4^{th}$ nucleosides from the 3'-most terminal nucleoside are bicyclic sugar moieties.

Embodiment 514: The method of embodiment 510 wherein each modified nucleoside comprises a modified sugar moiety, and wherein $1^{st}$, $2^{nd}$, $3^{rd}$, $4^{th}$ and $5^{th}$ nucleosides from the 3'-most terminal nucleoside are bicyclic sugar moieties.

Embodiment 515: The method of embodiment 510 wherein each modified nucleoside comprises a modified sugar moiety, and wherein $1^{st}$, $2^{nd}$, $3^{rd}$, $4^{th}$ $5^{th}$ and $6^{th}$ nucleosides from the 3'-most terminal nucleoside are bicyclic sugar moieties.

Embodiment 516: The method of embodiments 511-515 wherein the bicyclic sugar moiety of the modified oligonucleotide is selected from LNA and cEt.

Embodiment 517: The method of embodiment 515 wherein, each remaining nucleoside in the modified oligonucleotide comprises a modified sugar moiety selected from 2'-F, 2'-OMe, and 2'-MOE.

Embodiment 518: The method of embodiment 510 wherein each modified nucleoside comprises a modified sugar moiety, and wherein $1^{st}$ and $2^{nd}$ nucleosides from the 3'-most terminal nucleoside are 2'-F modified sugar moieties.

Embodiment 519: The method of embodiment 510 wherein each modified nucleoside comprises a modified sugar moiety, and wherein $1^{st}$, $2^{nd}$d and $3^{rd}$ nucleosides from the 3'-most terminal nucleoside are 2'-F modified sugar moieties.

Embodiment 520: The method of embodiment 510 wherein each modified nucleoside comprises a modified sugar moiety, and wherein $1^{st}$ $2^{nd}$ $3^{rd}$ and $4^{th}$ nucleosides from the 3'-most terminal nucleoside are 2'-F modified sugar moieties.

Embodiment 521: The method of embodiment 510 wherein each modified nucleoside comprises a modified sugar moiety, and wherein $1^{st}$, $2^{nd}$, $3^{rd}$ $4^{th}$ and $5^{th}$ nucleosides from the 3'-most terminal nucleoside are 2'-F modified sugar moieties.

Embodiment 522: The method of embodiment 510 wherein each modified nucleoside comprises a modified sugar moiety, and wherein $1^{st}$ $2^{nd}$, $3^{rd}$, $4^{th}$ $5^{th}$ and $6^{th}$ nucleosides from the 3'-most terminal nucleoside are 2'-F modified sugar moieties.

Embodiment 523: The method of embodiments 511-522, wherein each remaining nucleoside in the modified oligonucleotide comprises a modified sugar moiety selected from 2'-OMe and 2'-MOE.

Embodiment 524: The method of embodiment 509, wherein the modified nucleosides of the modified oligonucleotide comprise the same modification as one another.

Embodiment 525: The method of embodiment 524, wherein the modified nucleosides of the modified oligonucleotide each comprise the same 2'-substituted sugar moiety.

Embodiment 526: The method of embodiment 525, wherein the 2'-substituted sugar moiety of the modified oligonucleotide is selected from 2'-F, 2'-OMe, and 2'-MOE.

Embodiment 527: The method of embodiment 526, wherein the 2'-substituted sugar moiety of the modified oligonucleotide is 2'-MOE.

Embodiment 528: The method of embodiment 526, wherein the 2'-substituted sugar moiety of the modified oligonucleotide is 2'-OMe.

Embodiment 529: The method of embodiment 524, wherein the modified nucleosides of the modified oligonucleotide each comprise the same bicyclic sugar moiety.

Embodiment 530: The method of embodiment 529, wherein the bicyclic sugar moiety of the modified oligonucleotide is selected from LNA and cEt.

Embodiment 531: The method of embodiment 524, wherein the modified nucleosides of the modified oligonucleotide each comprises a sugar surrogate.

Embodiment 532: The method of embodiment 531, wherein the sugar surrogate of the modified oligonucleotide is a morpholino.

Embodiment 533: The method of embodiment 531, wherein the sugar surrogate of the modified oligonucleotide is a modified morpholino.

Embodiment 534: The method of embodiment 531, wherein the sugar surrogate of the modified oligonucleotide is a peptide nucleic acid.

Embodiment 535: The method of any of embodiments 397-534, wherein the modified oligonucleotide comprises at least one modified internucleoside linkage.

Embodiment 536: The method of embodiment 535, wherein the modified internucleoside linkage is a phosphorothioate internucleoside linkage.

Embodiment 537: The method of embodiment 535 or 536, wherein each internucleoside linkage is either a phosphodiester internucleoside linkage or a phosphorothioate internucleoside linkage.

Embodiment 538: The method of embodiment 537, wherein each internucleoside linkage is a modified internucleoside linkage.

Embodiment 539: The method of embodiment 535 or 536, comprising at least one phosphorothioate internucleoside linkage.

Embodiment 540: The method of embodiment 535, wherein each internucleoside linkage is a modified internucleoside linkage and wherein each internucleoside linkage comprises the same modification.

Embodiment 541: The method of embodiment 540, wherein each internucleoside linkage is a phosphorothioate internucleoside linkage.

Embodiment 542: The method of any of embodiments 397-541, wherein the antisense compound comprises at least one conjugate group.

Embodiment 543: The method of embodiment 542, wherein the conjugate group comprises Gal-NAc.

Embodiment 544: The method of any of embodiments 397-543, wherein the antisense compound consists of the modified oligonucleotide.

Embodiment 545: The method of any of embodiments 397-544, wherein the expression, translation, or amount or activity of the target protein is increased by at least 10%.

Embodiment 546: The method of any of embodiments 397-544, wherein the expression, translation, or amount or activity of the target protein is increased by at least 20%.

Embodiment 547: The method of any of embodiments 397-544, wherein the expression, translation, or amount or activity of the target protein is increased by at least 30%.

Embodiment 548: The method of any of embodiments 397-544, wherein the expression, translation, or amount or activity of the target protein is increased by at least 50%.

Embodiment 549: The method of any of embodiments 397-544, wherein the expression, translation, or amount or activity of the target protein is increased by at least 100%.

Embodiment 550: The method of any of embodiments 397-544, wherein the expression, translation, or amount or activity of the target protein is increased by at least 120%.

Embodiment 551: The method of any of embodiments 397-544, wherein the expression, translation, or amount or activity of the target protein is increased by at least 150%.

Embodiment 552: The method of any of embodiments 386-551, wherein the cell is in vitro.

Embodiment 553: The method of any of embodiments 386-551, wherein the cell is in a subject.

Embodiment 554: The method of embodiment 553, wherein the subject has a disease or condition and wherein at least one symptom of the disease or condition is ameliorated.

Embodiment 555: The method of embodiment 553 or 554, wherein the cell is in an animal.

Embodiment 556: The method of embodiment 555, wherein the animal is a human.

Embodiment 557: A method of increasing translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing translation of the target protein in the cell.

Embodiment 558: A method of decreasing suppression of translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby decreasing suppression of translation of the target protein in the cell.

Embodiment 559: A method of increasing the amount or activity of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing the amount or activity of the target protein in the cell.

Embodiment 560: A method of increasing expression of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing expression of the target protein in the cell.

Embodiment 561: The method of any of embodiments 557-560, wherein the translation suppression element region is the 5' untranslated region.

Embodiment 562: The method of any of embodiments 557-561, wherein the translation suppression element region contains one or more uORFs.

Embodiment 563: The method of any of embodiments 557-561, wherein the translation suppression element region contains one or more uORFs, but wherein the one or more uORFs do not suppress translation of the target transcript.

Embodiment 564: The method of any of embodiments 557-561, wherein the translation suppression element region does not contains a uORF.

Embodiment 565: The method of any of embodiments 557-563, wherein the target transcript encodes RNase H1.

Embodiment 566: The method of any of embodiments 557-561 or 564, wherein the target transcript encodes ACP1.

Embodiment 567: The method of any of embodiments 557-563, wherein the target transcript encodes LRP-PRC.

Embodiment 568: The method of any of embodiments 557-563, wherein the target transcript encodes SFXN3.

Embodiment 569: The method of any of embodiments 557-563, wherein the target transcript encodes MRPL11.

Embodiment 570: The method of any of embodiments 557-563, wherein the target transcript encodes THPO.

Embodiment 571: The method of any of embodiments 557-563, wherein the target transcript encodes CFTR.

Embodiment 572: The method of any of embodiments 557-564, wherein the target transcript encodes a protein selected from the group consisting of La/SSB, NPM1, TCP1-alpha, TCP1-epsilon, TCP1-beta, HSP90-AA1, hsp90-AB, HSPA1L, RAN, IMP9, Annexin A2, FTCD/58K, PC4/SUB1, VARS, and DHX36.

Embodiment 573: The method of any of embodiments 557-564, wherein the target transcript does not encode RNase H1.

Embodiment 574: The method of any of embodiments 557-563, wherein the modified oligonucleotide has a nucleobase sequence comprising at least 8 contiguous nucleobases of any of the nucleobase sequences of SEQ ID NOs: 8, 9, 11, or 12.

Embodiment 575: The method of any of embodiments 557-563, wherein the modified oligonucleotide has a nucleobase sequence comprising at least 10 contiguous nucleobases of any of the nucleobase sequences of SEQ ID NOs: 8, 9, 11, or 12.

Embodiment 576: The method of any of embodiments 557-563, wherein the modified oligonucleotide has a nucleobase sequence comprising at least 12 contiguous nucleobases of any of the nucleobase sequences of SEQ ID NOs: 8, 9, 11, or 12.

Embodiment 577: The method of any of embodiments 557-563, wherein the modified oligonucleotide has a nucleobase sequence comprising at least 14 contiguous nucleobases of any of the nucleobase sequences of SEQ ID NOs: 8, 9, 11, or 12.

Embodiment 578: The method of any of embodiments 557-563, wherein the modified oligonucleotide has a nucleobase sequence consisting of the nucleobase sequence of any of SEQ ID NOs: 8, 9, 11, or 12.

Embodiment 579: The method of any of embodiments 557-561 or 564 or 566, wherein the modified oligonucleotide has a nucleobase sequence comprising at least 8 contiguous nucleobases of any of the nucleobase sequences of SEQ ID NOs: 79 or 80.

Embodiment 580: The method of any of embodiments 557-561 or 564 or 566, wherein the modified oligonucleotide has a nucleobase sequence comprising at least 10 contiguous nucleobases of any of the nucleobase sequences of SEQ ID NOs: 79 or 80.

Embodiment 581: The method of any of embodiments 557-561 or 564 or 566, wherein the modified oligonucleotide has a nucleobase sequence comprising at least 12 contiguous nucleobases of any of the nucleobase sequences of SEQ ID NOs: 79 or 80.

Embodiment 582: The method of any of embodiments 557-561 or 564 or 566, wherein the modified oligonucleotide has a nucleobase sequence comprising at least 14 contiguous nucleobases of any of the nucleobase sequences of SEQ ID NOs: 79 or 80.

Embodiment 583: The method of any of embodiments 557-561 or 564 or 566, wherein the modified oligonucleotide has a nucleobase sequence consisting of the nucleobase sequence of any of SEQ ID NOs: 79 or 80.

Embodiment 584: The method of any of embodiments 557-573, wherein the modified oligonucleotide has a nucleobase sequence wherein at least 35% all the nucleobases are G or C nucleobases.

Embodiment 585: The method of any of embodiments 557-573, wherein the modified oligonucleotide has a nucleobase sequence wherein at least 40% all the nucleobases are G or C nucleobases.

Embodiment 586: The method of any of embodiments 557-573, wherein the modified oligonucleotide has a nucleobase sequence wherein at least 45% all the nucleobases are G or C nucleobases.

Embodiment 587: The method of any of embodiments 557-573, wherein the modified oligonucleotide has a nucleobase sequence wherein at least 50% all the nucleobases are G or C nucleobases.

Embodiment 588: The method of any of embodiments 557-573, wherein the modified oligonucleotide has a nucleobase sequence wherein at least 55% all the nucleobases are G or C nucleobases.

Embodiment 589: The method of any of embodiments 557-573, wherein the modified oligonucleotide has a nucleobase sequence wherein at least 60% all the nucleobases are G or C nucleobases.

Embodiment 590: The method of any of embodiments 557-573, wherein the modified oligonucleotide has a nucleobase sequence wherein at least 65% all the nucleobases are G or C nucleobases.

Embodiment 591: The method of any of embodiments 557-573, wherein the modified oligonucleotide has a nucleobase sequence wherein at least 70% all the nucleobases are G or C nucleobases.

Embodiment 592: The method of any of embodiments 557-573, wherein at least a portion of the nucleobase sequence of the modified oligonucleotide is complementary to a G-quartet.

Embodiment 593: The method of any of embodiments 557-573, wherein the modified oligonucleotide has a nucleobase sequence that is not complementary to a G-quartet.

Embodiment 594: The method of any of embodiments 557-593, wherein the modified oligonucleotide consists of 10 to 40 linked nucleosides.

Embodiment 595: The method of any of embodiments 557-593, wherein the modified oligonucleotide consists of 12 to 22 linked nucleosides.

Embodiment 596: The method of any of embodiments 557-593, wherein the modified oligonucleotide consists of 15 to 22 linked nucleosides.

Embodiment 597: The method of any of embodiments 557-593, wherein the modified oligonucleotide consists of 18 to 20 linked nucleosides.

Embodiment 598: The method of any of embodiments 557-593, wherein the modified oligonucleotide comprises at least one modified nucleoside.

Embodiment 599: The method of embodiment 598, wherein at least one modified nucleoside comprises a modified sugar moiety.

Embodiment 600: The method of embodiment 599, wherein at least one modified sugar moiety is a 2'-substituted sugar moiety.

Embodiment 601: The method of embodiment 600, wherein the 2'-substituent of at least one 2'-substituted sugar moiety is selected from among: 2'-OMe, 2'-F, and 2'-MOE.

Embodiment 602: The method of any of embodiments 600-601, wherein the 2'-substituent of at least one 2'-substituted sugar moiety is a 2'-MOE.

Embodiment 603: The method of any of embodiments 600-602, wherein the 2'-substituent of at least one 2'-substituted sugar moiety is not 2'OMe.

Embodiment 604: The method of any of embodiments 598-603, wherein at least one modified sugar moiety is a bicyclic sugar moiety.

Embodiment 605: The method of embodiment 604, wherein at least one bicyclic sugar moiety is LNA or cEt.

Embodiment 606: The method of any of embodiments 598-605, wherein at least one sugar moiety is a sugar surrogate.

Embodiment 607: The method of embodiment 606, wherein at least one sugar surrogate is a morpholino.

Embodiment 608: The method of embodiment 606, wherein at least one sugar surrogate is a modified morpholino.

Embodiment 609: The method of embodiment 606, wherein at least one sugar surrogate is a peptide nucleic acid.

Embodiment 610: The method of any of embodiment 598-609, wherein the modified oligonucleotide comprises at least 5 modified nucleosides, each independently comprising a modified sugar moiety.

Embodiment 611: The method of any of embodiment 598-609, wherein the modified oligonucleotide comprises at least 6 modified nucleosides, each independently comprising a modified sugar moiety.

Embodiment 612: The method of any of embodiment 598-609, wherein the modified oligonucleotide comprises at least 7 modified nucleosides, each independently comprising a modified sugar moiety.

Embodiment 613: The method of any of embodiment 598-609, wherein the modified oligonucleotide comprises at least 8 modified nucleosides, each independently comprising a modified sugar moiety.

Embodiment 614: The method of any of embodiment 598-609, wherein the modified oligonucleotide comprises at least 9 modified nucleosides, each independently comprising a modified sugar moiety.

Embodiment 615: The method of embodiment 598-609, wherein the modified oligonucleotide comprises at least 10 modified nucleosides, each independently comprising a modified sugar moiety.

Embodiment 616: The method of any of embodiments 598-609, wherein each nucleoside of the modified oligonucleotide is a modified nucleoside or an unmodified nucleoside.

Embodiment 617: The method of embodiment 616, wherein each unmodified nucleoside is a 2'-deoxy nucleoside.

Embodiment 618: The method of any of embodiments 616-617, wherein the modified oligonucleotide comprises at least 6 2'-deoxy nucleosides.

Embodiment 619: The method of any of embodiments 616-617, wherein the modified oligonucleotide comprises at least 7 2'-deoxy nucleosides.

Embodiment 620: The method of any of embodiments 616-617, wherein the modified oligonucleotide comprises at least 8 2'-deoxy nucleosides.

Embodiment 621: The method of any of embodiments 616-617, wherein the modified oligonucleotide comprises at least 9 2'-deoxy nucleosides.

Embodiment 622: The method of any of embodiments 616-617, wherein the modified oligonucleotide comprises at least 10 2'-deoxy nucleosides.

Embodiment 623: The method of any of embodiments 616-622, wherein the modified oligonucleotide contains no more than 4 contiguous 2'-deoxy nucleosides.

Embodiment 624: The method of any of embodiments 598-623, wherein the modified oligonucleotide comprises at least 15 modified nucleosides, each independently comprising a modified sugar moiety.

Embodiment 625: The method of embodiment 624, wherein each nucleoside of the modified oligonucleotide is a modified nucleoside, each independently comprising a modified sugar moiety.

Embodiment 626: The method of any of embodiments 598-625, wherein the modified oligonucleotide comprises at least two modified nucleosides comprising modified sugar moieties that are the same as one another.

Embodiment 627: The method of any of embodiments 598-626, wherein the modified oligonucleotide comprises at least two modified nucleosides comprising modified sugar moieties that are different from one another.

Embodiment 628: The method of any of embodiments 598-627, wherein the modified oligonucleotide comprises a modified region of at least 5 contiguous modified nucleosides.

Embodiment 629: The method of embodiment 628, wherein the modified oligonucleotide comprises a modified region of at least 10 contiguous modified nucleosides.

Embodiment 630: The method of embodiment 628, wherein the modified oligonucleotide comprises a modified region of at least 15 contiguous modified nucleosides.

Embodiment 631: The method of embodiment 628, wherein the modified oligonucleotide comprises a modified region of at least 18 contiguous modified nucleosides.

Embodiment 632: The method of embodiment 628, wherein the modified oligonucleotide comprises a modified region of at least 20 contiguous modified nucleosides.

Embodiment 633: The method of any of embodiments 626-632, wherein each modified nucleoside of the modified region has a modified sugar moiety independently selected from among: 2'-F, 2'-OMe, 2'-MOE, cEt, LNA, morpholino, modified morpholino, and peptide nucleic acid.

Embodiment 634: The method of any of embodiments 628-633, wherein the modified nucleosides of the modified region each comprise the same modification as one another.

Embodiment 635: The method of embodiment 634, wherein the modified nucleosides of the modified region each comprise the same 2'-substituted sugar moiety.

Embodiment 636: The method of embodiment 635, wherein the 2'-substituted sugar moiety of the modified nucleosides of the region of modified nucleosides is selected from 2'-F, 2'-OMe, and 2'-MOE.

Embodiment 637: The method of embodiment 635, wherein the 2'-substituted sugar moiety of the modified nucleosides of the region of modified nucleosides is 2'-MOE.

Embodiment 638: The method of embodiment 634, wherein the modified nucleosides of the region of modified nucleosides each comprise the same bicyclic sugar moiety.

Embodiment 639: The method of embodiment 638, wherein the bicyclic sugar moiety of the modified nucleosides of the region of modified nucleosides is selected from LNA and cEt.

Embodiment 640: The method of embodiment 634, wherein the modified nucleosides of the region of modified nucleosides each comprises a sugar surrogate.

Embodiment 641: The method of embodiment 640, wherein the sugar surrogate of the modified nucleosides of the region of modified nucleosides is a morpholino.

Embodiment 642: The method of embodiment 640, wherein the sugar surrogate of the modified nucleosides of the region of modified nucleosides is a modified morpholino.

Embodiment 643: The method of embodiment 640, wherein the sugar surrogate of the modified nucleosides of the region of modified nucleosides is a peptide nucleic acid.

Embodiment 644: The method of any of embodiments 623-643, wherein the modified nucleotide comprises no more than 4 contiguous naturally occurring nucleosides.

Embodiment 645: The method of any of embodiments 626-644, wherein each nucleoside of the modified oligonucleotide is a modified nucleoside.

Embodiment 646: The method of embodiment 645 wherein each modified nucleoside comprises a modified sugar moiety.

Embodiment 647: The method of embodiment 646, wherein the modified nucleosides of the modified oligonucleotide comprise the same modification as one another.

Embodiment 648: The method of embodiment 647, wherein the modified nucleosides of the modified oligonucleotide each comprise the same 2'-substituted sugar moiety.

Embodiment 649: The method of embodiment 648, wherein the 2'-substituted sugar moiety of the modified oligonucleotide is selected from 2'-F, 2'-OMe, and 2'-MOE.

Embodiment 650: The method of embodiment 649, wherein the 2'-substituted sugar moiety of the modified oligonucleotide is 2'-MOE.

Embodiment 651: The method of embodiment 649, wherein the 2'-substituted sugar moiety of the modified oligonucleotide is 2'-OMe.

Embodiment 652: The method of embodiment 647, wherein the modified nucleosides of the modified oligonucleotide each comprise the same bicyclic sugar moiety.

Embodiment 653: The method of embodiment 652, wherein the bicyclic sugar moiety of the modified oligonucleotide is selected from LNA and cEt.

Embodiment 654: The method of embodiment 646-647, wherein the modified nucleosides of the modified oligonucleotide each comprises a sugar surrogate.

Embodiment 655: The method of embodiment 654, wherein the sugar surrogate of the modified oligonucleotide is a morpholino.

Embodiment 656: The method of embodiment 654, wherein the sugar surrogate of the modified oligonucleotide is a modified morpholino.

Embodiment 657: The method of embodiment 654, wherein the sugar surrogate of the modified oligonucleotide is a peptide nucleic acid.

Embodiment 658: The method of any of embodiments 557-657, wherein the modified oligonucleotide comprises at least one modified internucleoside linkage.

Embodiment 659: The method of embodiment 658, wherein the modified internucleoside linkage is a phosphorothioate internucleoside linkage.

Embodiment 660: The method of embodiment 658 or 659, wherein each internucleoside linkage is either a phosphodiester internucleoside linkage or a phosphorothioate internucleoside linkage.

Embodiment 661: The method of embodiment 658, wherein each internucleoside linkage is a modified internucleoside linkage.

Embodiment 662: The method of any of embodiments 557-657, comprising at least one phosphorothioate internucleoside linkage.

Embodiment 663: The method of embodiment 658, wherein each internucleoside linkage is a modified internucleoside linkage and wherein each internucleoside linkage comprises the same modification.

Embodiment 664: The method of embodiment 663, wherein each internucleoside linkage is a phosphorothioate internucleoside linkage.

Embodiment 665: The method of any of embodiments 557-664, wherein the antisense compound comprises at least one conjugate group.

Embodiment 666: The method of embodiment 665, wherein the conjugate group comprises Gal-NAc.

Embodiment 667: The method of any of embodiments 557-666, wherein the antisense compound consists of the modified oligonucleotide.

Embodiment 668: The method of any of embodiments 557-667, wherein the expression, translation, or amount or activity of the target protein is increased by at least 10%.

Embodiment 669: The method of any of embodiments 557-667, wherein the expression, translation, or amount or activity of the target protein is increased by at least 20%.

Embodiment 670: The method of any of embodiments 557-667, wherein the expression, translation, or amount or activity of the target protein is increased by at least 30%.

Embodiment 671: The method of any of embodiments 557-667, wherein the expression, translation, or amount or activity of the target protein is increased by at least 50%.

Embodiment 672: The method of any of embodiments 557-667, wherein the expression, translation, or amount or activity of the target protein is increased by at least 100%.

Embodiment 673: The method of any of embodiments 557-667, wherein the expression, translation, or amount or activity of the target protein is increased by at least 120%.

Embodiment 674: The method of any of embodiments 557-667, wherein the expression, translation, or amount or activity of the target protein is increased by at least 150%.

Embodiment 675: The method of any of embodiments 557-674, wherein the cell is in vitro.

Embodiment 676: The method of any of embodiments 557-674, wherein the cell is in a subject.

Embodiment 677: The method of embodiment 676, wherein the subject has a disease or condition and wherein at least one symptom of the disease or condition is ameliorated.

Embodiment 678: The method of embodiment 676 or 677, wherein the cell is in an animal.

Embodiment 679: The method of embodiment 678, wherein the animal is a human.

Embodiment 680: The compound or method of any preceeding embodiment, wherein the modified oligonucleotide does not activate RNase H when bound to a target transcript.

Embodiment 681: The compound or method of any preceeding embodiment, wherein the modified oligonucleotide is not a gapmer.

Embodiment 682: A method of increasing translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing translation of the target protein in the cell.

Embodiment 683: A method of decreasing suppression of translation of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby decreasing suppression of translation of the target protein in the cell.

Embodiment 684: A method of increasing the amount or activity of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing the amount or activity of the target protein in the cell.

Embodiment 685: A method of increasing expression of a target protein in a cell, comprising contacting the cell with an antisense compound comprising a modified oligonucleotide, wherein the target protein is encoded by a target transcript comprising at least one translation suppression element and wherein the modified oligonucleotide is complementary to a target site within a translation suppression element region of the target transcript; and thereby increasing expression of the target protein in the cell.

Embodiment 686: The method of any of embodiments 682-685, wherein the translation suppression element region is the 5' untranslated region.

Embodiment 687: The method of any of embodiments 682-685, wherein the translation suppression element region is a stem-loop structure in the 5' untranslated region.

Embodiment 688: The method of any of embodiments 682-685, wherein the translation suppression element region is a stem in a stem-loop structure in the 5' untranslated region.

Embodiment 689: The method of any of embodiments 682-685, wherein the translation suppression element region is a loop in a stem-loop structure in the 5' untranslated region.

Embodiment 690: The method of any of embodiments 682-689, wherein the translation suppression element region contains one or more uORFs.

Embodiment 691: The method of any of embodiments 682-689, wherein the translation suppression element region contains one or more uORFs, but wherein the one or more uORFs do not suppress translation of the target transcript.

Embodiment 692: The method of any of embodiments 682-689, wherein the translation suppression element region does not contains a uORF.

Embodiment 693: The method of any of embodiments 682-691, wherein the target transcript encodes RNase H1.

Embodiment 694: The method of any of embodiments 682-692, wherein the target transcript encodes LDLr.

Embodiment 695: The method of any of embodiments 682-689, wherein the target transcript encodes ARF1.

Embodiment 696: The method of any of embodiments 682-692 or 694-695, wherein the modified oligonucleotide has a nucleobase sequence comprising at least 8 contiguous nucleobases of any of the nucleobase sequences of SEQ ID NOs: 80, 84, 85, 86, 87, 88, 89, 90, 92, 93, 95, 97, 99, or 100.

Embodiment 697: The method of any of embodiments 682-692 or 694-695, wherein the modified oligonucleotide has a nucleobase sequence comprising at least 10 contiguous nucleobases of any of the nucleobase sequences of SEQ ID NOs: 80, 84, 85, 86, 87, 88, 89, 90, 92, 93, 95, 97, 99, or 100.

Embodiment 698: The method of any of embodiments 682-692 or 694-695, wherein the modified oligonucleotide has a nucleobase sequence comprising at least 12 contiguous nucleobases of any of the nucleobase sequences of SEQ ID NOs: 80, 84, 85, 86, 87, 88, 89, 90, 92, 93, 95, 97, 99, or 100.

Embodiment 699: The method of any of embodiments 682-692 or 694-695, wherein the modified oligonucleotide has a nucleobase sequence comprising at least 14 contiguous nucleobases of any of the nucleobase sequences of SEQ ID NOs: 80, 84, 85, 86, 87, 88, 89, 90, 92, 93, 95, 97, 99, or 100.

Embodiment 700: The method of any of embodiments 682-692 or 694-695, wherein the modified oligonucleotide has a nucleobase sequence consisting of the nucleobase sequence of any of SEQ ID NOs: 80, 84, 85, 86, 87, 88, 89, 90, 92, 93, 95, 97, 99, or 100.

Embodiment 701: The method of any of embodiments 682-692 or 694-695, wherein the modified oligonucleotide has a nucleobase sequence consisting of the nucleobase sequence of any of SEQ ID NOs: 80, 84, 85, 86, 87, 88, 89, 90, 92, 93, 95, 97, 99, or 100.

Embodiment 702: The compound or method of any preceeding embodiment, wherein the modified oligonucleotide is not a gapmer.

Embodiment 703: The compound or method of any preceeding embodiment, wherein the target transcript is not: CFTR, FXN (Frataxin), HOTAIR, LAMA1, UTRN, EZH2, Suv3H1, NEST, DINO, Apoal, SSPN, MERTK, MECP2, MBNL1, FMR1, CD247, PTEN, KLF4, ATP2A2, NFE2L2, FoxP3, ANRIL, SMN, HBF, ACTB, or EPO.

Embodiment 704: The compound or method of any preceeding embodiment, wherein the target transcript is not an epigenetic regulator.

Embodiment 705: The compound or method of any preceeding embodiment, wherein the target protein is not frataxin.

Embodiment 706: The compound or method of any preceeding embodiment, wherein the target transcript is not frataxin.

Embodiment 707: The compound or method of any preceeding embodiment, wherein the target transcript is not a lncRNA.

Embodiment 708: A pharmaceutical composition comprising a prodrug of any preceeding embodiment.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Definitions

Unless otherwise indicated, the following terms have the following meanings:

As used herein, "target transcript" means a transcript that encodes a target protein. In certain embodiments, a target transcript contains a primary open reading frame that encodes a primary protein and one or more start sites at which translation of a polypeptide that is not the target protein may be initiated. In certain such embodiments, a target transcript contains a primary open reading frame and a uORF. In certain such embodiments, a target transcript contains a primary open reading frame and more than one uORF. In certain embodiments, a target transcript contains a primary open reading frame and does not contain a uORF. In certain embodiments, a target transcript contains a primary open reading frame and a translation suppression element.

As used herein, "translation suppression element," means any sequence and/or secondary structure in the 5'-UTR of a target transcript that reduces, inhibits, and/or suppresses translation of the target transcript. In certain embodiments, a translation suppression element comprises a uORF.

In certain embodiments, a translation suppression element does not comprise a uORF. In certain embodiments, a translation suppression element comprises one or more stem-loops. In certain embodiments, a translation suppression element comprises greater than 60%, greater than 70%, or greater than 80% GC content. In certain embodiments, the translation suppression element is a uORF. In certain embodiments, the translation suppression element is a stem-loop.

As used herein, "translation suppression element inhibitor," means any means any agent capable of specifically inhibiting the activity of a translation suppression element. In certain embodiments, the activity of a translation suppression element inhibitor is suppression of translation of the pORF polypeptide or protein on the same transcript. For example, translation suppression element inhibitors include nucleic acids (including antisense compounds and siRNA), peptides, antibodies, small molecules, and other agents capable of inhibiting the amount or activity of a translation suppression element.

As used herein, "translation suppression element region" means a portion of the target transcript that comprises one or more translation suppression elements. In certain embodiments, a translation suppression element region comprises a uORF. In certain embodiments, a translation suppression element region comprises more than one uORF. In certain embodiments, a translation suppression element region comprises a uORF and at least one translation suppression element that is not a uORF. In certain embodiments, a translation suppression element region comprises a translation suppression element that is not a uORF and does not contain a uORF.

As used herein, "GC content" means the percentage of total nucleosides in a particular portion of a nucleic acid or oligonucleotide that are either G or C or that base pair with G or C.

As used herein, "consecutive GC nucleosides" or "consecutive GC nucleotides" means a portion of adjacent nucleosides in a nucleic acid or oligonucleotide that are all either G or C or that base pair with G or C.

As used herein, "target protein" means a protein that one desires to increase in amount, concentration, or activity. In certain embodiments, the target protein is encoded by the primary open reading frame of a target transcript.

As used herein, "target transcript" means a transcript that encodes a target protein. In certain embodiments, a target transcript contains a primary open reading frame that encodes a primary protein and one or more start sites at which translation of a polypeptide that is not the target protein may be initiated. In certain such embodiments, a target transcript contains a primary open reading frame and a uORF. In certain such embodiments, a target transcript contains a primary open reading frame and more than one uORF.

As used herein, "primary open reading frame" or "pORF" means the portion of the target transcript that encodes the primary protein associated with the transcript. In certain embodiments, the pORF encodes the target protein.

As used herein, "primary protein" means a protein encoded by a primary open reading frame.

As used herein, "target site" means the portion of the target transcript having a nucleobase sequence that is complementary to a portion of the nucleobase sequence of a modified oligonucleotide. In certain embodiments, the modified oligonucleotide is complementary to the target site across the entire length of the modified oligonucleotide.

As used herein, "start site" means a group of nucleobases on a transcript at which a ribosomal subunit is recruited. In certain embodiments, a start site may result in initiation of translation. In certain embodiments, a start site is an AUG codon. In certain embodiments, a start site is a non-canonical start codon.

As used herein, "upstream open reading frame start site" or "uORF start site" means a start site that is upstream of the pORF start codon. In certain embodiments, a uORF start site initiates translation of a polypeptide that is not the target protein.

As used herein, "uORF start site region" means a portion of the target transcript that comprises a uORF start site. In certain embodiments, a uORF start site region comprises a uORF start site and the 100 nucleosides upstream and downstream of the uORF start site. In certain embodiments, a uORF start site region comprises a uORF start site and the 75 nucleosides upstream and downstream of the uORF start site. In certain embodiments, a uORF start site region comprises a uORF start site and the 50 nucleosides upstream and downstream of the uORF start site. In certain embodiments, a uORF start site region comprises a uORF start site and the 30 nucleosides upstream and downstream of the uORF start site. In certain embodiments, a uORF start site region comprises a uORF start site and the 20 nucleosides upstream and downstream of the uORF start site. In certain embodiments, a uORF start site region comprises the 5' untranslated region. In certain embodiments, a uORF start site region consists of the 5'-UTR.

As used herein, "uORF" or "upstream open reading frame" means a portion of a target transcript that comprises a start site upstream of (i.e. 5' of) the pORF and an in frame termination codon. In certain embodiments, a uORF is the portion of the target transcript that is translated when translation is initiated at a uORF start site. In certain embodiments, a uORF does not overlap with a pORF. In certain embodiments, a uORF does overlap with a pORF. In certain embodiments a uORF overlaps with another uORF. In certain embodiments, a uORF is out of frame with a pORF.

As used herein, "wild-type uORF start site" means a uORF start site that does not arise from a mutation.

As used herein, "wild-type uORF start site region" means the uORF start site region of a wild-type uORF start site.

As used herein, "a uORF start site that arises from a mutation" means a uORF start site, where the same portion of the target transcript on the wild-type allele does not contain a uORF start site.

As used herein, "uORF polypeptide" means a polypeptide encoded by a uORF. In certain embodiments, a uORF polypeptide is a protein.

As used herein, "uORF inhibitor" means any agent capable of specifically inhibiting the activity of a uORF. In certain embodiments, the activity of a uORF is suppression of translation of the pORF polypeptide or protein on the same transcript. In certain embodiments, the activity of a uORF is suppression of translation of the pORF polypeptide or protein on a different transcript. For example, uORF specific inhibitors include nucleic acids (including antisense compounds and siRNA), peptides, antibodies, small molecules, and other agents capable of inhibiting the amount or activity of a uORF.

As used herein, "suppression of translation of a target protein in a cell," means that translation of the target protein is less than the translation of the target protein in the absence of one or more TSEs.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluoroine at the 2' position. Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligonucleotide which is capable of hybridizing to a complementary oligonucleotide. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides.

In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage. Examples of modified oligonucleotides include single-stranded and double-stranded compounds, such as, antisense compounds, siRNAs, shRNAs, ssRNAs, and occupancy-based compounds.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, the sub-structures are nucleotides or nucleosides. In certain embodiments, an oligomeric compound comprises an oligonucleotide. In certain embodiments, an oligomeric compound consists of an oligonucleotide. In certain embodiments, an oligomeric compound consists of an antisense compound.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate group" means an atom or group of atoms bound to an oligonucleotide or oligomeric compound. In general, conjugate groups modify one or more properties of the oligonucleotide or oligomeric compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a measurable activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), translation, and post-translational modification.

As used herein, "translation" means the process in which a polypeptide (e.g. a protein) is translated from an mRNA. In certain embodiments, an increase in translation means an increase in the number of polypeptide (e.g. a protein) molecules that are made per copy of mRNA that encodes said polypeptide.

As used herein, "target nucleic acid" means a nucleic acid molecule to which an antisense compound is intended to hybridize.

As used herein, "mRNA" means an RNA molecule that encodes a protein.

As used herein, "pre-mRNA" means an RNA transcript that has not been fully processed into mRNA. Pre-RNA includes one or more intron.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense compound specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$), aryl, aralkyl, heterocyclic radical, heteroaryl, heteroarylalkyl, amino (—N(R$_{bb}$)(R$_{cc}$)), imino(=NR$_{bb}$), amido (—C(O)N(R$_{bb}$)(R$_{cc}$) or —N(R$_b$)C(O)R$_{aa}$), azido (—N$_3$), nitro (—NO$_2$), cyano (—CN), carbamido (—OC(O)N(R$_{bb}$)(R$_{cc}$) or —N(R$_{bb}$)C(O)OR$_{aa}$), ureido (—N(R$_{bb}$)C(O)N(R$_{bb}$)(R$_{cc}$)), thioureido (—N(R$_{bb}$)C(S)N(R$_{bb}$)—(R$_{cc}$)), guanidinyl (—N(R$_{bb}$)C(=NR$_{bb}$)N(R$_{bb}$)(R$_{cc}$)), amidinyl (—C(=NR$_{bb}$)N(R$_{bb}$)(R$_{cc}$) or —N(R$_{bb}$)C(=NR$_{bb}$)(R$_{aa}$)), thiol (—SR$_{bb}$), sulfinyl (—S(O)R$_{bb}$), sulfonyl (—S(O)$_2$R$_{bb}$) and sulfonamidyl (—S(O)$_2$N(R$_{bb}$)(R$_{cc}$) or —N(R$_{bb}$)S—(O)$_2$R$_{bb}$). Wherein each R$_{aa}$, R$_{bb}$ and R$_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "Intracerebroventricular" or "ICV" means administration into the ventricular system of the brain.

As used herein, "wherein the translation suppression element region comprises one and only one uORF," means that exactly one uORF is present in the translation suppression element region. In certain embodiments, exactly one uORF is present in the 5'-UTR.

The compounds described herein include variations in which one or more atoms are replaced with a non-radioactive isotope or radioactive isotope of the indicated element. For example, compounds herein that comprise hydrogen atoms encompass all possible deuterium substitutions for each of the 1H hydrogen atoms. Isotopic substitutions encompassed by the compounds herein include but are not limited to: 2H or 3H in place of 1H, 13C or 14C in place of 12C, 15N in place of 14N, 17O or 18O in place of 16O, and 33S, 34S, 35S, or 36S in place of 32S. In certain embodiments, non-radioactive isotopic substitutions may impart new properties on the oligomeric compound that are beneficial for use as a therapeutic or research tool. In certain embodiments, radioactive isotopic substitutions may make the compound suitable for research purposes such as imaging.

Certain Modified Oligonucleotides

In certain embodiments, the present invention provides antisense compounds. In certain embodiments, antisense compounds comprise a modified oligonucleotide. In certain embodiments, such antisense compounds comprise modified oligonucleotides and optionally one or more conjugate and/or terminal groups. In certain embodiments, an antisense compound consists of a modified oligonucleotide. In certain embodiments, modified oligonucleotides comprise one or more chemical modifications. Such chemical modifications include modifications of one or more nucleoside (including modifications to the sugar moiety and/or the nucleobase) and/or modifications to one or more internucleoside linkage.

a. Certain Modified Nucleosides

In certain embodiments, provided herein are antisense compounds comprising or consisting of oligonuleotides comprising at least one modified nucleoside. Such modified nucleosides comprise a modified sugar moeity, a modified nucleobase, or both a modified sugar moiety and a modified nucleobase.

i. Certain Sugar Moieties

In certain embodiments, antisense compounds of the invention comprise one or more modified nucleosides comprising a modified sugar moiety. Such antisense compounds comprising one or more sugar-modified nucleosides may have desirable properties, such as enhanced nuclease stability or increased binding affinity with a target nucleic acid relative to antisense compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, 0-allyl, 0-C$_1$-C$_{10}$ alkyl, O—C$_1$-C$_{10}$ substituted alkyl; O—C$_1$-C$_{10}$ alkoxy; O—C$_1$-C$_{10}$ substituted alkoxy, OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy.

In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2-substituent group selected from halo, allyl, amino, azido, O—C$_1$-C$_{10}$ alkoxy; O—C$_1$-C$_{10}$ substituted alkoxy, SH, CN, OCN, CF$_3$, OCF$_3$, O-alkyl, S-alkyl, N(R$_m$)-alkyl; O-alkenyl, S-alkenyl, or N(R$_m$)-alkenyl; O-alkynyl, S-alkynyl, N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$-, —[C(R$_a$)(R$_b$)]$_n$—O—, —C(R$_a$R$_b$)—N(R)—O— or, —C(R$_a$R$_b$)—O—N(R)—; 4'- CH$_2$-2', 4'-(CH$_2$)$_2$-2', 4'-(CH$_2$)$_3$-2', 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)-0-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:
x is 0, 1, or 2;
n is 1,2,3, or 4;
each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and
each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) R-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$-N(R)-2') BNA, (I) methyl carbocyclic (4'-CH$_2$—CH(CH$_3$)-2') BNA, (J) propylene carbocyclic (4'-(CH$_2$)$_3$-2') BNA, and (M) 4'-CH$_2$—O—CH$_2$-2' as depicted below.

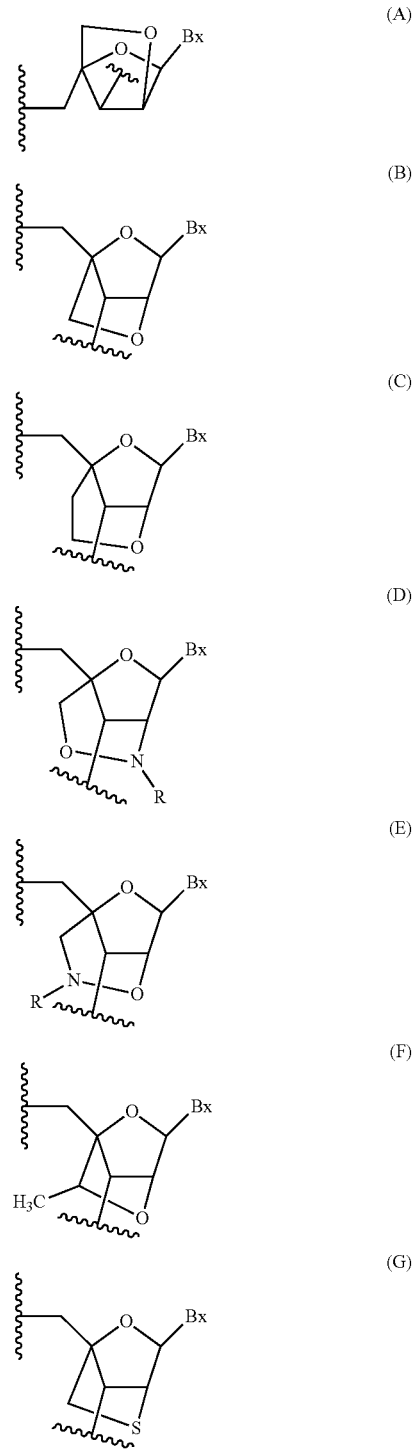

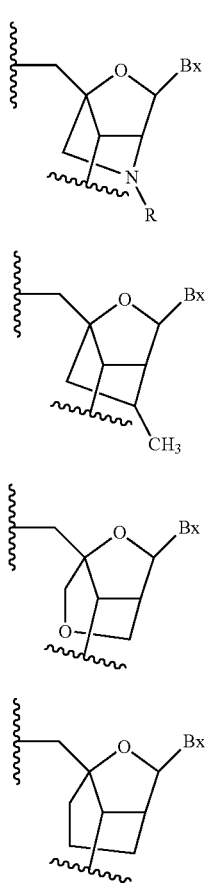

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J Org. Chem.*, 1998, 63, 10035-10039; Srivastava et al., *J Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. No. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surogates comprise a 4'-sulfer atom and a substitution at the 2-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F—HNA), and those compounds having Formula VII:

VII

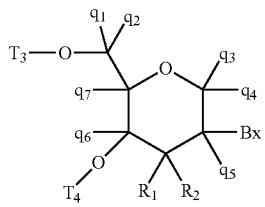

wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry,* 2002, 10, 841-854).

In certain embodiments, sugar surrogates comprise rings having more than 5 atoms and more than one heteroatom. For example nucleosides comprising morpholino sugar moieties and their use in oligomenc compounds has been reported (see for example: Braasch et al., *Biochemistry,* 2002, 41, 4503-4510; and U.S. Pat. Nos. 5,698,685; 5,166, 315; 5,185,444; and 5,034,506). As used here, the term "morpholino" means a sugar surrogate having the following structure:

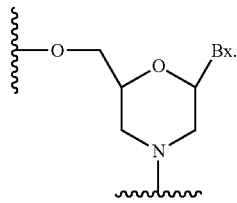

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

ii. Certain Modified Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and 0-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering,* Kroschwitz, J. I., Ed., John Wiley & Sons, 1990, 858-859; those disclosed by Englisch et al., *Angewandte Chemie, International Edition,* 1991, 30, 613; and those disclosed by Sanghvi, Y. S., Chapter 15, *Antisense Research and Applications,* Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121; 5,596,091; 5,614,617; 5,645,985; 5,681, 941; 5,750,692; 5,763,588; 5,830,653 and 6,005,096, certain of which are commonly owned with the instant application, and each of which is herein incorporated by reference in its entirety.

b. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R)

or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetyl (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., *ACS Symposium Series* 580; Chapters 3 and 4, 40-65). Further neutral internucleoside linkages include nonionic linkages comprising mixed N, O, S and CH$_2$ component parts.

c. Certain Motifs

In certain embodiments, the invention provides modified oligocucleotides. In certain embodiments, modified oligonucleotides comprise one or more modified sugars. In certain embodiments, modified oligonucleotides comprise one or more modified nucleobases. In certain embodiments, modified oligonucleotides comprise one or more modified internucleoside linkages. In certain embodiments, the modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, a modified oligonucleotide may be described by its sugar modification motif, internucleoside linkage motif and/or nucleobase modification motif (as used herein, nucleobase modification motif describes the chemical modifications to the nucleobases independent of the sequence of nucleobases).

In certain embodiments, every sugar moiety of the modified oligonucleotides of the present invention is modified. In certain embodiments, modified oligonucleotides include one or more unmodified sugar moiety.

d. Certain Overall Lengths

In certain embodiments, the present invention provides modified oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides modified oligonucleotides which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a modified oligonucleotides has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

e. Certain Oligonucleotides

In certain embodiments, oligonucleotides of the present invention are characterized by their modification motif and overall length. In certain embodiments, such parameters are each independent of one another.

I. Certain Oligomeric Compounds

In certain embodiments, the invention provides oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, abasic nucleosides, modified or unmodified nucleosides, and two or more nucleosides that are independently modified or unmodified.

In certain embodiments, antisense compounds are provided wherein the 5-terminal group comprises a 5'-terminal stabilized phosphate. A "5'-terminal stabilized phosphate" is a 5'-terminal phosphate group having one or more modifications that increase nuclease stability relative to a 5'-phosphate.

In certain embodiments, antisense compounds are provided wherein the 5-terminal group has Formula IIe:

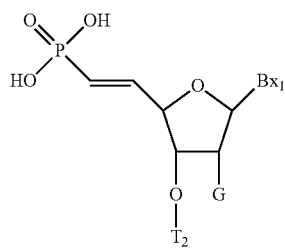

wherein:
Bx is uracil, thymine, cytosine, 5-methyl cytosine, adenine or guanine;
T2 is a phosphorothioate internucleoside linking group linking the compound of Formula IIe to the oligomeric compound; and G is halogen, OCH3, OCF3, OCH2CH3, OCH2CF3, OCH2-CH=CH2, O(CH2)2-OCH3, O(CH2)2-O(CH2)2-N(CH3)2, OCH2C(=O)—N(H)CH3, OCH2C(=O)—N(H)—(CH2)2-N(CH3)2 or OCH2-N(H)—C(=NH)NH2.

In certain embodiments, antisense compounds are provided wherein said 5-terminal compound has Formula IIe wherein G is F, OCH3 or O(CH2)$_2$—OCH3.

In certain embodiments, the 5'-terminal group is a 5'-terminal stabilized phosphate comprising a vinyl phosphonate represented by Formula IIe above.

f. Certain Conjugate Groups

In certain embodiments, the oligonucleotides or oligomeric compounds as provided herein are modified by covalent attachment of one or more conjugate groups. In general, conjugate groups modify one or more properties of the attached oligonucleotide or oligomeric compound including but not limited to pharmacodynamics, pharmacokinetics, stability, binding, absorption, cellular distribution, cellular uptake, charge and clearance. As used herein, "conjugate group" means a radical group comprising a group of atoms that are attached to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties. Conjugate groups are routinely used in the chemical arts and can include a conjugate linker that covalently links the conjugate group to an oligonucleotide or oligomeric compound. In certain embodiments, conjugate groups include a cleavable moiety that covalently links the conjugate group to an oligonucleotide or oligomeric compound. In certain embodiments, conjugate groups include a conjugate linker and a cleavable moiety to covalently link the conjugate group to an oligonucleotide or oligomeric compound. In certain embodiments, a conjugate group has the general formula:

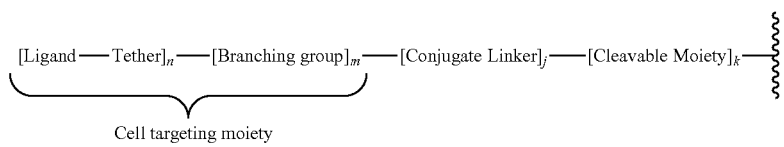

wherein n is from 1 to about 3, m is 0 when n is 1 or m is 1 when n is 2 or 3, j is 1 or 0, k is 1 or 0 and the sum of j and k is at least one.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

Conjugate groups are shown herein as radicals, providing a bond for forming covalent attachment to an oligomeric compound such as an oligonucleotide. In certain embodiments, the point of attachment on the oligomeric compound is at the 3-terminal nucleoside or modified nucleoside. In certain embodiments, the point of attachment on the oligomeric compound is the 3-oxygen atom of the 3-hydroxyl group of the 3' terminal nucleoside or modified nucleoside. In certain embodiments, the point of attachment on the oligomeric compound is at the 5-terminal nucleoside or modified nucleoside. In certain embodiments the point of attachment on the oligomeric compound is the 5'-oxygen atom of the 5-hydroxyl group of the 5'-terminal nucleoside or modified nucleoside. In certain embodiments, the point of attachment on the oligomeric compound is at any reactive site on a nucleoside, a modified nucleoside or an internucleoside linkage.

As used herein, "cleavable moiety" and "cleavable bond" mean a cleavable bond or group of atoms that is capable of being split or cleaved under certain physiological conditions. In certain embodiments, a cleavable moiety is a cleavable bond. In certain embodiments, a cleavable moiety comprises a cleavable bond. In certain embodiments, a cleavable moiety is a group of atoms. In certain embodiments, a cleavable moiety is selectively cleaved inside a cell or sub-cellular compartment, such as a lysosome. In certain embodiments, a cleavable moiety is selectively cleaved by endogenous enzymes, such as nucleases. In certain embodiments, a cleavable moiety comprises a group of atoms having one, two, three, four, or more than four cleavable bonds.

In certain embodiments, conjugate groups comprise a cleavable moiety. In certain such embodiments, the cleavable moiety covalently attaches the oligomeric compound to the conjugate linker. In certain such embodiments, the cleavable moiety covalently attaches the oligomeric compound to the cell-targeting moiety.

In certain embodiments, a cleavable bond is selected from among: an amide, a polyamide, an ester, an ether, one or both esters of a phosphodiester, a phosphate ester, a carbamate, a di-sulfide, or a peptide. In certain embodiments, a cleavable bond is one of the esters of a phosphodiester. In certain embodiments, a cleavable bond is one or both esters of a phosphodiester. In certain embodiments, the cleavable moiety is a phosphodiester linkage between an oligomeric compound and the remainder of the conjugate group. In certain embodiments, the cleavable moiety comprises a phosphodiester linkage that is located between an oligomeric compound and the remainder of the conjugate group. In certain embodiments, the cleavable moiety comprises a phosphate or phosphodiester. In certain embodiments, the cleavable moiety is attached to the conjugate linker by either a phosphodiester or a phosphorothioate linkage. In certain embodiments, the cleavable moiety is attached to the conjugate linker by a phosphodiester linkage. In certain embodiments, the conjugate group does not include a cleavable moiety.

In certain embodiments, the cleavable moiety is a cleavable nucleoside or a modified nucleoside. In certain embodiments, the nucleoside or modified nucleoside comprises an optionally protected heterocyclic base selected from a purine, substituted purine, pyrimidine or substituted pyrimidine. In certain embodiments, the cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine.

In certain embodiments, the cleavable moiety is 2'-deoxy nucleoside that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to the 3'-oxygen atom of the 3'-hydroxyl group of the 3'-terminal nucleoside or modified nucleoside by a phosphodiester linkage. In certain embodiments, the cleavable moiety is 2'-deoxy adenosine that is attached to the 5'-oxygen atom of the 5'-hydroxyl group of the 5'-terminal nucleoside or modified nucleoside by a phosphodiester linkage. In certain embodiments, the cleavable moiety is attached to a 2'-position of a nucleoside or modified nucleoside of an oligomeric compound.

As used herein, "conjugate linker" in the context of a conjugate group means a portion of a conjugate group comprising any atom or group of atoms that covalently link the cell-targeting moiety to the oligomeric compound either directly or through the cleavable moiety. In certain embodiments, the conjugate linker comprises groups selected from alkyl, amino, oxo, amide, disulfide, polyethylene glycol, ether, thioether (—S—) and hydroxylamino (—O—N(H)—). In certain embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus linking group. In certain embodiments, the conjugate linker comprises at least one phosphodiester group. In certain embodiments, the conjugate linker includes at least one neutral linking group.

In certain embodiments, the conjugate linker is covalently attached to the oligomeric compound. In certain embodiments, the conjugate linker is covalently attached to the oligomeric compound and the branching group. In certain embodiments, the conjugate linker is covalently attached to the oligomeric compound and a tethered ligand. In certain embodiments, the conjugate linker is covalently attached to the cleavable moiety. In certain embodiments, the conjugate linker is covalently attached to the cleavable moiety and the branching group. In certain embodiments, the conjugate linker is covalently attached to the cleavable moiety and a tethered ligand. In certain embodiments, the conjugate linker includes one or more cleavable bonds. In certain embodiments, the conjugate group does not include a conjugate linker.

As used herein, "branching group" means a group of atoms having at least 3 positions that are capable of forming covalent linkages to two or more tether-ligands and the remainder of the conjugate group. In general a branching group provides a plurality of reactive sites for connecting tethered ligands to the oligomeric compound through the conjugate linker and/or the cleavable moiety. In certain embodiments, the branching group comprises groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, the branching group is covalently attached to the conjugate linker. In certain embodiments, the branching group is covalently attached to the cleavable moiety. In certain embodiments, the branching group is covalently attached to the conjugate linker and each of the tethered ligands. In certain embodiments, the branching group comprises one or more cleavable bond. In certain embodiments, the conjugate group does not include a branching group.

In certain embodiments, conjugate groups as provided herein include a cell-targeting moiety that has at least one tethered ligand. In certain embodiments, the cell-targeting moiety comprises two tethered ligands covalently attached to a branching group. In certain embodiments, the cell-targeting moiety comprises three tethered ligands covalently attached to a branching group.

As used herein, "tether" means a group of atoms that connect a ligand to the remainder of the conjugate group. In certain embodiments, each tether is a linear aliphatic group comprising one or more groups selected from alkyl, substituted alkyl, ether, thioether, disulfide, amino, oxo, amide, phosphodiester and polyethylene glycol groups in any combination. In certain embodiments, each tether is a linear aliphatic group comprising one or more groups selected from alkyl, ether, thioether, disulfide, amino, oxo, amide and polyethylene glycol groups in any combination. In certain embodiments, each tether is a linear aliphatic group comprising one or more groups selected from alkyl, substituted alkyl, phosphodiester, ether and amino, oxo, amide groups in any combination. In certain embodiments, each tether is a linear aliphatic group comprising one or more groups selected from alkyl, ether and amino, oxo, amide groups in any combination. In certain embodiments, each tether is a linear aliphatic group comprising one or more groups selected from alkyl, amino and oxo groups in any combination. In certain embodiments, each tether is a linear aliphatic group comprising one or more groups selected from alkyl and oxo groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, tethers include one or more cleavable bond. In certain embodiments, each tethered ligand is attached to a branching group. In certain embodiments, each tethered ligand is attached to a branching group through an amide group. In certain embodiments, each tethered ligand is attached to a branching group through an ether group. In certain embodiments, each tethered ligand is attached to a branching group through a phosphorus linking group or neutral linking group. In certain embodiments, each tethered ligand is attached to a branching group through a phosphodiester group. In certain embodiments, each tether is attached to a ligand through either an amide or an ether group. In certain embodiments, each tether is attached to a ligand through an ether group.

In certain embodiments, each tether comprises from about 8 to about 20 atoms in chain length between the ligand and the branching group. In certain embodiments, each tether comprises from about 10 to about 18 atoms in chain length between the ligand and the branching group. In certain embodiments, each tether comprises about 13 atoms in chain length.

In certain embodiments, the present disclosure provides ligands wherein each ligand is covalently attached to the remainder of the conjugate group through a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose.

In certain embodiments, each ligand is N-acetyl galactoseamine (GalNAc). In certain embodiments, the targeting moiety comprises 1 to 3 ligands. In certain embodiments, the targeting moiety comprises 3 ligands. In certain embodiments, the targeting moiety comprises 2 ligands. In certain embodiments, the targeting moiety comprises 1 ligand. In certain embodiments, the targeting moiety comprises 3 N-acetyl galactoseamine ligands. In certain embodiments, the targeting moiety comprises 2 N-acetyl galactoseamine ligands. In certain embodiments, the targeting moiety comprises 1 N-acetyl galactoseamine ligand.

In certain embodiments, each ligand is a carbohydrate, carbohydrate derivative, modified carbohydrate, multivalent carbohydrate cluster, polysaccharide, modified polysaccharide, or polysaccharide derivative. In certain embodiments, each ligand is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3-O—[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3,4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-gluco-heptopyranoside.

In certain embodiments, conjugate groups as provided herein comprise a carbohydrate cluster. As used herein, "carbohydrate cluster" means a portion of a conjugate group wherein two or more carbohydrate residues are attached to a branching group through tether groups. (see, e.g., Maier et al., "Synthesis of Antisense Oligonucleotides Conjugated to a Multivalent Carbohydrate Cluster for Cellular Targeting," *Bioconjugate Chemistry*, 2003, (14): 18-29, which is incorporated herein by reference in its entirety, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808, for examples of carbohydrate conjugate clusters).

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

In certain embodiments, conjugate groups are provided wherein the cell-targeting moiety has the formula:
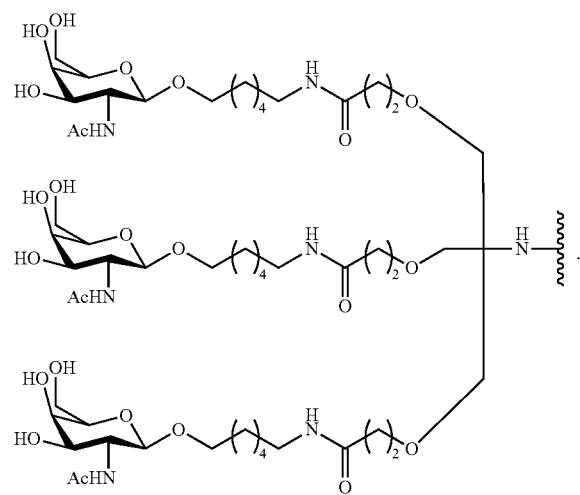
In certain embodiments, conjugate groups are provided wherein the cell-targeting moiety has the formula:
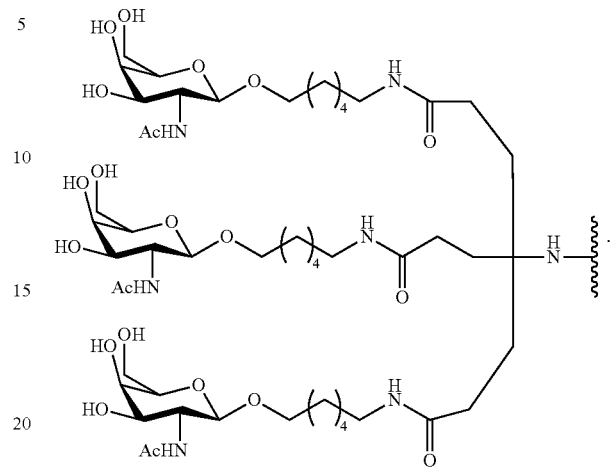
In certain embodiments, conjugate groups are provided wherein the cell-targeting moiety has the formula:
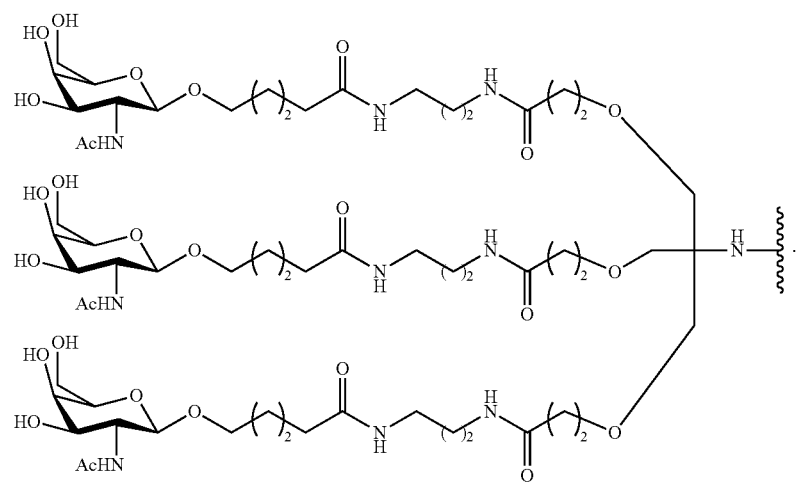

In certain embodiments, conjugate groups have the formula:

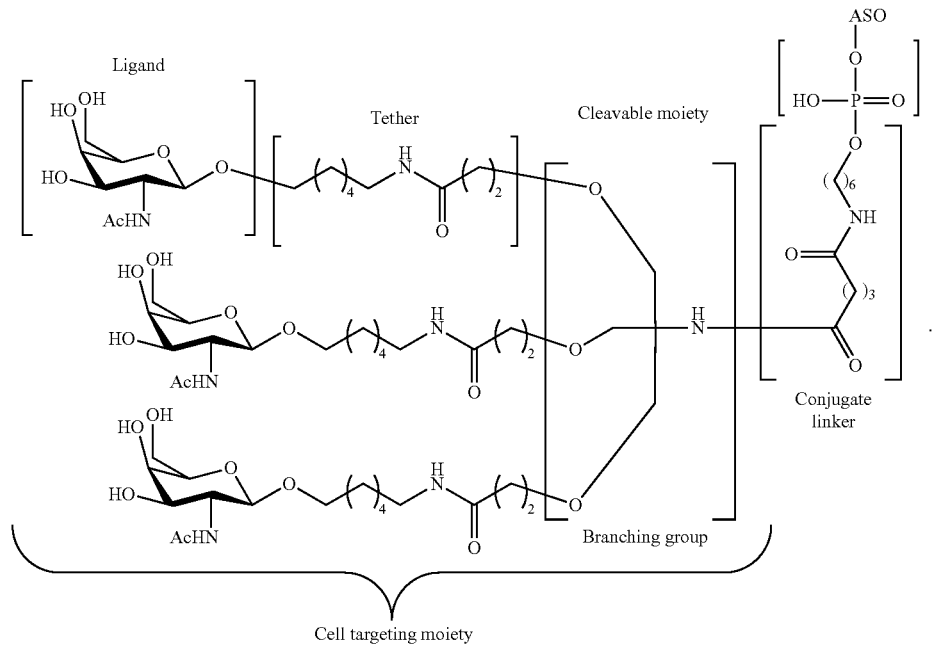

Representative United States patents, United States patent application publications, and international patent application publications that teach the preparation of certain of the above noted conjugate groups, conjugated oligomeric compounds such as antisense compounds comprising a conjugate group, tethers, conjugate linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/0148740, US 2011/0123520, WO 2013/033230 and WO 2012/037254, each of which is incorporated by reference herein in its entirety.

Representative publications that teach the preparation of certain of the above noted conjugate groups, conjugated oligomeric compounds such as antisense compounds comprising a conjugate group, tethers, conjugate linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584, RENSEN et al., "Design and Synthesis of Novel N-Acetyl-galactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" Tetrahedron, 1997, 53(2), 759-770, each of which is incorporated by reference herein in its entirety.

In certain embodiments, conjugate groups include without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxy-cholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

Some nonlimiting examples of conjugate linkers include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a non-limiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

B. Antisense Compounds

In certain embodiments, modified oligonucleotides provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

a. Certain Antisense Compounds

In certain embodiments, a modified oligonucleotide described herein has a nucleobase sequence comprising at least 14 contiguous nucleobases of any of the nucleobase sequences of SEQ ID NOs: 3, 4, 5, 6, 7, 8, 9, 10, 11, 12, 13, 14, 15, 16, 26, 27, 28, 29, 30, 31, 32, 33, 34, 35, 36, 37, 38, 39, 40, 45, 54, 55, 56, 57, 58, 59, 60, 61, 62, 63, 64, 65, 66, 67, 68, 69, 70, 71, 72, 73, 74, 75, 76, or 77.

In certain embodiments, a modified oligonucleotide described herein has a nucleobase sequence comprising at least 14 contiguous nucleobases of any of the nucleobase sequences of SEQ ID NOs: 17, 18, 19, 41, or 32.

In certain embodiments, a modified oligonucleotide described herein has a nucleobase sequence comprising at least 14 contiguous nucleobases of any of the nucleobase sequences of SEQ ID NO: 21.

In certain embodiments, a modified oligonucleotide described herein has a nucleobase sequence comprising at least 14 contiguous nucleobases of any of the nucleobase sequences of SEQ ID NOs: 25 or 44.

In certain embodiments, a modified oligonucleotide described herein has a nucleobase sequence comprising at least 14 contiguous nucleobases of any of the nucleobase sequences of SEQ ID NO: 23.

In certain embodiments, a modified oligonucleotide described herein has a nucleobase sequence comprising at least 14 contiguous nucleobases of any of the nucleobase sequences of SEQ ID NOs: 79, 80, 84, 85, 86, 87, 88, 89, 90, 92, or 93.

In certain embodiments, a modified oligonucleotide described herein has a nucleobase sequence comprising at least 14 contiguous nucleobases of any of the nucleobase sequences of SEQ ID NOs: 82 or 83.

In certain embodiments, a modified oligonucleotide described herein has a nucleobase sequence comprising at least 14 contiguous nucleobases of any of the nucleobase sequences of SEQ ID NO: 95.

In certain embodiments, a modified oligonucleotide described herein has a nucleobase sequence comprising at least 14 contiguous nucleobases of any of the nucleobase sequences of SEQ ID NO: 97.

In certain embodiments, a modified oligonucleotide described herein has a nucleobase sequence comprising at least 14 contiguous nucleobases of any of the nucleobase sequences of SEQ ID NOs: 99, 101, 102, 103, or 104.

In certain embodiments, a modified oligonucleotide described herein has a nucleobase sequence consisting of the nucleobase sequence of any of SEQ ID NOs: 3, 4, 5, 6, 7, 8, 9, 10, 11, 12, 13, 14, 15, 16, 26, 27, 28, 29, 30, 31, 32, 33, 34, 35, 36, 37, 38, 39, 40, 45, 54, 55, 56, 57, 58, 59, 60, 61, 62, 63, 64, 65, 66, 67, 68, 69, 70, 71, 72, 73, 74, 75, 76, or 77.

In certain embodiments, a modified oligonucleotide described herein has a nucleobase sequence consisting of the nucleobase sequence of any of SEQ ID NOs: 17, 18, 19, 41, or 32.

In certain embodiments, a modified oligonucleotide described herein has a nucleobase sequence consisting of the nucleobase sequence of SEQ ID NO: 21.

In certain embodiments, a modified oligonucleotide described herein has a nucleobase sequence consisting of the nucleobase sequence of any of SEQ ID NOs: 25 or 44.

In certain embodiments, a modified oligonucleotide described herein has a nucleobase sequence consisting of the nucleobase sequence of SEQ ID NO: 23.

In certain embodiments, a modified oligonucleotide described herein has a nucleobase sequence consisting of the nucleobase sequence of any of SEQ ID NOs: 79, 80, 84, 85, 86, 87, 88, 89, 90, 92, or 93.

In certain embodiments, a modified oligonucleotide described herein has a nucleobase sequence consisting of the nucleobase sequence of any of SEQ ID NOs: 82 or 83.

In certain embodiments, a modified oligonucleotide described herein has a nucleobase sequence consisting of the nucleobase sequence of SEQ ID NO: 95.

In certain embodiments, a modified oligonucleotide described herein has a nucleobase sequence consisting of the nucleobase sequence of SEQ ID NO: 97.

In certain embodiments, a modified oligonucleotide described herein has a nucleobase sequence consisting of the nucleobase sequence of any of SEQ ID NOs: 99, 101, 102, 103, or 104.

In certain embodiments, the present disclosure provides methods for increasing the expression of RNAse H1 by contacting a cell with a modified oligonucleotide described herein has a nucleobase sequence comprising at least 14 contiguous nucleobases of any of the nucleobase sequences of SEQ ID NOs: 3, 4, 5, 6, 7, 8, 9, 10, 11, 12, 13, 14, 15, 16, 26, 27, 28, 29, 30, 31, 32, 33, 34, 35, 36, 37, 38, 39, 40, 45, 54, 55, 56, 57, 58, 59, 60, 61, 62, 63, 64, 65, 66, 67, 68, 69, 70, 71, 72, 73, 74, 75, 76, or 77.

In certain embodiments, the present disclosure provides methods for increasing the expression of LRPPRC by contacting a cell with a modified oligonucleotide described herein has a nucleobase sequence comprising at least 14 contiguous nucleobases of any of the nucleobase sequences of SEQ ID NOs: 17, 18, 19, 41, or 32.

In certain embodiments, the present disclosure provides methods for increasing the expression of SFXN3 by contacting a cell with a modified oligonucleotide described herein has a nucleobase sequence comprising at least 14 contiguous nucleobases of the nucleobase sequences of SEQ ID NO: 21.

In certain embodiments, the present disclosure provides methods for increasing the expression of THPO by contacting a cell with a modified oligonucleotide described herein has a nucleobase sequence comprising at least 14 contiguous nucleobases of any of the nucleobase sequences of SEQ ID NOs: 25 or 44.

In certain embodiments, the present disclosure provides methods for increasing the expression of MRPL11 by contacting a cell with a modified oligonucleotide described herein has a nucleobase sequence comprising at least 14 contiguous nucleobases of the nucleobase sequences of SEQ ID NO: 23.

In certain embodiments, the present disclosure provides methods for increasing the expression of ACP1 by contacting a cell with a modified oligonucleotide described herein has a nucleobase sequence comprising at least 14 contiguous nucleobases of any of the nucleobase sequences of SEQ ID NOs: 79, 80, 84, 85, 86, 87, 88, 89, 90, 92, or 93.

In certain embodiments, the present disclosure provides methods for increasing the expression of CFTR by contacting a cell with a modified oligonucleotide described herein has a nucleobase sequence comprising at least 14 contiguous nucleobases of any of the nucleobase sequences of SEQ ID NOs: 82 or 83.

In certain embodiments, the present disclosure provides methods for increasing the expression of ARF1 by contacting a cell with a modified oligonucleotide described herein has a nucleobase sequence comprising at least 14 contiguous nucleobases of the nucleobase sequences of SEQ ID NO: 95.

In certain embodiments, the present disclosure provides methods for increasing the expression of USP16 by contacting a cell with a modified oligonucleotide described herein has a nucleobase sequence comprising at least 14 contiguous nucleobases of the nucleobase sequences of SEQ ID NO: 97.

In certain embodiments, the present disclosure provides methods for increasing the expression of LDLr by contacting a cell with a modified oligonucleotide described herein has a nucleobase sequence comprising at least 14 contiguous nucleobases of any of the nucleobase sequences of SEQ ID NOs: 99, 101, 102, 103, or 104.

b. Certain Antisense Activities and Mechanisms

The 5'-UTR has emerged as playing an important role in the regulation of translation of many transcripts. In certain embodiments, the 5'-UTR contains translation suppression elements (TSEs), which serve to suppress translation of a target protein. In certain embodiments, translation suppression elements are uORFs. In certain embodiments, translation suppression elements are G-quartets. In certain embodiments, translation suppression elements are stem-loops. Disruption of a TSE will decrease the TSE's suppression of translation of a given transcript and will therefore result in an increase in translation of a target protein. In certain embodiments, antisense compounds are used to disrupt a TSE and to increase translation of a target protein.

Upstream open reading frames have emerged as an important mechanism by which translation is regulated. Approximately 50% of human transcripts have uORFs and most appear to be functional. When functional, uORFs typically reduce the translation of a polypeptide or protein from the downstream pORF. Characteristics of uORFs such as the strength of Kozak sequence and/or the distance from the 5'cap, affect the effectiveness of each uORF in reducing the translation of the downstream protein. Other factors, such as the secondary structure of the uORF or the number of uORFs per transcript also affect the effectiveness of each uORF in reducing the translation of the downstream protein. Certain embodiments of the present disclosure provide uORF inhibitors (e.g. antisense compounds) that serve to block the initiation of translation from a uORF. In certain embodiments, the uORF inhibitors do not activate RNase H. In certain such embodiments, translation of the protein encoded by a downstream ORF (e.g., the pORF) is enhanced. Certain embodiments of the present invention block the initiation of translation from a uORF with a uORF inhibitor. In certain such embodiments, translation of the protein encoded by the downstream ORF (e.g., the pORF) is enhanced. Certain embodiments of the present disclosure provide TSE inhibitors and/or uORF inhibitors (e.g. antisense compounds) that when bound to a complementary target transcript, do not activate RNase H.

Certain embodiments of the present disclosure provide TSE inhibitors and/or uORF inhibitors (e.g. antisense compounds), wherein the antisense compounds are modified oligonucleotides that are not gapmers.

Upstream open reading frames can regulate translation of polypeptides or proteins encoded by pORFs by a variety of mechanisms. The polypeptide or protein encoded by the uORF may be translated, and the resulting uORF polypeptide may block translation of the polypeptide or protein encoded by the pORF on the same mRNA molecule (cis regulation) or on a separate mRNA molecule (trans regulation). In another example of cis regulation, the ribosomal subunits may dissociate from the mRNA following translation of the uORF polypeptide, thus failing to recognize and translate the pORF polypeptide or protein. Alternatively, the uORF stop codon may be recognized as a premature stop codon and initiate nonsense mediated decay. The extent to which a uORF suppresses translation of a pORF polypeptide or protein depends on how often it is recognized by the translational machinery, which is in turn affected by many factors, including the strength of the associated Kozak sequence, the number of uORFs in the 5'-UTR, the position of the stop codon, and the secondary structure of the uORF.

uORF inhibitors may be employed to disrupt, alter, or exploit any of these mechanisms. In certain embodiments, uORF inhibitors are antisense compounds, and antisense compounds may be employed to disrupt, alter, or exploit any of these mechanisms. In certain embodiments, uORF inhibitors are antisense compounds, and antisense compounds may be employed to disrupt, alter, or exploit any of these mechanisms to increase expression of a target protein in a cell.

In certain embodiments, a uORF inhibitor (e.g. an antisense compound) disrupts one or more of the factors that contribute to the recognition of a uORF start site by a ribosomal subunit. In certain embodiments, a uORF inhibitor (e.g. an antisense compound) may prevent or decrease one or more of the uORF mediated translational suppressors of pORF polypeptide or protein translation discussed above. For example, in certain embodiments, a uORF inhibitor (e.g. an antisense compound) will disrupt one or more elements of a Kozak sequence, and thereby inhibit recognition of a uORF start site by a ribosomal subunit. For example, in certain embodiments, an antisense compound complementary to a portion of a uORF start site may prevent one or more ribosomal subunits from recognizing a Kozak consensus sequence. In certain embodiments, an antisense compound complementary to a portion of a uORF start site may prevent one or more ribosomal subunits from recognizing a Kozak consensus sequence and would therefore cause the ribosome to pass by the uORF start site and initiate translation at a downstream start site (e.g. the pORF start site). A uORF inhibitor (e.g. an antisense compound) would thereby increase the amount or activity of the target protein encoded by the pORF.

In certain embodiments, an antisense compound complementary to a portion of a target transcript upstream of a uORF start site may prevent one or more ribosomal subunits from recognizing a Kozak consensus sequence. In certain embodiments, an antisense compound complementary to a portion of a target transcript upstream of a uORF start site may prevent one or more ribosomal subunits from recognizing the uORF start site. In certain embodiments, an antisense compound complementary to a portion of a target transcript 10 nucleobases upstream of a uORF start site may prevent one or more ribosomal subunits from recognizing a Kozak consensus sequence. In certain embodiments, an antisense compound complementary to a portion of a target transcript 20 nucleobases upstream of a uORF start site may prevent one or more ribosomal subunits from recognizing a Kozak consensus sequence. In certain embodiments, an antisense compound complementary to a portion of a target transcript 30 nucleobases upstream of a uORF start site may prevent one or more ribosomal subunits from recognizing a Kozak consensus sequence. In certain embodiments, an antisense compound complementary to a portion of a target transcript 40 nucleobases upstream of a uORF start site may prevent one or more ribosomal subunits from recognizing a Kozak consensus sequence. In certain embodiments, an antisense compound complementary to a portion of a target transcript 50 nucleobases upstream of a uORF start site may prevent one or more ribosomal subunits from recognizing a Kozak consensus sequence. In certain embodiments, an antisense compound complementary to a portion of a target transcript 60 nucleobases upstream of a uORF start site may prevent one or more ribosomal subunits from recognizing a Kozak consensus sequence. In certain embodiments, an antisense compound complementary to a portion of a target transcript at least 60 nucleobases upstream of a uORF start site may prevent one or more ribosomal subunits from recognizing a Kozak consensus sequence. Therefore, in certain embodiments, an antisense compound complementary to a portion of a target transcript upstream of a uORF start site would increase the amount or activity the target protein encoded by the pORF.

In certain embodiments, an antisense compound complementary to a portion of a target transcript downstream of a uORF start site may prevent one or more ribosomal subunits from recognizing a Kozak consensus sequence. In certain embodiments, an antisense compound complementary to a portion of a target transcript downstream of a uORF start site may prevent one or more ribosomal subunits from recognizing the uORF start site. Therefore, in certain embodiments, an antisense compound complementary to a portion of a target transcript downstream of a uORF start site would increase the amount or activity the target protein encoded by the pORF.

In certain embodiments, disruption one or more of the factors that contribute to the recognition of a uORF start site by a ribosomal subunit by a uORF inhibitor (e.g. an antisense compound) increases expression of a downstream pORF. For example, a uORF inhibitor (e.g. an antisense compound) may prevent the dissociation of ribosomal subunits after uORF polypeptide translation and thereby increase expression of a downstream pORF. For example, a uORF inhibitor (e.g. an antisense compound) may prevent the recognition of the uORF termination codon as premature and prevent nonsense-mediated decay of the transcript comprising the pORF.

In certain embodiments the ribosomal subunits recognize a uORF start site and after translation of all or part of the uORF polypeptide, the ribosomal subunits dissociate from the transcript before recognition of the pORF start site. In certain embodiments, the ribosomal subunits are the 60s ribosomal subunit and/or the 40s ribosomal subunit. In certain embodiments, a uORF inhibitor (e.g. an antisense compound) may increase the amount of translation reinitiation at the pORF after uORF polypeptide translation. For example, in certain embodiments, a uORF inhibitor (e.g. an antisense compound) prevents the amount of the 60s ribosomal subunit and/or the 40s ribosomal subunit that dissociate from the transcript after translation of all or part of the uORF polypeptide and thereby increases translation of the pORF polypeptide or protein.

In certain embodiments, a uORF inhibitor is a small molecule. In certain embodiments, a uORF inhibitor is an antibody. In certain embodiments, a uORF inhibitor is a polypeptide. In certain embodiments, a uORF inhibitor (e.g. a small molecule, antibody, polypeptide, and/or siRNA) increases the amount or activity a target protein encoded by a pORF via any of the mechanisms described herein.

Upstream open reading frames are one type of translation suppression element. In addition to uORFs, translation can be regulated by other types of translation suppression elements (TSEs) in the 5'-UTR. Translation may be suppressed by structural elements in the 5'-UTR, such as stem-loops and hairpins. In certain embodiments, the extent to which a structural element suppresses translation may be correlated with the sequence and/or stability of the structural element. For example, the extent to which a structural element suppresses translation may increase as the distance between the 5'-cap of the target transcript and the structural element decreases. For another example, in certain embodiments, GC content and/or the number of consecutive GC nucleosides in the structural element may positively correlate with the extent to which translation is suppressed, due to increased stability of the structural element. Thus, in certain embodiments, transcripts with a 5'-UTR containing multiple stretches of at least 3 consecutive GC nucleosides may comprise at least one TSE. In certain embodiments, transcripts with a 5'-UTR containing at least one stretch of at least 7 GC nucleosides may comprise at least one TSE.

TSEs that are structural elements may sterically block one or more ribosomal subunits from accessing the coding region. Without wishing to be bound by mechanism, TSE inhibitors may increase translation of a target protein by relieving such steric blockage. In certain embodiments, antisense compounds that are complementary to at least a portion of a TSE structural element alter the structure of the structural element, resulting in increased translation of the target protein. In certain embodiments, such antisense compounds unfold the structural element. In certain embodiments, antisense compounds that are TSE inhibitors have at least 60% GC content. In certain embodiments, antisense compounds that are TSE inhibitors have at least 70% GC content. In certain embodiments, antisense compounds that are TSE inhibitors have at least 80% GC content. In certain embodiments, antisense compounds that are TSE inhibitors have at least 90% GC content. In certain embodiments, antisense compounds that are TSE inhibitors have 100% GC content. In certain embodiments, antisense compounds that are TSE inhibitors have 3, 4, 5, 6, 7, 8, 9, 10, 11, 12, 13, 14, 15, 16, 17, 18, 19, or at least 20 consecutive GC nucleosides. In certain embodiments, antisense compounds that are TSE inhibitors are complementary to the stem portion of a stem-loop in the 5'-UTR of the target transcript. In certain embodiments, antisense compounds that are TSE inhibitors are complementary to a hairpin in the 5'-UTR of the target transcript.

A third type of TSE is a G quartet. In certain embodiments, the extent to which a G quartet suppresses translation may increase as the distance between the 5'-cap of the target transcript and the G quartet decreases.

A fourth type of TSE is a stem-loop structure. In certain embodiments, transcripts having a stem-loop structure within the 5'-UTR suppress translation of the target protein. In certain embodiments, the extent to which a stem-loop suppresses translation may increase as the distance between the 5'-cap of the target transcript and the stem-loop decreases.

c. Certain Compositions and Methods for Increasing Antisense Activity

In certain embodiments the present disclosure provides methods for increase the activity of an antisense compound in a cell, comprising contact the cell with a translation suppression element inhibitor and thereby increasing the activity of an antisense compound.

In certain embodiments, a translation suppression element inhibitor (e.g. an antisense compound) as described herein increases the amount or activity of a target protein in a cell. In certain embodiments, a uORF inhibitor (e.g. an antisense compound) as described herein increases the amount or activity of a target protein in a cell. In certain embodiments, the target protein plays a role in antisense activity. Therefore, in certain embodiments, increasing the amount or activity of a target protein may also increase the amount or activity of an antisense compound. For example, in certain embodiments, the target protein may play a role in subcellular localization of antisense compounds. In certain embodiments, the target protein may play a role in RNA binding. In certain embodiments, the target protein may play a role in nuclear transport. In certain embodiments, the target protein may play a role in membrane binding. In certain embodiments, the target protein may play a role in DNA binding. In certain embodiments, the target protein may play a role in nuclear import. In certain embodiments, the target protein is a heat shock protein.

In certain embodiments, a translation suppression element inhibitor is used to increase the amount or activity of a target protein that plays a role in antisense activity, thereby increasing the amount or activity of an antisense compound. In this manner, a translation suppression element inhibitor may be used to increase the activity of an antisense compound by contacting a cell with the translation suppression element inhibitor and then contacting the cell with an antisense compound. In certain embodiments, a uORF inhibitor is used to increase the amount or activity of a target protein that plays a role in antisense activity, thereby increasing the amount or activity of an antisense compound. In this manner, a uORF inhibitor may be used to increase the activity of an antisense compound by contacting a cell with the uORF inhibitor and then contacting the cell with an antisense compound.

For example, in certain embodiments, the target protein is RNase H. In certain embodiments, a translation suppression element inhibitor targeted to the 5'-UTR of RNase H increases the amount or activity of RNase H protein in a cell, thereby increasing antisense activity in the cell. In certain embodiments, the target protein is La/SSB. In certain embodiments, a translation suppression element inhibitor targeted to the 5'-UTR of La/SSB increases the amount or activity of La/SSB protein in a cell, thereby increasing antisense activity in the cell. In certain embodiments, the target protein is NPM1. In certain embodiments, a translation suppression element inhibitor targeted to the 5'-UTR of NPM1 increases the amount or activity of NPM1 protein in a cell, thereby increasing antisense activity in the cell. In certain embodiments, the target protein is TCP1-alpha. In certain embodiments, a translation suppression element inhibitor targeted to the 5'-UTR of TCP1-alpha increases the amount or activity of TCP1-alpha protein in a cell, thereby increasing antisense activity in the cell.

In certain embodiments, the target protein is TCP1-epsilon. In certain embodiments, a translation suppression element inhibitor targeted to the 5'-UTR of TCP1-epsilon increases the amount or activity of TCP1-epsilon protein in a cell, thereby increasing antisense activity in the cell. In certain embodiments, the target protein is TCP1-beta. In certain embodiments, a translation suppression element inhibitor targeted to the 5'-UTR of TCP1-beta increases the amount or activity of TCP1-beta protein in a cell, thereby increasing antisense activity in the cell. In certain embodiments, the target protein is HSP90-AA1. In certain embodiments, a translation suppression element inhibitor targeted to the 5'-UTR of HSP90-AA1 increases the amount or activity of HSP90-AA1 protein in a cell, thereby increasing antisense activity in the cell. In certain embodiments, the target protein is HSP90-AB. In certain embodiments, a translation suppression element inhibitor targeted to the 5'-UTR of HSP90-AB increases the amount or activity of HSP90-AB protein in a cell, thereby increasing antisense activity in the cell. In certain embodiments, the target protein is HSPA1L. In certain embodiments, a translation suppression element inhibitor targeted to the 5'-UTR of HSPA1L increases the amount or activity of HSPA1L protein in a cell, thereby increasing antisense activity in the cell. In certain embodiments, the target protein is RAN. In certain embodiments, a translation suppression element inhibitor targeted to the 5'-UTR of RAN increases the amount or activity of RAN protein in a cell, thereby increasing antisense activity in the cell.

In certain embodiments, the target protein is IMP9. In certain embodiments, a translation suppression element inhibitor targeted to the 5'-UTR of IMP9 increases the amount or activity of IMP9 protein in a cell, thereby increasing antisense activity in the cell. In certain embodiments, the target protein is Annexin A2. In certain embodiments, a translation suppression element inhibitor targeted to the 5'-UTR of Annexin A2 increases the amount or activity of Annexin A2 protein in a cell, thereby increasing antisense activity in the cell. In certain embodiments, the target protein is FTCD/58k. In certain embodiments, a translation suppression element inhibitor targeted to the 5'-UTR of FTCD/58k increases the amount or activity of FTCD/58k protein in a cell, thereby increasing antisense activity in the cell.

In certain embodiments, the target protein is PC4/SUB1. In certain embodiments, a translation suppression element inhibitor targeted to the 5'-UTR of PC4/SUB1 increases the amount or activity of PC4/SUB1 protein in a cell, thereby increasing antisense activity in the cell. In certain embodiments, the target protein is VARS. In certain embodiments, a translation suppression element inhibitor targeted to the 5'-UTR of VARS increases the amount or activity of VARS protein in a cell, thereby increasing antisense activity in the cell. In certain embodiments, the target protein is DHX36. In certain embodiments, a translation suppression element inhibitor targeted to the 5'-UTR of DHX36 increases the amount or activity of DHX36 protein in a cell, thereby increasing antisense activity in the cell.

For example, in certain embodiments, the target protein is RNase H. In certain embodiments, a uORF inhibitor targeted to the 5'-UTR of RNase H increases the amount or activity of RNase H protein in a cell, thereby increasing antisense activity in the cell. In certain embodiments, the target protein is La/SSB. In certain embodiments, a uORF inhibitor targeted to the 5'-UTR of La/SSB increases the amount or activity of La/SSB protein in a cell, thereby increasing antisense activity in the cell. In certain embodiments, the target protein is NPM1. In certain embodiments, a uORF inhibitor targeted to the 5'-UTR of NPM1 increases the amount or activity of NPM1 protein in a cell, thereby increasing antisense activity in the cell. In certain embodiments, the target protein is TCP1-alpha. In certain embodiments, a uORF inhibitor targeted to the 5'-UTR of TCP1-alpha increases the amount or activity of TCP1-alpha protein in a cell, thereby increasing antisense activity in the cell.

In certain embodiments, the target protein is TCP1-epsilon. In certain embodiments, a uORF inhibitor targeted to the 5'-UTR of TCP1-epsilon increases the amount or activity of TCP1-epsilon protein in a cell, thereby increasing antisense activity in the cell. In certain embodiments, the target protein is TCP1-beta. In certain embodiments, a uORF inhibitor targeted to the 5'-UTR of TCP1-beta increases the amount or activity of TCP1-beta protein in a cell, thereby increasing antisense activity in the cell. In certain embodiments, the target protein is HSP90-AA1. In certain embodiments, a uORF inhibitor targeted to the 5'-UTR of HSP90-AA1 increases the amount or activity of HSP90-AA1 protein in a cell, thereby increasing antisense activity in the cell. In certain embodiments, the target protein is HSP90-AB. In certain embodiments, a uORF inhibitor targeted to the 5'-UTR of HSP90-AB increases the amount or activity of HSP90-AB protein in a cell, thereby increasing antisense activity in the cell. In certain embodiments, the target protein is HSPA1L. In certain embodiments, a uORF inhibitor targeted to the 5'-UTR of HSPA1L increases the amount or activity of HSPA1L protein in a cell, thereby increasing antisense activity in the cell. In certain embodiments, the target protein is RAN. In certain embodiments, a uORF inhibitor targeted to the 5'-UTR of RAN increases the amount or activity of RAN protein in a cell, thereby increasing antisense activity in the cell.

In certain embodiments, the target protein is IMP9. In certain embodiments, a uORF inhibitor targeted to the 5'-UTR of IMP9 increases the amount or activity of IMP9 protein in a cell, thereby increasing antisense activity in the cell. In certain embodiments, the target protein is Annexin A2. In certain embodiments, a uORF inhibitor targeted to the 5'-UTR of Annexin A2 increases the amount or activity of Annexin A2 protein in a cell, thereby increasing antisense activity in the cell. In certain embodiments, the target protein is FTCD/58k. In certain embodiments, a uORF inhibitor targeted to the 5'-UTR of FTCD/58k increases the amount or activity of FTCD/58k protein in a cell, thereby increasing antisense activity in the cell.

In certain embodiments, the target protein is PC4/SUB1. In certain embodiments, a uORF inhibitor targeted to the 5'-UTR of PC4/SUB1 increases the amount or activity of PC4/SUB1 protein in a cell, thereby increasing antisense activity in the cell. In certain embodiments, the target protein is VARS. In certain embodiments, a uORF inhibitor targeted to the 5'-UTR of VARS increases the amount or activity of VARS protein in a cell, thereby increasing antisense activity in the cell. In certain embodiments, the target protein is DHX36. In certain embodiments, a uORF inhibitor targeted to the 5'-UTR of DHX36 increases the amount or activity of DHX36 protein in a cell, thereby increasing antisense activity in the cell.

In certain embodiments, the target protein is LDLr. Increasing expression of the LDLr protein decreases cholesterol levels.

In certain embodiments, the target protein is CFTR. Mutations in the CFTR gene lead to cystic fibrosis. In certain embodiments, increasing expression of the CFTR protein may ameliorate one or more symptoms of cystic fibrosis.

d. Certain Compositions and Methods for Decreasing Antisense Activity

In certain embodiments, antisense compounds disclosed herein may target microRNAs or other naturally occurring non-coding transcripts that are complementary to a uORF region or a translation suppression element. Certain such antisense compounds would therefore inhibit expression of a target transcript by increasing the effect of a translation suppression element or uORF. For example, in certain embodiments, a non-coding transcript, such as a microRNA may be complementary to a uORF or uORF region and serve to increase expression of a target protein. An antisense compound complementary to the microRNA would sequester the microRNA and the uORF would then suppress translation of the target protein. In such a manner, an antisense compound would inhibit expression of a target protein.

C. Certain Target Genes

The present disclosure provides compounds and methods that may be used to increase expression of any target protein, provided there is at least one uORF on a transcript encoding the target protein. The present disclosure also provides compounds and methods that may be used to increase expression of any target protein, provided there is at least one TSE on a transcript encoding the target protein. In certain embodiments, the at least one TSE comprises a uORF. In certain embodiments, there are at least two TSEs on a transcript encoding a target protein. In certain embodiments neither of the at least two TSEs comprise a uORF. In certain embodiments, one of the at least two TSEs comprises a uORF. In certain embodiments, both of the at least two TSEs comprise a uORF. In certain embodiments, a deficiency of the target protein is associated with disease and so increasing the amount or activity of the protein is expected to ameliorate one or more symptoms of the disease or delay the onset of one or more symptoms of the disease. Table 1 and Table 2, below, list certain genes and associated diseases. In certain embodiments, a target transcript is encoded by a gene listed in Table 1 or Table 2. In certain embodiments, the associated disease or disorder in Table 1 or Table 2 is treated by use of an antisense compound of the present invention targeting such transcript. The diseases associated with each gene in Table 1 include diseases that arise due to or are correlated with an insufficiency of the corresponding uORF-containing gene as well as diseases that could be ameliorated by up-regulation of the corresponding uORF-containing gene. The diseases associated with each gene in Table 2 include diseases that correlate with a mutation or SNP that introduces a uORF in the corresponding gene.

In certain embodiments, antisense compounds are targeted to one or more TSEs in the 5'UTR of a gene in Table 1 or Table 2. In certain embodiments, antisense compounds are not targeted to one or more TSEs in the 5'UTR of a gene in Table 1 or Table 2.

TABLE 1 uORF-containing genes and associated diseases

| Gene | NCBI Gene ID | Associated disease(s) |
|---|---|---|
| ABCA1 | 19 | Cardiovascular, Dry AMD, dyslipidemia, and atherosclerosis |
| ABCB11 | 8647 | Cholestasis, primary sclerosing cholangitis abd biliary cirrhosis |
| ABCC2 | 1244 | Dubin-Johnson syndrome- but overexpressed in cancer |
| ABCG5 | 64240 | Cholestasis, primary sclerosing cholangitis and biliary cirrhosis |
| ADAM10 | 102 | Alzheimer's Disease |
| ALB | 213 | liver disease, nephrotic syndrome, renal disease, and analbuminemia |
| ANK1 | 286 | Hereditary spherocytosis |
| APOE | 348 | Cancer, melanoma, pulmonary hypertension, dyslipidemia, atherosclerosis, Alzheimer disease, Lipoprotein glomerulepathy, and Sea-blue histiocyte disease |
| ATP2A2 | 488 | cardiac diseases, congenital heart disease, aortic aneurysms, aortic dissections, arrhythmia, cardiomyopathy, congestive heart failure, Darier-White disease, muscular dystrophy, and Acrokeratosis verruciformis |
| ATP7B | 540 | wilson disease, and menkes disease. |
| ATRX | 546 | alpha-thalassemia myelodysplasia syndrome, somatic, and mental retardation-hypotonic facies syndrome, x-linked. |
| ATXN1 | 6310 | Spinocerebellar ataxia-1 |
| ATXN1L | 342371 | Spinocerebellar ataxia-1 |
| BAX | 581 | Cancer |
| BCL2L11 | 10018 | Cancer, e.g. human T-cell acute lymphoblastic leukemia and lymphoma |
| BDNF | 627 | neurodegeneration diseases, amyotrophic lateral sclerosis, Alzheimer's Disease, Huntington's disease (HD), or Parkinson's Disease (PD) |
| BLM | 641 | bloom syndrome, and rothmund-thomson syndrome. |
| BRCA1 | 672 | Cancer, e.g. breast cancer, pancreatic cancer |
| C/EBPa | 1050 | B-cell maligancy (B-ALL, DLBCL), AML |
| CA2 | 760 | autoimmune retinopathy, and multifocal fibrosclerosis. |
| CASP8 | 841 | CASP8 deficiency, breast cancer, HCC, lung cancer |
| CCBE1 | 147372 | hennekam syndrome, and immune hydrops fetalis. |
| CD36 | 948 | platelet glycoprotein IV deficiency, coronary heart disease, CHDS7 |
| CD3D | 915 | severe combined immune deficiency, autosomal recessive, t cell-negative, b cell-positive, nk cell-positive, cd3d-related, and immunodeficiency 19. |
| CDKN1B | 1027 | cancer, multiple endocrine neoplasia |
| CDKN2A | 1029 | cancer, melanoma |
| CEP290 | 80184 | Leber's congenital amaurosis (LCA), Bardet--Biedl syndrome (BBS), Joubert syndrome, Meckel syndrome, Sior-Loken syndrome. |
| CFH | 3075 | C3 glomerulopathy, AMD, PNH, RA etc |
| CFTR | 1080 | Cystic fibrosis, Disseminated bronchiectasis, congenital bilateral absence of vas deferens (CBAVD) |
| CHRNA4 | 1137 | nicotine addiction |
| CHRNA5 | 1138 | nicotine addiction |
| CNTF | 1270 | Multiple Sclerosis |
| CNTFR | 1271 | Multiple Sclerosis |
| COL1A1 | 1277 | Osteogenesis Imperfecta Type I |
| CR1 | 1378 | Alzherimer's Disease |
| CSPP1 | 79848 | joubert syndrome 21, and joubert syndrome with jeune asphyxiating thoracic dystrophy. |
| CTNND2 | 1501 | Cri-du-chat syndrome |
| CTNS | 1497 | intermediate cystinosis, and cystinosis, atypical nephropathic |
| CYP1B1 | 1545 | Glaucoma, Peters anomaly |
| DBT | 1629 | maple syrup urine disease type 2, and maple syrup urine disease type 1a |
| DCAF17 | 80067 | sakati syndrome, and hypogonadism, alopecia, diabetes mellitus, mental retardation, and extrapyramidal syndrome |
| DNASE1 | 1773 | cystic fibrosis, acute bronchitis |
| DDIT3 | 1649 | Myxoid liposarcoma |
| DICER1 | 23405 | DICER1 syndrome, pleuropulmonary blastoma, cystic nephroma, Sertoli-Leydig tumors, multiodular goiter, cancer |
| DRD3 | 1814 | mood disorders |
| EED | 8726 | HIV-1 |

TABLE 1-continued uORF-containing genes and associated diseases

| Gene | NCBI Gene ID | Associated disease(s) |
|---|---|---|
| EFNB1 | 1947 | CFNS |
| EPO | 2056 | erythropoiesis and anemia |
| ESR1 | 2099 | inhibits ERBB1, breast cancer |
| ETHE1 | 23474 | ethylmalonic encephalopathy |
| EXH2 | 2146 | weaver syndrome, ezh2-related overgrowth, lymphomas and leukemias |
| F8 (and F2, 3, 5, 7, 11, 13) | 2147, '52, '53, '55, '57, '60 | Hemophilia, bleeding |
| FAP | 2191 | glomuvenous malformations |
| FMR1 | 2332 | Fragile X syndrome and premature ovarian failure |
| FNDC5 | 252995 | Obesity, Type 2 Diabetes |
| FXN | 2395 | Friedreich's ataxia |
| GALNS | 2588 | mucopolysaccharidosis iv, and kniest dysplasia |
| GATA3 | 2625 | Cancer |
| GBA | 2629 | Synucleinopathies, Gaucher's disease |
| GCH1 | 2643 | gtp cyclohydrolase I deficiency, Parkinson's disease, movement disorders, CNS disease, doparesponsive dystonia, hyperpehnylalaninemia, and atypical severe phenylketonuria |
| GCK | 2645 | Obesity, Type 2 Diabetes, and Hyperinsulinemic hypoglycemia |
| GH2 | 2689 | idiopathic short stature, growth delay |
| GRN | 2896 | autoimmune, inflammatory, demential, FTD, cancer, e.g. hepatic cancer |
| HBB | 3043 | thallasemia, sickle cell disease, and anemia |
| HBD | 3045 | thallasemia, sickle cell disease, and anemia |
| HBE1 | 3046 | thallasemia, sickle cell disease, and anemia |
| HBG1 | 3047 | Anemia (e.g., Fanconi's anemia), thalassemia (e.g., beta-thalassemia etc.), sickle cell disease, leukemia, cellular dyscrasia, dyserythropoiesis, anisocytosis and poikilocytosis. |
| HBG2 | 3048 | thallasemia, sickle cell disease, and anemia |
| HCRT | 3060 | Narcolepsy/Excessive Daytime Sleepiness |
| HGF | 3082 | Ischemic disease, restenosis after percutaneous transluminal coronary angioplasty (PTCA), arteriosclerosis, insufficiency of peripheral curculation, myocardial infarction, myocardia, peripheral angiostenosis cardiac insufficiency, nerve degeneration, neuropathy, neurotoxin induced lesions, innjury of nerve cell, lesions of nerve cell by infection, epliepsy, head trauma, dementia, cerebral stroke, cerebral infarction, amyotrophic lateral sclerosis, Parkinson's disease, Alzheimer's disease, cancer, tumor, liver cirrhosis, Nonalcoholic fatty liver disease, renal fibrosis, rhabdomyolysis, pulmonary fibrosis, blood coagulopathy, adenosine deaminase deficiency, Chronic Ulcerative Colitis, Crohn's Disease, necrotizing enterocolitis, severe acute gastroenteritis, chronic gastroenteritis, cholera, chronic infections of the bowel, AIDS, pustulous fibrosis, fibrosis, osteoporosis, Arterial sclerosis, chronic glomerulonephritis, cutis keloid formation, progressive systemic sclerosis (PSS), liver fibrosis, pulmonary fibrosis, cystic fibrosis, chronic graft versus host disease, scleroderma (local and systemic), Peyronie's disease, penis fibrosis, inner accretion after surgery, myelofibrosis, idiopathic retroperitoneal fibrosis, hemophilia, decubitus ulcer, scar, atopic dermatitis, or skin damage following a skin graft |
| HNF4a | 3172 | HCC, fibrosis |
| HR | 55806 | atrichia with papular lesions, and hypotrichosis 4 |
| HSD17B4 | 3295 | D-bifunctional protein deficiency |
| IDO1 | 3620 | autoimmune and inflammatory diseases |
| IFNE and other interferon genes | 338376, others | Cancer, HBV, and other virus infection |
| IFRD1 | 3475 | Cystic fibrosis, Chronic obstructive pulmonary disease (COPD), inflammation, lung cancer, sensory/motor neuropathy, a neuronal injury |
| IGF1 | 3479 | CNS diseases, metabolic disease, delayed growth, cancer |
| IGF1R | 3480 | Insulin-like growth factor I resistance |
| IGF2 | 3481 | Russell-Silver syndrome |
| IGF2BP2 | 10644 | Type 2 diabetes, insulin resistance susceptibility |
| IGFBP3 | 3486 | growth delay |
| IGHMBP2 | 3508 | progressive multifocal leukoencephalopathy, and spinal muscular atrophy with respiratory distress 1 |
| IL6 | 3569 | infectious disease, vaccination, and cancer |
| INS | 3630 | Diabetes or related disorders thereof, and insulin resistant non diabetic state, obesity, impaired glucose tolerance (IGT), Metabolic Syndrome, MODY syndrome, Polycystic Overy Syndrome, cancer, inflammation, hirsuitism, and hypertension. |
| IQGAP1 | 8826 | Cancer, obesity, diabetes, multiple sclerosis, neoplastic transformation, inflammation, Nonsmall cell lung carcinoma (NSCLSs), hypercholesterolemia, liposarcoma, gastric cancer, immunodeficiency, glomerulonephritis, venous thrombosis, glioma |

TABLE 1-continued uORF-containing genes and associated diseases

| Gene | NCBI Gene ID | Associated disease(s) |
|---|---|---|
| IQGAP2 | 10788 | Obesity, diabetes, multiple sclerosis, neoplastic transformation, inflammation, Nonsmall cell lung carcinoma (NSCLCs), hypercholesterolemia, liposarcoma, gastric cancer, immunodeficiency, glomerulonephritis, venous thrombosis, glimoa |
| IRF6 | 3664 | van der Woude syndrome |
| IRS2 | 8660 | Alzheimer's disease, Parkinson's disease, amyotrophic lateral sclerosis, insulin resistance, diabetes, Polycystic Ovary Syndrome, atherosclerosis cancer |
| ITGA7 | 3679 | muscular dystrophy, congenital, due to itga7 deficiency, and congenital muscular dystrophy due to integrin alpha-7 deficiency |
| JAG1 | 182 | Alagille syndrome |
| KCNJ11 | 3767 | Congenital hyperinsulinism, hyperinsulinemic hypoglycemia, 2 |
| KCNMA1 | 3778 | vascular disease, kidney disease, Obesity, Type 2 Diabetes, inflammatory disease, autoimmune disease, and cancer, e.g. kidney, lung, or ovarian cancer |
| KCNMB1 | 3779 | vascular disease, kidney disease, Obesity, Type 2 Diabetes, inflammatory disease, autoimmune disease, and cancer, e.g. kidney, lung, or ovarian cancer |
| KCNMB2 | 10242 | vascular disease, kidney disease, Obesity, Type 2 Diabetes, inflammatory disease, autoimmune disease, and cancer, e.g. kidney, lung, or ovarian cancer |
| KCNMB3 | 27094 | vascular disease, kidney disease, Obesity, Type 2 Diabetes, inflammatory disease, autoimmune disease, and cancer, e.g. kidney, lung, or ovarian cancer |
| KCNQ3 | 3786 | kcnq3-related benign familial neonatal epilepsy, and seizures, benign neonatal, type 2 |
| KLF4 | 9314 | thallasemia, sickle cell disease, and anemia |
| KMT2D | 8085 | Kabuki Syndrome |
| LDLR | 3949 | dyslipidemias, atherosclerosis, and hypercholesterolemia, cardiovascular disease |
| LRP1 | 4035 | Cancer, melanoma |
| LRP5, LRP5L | 4041, 91355 | exudative vitreoretinopathy 4, and hyperostosis, endosteal |
| LRP8 | 7804 | Cancer, melanoma |
| LRPPRC | 10128 | Leigh syndrome Frencn-Canadian type, Cytochrome c oxidase deficiency |
| MBTPS1 | 8720 | Colitis, obesity, diabetes, hypercholesterolemia, dyslipidemia, Crimean-Congo hemorrhagic fever, chondrodysplasia |
| MECP2 | 4204 | Rett Syndrome, MECP2-related severe neonatal encephalopathy, Angelman syndrome, and PPM-X syndrome |
| MSRA | 4482 | cancer, macular degeneration, eye aging, cataract |
| MSX2 | 4488 | tooth agenesis (dentin dysplasia), developmental disorders e.g. Craniosynostosis and Parietal foramina |
| MTR | 4548 | Homocystinuria |
| MUTYH | 4595 | Familial adenomatous polyposis |
| MYCN | 4613 | Feingold syndrome |
| MYF6 | 4618 | Centronuclear Myopathy 3 |
| NAMPT | 10135 | cancer, cytopenia of the myeloid or lymphoid lineage, neutropenia, leukaemia, acute myeloid leukaemia (AML), atherosclerosis, inflammatory bowel disease, Crohn's disease, ulcerative colitis, psoriasis, arthritis, chronic ulcer, ischemic stroke, myocardial infarction, angina and vascular dementia, inflammation, nonalcoholic fatty liver disease |
| NANOG | 79923 | diabetes, osteoarthritis, rheumatoid arthritis, cancer, Duchenne muscular dystrophy, Parkinson's, Alzheimer's, Gaucher disease, type I diabetes, spinal cord injury, burns (tissue regeneration) |
| NEU4 | 129807 | cancer, diabetes, Tay Sachs disease, inflammatory bowel disease, Crohn's disease, ulcerative colitis, psoriasis, arthritis, inflammation, insulin resistance syndrome, hypcrlipidemia, fatty liver disease, cachexia, obesity, atherosclerosis, artcriosccrlosis, elevated blood pressure, viral infection |
| NF1 | 4763 | neurofibromatosis and cancer, e.g., neurofibrosarcoma, malignant peripheral nerve sheath tumors, and myelomonocytic leukemia |
| NKX2-3, -5, -8 | 159296, 1482, 26257 | cancer, e.g., lung cancer |
| NOD2 | 64127 | Crohn disease |
| NR5A1 | 2516 | nr5a1-related 46,xy dsd adn 46,xy cgd, and adrenocortical insufficiency, without ovarian defect |
| NRF1 | 4899 | Alzheimer's disease, Parkinson's disease, amyotrophic lateral sclerosis, insulin resistance, diabetes, hepatic tumor, non-small cell bronchopulmonary cancer, mitochondrial disease |
| NSD1 | 64324 | Sotos syndrome (cerebral gigantism)autosomal dominant disorder. The cause is haploinsufficiency of the NSD1 gene |
| PAH | 5053 | Phenylketonuria (PKU) |
| PARK2 | 5071 | Parkinson's |
| PKD1 | 5310 | Polycystic kidney disease |

TABLE 1-continued uORF-containing genes and associated diseases

| Gene | NCBI Gene ID | Associated disease(s) |
|---|---|---|
| PLAT | 5327 | ischemic stroke |
| PON1, 2 | 5444, 5445 | diabetes, obesity, hypercholesterolemia, high blood pressure, atherosclerosis, coronary heart disease, autism/autism spectrum disorder, epliepsy, cancer, inflammation, stroke, trauma, a renal disease, rheumatoid arthritis, Fish-Eye disease, purpura, Polycystic Ovary Syndrome, hyperthyroidism, a hepatic diseases, vascular dementia, an infectious disease |
| PPARD | 5467 | Metabolic disease |
| PRKAR1A | 5573 | Carney complex |
| PRPF31 | 26121 | adRP |
| PTEN | 5728 | cancer |
| PYCR1 | 5831 | cystic fibrosis, myocardial fibrosis, myelofibrosis, hepatic fibrosis, interstital lung fibrosis, neoplastic fibrosis, pancreatic fibrosis, pulmonary fibrosis, subepidermal fibrosis, panmural fibrosis of the bladder, proliferative fibrosis, replacement fibrosis, retroperitoneal fibrosis and root sleeve fibrosis, osteogenesis imperfecta, Ehlers-Danlos syndrome, chondrodysplasias, Marfan syndrome, Alport syndrome, familial aortic aneurysm, achondroplasia, mucopolysaccharidoses, osteroporosis, oseopetrosis, Paget's disease, rickets, osteomalacia, hyperparathyroidism, renal osteodystrophy, osteonecrosis, osteomyelitis, osteoma, osteoid osteoma, osteoblastoma, osteocarcoma, osteochondroma, chondroma, chondroblastoma, chondromyxoid fibroma, chondrosarcoma, fibrous cortical defect, nonossifyinh fibroma, fibrous dysplasia, fibrosarcoma, malignant fibrous histiocytoma, Ewing's sarcoma |
| RB1, RBL1, RBL2 | 5925, 5933, 5934 | cancer, e.g. bladder cancer, osteosarcoma, retinoblastoma, small cell lung cancer |
| RBBP4 | 5928 | intermediate charcot-marie-tooth neuropathy, retinoblastoma, Alzheimer's |
| RNASEH1 | 246243 | leishmaniasis, a disease or disorder associated with mitochondrial dysfunction, cancer, Aicardi-Goutieres syndrome, AIDS |
| ROR2 | 4920 | brachydactyly, type b1, and brachdactyly type b |
| RPS14 | 6208 | 5q syndrome (myelodysplastic syndrome) |
| RPS19 | 6223 | Diamond-Blackfan Anemia |
| SCN1A | 6323 | convulsion, pain, paralysis, hyperkalemic perioidic paralysis, paramyotonia, congenita, potassium-aggravated myotonia, long Q-T syndrome 3, motor endplate disease, ataxia, colitis, ileitis, inflammatory bowel syndrome, hypertension, congestive heart failure, benign prostrate hyperplasia, impotence, muscular dystrophy, multiple sclerosis, epilepsy, autism, migraine, severe myoclonic epilepsy of infancy (SMEI or Dravet's syndrome) |
| SCN2A | 6326 | epileptic encephalopathy, early infantile, 11, and benign familial neonatal-infantile seizures |
| SERPINF1 | 5176 | cancer, choroidal neovascularization, cardiovascular disease, diabetes, and osteogenesis inperfecta |
| SERPING1 | 710 | Hereditary Angioedema |
| SHBG | 6462 | disorders of mood and affect, a memory dysfunction disease or disorder, an amnestic disease or disorder, a motor and tic disorder, substance abuse disease or disorder, a psychotic disease or disorder, an anxiety disease or disorder, schizophrenia, schizofreniform disorder, schizoaffective disorder, and delusional disorder, panic disorder, phobias, an obsessive-compulsive disorder, posttraumatic stress disorder, infertility, hirsutism, Tourette's disorder, Asperger syndrome, hypothyroidism, fibromyalgia, chronic fatigue syndrome, hypothalamic-pituitary axis dysregulation, chronic sleep deprivation, alopecia, prostate cancer, breast cancer, polycystic ovary syndrome, osteoporosis, hyperinsulinemia, glucose intolerance, insulin resistance, diabetes |
| SIRT1 | 23411 | cancer, Alzheimer's Disease (AD), Huntington's disease, Parkinson's disease, Amyotrophic Lateral Sclerosis (ALS), Multiple Sclerosis, Duchene muscular dystrophy, skeletal muscle atrophy, Becker's dystrophy, myotonic dystrophy, insulin resistance, diabetes, obesity, Hypercholesterolemia, dyslipidemia hyperlipidemia, sensory neuropathy, autonomic neuropathy, motor neuropathy, retinopathy, heptitis, fatty liver disease, age-related macular degeneration, osteoporosis, leukemia, bone resorption, dementia, Bell's Palsy, atherosclerosis, cardiac dysrhymias, chronic congestive heart failure, ischemic stroke, coronary artery disease, cardiac muscle disease, chronic renal failure, ulceration, cataract, presbiopia, glomerulonephritis, Guillan-Barre syndrome, hemorrhagic stroke, rheumatoid arthritis, inflammatory bowel disease, SLE, Crohn's desease, osteoarthritis, Chronic Obstructive Pulmonary Disease (COPD), pneumonia, urinary incontinence, mitochondrial myopathy, encephalopathy, Leber's disease, Leigh encephalopathia, Pearson's disease, lactic acidosis, mitochondrial encephalopathy, lactic acidosis and stroke like symptoms (MELAS), inflammation |
| SLC1A2 | 6506 | ALS |
| SMAD7 | 4092 | Acute kidney injury (anti-TGFb), colorectal cancer |
| SMCHD1 | 23347 | FSHD |

TABLE 1-continued uORF-containing genes and associated diseases

| Gene | NCBI Gene ID | Associated disease(s) |
|---|---|---|
| SMN1, SMN2 | 6606, 6607 | Spinal muscular atrophy |
| SNX27 | 81609 | Downs' Syndrome |
| SPINK1 | 6690 | Pancreatits |
| SRB1 | 949 | Cardiovascular disease |
| SRY | 6736 | Gonadal dysgenesis |
| ST7, ST7L | 7982, 54879 | cancer, e.g. myeloid cancer, head and neck squamous cell carcinomas, breast cancer, colon carcinoma, and prostate cancer |
| STAT3 | 6774 | tissue regeneration and Hyper-IgE recurrent infection syndrome |
| TFE3 | 7030 | diabetes, obesity, impaired glucose tolerance (IGT) and Metabolic Syndrome, Polycystic Ovary Syndrome, atherosclerosis, cancer, Alzheimer's disease, Parkinson's disease, amyotrophic lateral sclerosis, diabetic retinopathy, diabetic neuropathy, diabetic amyotrophy, diabetic nephropathy, diabetic cardiomyopathy, angina, myocardial infarction, stroke, a peripheral vascular disease |
| TFEB | 7942 | Lysosomal storage diseases |
| TGFB3 | 7043 | Rienhoff syndrome |
| THPO | 7066 | Myelosuppressive chemo, Bleeding disorders |
| TP63 | 8626 | cancer, tumor, Corneal dystrophy, premature menopause, alopecia, cctrodaclyly-ectodermal dysplasia-cleft syndrome, Hay-Wells syndrome, limb mammary syndrome, acro-dermato-ungual-lacrimal-tooth syndrome, nonsyndromic split-hand/foot malformation, isolated cleft lip/palate, Rapp-Hodgkin syndrome |
| TP73 | 7161 | Cancer |
| UCP2 | 7351 | cancer, obesity, cachexia, anorexia nervosa, bulimia nerv osa, diabetes, hypcrinsulincmia, glucose intolerance, atherosclerosis, inflammation |
| USP9Y/ SP3 | 8287 | Y chromosome infertility |
| UTRN | 7402 | muscular dystrophies, Duchenne muscular dystrophy (DMD), Bekcer Muscular Dystrophy (BMD), and myotonic dystrophy |
| VEGFA | 7422 | diabetes, coronary artery disease, congestive heart failure, and peripheral vascular disease, cancer, infectious diseases, rheumatoid arthritis, DiGeorge syndrome, HHT, cavernous hemangioma, atherosclerosis, transplant ateriopathy, obesity, psoriasis, warts, allergic dermatitis, scar keloids, pyogenic granulomas, blistering disease, Kaposi sarcoma, persistent hyperplastic vitreous syndrome, Autosomal dominant polycystic kidney disease (ADPKD), diabetic retinopathy, retinopathy of prematurity, macular degeneration, choroidal neovacularization, primary pulmonary hypertension, asthma, nasal polyps, inflammatory bowel disease, Alzheimer's disease, Parkinson's disease, amyotrophic lateral sclerosis, periodontal disease, ascites, peritoneal adhesions, endometriosis, uterine bleeding, ovarian cysts, ovarian hyperstimulation, arthritis, synovitis, osteomyelitis, and/or osteophyte formation, ulceration, verruca, vulgaris, angiofibroma of tuberous sclerosis, pot-wine stains, Sturge Weber syndrome, Kippel-Tranaunay-Weber syndrome, Olser-Weber-Rendu syndrome |

TABLE 2

Genes with mutations or SNPs that create uORFs and associated diseases

| Gene | NCBI Gene ID | Associated disease(s) |
|---|---|---|
| ATP7B | 540 | wilson disease, and menkes disease. |
| ATRX | 546 | alpha-thalassemia myelodysplasia syndrome, somatic, and mental retardation-hypotonic facies syndrome, x-linked. |
| BLM | 641 | bloom syndrome, and rothmund-thomson syndrome. |
| BRCA1 | 672 | primary peritoneal carcinoma, and hereditary site-specific ovarian cancer syndrome. |
| CA2 | 760 | autoimmune retinopathy, and multifocal fibrosclerosis. |
| CCBE1 | 147372 | hennekam syndrome, and immune hydrops fetalis. |
| CD3D | 915 | severe combined immune deficiency, autosomal recessive, t cell-negative, b cell-positive, nk cell-positive, cd3d-related, and immunodeficiency 19. |
| CD4 | 920 | okt4 epitope deficiency, and lymphatic system disease. |
| CDKN2A | 1029 | Melanoma predisposition, Melanoma |
| CFL2 | 1073 | cfl2-related nemaline myopathy, and nemaline myopathy 7, autosomal recessive. |
| CFTR | 1080 | Cystic fibrosis, Disseminated bronchiectasis |
| CSPP1 | 79848 | joubert syndrome 21, and joubert syndrome with jeune asphyxiating thoracic dystrophy. |
| CTNS | 1497 | intermediate cystinosis, and cystinosis, atypical nephropathic |
| DBT | 1629 | maple syrup urine disease type 2, and maple syrup urine disease type 1a |

TABLE 2-continued

Genes with mutations or SNPs that create uORFs and associated diseases

| Gene | NCBI Gene ID | Associated disease(s) |
|---|---|---|
| DCAF17 | 80067 | sakati syndrome, and hypogonadism, alopecia, diabetes mellitus, mental retardation, and extrapyramidal syndrome |
| DCLRE1C | 64421 | severe combined immunodeficiency, athabascan type, and artemis deficiency. |
| DFNB31 | 25861 | deafness, autosomal recessive 31, and dfnb31 nonsyndromic hearing loss and deafness. |
| DLG4 | 1742 | schizophrenia. |
| DMD | 1756 | duchenne muscular dystrophy, and becker muscular dystrophy. |
| DNASE1 | 1773 | cystic fibrosis, acute bronchitis |
| ETHE1 | 23474 | ethylmalonic encephalopathy |
| GALNS | 2588 | mucopolysaccharidosis iv, and kniest dysplasia |
| GCH1 | 2643 | Levodopa responsive dystonia |
| HAMP | 57817 | Juvenile hemochromatosis, thalassemia |
| HBB | 3043 | Beta-Thalassemia |
| HMBS | 3145 | histrionic personality disorder, and acute porphyria. |
| HR | 55806 | atrichia with papular lesions, and hypotrichosis 4 |
| IGHMBP2 | 3508 | progressive multifocal leukoencephalopathy, and spinal muscular atrophy with respiratory distress 1 |
| IRF6 | 3664 | Van der Woude syndrome |
| ITGA7 | 3679 | muscular dystrophy, congenital, due to itga7 deficiency, and congenital muscular dystrophy due to integrin alpha-7 deficiency |
| ITGB2 | 3689 | leukocyte adhesion deficiency type 1, and leukocyte adhesion deficiency. |
| KCNJ11 | 3767 | Congenital hyperinsulinism, hyperinsulinemic hypoglycemia, 2 |
| KCNQ3 | 3786 | kcnq3-related benign familial neonatal epilepsy, and seizures, benign neonatal, type 2 |
| LDLR | 3949 | Cardiovascular disease, Familial hypercholesterolemia |
| LRP5, LRP5L | 4041, 91355 | exudative vitreoretinopathy 4, and hyperostosis, endosteal |
| MECP2 | 4204 | autism susceptibility, x-linked 3, and bruxism. |
| MLH1 | 4292 | mlh 1-related lynch syndrome, and solitary rectal ulcer syndrome. |
| MSH6 | 2956 | msh6-related lynch syndrome, colorectal cancer, hereditary nonpolyposis, type 5 |
| MUTYH | 4595 | adenomas, multiple colorectal, stomach cancer. |
| NR5A1 | 2516 | nr5al-related 46,xy dsd and 46,xy cgd, and adrenocortical insufficiency, without ovarian defect |
| PALB2 | 79728 | fanconi anemia, complementation group n, and pancreatic cancer susceptibility 3. |
| PANK2 | 80025 | classic pantothenate kinase-associated neurodegeneration, and harp syndrome. |
| PEX7 | 5191 | peroxisome biogenesis disorder 9b, and rhizomelic chondrodysplasia punctata. |
| PHYH | 5264 | phyh-related refsum disease, and refsum disease. |
| PIK3R5 | 23533 | ataxia-oculomotor apraxia 3, and spinocerebellar ataxia autosomal recessive 1 |
| POMC | 5443 | Proopiomelanocortin deficiency |
| POMT1 | 10585 | pomt1-related muscle diseases, and walker-warburg syndrome. |
| ROR2 | 4920 | brachydactyly, type b1, and brachydactyly type b |
| SCN2A | 6326 | epileptic encephalopathy, early infantile, 11, and benign familial neonatal-infantile seizures |
| SGCA | 6442 | sarcoglycanopathies, and limb-girdle muscular dystrophy, type 2d. |
| SGCD | 6444 | limb-girdle muscular dystrophy type 2f, and delta-sarcoglycanopathy. |
| SLC16A1 | 6566 | erythrocyte lactate transporter defect, and exercise-induced hyperinsulinemic hypoglycemia. |
| SLC19A3 | 80704 | basal ganglia disease, and biotin-responsive basal ganglia disease. |
| SLC2A2 | 6514 | fanconi bickel syndrome,fanconi syndrome |
| SLC7A9 | 11136 | stinuria, and aminoaciduria. |
| SPINK1 | 6690 | Hereditary pancreatitis |
| SRY | 6736 | Gonadal dysgenesis |
| STIL | 6491 | primary autosomal recessive microcephaly type 7, and ideomotor apraxia. |
| TK2 | 7084 | mitochondrial dna depletion syndrome, myopathic form, and tk2-related mitochondrial dna depletion syndrome, myopathic form. |
| TMPRSS3 | 64699 | deafness, autosomal recessive 8/10, and dfnb 8/10 nonsyndromic hearing loss and deafness. |
| TP53 | 7157 | hepatocellular carcinoma, and osteosarcoma |
| TPI1 | 7167 | hemolytic anemia due to triosephosphate isomerase deficiency, and triose phosphate-isomerase deficiency. |
| TPM3 | 7170 | nemaline myopathy, and nemaline myopathy 1 |
| TRMU | 55687 | liver failure acute infantile, and melas, mt-th-related. |
| TSEN54 | 283989 | tsen54-related pontocerebellar hypoplasia, and pontocerebellar hypoplasia type 4. |
| ZEB1 | 6935 | corneal dystrophy, posterior polymorphous, 3, and corneal dystrophy, fuchs endothelial, 6. |

In certain embodiments, a uORF inhibitor (e.g. an antisense compound), inhibits ribosomal recognition or uORF activity of a uORF start site on the CDKN2A transcript and thereby increases expression of CDKN2A. In certain embodiments, a uORF inhibitor (e.g. an antisense compound), inhibits ribosomal recognition or uORF activity of a uORF start site on the CFTR transcript and thereby increases expression of CFTR. In certain embodiments, a uORF inhibitor (e.g. an antisense compound), inhibits ribosomal recognition or uORF activity of a uORF start site on the FXII transcript and thereby increases expression of FXII. In certain embodiments, a uORF inhibitor (e.g. an antisense compound), inhibits ribosomal recognition or uORF activity of a uORF start site on the GCH1 transcript and thereby increases expression of GCH1. In certain embodiments, a uORF inhibitor (e.g. an antisense compound), inhibits ribosomal recognition or uORF activity of a uORF start site on the HAMP transcript and thereby increases expression of HAMP.

In certain embodiments, a uORF inhibitor (e.g. an antisense compound), inhibits ribosomal recognition or uORF activity of a uORF start site on the HBB transcript and thereby increases expression of HBB. In certain embodiments, a uORF inhibitor (e.g. an antisense compound), inhibits ribosomal recognition or uORF activity of a uORF start site on the IRF6 transcript and thereby increases expression of IRF6. In certain embodiments, a uORF inhibitor (e.g. an antisense compound), inhibits ribosomal recognition or uORF activity of a uORF start site on the KCNJ11 transcript and thereby increases expression of KCNJ11. In certain embodiments, a uORF inhibitor (e.g. an antisense compound), inhibits ribosomal recognition or uORF activity of a uORF start site on the LDLR transcript and thereby increases expression of LDLR. In certain embodiments, a uORF inhibitor (e.g. an antisense compound), inhibits ribosomal recognition or uORF activity of a uORF start site on the PEX7 transcript and thereby increases expression of PEX7.

In certain embodiments, a uORF inhibitor (e.g. an antisense compound), inhibits ribosomal recognition or uORF activity of a uORF start site on the POMC transcript and thereby increases expression of POMC. In certain embodiments, a uORF inhibitor (e.g. an antisense compound), inhibits ribosomal recognition or uORF activity of a uORF start site on the PRKAR1A transcript and thereby increases expression of PRKAR1A. In certain embodiments, a uORF inhibitor (e.g. an antisense compound), inhibits ribosomal recognition or uORF activity of a uORF start site on the SPINK1 transcript and thereby increases expression of SPINK1. In certain embodiments, a uORF inhibitor (e.g. an antisense compound), inhibits ribosomal recognition or uORF activity of a uORF start site on the SRY transcript and thereby increases expression of SRY.

In certain embodiments, a TSE inhibitor (e.g. an antisense compound) may be used to upregulate a expression of ATM, lipoprotein lipase (LPL), DMD, sphingomyelinase, Factor VIII, insulin, growth hormone, thyroid stimulating hormone, follicle stimulating hormone, or hepcidin.

D. Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water.

In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

E. Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense compound is delivered by injection or infusion once every month, every two months, every 90 days, every 3 months, every 6 months, twice a year or once a year.

F. Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

In certain embodiments, the present invention may be used to increase expression of a protein, which sensitizes the cell to other treatment. For example, in certain embodiments, the invention may be used to increase expression of RNase H. Cells with increased RNase H may be more sensitive to subsequent treatment with RNase H-dependent antisense compounds.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^m$CGAUCG," wherein $^m$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1: Effects of Antisense Oligonucleotides Targeting the uORF of RNase H1 on RNase H1 Protein Expression Human RNase H1 mRNA (GENBANK accession number NM_001286834.1, designated herein as SEQ ID NO: 1) comprises an upstream open reading frame (uORF). Antisense oligonucleotides designed to target the start codon of the uORF of human RNase H1 were tested for their effects on RNase H1 expression in vitro. These antisense oligonucleotides, described in Table 3, were uniformly modified in order to avoid inducing cleavage of the target RNA. The start and stop sites listed in Table 3 indicate the positions on SEQ ID NO: 1 that the antisense oligonucleotides target. The targeted uORF begins at position 86. HeLa cells were transfected with Lipofectamine RNAiMAX (Life Technologies) and one of the antisense oligonucleotides at a final concentration of 25 nM or were mock transfected as a control. Thirty hours after transfection, the cells were lysed, and expression of RNase H1 was analyzed by western blot and RT-PCR. The primary antibody used for the western blot was made as described in Wu et al. *Determination of the Role of the Human RNase H1 in the Pharmacology of DNA-like Antisense Drugs. J. Biol. Chem.* 279, 17181 (2004), and the secondary antibody was purchased from Biorad (catalog #170-6515). The western blot was quantified using Image J, and the results are shown in Table 3 as percent protein levels relative to mock transfected cells following normalization to the Annexin A2 loading control. The RT-PCR results are shown in Table 3 as percent mRNA levels relative to mock transfected cells following normalization to Ribogreen. The results show that antisense oligonucleotides targeting a portion of the RNase H1 uORF that includes the uORF start codon increased RNase H1 expression. Furthermore, certain antisense oligonucleotides did not significantly affect RNase H1 mRNA levels, indicating that the increased RNase H1 expression exhibited by those oligonucleotides occurred mainly via increased translation.

TABLE 3

RNase H1 expression

| Isis No. | Sequence | Start Site | Stop Site | RNase H1 protein (% mock) | RNase H1 mRNA (% mock) | SEQ ID NO. |
|---|---|---|---|---|---|---|
| 761909 | $C_{mo}A_{mo}U_{mo}U_{mo}U_{mo}C_{mo}G_{mo}A_{mo}C_{mo}U_{mo}C_{mo}C_{mo}C_{mo}G_{mo}G_{mo}C_{m}$ | 73 | 88 | 166 | 106 | 3 |
| 761910 | $A_{mo}G_{mo}C_{mo}A_{mo}U_{mo}U_{mo}U_{mo}C_{mo}G_{mo}A_{mo}C_{mo}U_{mo}C_{mo}C_{mo}C_{mo}G_{m}$ | 75 | 90 | 146 | 113 | 4 |
| 761911 | $G_{mo}A_{mo}A_{mo}G_{mo}C_{mo}A_{mo}U_{mo}U_{mo}U_{mo}C_{mo}G_{mo}A_{mo}C_{mo}U_{mo}C_{mo}C_{m}$ | 77 | 92 | 139 | 114 | 5 |
| 761912 | $G_{mo}G_{mo}G_{mo}A_{mo}A_{mo}G_{mo}C_{mo}A_{mo}U_{mo}U_{mo}U_{mo}C_{mo}G_{mo}A_{mo}C_{mo}U_{m}$ | 79 | 94 | 106 | 109 | 6 |
| 761913 | $C_{mo}C_{mo}G_{mo}G_{mo}G_{mo}A_{mo}A_{mo}G_{mo}C_{mo}A_{mo}U_{mo}U_{mo}U_{mo}C_{mo}G_{mo}A_{m}$ | 81 | 96 | 104 | 113 | 7 |

Subscripts: "m" indicates a 2'-O-methyl modification, and "o" indicates a phosphodiester internucleoside linkage.

Example 2: Time Course of RNase H1 Protein Expression Following Treatment with an Antisense Oligonucleotide Targeting the uORF In Vitro HeLa cells were transfected with 25 nM Isis No. 761909 (see Table 3). At various time points following transfection, the cells were harvested and RNase H1 expression was analyzed by western blot as described in Example 1. The results are shown in Table 4 as the percent RNase H1 protein expression relative to cells that did not receive antisense oligonucleotide treatment (harvested at the 0 hour time point) following normalization to the Annexin A2 loading control. The results show that the induction of RNase H1 expression was observed within 4 hours following transfection, and maximal expression was observed at approximately 12 hours following transfection.

TABLE 4

RNase H1 expression RNase H1 (% 0 h) following transfection with 25 nM 761909

| 4 h | 8 h | 12 h | 15 h |
|---|---|---|---|
| 143 | 145 | 214 | 176 |

Example 3: Dose Response Effect of an Antisense Oligonucleotide Targeting the uORF of RNase H1 on RNase H1 Protein Expression In Vitro Isis No. 761909 (see Table 3) was tested at five different doses for its effect on RNase H1 expression in vitro. HeLa cells were transfected with 761909 at a concentration listed in Table 5 or were not treated as a control. Fifteen hours after transfection, RNase H1 expression was analyzed as described in Example 1. The results are shown in Table 5 as the percent protein levels relative to untreated control cells following normalization to the Annexin A2 loading control and as mRNA levels relative to untreated control cells following normalization to Ribogreen. The results show that an antisense oligonucleotide targeting a portion of the RNase H1 uORF increased RNase H1 protein levels in a dose dependent manner; and mRNA levels did not increase, indicating that the antisense oligonucleotide increased RNase H1 expression via increased translation.

TABLE 5

RNase H1 expression following transfection with 761909

| 761909 concentration (nM) | Protein (% untreated cells) | mRNA (% untreated cells) |
|---|---|---|
| 10 | 108 | 100 |
| 15 | 93 | 100 |
| 20 | 183 | 96 |
| 25 | 169 | 92 |
| 30 | 182 | 96 |

Example 4: Effects of Antisense Oligonucleotides Targeting the 5'-Untranslated Region Upstream of the RNase H1 uORF on RNase H1 Protein Expression Antisense oligonucleotides designed to target the 5'-untranslated region upstream of the uORF of human RNase H1 were tested for their effects on RNase H1 protein expression in vitro. These antisense oligonucleotides, described in Table 6, were uniformly modified in order to avoid inducing cleavage of the target RNA. The start and stop sites listed in Table 6 indicate the positions on SEQ ID NO: 1 that the antisense oligonucleotides target. Isis 761909 was included for reference. HeLa cells were transfected with 20 nM antisense oligonucleotide or were mock transfected as a control. Fifteen hours after transfection, RNase H1 expression was analyzed as described in Example 1. The results are shown in Table 6 below as percent protein expression relative to mock transfected cells following normalization to the γ-tubulin loading control and percent mRNA levels relative to mock transfected cells following normalization to Ribogreen. The results show that antisense oligonucleotides do not necessarily need to target the start codon of an uORF in order to induce increased translation of the target. Antisense oligonucleotides that target the 5'-untranslated region upstream of an uORF and antisense oligonucleotides that target at least a portion of the uORF itself can induce translation of the target. Furthermore, the antisense oligonucleotides targeting the 5'-untranslated region upstream of the uORF did not increase mRNA levels, indicating that they increased RNase H1 expression via increased translation.

TABLE 6

RNase H1 expression

| Isis No. | Sequence | Start Site | Stop Site | Protein (% mock) | mRNA (% mock) | SEQ ID NO. |
|---|---|---|---|---|---|---|
| 761918 | $U_{mo}C_{mo}A_{mo}C_{mo}C_{mo}G_{mo}G_{mo}C_{mo}G_{mo}C_{mo}G_{mo}G_{mo}G_{mo}A_{mo}A_{mo}G_{m}$ | 14 | 29 | 155 | 96 | 8 |
| 761919 | $C_{mo}U_{mo}C_{mo}A_{mo}A_{mo}C_{mo}A_{mo}C_{mo}C_{mo}G_{mo}C_{mo}A_{mo}C_{mo}U_{mo}U_{mo}C_{m}$ | 32 | 47 | 214 | 100 | 9 |
| 761917 | $A_{mo}C_{mo}U_{mo}C_{mo}C_{mo}C_{mo}G_{mo}G_{mo}C_{mo}C_{mo}C_{mo}A_{mo}G_{mo}C_{mo}G_{mo}U_{m}$ | 66 | 81 | 116 | 98 | 10 |
| 761916 | $C_{mo}G_{mo}A_{mo}C_{mo}U_{mo}C_{mo}C_{mo}C_{mo}G_{mo}G_{mo}C_{mo}C_{mo}C_{mo}A_{mo}G_{mo}C_{m}$ | 68 | 83 | 142 | 96 | 11 |
| 761915 | $U_{mo}U_{mo}C_{mo}G_{mo}A_{mo}C_{mo}U_{mo}C_{mo}C_{mo}C_{mo}G_{mo}G_{mo}C_{mo}C_{mo}C_{mo}A_{m}$ | 70 | 85 | 218 | 96 | 12 |
| 761909 | $C_{mo}A_{mo}U_{mo}U_{mo}U_{mo}C_{mo}G_{mo}A_{mo}C_{mo}U_{mo}C_{mo}C_{mo}C_{mo}G_{mo}G_{mo}C_{m}$ | 73 | 88 | 151 | 94 | 3 |

Subscripts: "m" indicates a 2'-O-methyl modification, and "o" indicates a phosphodiester internucleoside linkage.

Example 5: Effects of Antisense Oligonucleotides of Varying Lengths on RNase H1 Protein Expression Antisense oligonucleotides of varying lengths designed to target at least a portion of the uORF of human RNase H1 were tested for their effects on RNase H1 expression in vitro. These antisense oligonucleotides, described in Table 7, were uniformly modified in order to avoid inducing cleavage of the target RNA. The start and stop sites listed in Table 7 indicate the positions on SEQ ID NO: 1 that the antisense oligonucleotides target. HeLa cells were transfected with 20 nM antisense oligonucleotide or were mock transfected as a control. Fifteen hours after transfection, RNase H1 expression was analyzed as described in Example 1. The results are shown in Table 7 below as the percent protein expression relative to mock transfected cells following normalization to the γ-tubulin loading control and percent mRNA levels relative to mock transfected cells following normalization to Ribogreen. The results show that antisense oligonucleotides of various lengths increased RNase H1 expression mainly via increased translation of the target.

TABLE 7

RNase H1 expression following transfection with 5'-UTR targeting antisense oligonucleotides

| Isis No. | Sequence | Start Site | Stop Site | Length | Protein (% mock) | mRNA (% mock) | SEQ ID NO. |
|---|---|---|---|---|---|---|---|
| 761928 | $C_{mo}A_{mo}U_{mo}U_{mo}U_{mo}C_{mo}G_{mo}A_{mo}C_{mo}U_{mo}C_{mo}C_{m}$ | 77 | 88 | 12 | 143 | 104 | 13 |
| 761927 | $C_{mo}A_{mo}U_{mo}U_{mo}U_{mo}C_{mo}G_{mo}A_{mo}C_{mo}U_{mo}C_{mo}C_{mo}C_{mo}G_{m}$ | 75 | 88 | 14 | 142 | 101 | 14 |
| 761909 | $C_{mo}A_{mo}U_{mo}U_{mo}U_{mo}C_{mo}G_{mo}A_{mo}C_{mo}U_{mo}C_{mo}C_{mo}C_{mo}G_{mo}G_{mo}C_{m}$ | 73 | 88 | 16 | 244 | 94 | 3 |
| 761926 | $C_{mo}A_{mo}U_{mo}U_{mo}U_{mo}C_{mo}G_{mo}A_{mo}C_{mo}U_{mo}C_{mo}C_{mo}C_{mo}G_{mo}G_{mo}C_{mo}C_{mo}C_{m}$ | 71 | 88 | 18 | 187 | 110 | 15 |
| 761925 | $C_{mo}A_{mo}U_{mo}U_{mo}U_{mo}C_{mo}G_{mo}A_{mo}C_{mo}U_{mo}C_{mo}C_{mo}C_{mo}G_{mo}G_{mo}C_{mo}C_{mo}C_{mo}A_{mo}G_{m}$ | 69 | 88 | 20 | 126 | 100 | 16 |

Subscripts: "m" indicates a 2'-O-methyl modification, and "o" indicates a phosphodiester internucleoside linkage.

Example 6: Effects of Antisense Oligonucleotides Targeting the uORF of Mouse LRPPRC on LRPPRC Protein Expression Mouse Leucine-Rich PPR-Motif Containing (LRPPRC) mRNA (GENBANK accession number NM_028233.2, designated herein as SEQ ID NO: 2) comprises an upstream open reading frame. Antisense oligonucleotides with various lengths and internucleoside linkages designed to target the start codon of the uORF of mouse LRPPRC were tested for their effects on LRPPRC protein expression in vitro. These antisense oligonucleotides, described in Table 8, were uniformly modified in order to avoid inducing cleavage of the target RNA. The start and stop sites listed in Table 8 indicate the positions on SEQ ID NO: 2 that the antisense oligonucleotides target. The targeted uORF begins at position 70. MHT cells were transfected with Lipofectamine RNAiMAX (Life Technologies) and an antisense oligonucleotide at a concentration listed in Table 8 or were untreated as a control. Fifteen hours after transfection, the cells were lysed, and a western blot was performed with an LRPPRC antibody purchased from Abcam (catalog #ab97505) to analyze expression of LRPPRC. The western blot was quantified using Image J, and the results are shown in Table 8 below as the percent expression relative to untreated control cells following normalization to the loading control (Annexin A2 for 761932 and 761933, and hnRNP K for 759704 and 761930). The results show that antisense oligonucleotides of various lengths targeting the start codon of the uORF of mouse LRPPRC increased LRPPRC expression, including oligonucleotides comprising phosphodiester internucleoside linkages and an oligonucleotide comprising phosphorothioate internucleoside linkages. Thus, the results in Table 8 along with the results in the Examples above show that various antisense oligonucleotides targeting at least a portion of an uORF can increase expression of multiple targets

TABLE 8

LRPPRC expression

| Isis No. | Sequence | Start Site | Stop Site | Concentration (nM) | LRPPRC (% UTC) | SEQ ID NO. |
|---|---|---|---|---|---|---|
| 761932 | $C_{mo}A_{mo}U_{mo}U_{mo}G_{mo}U_{mo}U_{mo}U_{mo}U_{mo}U_{mo}U_{mo}$ $G_{mo}U_{mo}C_{mo}U_{mo}U_{mo}C_{mo}C_{m}$ | 55 | 72 | 10 | 127 | 17 |
| | | | | 20 | 184 | |
| | | | | 30 | 214 | |
| | | | | 40 | 173 | |
| | | | | 50 | 178 | |
| | | | | 60 | 228 | |
| 761933 | $C_{ms}A_{ms}U_{ms}U_{ms}G_{ms}U_{ms}U_{ms}U_{ms}U_{ms}U_{ms}U_{ms}$ $G_{ms}U_{ms}C_{ms}U_{ms}U_{ms}C_{ms}C_{m}$ | 55 | 72 | 10 | 123 | 17 |
| | | | | 20 | 141 | |
| | | | | 30 | 126 | |
| | | | | 40 | 131 | |
| | | | | 50 | 105 | |
| 759704 | $C_{mo}A_{mo}U_{mo}U_{mo}G_{mo}U_{mo}U_{mo}U_{mo}U_{mo}U_{mo}$ $U_{mo}U_{mo}G_{mo}U_{mo}C_{mo}U_{mo}U_{m}$ | 57 | 72 | 10 | 187 | 18 |
| | | | | 20 | 182 | |
| | | | | 30 | 189 | |
| | | | | 40 | 170 | |
| | | | | 50 | 243 | |
| | | | | 60 | 203 | |
| 761930 | $C_{mo}A_{mo}U_{mo}U_{mo}G_{mo}U_{mo}U_{mo}U_{mo}U_{mo}U_{mo}$ $U_{mo}U_{mo}G_{mo}U_{mo}C_{mo}U_{mo}U_{mo}C_{mo}C_{mo}$ $G_{mo}U_{m}$ | 53 | 72 | 10 | 164 | 19 |
| | | | | 20 | 149 | |
| | | | | 30 | 218 | |
| | | | | 40 | 142 | |
| | | | | 50 | 219 | |
| | | | | 60 | 255 | |

Subscripts: "m" indicates a 2'-O-methyl modification, "o" indicates a phosphodiester internucleoside linkage, and "s" indicates a phosphorothioate internucleoside linkage.

Example 7: Effect of Antisense Oligonucleotide Targeting the uORF of Human SFXN3 on SFXN3 Protein Expression Human Sideroflexin 3 (SFXN3) mRNA (GENBANK accession number NM_030971.3, designated herein as SEQ ID NO: 20) comprises an upstream open reading frame. An antisense oligonucleotide designed to target the start codon of the uORF of human SFXN3 was tested for its effect on SFXN3 protein expression in vitro. The antisense oligonucleotide, described in Table 9, was uniformly modified in order to avoid inducing cleavage of the target RNA. The start and stop sites listed in Table 9 indicate the positions on SEQ ID NO: 20 that the antisense oligonucleotide targets. The targeted uORF begins at position 388. HeLa cells were transfected with Lipofectamine RNAiMAX (Life Technologies) and an antisense oligonucleotide at a concentration listed in Table 9 or were untreated as a control. Ten hours after transfection, the cells were lysed, and SFXN3 mRNA and protein expression were analyzed by RT-PCR and western blot, respectively. The western blot was performed with an SFXN3 antibody purchased from Abcam (catalog #ab181163) and quantified using Image J. The results are shown in Table 9 below as the percent protein expression relative to untreated control cells ("UTC") following normalization to the loading control (Ku70, detected with Abcam antibody, catalog #ab3114). SFXN3 mRNA levels normalized to Ribogreen are also shown. The results show that an antisense oligonucleotide targeting the start codon of the uORF of human SFXN3 increased SFXN3 protein expression. SFXN3 mRNA levels did not increase, indicating that the antisense oligonucleotide increased SFXN3 expression via increased translation.

TABLE 9

SFXN3 expression

| Isis No. | Sequence | Start Site | Stop Site | Concentration (nM) | Protein (% UTC) | mRNA (% UTC) | SEQ ID NO. |
|---|---|---|---|---|---|---|---|
| 759677 | $C_{mo}A_{mo}U_{mo}C_{mo}A_{mo}C_{mo}G_{mo}$ $C_{mo}G_{mo}G_{mo}G_{mo}$ $A_{mo}C_{mo}G_{mo}U_{mo}C_{m}$ | 375 | 390 | 10 | 100 | 106 | 21 |
|  |  |  |  | 20 | 120 | 102 |  |
|  |  |  |  | 30 | 124 | 97 |  |
|  |  |  |  | 40 | 126 | 94 |  |
|  |  |  |  | 60 | 134 | 109 |  |
|  |  |  |  | 80 | 133 | 103 |  |
|  |  |  |  | 100 | 125 | 107 |  |

Subscripts: "m" indicates a 2'-O-methyl modification, "o" indicates a phosphodiester internucleoside linkage.

Example 8: Effect of Antisense Oligonucleotide Targeting the uORF of Mouse MRPL11 on MRPL11 Protein Expression Mouse Mitochondrial Ribosomal protein LII (MRPL11) mRNA (GENBANK accession number NM_025553.4, designated herein as SEQ ID NO: 22) comprises an upstream open reading frame. An antisense oligonucleotide designed to target the start codon of the uORF of mouse MRPL11 was tested for its effect on MRPL11 protein expression in vitro. The antisense oligonucleotide, described in Table 10, was uniformly modified in order to avoid inducing cleavage of the target RNA. The start and stop sites listed in Table 10 indicate the positions on SEQ ID NO: 22 that the antisense oligonucleotide targets. The targeted uORF begins at position 24. bEND cells were transfected with Lipofectamine RNAiMAX (Life Technologies) and an antisense oligonucleotide at a concentration listed in Table 10 or were untreated as a control. Ten hours after transfection, the cells were lysed, and MRPL11 mRNA and protein expression were analyzed by RT-PCR and western blot, respectively. The western blot was performed with an MRPL11 antibody purchased from Abcam (catalog #ab2066s) and quantified using Image J. The results are shown in Table 10 below as the percent protein expression relative to untreated control cells ("UTC") following normalization to the loading control (GAPDH, detected with Santa Cruz Biotechnology antibody, catalog #sc-32233). MRPL11 mRNA levels normalized to Ribogreen are also shown. The results show that an antisense oligonucleotide targeting the start codon of the uORF of mouse MRPL11 increased MRPL11 protein expression. MRPL11 mRNA levels did not increase, indicating that the antisense oligonucleotide increased MRPL11 expression via increased translation.

TABLE 10

MRPL11 expression

| Isis No. | Sequence | Start Site | Stop Site | Concentration (nM) | Protein (% UTC) | mRNA (% UTC) | SEQ ID NO. |
|---|---|---|---|---|---|---|---|
| 773534 | $C_{mo}A_{mo}U_{mo}U_{mo}U_{mo}U_{mo}G_{mo}$ $G_{mo}G_{mo}U_{mo}C_{mo}$ $A_{mo}G_{mo}A_{mo}G_{mo}G_{mo}U_{mo}G_{m}$ | 9 | 26 | 5 | 95 | 93 | 23 |
| | | | | 10 | 146 | 95 | |
| | | | | 20 | 137 | 96 | |
| | | | | 40 | 134 | 109 | |
| | | | | 80 | 125 | 104 | |

Subscripts: "m" indicates a 2'-O-methyl modification, "o" indicates a phosphodiester internucleoside linkage.

Example 9: Effects of Antisense Oligonucleotides Targeting the uORF of Human THPO on THPO Protein Expression Human Thrombopoietin (THPO) mRNA (GENBANK accession number NM_000460.3, designated herein as SEQ ID NO: 24) comprises seven upstream open reading frames. An antisense oligonucleotide designed to target the start codon of the last uORF of human THPO was tested for its effect on THPO protein expression in vitro. The antisense oligonucleotide, described in Table 11, was uniformly modified in order to avoid inducing cleavage of the target RNA. The start and stop sites listed in Table 11 indicate the positions on SEQ ID NO: 24 that the antisense oligonucleotide targets. The targeted uORF begins at position 210. Hep3B cells were transfected with Lipofectamine RNAiMAX (Life Technologies) and an antisense oligonucleotide at a concentration listed in Table 11 or cells were untreated as a control. Ten hours after transfection, medium was changed to serum-free medium and cells were incubated for an additional 12 hr. Proteins from the medium were precipitated using trichloroacetic acid, and THPO protein expression was analyzed by western blot using a THPO antibody purchased from Abcam (catalog #ab196026) and quantified using Image J. The results are shown in Table 11 below as the percent protein expression relative to untreated control cells ("UTC") following normalization to the loading control (Transferrin). The results show that an antisense oligonucleotide targeting the start codon of the uORF of human THPO increased THPO protein expression.

TABLE 11

THPO expression

| Isis No. | Sequence | Start Site | Stop Site | Concentration (nM) | Protein (% UTC) | SEQ ID NO. |
|---|---|---|---|---|---|---|
| 806734 | $C_{mo}A_{mo}U_{mo}G_{mo}G_{mo}A_{mo}G_{mo}$ $G_{mo}C_{mo}G_{mo}G_{mo}$ $C_{mo}U_{mo}U_{mo}A_{mo}G_{mo}G_{mo}C_{m}$ | 195 | 212 | 5 | 155 | 25 |
| | | | | 10 | 176 | |
| | | | | 20 | 167 | |
| | | | | 40 | 172 | |
| | | | | 60 | 130 | |

Subscripts: "m" indicates a 2'-O-methyl modification, "o" indicates a phosphodiester internucleoside linkage.

Example 10: Effects of Mismatched Antisense Oligonucleotides Targeting the uORF of RNase H1 on RNase H1 Protein Expression Antisense oligonucleotides designed to target the start codon of the uORF of human RNase H1 with two mismatches between the antisense oligonucleotide and the target sequence were tested for their effects on RNase H1 expression in vitro. These antisense oligonucleotides, described in Table 12, were uniformly modified in order to avoid inducing cleavage of the target RNA. The start and stop sites listed in Table 12 indicate the positions on SEQ ID NO: 1 that the antisense oligonucleotides target, and the mismatched nucleotides are bolded. The targeted uORF begins at position 86. HeLa cells were transfected with Lipofectamine RNAiMAX (Life Technologies) and an antisense oligonucleotide at a final concentration of 25 nM or were mock transfected as a control. Twenty-four hours after transfection, the cells were lysed, and expression of RNase H1 was analyzed by western blot as described in Example 1. The results are shown in Table 12 as percent protein levels relative to mock transfected cells following normalization to the Ku70 loading control. The results show that antisense oligonucleotides with mismatches to the uORF start codon or near to the uORF start codon had little to no effect on RNase H1 protein expression, whereas antisense oligonucleotides with mismatches further away from the uORF start codon increased RNase H1 protein expression.

TABLE 12

RNase H1 expression

| Isis No. | Sequence | Start Site | Stop Site | RNase H1 protein (% mock) | SEQ ID NO. |
|---|---|---|---|---|---|
| 773519 | $G_{mo}U_{mo}U_{mo}U_{mo}U_{mo}C_{mo}G_{mo}A_{mo}C_{mo}U_{mo}C_{mo}C_{mo}C_{mo}G_{mo}G_{mo}C_{m}$ | 73 | 88 | 96 | 26 |
| 773520 | $C_{mo}\mathbf{A}_{mo}\mathbf{A}_{mo}\mathbf{A}_{mo}U_{mo}C_{mo}G_{mo}A_{mo}C_{mo}U_{mo}C_{mo}C_{mo}C_{mo}G_{mo}G_{mo}C_{m}$ | 73 | 88 | 82 | 27 |
| 773521 | $C_{mo}A_{mo}U_{mo}U_{mo}\mathbf{A}_{mo}\mathbf{G}_{mo}G_{mo}A_{mo}C_{mo}U_{mo}C_{mo}C_{mo}C_{mo}G_{mo}G_{mo}C_{m}$ | 73 | 88 | 103 | 28 |
| 773522 | $C_{mo}A_{mo}U_{mo}U_{mo}U_{mo}C_{mo}\mathbf{C}_{mo}\mathbf{U}_{mo}C_{mo}U_{mo}C_{mo}C_{mo}C_{mo}G_{mo}G_{mo}C_{m}$ | 73 | 88 | 89 | 29 |
| 773523 | $C_{mo}A_{mo}U_{mo}U_{mo}U_{mo}C_{mo}G_{mo}A_{mo}\mathbf{G}_{mo}\mathbf{A}_{mo}C_{mo}C_{mo}C_{mo}G_{mo}G_{mo}C_{m}$ | 73 | 88 | 121 | 30 |
| 773524 | $C_{mo}A_{mo}U_{mo}U_{mo}U_{mo}C_{mo}G_{mo}A_{mo}C_{mo}U_{mo}\mathbf{G}_{mo}\mathbf{G}_{mo}C_{mo}G_{mo}G_{mo}C_{m}$ | 73 | 88 | 158 | 31 |
| 773525 | $C_{mo}A_{mo}U_{mo}U_{mo}U_{mo}C_{mo}G_{mo}A_{mo}C_{mo}U_{mo}C_{mo}C_{mo}\mathbf{G}_{mo}\mathbf{C}_{mo}G_{mo}C_{m}$ | 73 | 88 | 150 | 32 |
| 773526 | $C_{mo}A_{mo}U_{mo}U_{mo}U_{mo}C_{mo}G_{mo}A_{mo}C_{mo}U_{mo}C_{mo}C_{mo}C_{mo}G_{mo}\mathbf{C}_{mo}\mathbf{G}_{m}$ | 73 | 88 | 153 | 33 |

Subscripts: "m" indicates a 2'-O-methyl modification, and "o" indicates a phosphodiester internucleoside linkage.

Example 11: Effects of Antisense Oligonucleotides Comprising Various Modifications Antisense oligonucleotides targeting the start codon of the uORF in human RNase H1 (SEQ ID NO: 1) or mouse LRPPRC (SEQ ID NO: 2) were designed with various lengths and with various modifications to the internucleoside linkages and to the sugars. These antisense oligonucleotides were tested for their effects on target protein expression in vitro. HEK293 cells (RNase H1 targeting oligonucleotides) or MHT cells (LRPPRC targeting oligonucleotides) were transfected with Lipofectamine RNAiMAX (Life Technologies) and an antisense oligonucleotide at a concentration listed in the tables below. Ten hours after transfection, the cells were lysed, and target protein expression was analyzed by western blot as described in Example 1 (for RNase H1) or Example 6 (for LRPPRC). The results are shown in the tables below as the percent protein expression relative to untreated control cells ("UTC") following normalization to the loading control (Ku70, γ-tubulin, Annexin A2, or a non-specific band detected by the primary antibody). The results show that antisense oligonucleotides of various lengths and with modified internucleoside linkages and various 2'-modifications and bicyclic nucleosides increased target protein expression.

TABLE 13

RNase H1 expression

| Isis No. | Sequence | Start Site | Stop Site | Length | Concentration (nM) | Protein (% mock) | SEQ ID NO. |
|---|---|---|---|---|---|---|---|
| 783683 | $C_{ms}A_{ms}U_{ms}U_{ms}U_{ms}C_{ms}G_{ms}A_{ms}C_{ms}U_{ms}$ $C_{ms}C_m$ | 77 | 88 | 12 | 20 | 191 | 34 |
| 783681 | $C_{ms}A_{ms}U_{ms}U_{ms}U_{ms}C_{ms}G_{ms}A_{ms}C_{ms}U_{ms}$ $C_{ms}C_{ms}C_{ms}G_m$ | 75 | 88 | 14 | 20 | 178 | 35 |
| 783682 | $C_{ms}A_{ms}U_{ms}U_{ms}U_{ms}C_{ms}G_{ms}A_{ms}C_{ms}U_{ms}$ $C_{ms}C_{ms}C_{ms}G_{ms}G_{ms}C_m$ | 73 | 88 | 16 | 20 | 186 | 3 |
| 783679 | $C_{ms}A_{ms}U_{ms}U_{ms}U_{ms}C_{ms}G_{ms}A_{ms}C_{ms}U_{ms}$ $C_{ms}C_{ms}C_{ms}G_{ms}G_{ms}C_{ms}C_{ms}C_m$ | 71 | 88 | 18 | 20 | 149 | 15 |
| 783680 | $C_{ms}A_{ms}U_{ms}U_{ms}U_{ms}C_{ms}G_{ms}A_{ms}C_{ms}U_{ms}$ $C_{ms}C_{ms}C_{ms}G_{ms}G_{ms}C_{ms}C_{ms}C_{ms}A_{ms}G_m$ | 69 | 88 | 20 | 20 | 83 | 16 |

Subscripts: "m" indicates a 2'-O-methyl modification, and "s" indicates a phosphorothioate internucleoside linkage.

TABLE 14

RNase H1 expression

| Isis No. 783679 concentration (nM) | Protein (% UTC) |
|---|---|
| 5 | 140 |
| 10 | 179 |
| 20 | 186 |
| 40 | 174 |
| 60 | 195 |

TABLE 15

RNase H1 expression

| Isis No. | Sequence | Start Site | Stop Site | Length | Concentration (nM) | Protein (% mock) | SEQ ID NO. |
|---|---|---|---|---|---|---|---|
| 783674 | $^mC_{es}A_{es}T_{es}T_{es}T_{es}{}^mC_{es}G_{es}A_{es}{}^mC_{es}T_{es}{}^mC_{es}{}^mC_e$ | 77 | 88 | 12 | 20 | 70 | 36 |
| 783673 | $^mC_{es}A_{es}T_{es}T_{es}T_{es}{}^mC_{es}G_{es}A_{es}{}^mC_{es}T_{es}{}^mC_{es}$ $^mC_{es}{}^mC_{es}G_e$ | 75 | 88 | 14 | 20 | 104 | 37 |
| 759304 | $^mC_{es}A_{es}T_{es}T_{es}T_{es}{}^mC_{es}G_{es}A_{es}{}^mC_{es}T_{es}{}^mC_{es}$ $^mC_{es}{}^mC_{es}G_{es}G_{es}{}^mC_e$ | 73 | 88 | 16 | 20 | 136 | 38 |
| 773517 | $^mC_{es}A_{es}T_{es}T_{es}T_{es}{}^mC_{es}G_{es}A_{es}{}^mC_{es}T_{es}{}^mC_{es}$ $^mC_{es}{}^mC_{es}G_{es}G_{es}{}^mC_{es}{}^mC_{es}{}^mC_e$ | 71 | 88 | 18 | 20 | 178 | 39 |
| 773516 | $^mC_{es}A_{es}T_{es}T_{es}T_{es}{}^mC_{es}G_{es}A_{es}{}^mC_{es}T_{es}{}^mC_{es}$ $^mC_{es}{}^mC_{es}G_{es}G_{es}{}^mC_{es}{}^mC_{es}{}^mC_{es}A_{es}G_e$ | 69 | 88 | 20 | 20 | 122 | 40 |

Subscripts: "e" indicates a 2'-O-methoxyethyl modification, and "s" indicates a phosphorothioate internucleoside linkage.
Superscript "m" in front of a "C" indicates a 5'-methylcytosine.

TABLE 16

| Isis No. 759304 concentration (nM) | Protein (% UTC) |
|---|---|
| 5 | 137 |
| 10 | 211 |
| 20 | 218 |
| 40 | 208 |
| 60 | 193 |

TABLE 17

RNase H1 expression

| Isis No. | Sequence | Start Site | Stop Site | Length | Concentration (nM) | Protein (% mock) | SEQ ID NO. |
|---|---|---|---|---|---|---|---|
| 783678 | $^mC_{eo}A_{eo}T_{eo}T_{eo}T_{eo}{}^mC_{eo}G_{eo}A_{eo}{}^mC_{eo}T_{eo}{}^mC_{eo}{}^mC_e$ | 77 | 88 | 12 | 5 | 187 | 36 |
| 783677 | $^mC_{eo}A_{eo}T_{eo}T_{eo}T_{eo}{}^mC_{eo}G_{eo}A_{eo}{}^mC_{eo}T_{eo}{}^mC_{eo}{}^mC_{eo}{}^mC_{eo}G_e$ | 75 | 88 | 14 | 5 | 144 | 37 |
| 759388 | $^mC_{eo}A_{eo}T_{eo}T_{eo}T_{eo}{}^mC_{eo}G_{eo}A_{eo}{}^mC_{eo}T_{eo}{}^mC_{eo}{}^mC_{eo}{}^mC_{eo}G_{eo}G_{eo}{}^mC_e$ | 73 | 88 | 16 | 5 | 148 | 38 |
| 783676 | $^mC_{eo}A_{eo}T_{eo}T_{eo}T_{eo}{}^mC_{eo}G_{eo}A_{eo}{}^mC_{eo}T_{eo}{}^mC_{eo}{}^mC_{eo}{}^mC_{eo}G_{eo}G_{eo}{}^mC_{eo}{}^mC_{eo}{}^mC_e$ | 71 | 88 | 18 | 5 | 101 | 39 |
| 783675 | $^mC_{eo}A_{eo}T_{eo}T_{eo}T_{eo}{}^mC_{eo}G_{eo}A_{eo}{}^mC_{eo}T_{eo}{}^mC_{eo}{}^mC_{eo}{}^mC_{eo}G_{eo}G_{eo}{}^mC_{eo}{}^mC_{eo}{}^mC_{eo}A_{eo}G_e$ | 69 | 88 | 20 | 5 | 84 | 40 |

Subscripts: "e" indicates a 2'-O-methoxyethyl modification, and "s" indicates a phosphorothioate internucleoside linkage.
Superscript "m" in front of a "C" indicates a 5'-methylcytosine.

TABLE 18

RNase H1 expression

| Isis No. | Sequence | Start Site | Stop Site | Concentration (nM) | Protein (% UTC) | SEQ ID NO. |
|---|---|---|---|---|---|---|
| 766733 | $C_{fo}A_{fo}U_{fo}U_{fo}U_{fo}C_{fo}G_{fo}A_{fo}C_{fo}U_{fo}C_{fo}C_{fo}C_{fo}G_{fo}G_{fo}C_f$ | 73 | 88 | 5 | 115 | 3 |
|  |  |  |  | 10 | 126 |  |
|  |  |  |  | 20 | 137 |  |
|  |  |  |  | 40 | 134 |  |
|  |  |  |  | 60 | 127 |  |

Subscripts: "f" indicates a 2'-fluoro modification, "o" indicates a phosphodiester internucleoside linkage.

TABLE 19

RNase H1 expression

| Isis No. | Sequence | Start Site | Stop Site | Concentration (nM) | Protein (% UTC) | SEQ ID NO. |
|---|---|---|---|---|---|---|
| 768080 | $^mC_{es}A_{es}T_{es}T_{es}T_{es}{}^mC_{es}G_{es}A_{es}{}^mC_{es}T_{es}{}^mC_{es}{}^mC_{es}{}^mC_{es}C_{fs}G_{fs}G_{fs}C_f$ | 73 | 88 | 5 | 150 | 38 |
|  |  |  |  | 10 | 125 |  |
|  |  |  |  | 20 | 100 |  |
|  |  |  |  | 40 | 81 |  |
|  |  |  |  | 60 | 78 |  |

Subscripts: "e" indicates a 2'-O-methoxyethyl modification, "f" indicates a 2'-fluoro modification, "s" indicates a phosphorothioate internucleoside linkage.
Superscript "m" in front of a "C" indicates a 5'-methylcytosine.

TABLE 20

RNase H1 expression

| Isis No. | Sequence | Start Site | Stop Site | Concentration (nM) | Protein (% UTC) | SEQ ID NO. |
|---|---|---|---|---|---|---|
| 766741 | $^mC_{es}A_{es}T_{es}T_{es}T_{es}{}^mC_{es}G_{es}A_{es}$ $^mC_{es}T_{es}{}^mC_{es}{}^mC_{es}{}^mC_{es}$ $G_{ks}G_{ks}{}^mC_k$ | 73 | 88 | 5 | 126 | 38 |
|  |  |  |  | 10 | 151 |  |
|  |  |  |  | 20 | 122 |  |
|  |  |  |  | 40 | 121 |  |
|  |  |  |  | 80 | 62 |  |

Subscripts: "e" indicates a 2'-O-methoxyethyl modification, "k" indicates a cEt bicyclic nucleoside, "s" indicates a phosphorothioate internucleoside linkage.
Superscript "m" in front of a "C" indicates a 5'-methylcytosine.

TABLE 21

RNase H1 expression

| Isis No. | Sequence | Start Site | Stop Site | Concentration (nM) | Protein (% mock) | SEQ ID NO. |
|---|---|---|---|---|---|---|
| 806735 | $C_{ms}A_{ms}U_{ms}U_{ms}U_{ms}C_{ms}G_{ms}A_{ms}C_{ms}U_{ms}C_{ms}$ $C_{ms}C_{ms}G_{ms}G_{ks}{}^mC_k$ | 73 | 88 | 20 | 152 | 3 |
| 806736 | $C_{ms}A_{ms}U_{ms}U_{ms}U_{ms}C_{ms}G_{ms}A_{ms}C_{ms}U_{ms}C_{ms}$ $C_{ms}C_{ms}G_{ks}G_{ks}{}^mC_k$ | 73 | 88 | 20 | 165 | 3 |
| 806737 | $C_{ms}A_{ms}U_{ms}U_{ms}U_{ms}C_{ms}G_{ms}A_{ms}C_{ms}U_{ms}C_{ms}$ $C_{ms}{}^mC_{ks}G_{ks}G_{ks}{}^mC_k$ | 73 | 88 | 20 | 183 | 3 |
| 806738 | $C_{ms}A_{ms}U_{ms}U_{ms}U_{ms}C_{ms}G_{ms}A_{ms}C_{ms}U_{ms}C_{ms}$ $^mC_{ks}{}^mC_{ks}G_{ks}G_{ks}{}^mC_k$ | 73 | 88 | 20 | 145 | 3 |

Subscripts: "m" indicates a 2'-O-methyl modification, "k" indicates a cEt bicyclic nucleoside, and "s" indicates a phosphorothioate internucleoside linkage.
Superscript "m" in front of a "C" indicates a 5'-methylcytosine.

TABLE 22

LRPPRC expression

| Isis No. | Sequence | Start Site | Stop Site | Concentration (nM) | Protein (% mock) | SEQ ID NO. |
|---|---|---|---|---|---|---|
| 806739 | $C_{ms}A_{ms}U_{ms}U_{ms}G_{ms}U_{ms}U_{ms}U_{ms}U_{ms}U_{ms}U_{ms}$ $G_{ms}U_{ms}C_{ms}U_{ms}U_{ms}{}^mC_{ks}{}^mC_k$ | 55 | 72 | 20 | 149 | 17 |
| 806740 | $C_{ms}A_{ms}U_{ms}U_{ms}G_{ms}U_{ms}U_{ms}U_{ms}U_{ms}U_{ms}U_{ms}$ $G_{ms}U_{ms}C_{ms}U_{ms}T_{ks}{}^mC_{ks}{}^mC_k$ | 55 | 72 | 20 | 191 | 41 |
| 806741 | $C_{ms}A_{ms}U_{ms}U_{ms}G_{ms}U_{ms}U_{ms}U_{ms}U_{ms}U_{ms}U_{ms}$ $G_{ms}U_{ms}C_{ms}T_{ks}T_{ks}{}^mC_{ks}{}^mC_k$ | 55 | 72 | 20 | 212 | 42 |
| 806742 | $C_{ms}A_{ms}U_{ms}U_{ms}G_{ms}U_{ms}U_{ms}U_{ms}U_{ms}U_{ms}U_{ms}$ $G_{ms}U_{ms}{}^mC_{ks}T_{ks}T_{ks}{}^mC_{ks}{}^mC_k$ | 55 | 72 | 20 | 213 | 42 |

Subscripts: "m" indicates a 2'-O-methyl modification, "k" indicates a cEt bicyclic nucleoside, and "s" indicates a phosphorothioate internucleoside linkage.
Superscript "m" in front of a "C" indicates a 5'-methylcytosine.

Example 12: Effects of Antisense Oligonucleotides Targeting the uORF of Mouse LRPPRC In Vivo Isis No. 761933 (see Example 6) was tested for its effect on LRPPRC protein expression in vivo. Groups of three or four male, seven week old BALB/c mice were systemically administered Isis No. 761933, at a dose listed in the tables below, or saline by subcutaneous injection. Animals were sacrificed (Table 23) or received a second dose (Table 24) 48 hours later. Animals that received a second dose were sacrificed 48 hours after the second dose. Liver homogenates were prepared, and LRPPRC protein expression was analyzed by western blot, as described in Example 6. The results are shown in the tables below as the percent expression relative to saline treated animals following normalization to the loading control (GAPDH or hnRNP K). The results show that LRPPRC protein expression was increased in vivo following treatment with an antisense oligonucleotide targeting the LRPPRC uORF.

TABLE 23

| LRPPRC expression following single dose in vivo | |
|---|---|
| Isis No. 761933 dose (mg/kg) | Protein (% UTC) |
| 75 | 137 |

TABLE 24

| LRPPRC expression following two doses in vivo | |
|---|---|
| Isis No. 761933 dose (mg/kg) | Protein (% UTC) |
| 3.125 | 109 |
| 6.25 | 124 |
| 12.5 | 136 |
| 25 | 183 |
| 50 | 169 |
| 100 | 109 |
| 200 | 98 |

Example 13: Effects of Antisense Oligonucleotides Targeting the uORF of Mouse THPO In Vivo Mouse Thrombopoietin (THPO) mRNA (GENBANK accession number NM_009379.2, designated herein as SEQ ID NO: 43) comprises an upstream open reading frame. Isis No. 809793 (see the table below) was designed to target the start codon of the uORF of mouse THPO and tested for its effect on THPO protein expression in vivo. The start and stop sites listed in Table 25 indicate the positions on SEQ ID NO: 43 that the antisense oligonucleotide targets. Groups of three mice were systemically administered Isis No. 809793, at a dose listed in the table below, or saline by subcutaneous injection. The animals were sacrificed 48 hours later, and serum and bone marrow was collected. Serum THPO protein expression was analyzed by western blot, as described in Example 9, and bone marrow THPO mRNA expression was analyzed by RT-PCR. Bone marrow THPO mRNA levels were unaffected by the antisense oligonucleotide treatment (data not shown). The results shown in the table below are the average of two independent experiments and are shown as the percent expression relative to saline treated animals following normalization to the loading control (Transferrin). The results show that THPO protein expression was increased in vivo following treatment with an antisense oligonucleotide targeting the THPO uORF.

TABLE 25

| Mouse THPO expression | | | | | | |
|---|---|---|---|---|---|---|
| Isis No. | Sequence | Start Site | Stop Site | Dose (mg/kg) | THPO protein (% mock) | SEQ ID NO. |
| 809793 | $C_{ms}A_{ms}U_{ms}G_{ms}G_{ms}A_{ms}G_{ms}G_{ms}C_{ms}G_{ms}$ $G_{ms}C_{ms}U_{ms}U_{ms}G_{ms}A_{ms}G_{m}$ | 309 | 325 | 12.5 | 146 | 44 |
| | | | | 25 | 457 | |
| | | | | 50 | 240 | |
| | | | | 75 | 244 | |

Subscripts: "m" indicates a 2'-O-methyl modification, and "s" indicates a phosphorothioate internucleoside linkage.

Example 14: Inhibition of a uORF Targeting Oligonucleotide with a Complementary Oligonucleotide In order to test whether increased translation that is mediated by an oligonucleotide targeting a uORF could be reversed, the effect of an oligonucleotide complementary to the uORF targeting oligonucleotide was tested in vitro. HeLa cells were transfected with 20 nM of Isis No. 761909, as described in Example 1. Five hours later, the cells were transfected with a concentration of Isis No. 761929, which is complementary to Isis No. 761909, listed in the table below. Five hours after the second transfection, cells were lysed and RNase H1 protein expression was analyzed as described in Example 1, with γ-tubulin used as the loading control. The results are shown in the table below as the percent expression relative to mock transfected cells following normalization to the γ-tubulin loading control. The results show that an oligonucleotide targeted to a uORF targeting oligonucleotide blocked the uORF targeting oligonucleotide's ability to increase translation in a dose dependent manner.

Isis No. 761930 for 7 hours, and incubated with pre-warmed medium lacking methionine (Invitrogen, RPMI 1640) at 37° C. for 30 minutes. Cells were then pulse-labeled with 35 µCi/ml $S^{35}$-methionine in RPMI1640 medium for 20 minutes and chased with 1 mM methionine for 40 minutes. Cells were washed with cold PBS containing 10 µg/ml cycloheximide and cell lysate were prepared using IP buffer (Life Technologies). Immunoprecipitation was conducted using anti-LRPPRC antibody (Proteintech) at 4° C. for 3 hours. After 4 washes, the precipitated proteins were analyzed on a 4-12% SDS-PAGE gel, transferred to a membrane, and visualized by autoradiography. The LRPPRC band in the immunoprecipitate from the mock treated cells was significantly lighter than in the immunoprecipitate from the Isis No. 761930 treated cells (data not shown), further confirming that antisense oligonucleotides targeting a uORF increase protein expression via increasing target protein translation. Furthermore, the lysate inputs for both the mock and Isis No. 761930 transfected cells were also analyzed via autoradiography and were very similar, indicating that the increased translation was target specific.

TABLE 26

RNase H1 expression

| Isis No. | Sequence | Concentration 761909 (nM) | Concentration 761929 (nM) | RNase H1 protein (% mock) | SEQ ID NO. |
|---|---|---|---|---|---|
| 761929 | $G_{mo}C_{mo}C_{mo}G_{mo}G_{mo}G_{mo}A_{mo}$ | 20 | 0 | 185 | 45 |
|  | $G_{mo}U_{mo}C_{mo}G_{mo}A_{mo}A_{mo}A_{mo}$ | 20 | 10 | 161 |  |
|  | $U_{mo}G_m$ | 20 | 20 | 120 |  |
|  |  | 20 | 30 | 103 |  |
|  |  | 20 | 40 | 97 |  |

Subscripts: "m" indicates a 2'-O-methyl modification and "o" indicates a phosphodiester internucleoside linkage.

Example 15: Inhibition of a uORF Targeting Oligonucleotide by Globally Blocking Translation In order to test whether increases in protein expression mediated by antisense oligonucleotides targeting a uORF are due to increased protein stability, translation was blocked following transfection of the oligonucleotide. HeLa cells were transfected with Isis No. 761909 (see Example 1) or mock transfected. Twelve hours later, cells were treated with DMSO or 15 µg/ml cycloheximide at 37° C. Cells were then collected at various time points and cell lysates were prepared and subjected to western analysis, as described in Example 1. A duplicate SDS-PAGE gel was silver-stained and served as loading control. RNase H1 protein levels were calculated relative to mock transfected cells following normalization to the loading control. The results (data not shown) showed that the rates of reduction of RNase H1 protein levels following cycloheximide treatment were similar for mock and Isis No. 761909 transfected cells. Thus, these results, along with the lack of increase in mRNA shown in several above examples, show that increases in protein expression mediated by antisense oligonucletoides targeting a uORF are due to increased protein translation.

Example 16: Effect of a uORF Targeting Antisense Oligonucleotide on Nascent Protein Translation In order to further confirm that antisense oligonucleotides targeting a uORF mediate an increase in translation of new protein, pulse-chase labeling and immunoprecipitation of LRPPRC was performed. MHT cells were transfected with

Example 17: Effect of an Antisense Oligonucleotide Targeting the uORF of RNase H1 on RNase H1 Activity In order to test whether the increase in RNase H1 protein levels mediated by antisense oligonucleotides targeting a RNase H1 uORF results in an increase in RNase H1 activity, cells were first transfected with Isis No. 761909 (see Example 1) or a control oligonucleotide that does not target RNase H1, Isis No. 759704, then transfected with an antisense oligonucleotide targeting U16 snoRNA or NCL1 mRNA. Ten hours after the first transfection, the cells were reseeded at approximately 50% confluency. Cells were transfected a second time 14 hours later with Isis No. 462026 (U16) or Isis No. 110074 (NCL1) for an additional 4 hours. Cells were then collected, lysed, and U16 snoRNA or NCL1 mRNA levels were analyzed by RT-qPCR using TaqMan primer probe sets. The primer probe set sequences used were: Forward: 5'-CTTGCAATGATGTCGTAAT-TTGC-3', SEQ ID NO: 46, Reverse: 5'-TCGT-CAACCTTCTGTACCAGCTT-3', SEQ ID NO: 47, and Probe: 5'-TTACTCTGTTCTCAGCGACAGTTGCCTGC-3', SEQ ID NO: 48 for U16; and Forward: 5'-GCTTGGCTTCTTCTGGACTCA-3', SEQ ID NO: 49, Reverse: 5'-TCGCGAGCTTCACCATGA-3', SEQ ID NO: 50, and Probe: 5'-CGCCACTTGTCCGCTTCACACTCC-3', SEQ ID NO: 51 for NCL1. The results are shown in the tables below as the percent RNA levels relative to untreated control cells that were not transfected with any oligonucleotide, normalized to total RNA as measured using Ribogreen. The results show that Isis No. 761909 targeting a RNase H1 uORF increased the antisense activity of U16 and NCl1 antisense oligonucleotides.

TABLE 27

U16 snoRNA expression

| 1st ASO | | | SEQ | 2nd ASO | | | | SEQ |
|---|---|---|---|---|---|---|---|---|
| Isis No. | Sequence | Concentration (nM) | ID No. | Isis No. | Sequence | Concentration (nM) | mRNA (%) | ID No. |
| Control 759704 | $C_{mo} A_{mo} U_{mo} U_{mo}$ $G_{mo} U_{mo} U_{mo} U_{mo}$ $U_{mo} U_{mo} U_{mo} G_{mo}$ $U_{mo} C_{mo} U_{mo} U_{m}$ | 20 20 20 20 20 | 18 | 462026 | $^mC_{es}A_{es}G_{es}{}^mC_{es}A_{es}G_{ds}$ $G_{ds}{}^mC_{ds}A_{ds}A_{ds}{}^mC_{ds}$ $T_{ds}G_{ds}T_{ds}{}^mC_{ds}G_{es}{}^mC_{es}$ $T_{es}G_{es}A_{e}$ | 1.25 2.5 5 10 20 | 97 98 97 83 75 | 52 |
| uORF 761909 | $C_{mo}A_{mo}U_{mo}U_{mo}U_{mo}$ $C_{mo}G_{mo}A_{mo}C_{mo}$ $U_{mo}C_{mo}C_{mo}C_{mo}$ $G_{mo}G_{mo}C_{m}$ | 20 20 20 20 20 | 3 | 462026 | $^mC_{es}A_{es}G_{es}{}^mC_{es}A_{es}G_{ds}$ $G_{ds}{}^mC_{ds}A_{ds}A_{ds}{}^mC_{ds}$ $T_{ds}G_{ds}T_{ds}{}^mC_{ds}G_{es}$ $^mC_{es}T_{es}G_{es}A_{e}$ | 1.25 2.5 5 10 20 | 90 76 70 61 49 | 52 |

Subscripts: "e" indicates a 2'-O-methoxyethyl modification, "d" indicates a 2'-deoxynucleoside, and "s" indicates a phosphorothioate internucleoside linkage.
Superscript "m" in front of a "C" indicates a 5'-methylcytosine.

TABLE 28

NCL1 mRNA expression

| 1st ASO | | | SEQ | 2nd ASO | | | | SEQ |
|---|---|---|---|---|---|---|---|---|
| Isis No. | Sequence | Concentration (nM) | ID No. | Isis No. | Sequence | Concentration (nM) | mRNA (%) | ID No. |
| Control 759704 | $C_{mo} A_{mo} U_{mo} U_{mo}$ $G_{mo} U_{mo} U_{mo} U_{mo}$ $U_{mo} U_{mo} U_{mo} G_{mo}$ $U_{mo} C_{mo} U_{mo} U_{m}$ | 20 20 20 20 20 | 18 | 110074 | $G_{es}T_{es}{}^mC_{es}A_{es}T_{es}{}^mC_{ds}$ $G_{ds}T_{ds}{}^mC_{ds}A_{ds}T_{ds}$ $^mC_{ds}{}^mC_{ds}T_{ds}{}^mC_{ds}A_{es}$ $T_{es}{}^mC_{es}A_{es}T_{e}$ | 1.25 2.5 5 10 20 | 96 95 96 79 45 | 53 |
| uORF 761909 | $C_{mo}A_{mo}U_{mo}U_{mo}U_{mo}$ $C_{mo}G_{mo}A_{mo}C_{mo}$ $U_{mo}C_{mo}C_{mo}C_{mo}G_{mo}$ $G_{mo}C_{m}$ | 20 20 20 20 20 | 3 | 110074 | $G_{es}T_{es}{}^mC_{es}A_{es}T_{es}{}^mC_{ds}$ $G_{ds}T_{ds}{}^mC_{ds}A_{ds}T_{ds}$ $^mC_{ds}{}^mC_{ds}T_{ds}{}^mC_{ds}A_{es}$ $T_{es}{}^mC_{es}A_{es}T_{e}$ | 1.25 2.5 5 10 20 | 93 91 87 62 32 | 53 |

Subscripts: "e" indicates a 2'-O-methoxyethyl modification, "d" indicates a 2'-deoxynucleoside, and "s" indicates a phosphorothioate internucleoside linkage.
Superscript "m" in front of a "C" indicates a 5'-methylcytosine.

Example 18: Effects of Antisense Oligonucleotides Targeting the 5'-Untranslated Region of RNase H1

Antisense oligonucleotides designed to target the 5'-untranslated region upstream of the uORF of human RNase H1 were tested for their effects on RNase H1 protein expression in vitro. The start and stop sites listed in the tables below indicate the positions on SEQ ID NO: 1 that the antisense oligonucleotides target. HEK 293 cells were transfected with 20 nM antisense oligonucleotide or were mock transfected as a control. Ten hours after transfection, RNase H1 protein expression was analyzed as described in Example 1. The results are shown in the tables below as percent protein expression relative to mock transfected cells following normalization to the GAPDH loading control. The results show that many antisense oligonucleotides targeting the 5'-untranslated region upstream of the RNase H1 uORF induced translation of the target.

TABLE 29

RNase H1 expression

| Isis No. | Sequence | Start Site | Stop Site | Protein (% mock) | SEQ ID NO. |
|---|---|---|---|---|---|
| 761772 | $A_{mo} A_{mo} G_{mo} A_{mo} U_{mo} G_{mo} A_{mo} C_{mo} G_{mo}$ $C_{mo} A_{mo} C_{mo} G_{mo} U_{mo} C_{mo} U_{m}$ | 1 | 16 | 142 | 54 |
| 761773 | $G_{mo} G_{mo} A_{mo} A_{mo} G_{mo} A_{mo} U_{mo} G_{mo} A_{mo}$ $C_{mo} G_{mo} C_{mo} A_{mo} C_{mo} G_{mo} U_{m}$ | 3 | 18 | 155 | 55 |

TABLE 29-continued

RNase H1 expression

| Isis No. | Sequence | Start Site | Stop Site | Protein (% mock) | SEQ ID NO. |
|---|---|---|---|---|---|
| 761774 | $C_{mo}$ $G_{mo}$ $G_{mo}$ $G_{mo}$ $A_{mo}$ $A_{mo}$ $G_{mo}$ $A_{mo}$ $U_{mo}$ $G_{mo}$ $A_{mo}$ $C_{mo}$ $G_{mo}$ $C_{mo}$ $A_{mo}$ $C_m$ | 5 | 20 | 179 | 56 |
| 761775 | $C_{mo}$ $G_{mo}$ $C_{mo}$ $G_{mo}$ $G_{mo}$ $G_{mo}$ $A_{mo}$ $A_{mo}$ $G_{mo}$ $A_{mo}$ $U_{mo}$ $G_{mo}$ $A_{mo}$ $C_{mo}$ $G_{mo}$ $C_m$ | 7 | 22 | 259 | 57 |

TABLE 30

RNase H1 expression

| Isis No. | Sequence | Start Site | Stop Site | Protein (% mock) | SEQ ID NO. |
|---|---|---|---|---|---|
| 761778 | $C_{mo}$ $A_{mo}$ $C_{mo}$ $C_{mo}$ $G_{mo}$ $G_{mo}$ $C_{mo}$ $G_{mo}$ $C_{mo}$ $G_{mo}$ $G_{mo}$ $G_{mo}$ $A_{mo}$ $A_{mo}$ $G_{mo}$ $A_m$ | 13 | 28 | 132 | 58 |
| 761779 | $G_{mo}$ $U_{mo}$ $C_{mo}$ $A_{mo}$ $C_{mo}$ $C_{mo}$ $G_{mo}$ $G_{mo}$ $C_{mo}$ $G_{mo}$ $C_{mo}$ $G_{mo}$ $G_{mo}$ $G_{mo}$ $A_{mo}$ $A_m$ | 15 | 30 | 164 | 59 |
| 761780 | $C_{mo}$ $C_{mo}$ $G_{mo}$ $U_{mo}$ $C_{mo}$ $A_{mo}$ $C_{mo}$ $C_{mo}$ $G_{mo}$ $G_{mo}$ $C_{mo}$ $G_{mo}$ $C_{mo}$ $G_{mo}$ $G_{mo}$ $G_m$ | 17 | 32 | 182 | 60 |
| 761781 | $U_{mo}$ $U_{mo}$ $C_{mo}$ $C_{mo}$ $G_{mo}$ $U_{mo}$ $C_{mo}$ $A_{mo}$ $C_{mo}$ $C_{mo}$ $G_{mo}$ $G_{mo}$ $C_{mo}$ $G_{mo}$ $C_{mo}$ $G_m$ | 19 | 34 | 226 | 61 |
| 761782 | $A_{mo}$ $C_{mo}$ $U_{mo}$ $U_{mo}$ $C_{mo}$ $C_{mo}$ $G_{mo}$ $U_{mo}$ $C_{mo}$ $A_{mo}$ $C_{mo}$ $C_{mo}$ $G_{mo}$ $G_{mo}$ $C_{mo}$ $G_m$ | 21 | 36 | 229 | 62 |
| 761783 | $G_{mo}$ $C_{mo}$ $A_{mo}$ $C_{mo}$ $U_{mo}$ $U_{mo}$ $C_{mo}$ $C_{mo}$ $G_{mo}$ $U_{mo}$ $C_{mo}$ $A_{mo}$ $C_{mo}$ $C_{mo}$ $G_{mo}$ $G_m$ | 23 | 38 | 259 | 63 |
| 761784 | $C_{mo}$ $C_{mo}$ $G_{mo}$ $C_{mo}$ $A_{mo}$ $C_{mo}$ $U_{mo}$ $U_{mo}$ $C_{mo}$ $C_{mo}$ $G_{mo}$ $U_{mo}$ $C_{mo}$ $A_{mo}$ $C_{mo}$ $C_m$ | 25 | 40 | 237 | 64 |

TABLE 31

RNase H1 expression

| Isis No. | Sequence | Start Site | Stop Site | Protein (% mock) | SEQ ID NO. |
|---|---|---|---|---|---|
| 761785 | $C_{mo}$ $A_{mo}$ $C_{mo}$ $C_{mo}$ $G_{mo}$ $C_{mo}$ $A_{mo}$ $C_{mo}$ $U_{mo}$ $U_{mo}$ $C_{mo}$ $C_{mo}$ $G_{mo}$ $U_{mo}$ $C_{mo}$ $A_m$ | 27 | 42 | 170 | 65 |
| 761786 | $A_{mo}$ $A_{mo}$ $C_{mo}$ $A_{mo}$ $C_{mo}$ $C_{mo}$ $G_{mo}$ $C_{mo}$ $A_{mo}$ $C_{mo}$ $U_{mo}$ $U_{mo}$ $C_{mo}$ $C_{mo}$ $G_{mo}$ $U_m$ | 29 | 44 | 186 | 66 |
| 761787 | $U_{mo}$ $C_{mo}$ $A_{mo}$ $A_{mo}$ $C_{mo}$ $A_{mo}$ $C_{mo}$ $C_{mo}$ $G_{mo}$ $C_{mo}$ $A_{mo}$ $C_{mo}$ $U_{mo}$ $U_{mo}$ $C_{mo}$ $C_m$ | 31 | 46 | 197 | 67 |
| 761788 | $G_{mo}$ $C_{mo}$ $U_{mo}$ $C_{mo}$ $A_{mo}$ $A_{mo}$ $C_{mo}$ $A_{mo}$ $C_{mo}$ $C_{mo}$ $G_{mo}$ $C_{mo}$ $A_{mo}$ $C_{mo}$ $U_{mo}$ $U_m$ | 33 | 48 | 210 | 68 |
| 761789 | $G_{mo}$ $C_{mo}$ $G_{mo}$ $C_{mo}$ $U_{mo}$ $C_{mo}$ $A_{mo}$ $A_{mo}$ $C_{mo}$ $A_{mo}$ $C_{mo}$ $C_{mo}$ $G_{mo}$ $C_{mo}$ $A_{mo}$ $C_m$ | 35 | 50 | 211 | 69 |
| 761790 | $C_{mo}$ $G_{mo}$ $G_{mo}$ $C_{mo}$ $G_{mo}$ $C_{mo}$ $U_{mo}$ $C_{mo}$ $A_{mo}$ $A_{mo}$ $C_{mo}$ $A_{mo}$ $C_{mo}$ $C_{mo}$ $G_{mo}$ $C_m$ | 37 | 52 | 202 | 70 |
| 761791 | $G_{mo}$ $C_{mo}$ $C_{mo}$ $G_{mo}$ $G_{mo}$ $C_{mo}$ $G_{mo}$ $C_{mo}$ $U_{mo}$ $C_{mo}$ $A_{mo}$ $A_{mo}$ $C_{mo}$ $A_{mo}$ $C_{mo}$ $C_m$ | 39 | 54 | 173 | 71 |
| 761792 | $C_{mo}$ $C_{mo}$ $G_{mo}$ $C_{mo}$ $C_{mo}$ $G_{mo}$ $G_{mo}$ $C_{mo}$ $G_{mo}$ $C_{mo}$ $U_{mo}$ $C_{mo}$ $A_{mo}$ $A_{mo}$ $C_{mo}$ $A_m$ | 41 | 56 | 120 | 72 |

TABLE 32

RNase H1 expression

| Isis No. | Sequence | Start Site | Stop Site | Protein (% mock) | SEQ ID NO. |
|---|---|---|---|---|---|
| 761776 | $G_{mo}$ $G_{mo}$ $C_{mo}$ $G_{mo}$ $C_{mo}$ $G_{mo}$ $G_{mo}$ $G_{mo}$ $A_{mo}$ $A_{mo}$ $G_{mo}$ $A_{mo}$ $U_{mo}$ $G_{mo}$ $A_{mo}$ $C_m$ | 9 | 24 | 130 | 73 |
| 761794 | $C_{mo}$ $G_{mo}$ $A_{mo}$ $G_{mo}$ $C_{mo}$ $C_{mo}$ $G_{mo}$ $C_{mo}$ $C_{mo}$ $G_{mo}$ $G_{mo}$ $C_{mo}$ $G_{mo}$ $C_{mo}$ $U_{mo}$ $C_m$ | 45 | 60 | 92 | 74 |
| 761796 | $G_{mo}$ $G_{mo}$ $C_{mo}$ $G_{mo}$ $C_{mo}$ $G_{mo}$ $A_{mo}$ $G_{mo}$ $C_{mo}$ $C_{mo}$ $G_{mo}$ $C_{mo}$ $C_{mo}$ $G_{mo}$ $G_{mo}$ $C_m$ | 49 | 64 | 94 | 75 |
| 761798 | $C_{mo}$ $G_{mo}$ $U_{mo}$ $G_{mo}$ $G_{mo}$ $G_{mo}$ $C_{mo}$ $G_{mo}$ $C_{mo}$ $G_{mo}$ $A_{mo}$ $G_{mo}$ $C_{mo}$ $C_{mo}$ $G_{mo}$ $C_m$ | 53 | 68 | 84 | 76 |
| 761800 | $C_{mo}$ $C_{mo}$ $A_{mo}$ $G_{mo}$ $C_{mo}$ $G_{mo}$ $U_{mo}$ $G_{mo}$ $G_{mo}$ $G_{mo}$ $C_{mo}$ $G_{mo}$ $C_{mo}$ $G_{mo}$ $A_{mo}$ $G_m$ | 57 | 72 | 71 | 77 |

Subscripts: "m" indicates a 2'-O-methyl modification, and "o" indicates a phosphodiester internucleoside linkage.

Example 19: Effects of Antisense Oligonucleotides Targeting the 5'-Untranslated Region of ACP1

Antisense oligonucleotides designed to target the 5'-untranslated region of cytoplasmic phosphotyrosine protein phosphatase (ACP1), which does not comprise a uORF, were tested for their effects on ACP1 protein expression in vitro. The antisense oligonucleotides target the human ACP1 mRNA (GENBANK accession number NM_004300.3, designated herein as SEQ ID NO: 78) and were designed to target at least one stem loop structure in the 5'-untranslated region. The start and stop sites listed in the table below indicate the positions on SEQ ID NO: 78 that the antisense oligonucleotides target. HEK 293 cells were transfected with a concentration of antisense oligonucleotide shown in the table below or were not transfected as a control. Ten hours after transfection, ACP1 protein expression was analyzed by western blot using an Abcam antibody to ACP1 (catalog #ab166896). The results are shown in the tables below as percent protein expression relative to untreated control cells following normalization to the p32 loading control. The results show that the antisense oligonucleotides targeting the 5'-untranslated region of human ACP1 induced translation of the target.

TABLE 33

ACP1 expression

| Isis No. | Sequence | Start Site | Stop Site | Concentration (nM) | Protein (% mock) | SEQ ID NO. |
|---|---|---|---|---|---|---|
| 812652 | $C_{mo}$ $G_{mo}$ $A_{mo}$ $C_{mo}$ $G_{mo}$ $C_{mo}$ $G_{mo}$ $G_{mo}$ $C_{mo}$ $G_{mo}$ $C_{mo}$ $A_{mo}$ $G_{mo}$ $G_{mo}$ $C_{mo}$ $G_m$ | 36 | 51 | 5 | 112 | 79 |
| | | | | 10 | 130 | |
| | | | | 20 | 116 | |
| | | | | 40 | 165 | |
| | | | | 80 | 172 | |
| 812658 | $G_{mo}$ $C_{mo}$ $G_{mo}$ $C_{mo}$ $A_{mo}$ $G_{mo}$ $G_{mo}$ $C_{mo}$ $G_{mo}$ $C_{mo}$ $A_{mo}$ $C_{mo}$ $U_{mo}$ $G_{mo}$ $C_{mo}$ $C_{mo}$ $A_{mo}$ $C_m$ | 27 | 44 | 5 | 121 | 80 |
| | | | | 10 | 161 | |
| | | | | 20 | 164 | |
| | | | | 40 | 119 | |
| | | | | 80 | 129 | |

Subscripts: "m" indicates a 2'-O-methyl modification, and "o" indicates a phosphodiester internucleoside linkage.

Example 20: Effects of Antisense Oligonucleotides Targeting the 5'-Untranslated Region Downstream of the CFTR uORF Start Codon on CFTR Protein Expression Antisense oligonucleotides designed to target the 5'-untranslated region downstream of the uORF start codon of human cystic fibrosis transmembrane conductance regulator (CFTR) were tested for their effects on CFTR protein expression in vitro. These antisense oligonucleotides, described in the table below, were designed to target the CFTR mRNA (GENBANK accession number NM_000492.3, designated herein as SEQ ID NO: 81) and were uniformly modified in order to avoid inducing cleavage of the target RNA. The start and stop sites listed in the table below indicate the positions on SEQ ID NO: 81 that the antisense oligonucleotides target. One uORF begins at position 13 of SEQ ID NO: 81. Isis No. 786455 targets a portion of the uORF that is just downstream of the uORF start codon. Isis No. 786456 targets a stem loop structure further downstream.

HT-29 cells were transfected with a concentration of antisense oligonucleotide listed in the table below or were mock transfected as a control. Twelve or twenty-two hours after transfection, CFTR expression was analyzed by western blot using Anti-CFTR purchased from EMD Millipore (catalog #05-583, clone M3A7). The results are shown in the table below as percent protein expression relative to mock transfected cells following normalization to the HSP90 loading control. The results show that the antisense oligonucleotides increased CFTR protein expression.

TABLE 34

CFTR expression

| Isis No. | Sequence | Start Site | Stop Site | Time point (h) | Concentration (nM) | Protein (% mock) | SEQ ID NO. |
|---|---|---|---|---|---|---|---|
| 786455 | $U_{ms}$ $U_{ms}$ $C_{ms}$ $U_{ms}$ $C_{ms}$ $U_{ms}$ $G_{ms}$ $A_{ms}$ $C_{ms}$ $C_{ms}$ $U_{ms}$ $G_{ms}$ $C_{ms}$ $U_{ms}$ $G_{ms}$ $U_{ms}$ $G_{ms}$ $A_{m}$ | 19 | 36 | 12 | 12.5 | 142 | 82 |
|  |  |  |  |  | 25 | 151 |  |
|  |  |  |  |  | 50 | 150 |  |
|  |  |  |  |  | 100 | 86 |  |
|  |  |  |  | 22 | 12.5 | 59 |  |
|  |  |  |  |  | 25 | 93 |  |
|  |  |  |  |  | 50 | 146 |  |
|  |  |  |  |  | 100 | 192 |  |
| 786456 | $C_{ms}$ $C_{ms}$ $A_{ms}$ $A_{ms}$ $A_{ms}$ $G_{ms}$ $A_{ms}$ $C_{ms}$ $C_{ms}$ $U_{ms}$ $A_{ms}$ $C_{ms}$ $U_{ms}$ $A_{ms}$ $C_{ms}$ $U_{ms}$ $C_{ms}$ $U_{m}$ | 60 | 77 | 22 | 12.5 | 105 | 83 |
|  |  |  |  |  | 25 | 140 |  |
|  |  |  |  |  | 50 | 186 |  |
|  |  |  |  |  | 75 | 186 |  |
|  |  |  |  |  | 100 | 390 |  |
|  |  |  |  |  | 150 | 181 |  |
|  |  |  |  |  | 200 | 262 |  |

Subscripts: "m" indicates a 2'-O-methyl modification, and "s" indicates a phosphorothioate internucleoside linkage.

Example 21: Identification of a Translation Suppression Element that does not Comprise a uORF In order to test the effect of portions of the RNase H1 5'-UTR sequence on RNase H1 expression, the wild type and mutant 5'-UTR sequences were cloned into a plasmid and fused to firefly luciferase. Renila luciferase was cloned into the same plasmids for normalization. The plasmids were transfected into HeLa cells and firefly and Renila luciferase activities were detected using standard methods. The mutants and their firefly luciferase activity relative to the wild type 5'-UTR reporters, normalized to Renila luciferase activity, are shown in the table below. The nucleotide positions reported in the table below refer to the positions of the 5'-UTR of SEQ ID NO: 1 that were mutated or deleted. The results are the averages of multiple experiments and show that the mutation and/or deletion of portions of the 5'-UTR sequence of RNase H1, including portions that do not comprise a uORF, resulted in increased expression in a reporter system, indicating that the mutated portions are part of a translation suppression element.

TABLE 35

Firefly luciferase activity

| Mutation | Deletion | Firefly luciferase activity (%) |
|---|---|---|
| AUG -> UUG (uORF start codon) | n/a | 770 |
| AUG -> UUG (uORF start codon) | Nucleotides 30-60 | 980 |
| GACGGAAGT-> CAGCCTTCA, nucleotides 28-36 | n/a | 1380 |
| CGGTG->GCCAC nucleotides 38-42 | n/a | 680 |
| CGGTG->GCCAC & CGCCG->GCGGC, nucleotides 38-42 & 48-52 | n/a | 600 |

Example 22: Effects of Antisense Oligonucleotides Targeting the uORF of Mouse LRPPRC In Vivo Isis No. 806740 (see Example 11) was tested for its effect on LRPPRC protein expression in vivo. Groups of three, male, seven week old BALB/c mice were systemically administered Isis No. 806740, at a dose listed in the table below, or saline by subcutaneous injection. 48 hours later, the mice received a second dose listed in the table below. Animals were sacrificed 48 hours after the second dose. Liver homogenates were prepared, and LRPPRC protein expression was analyzed by western blot, as described in Example 6. The results are shown in the tables below as the percent expression relative to saline treated animals following normalization to the loading control (PSF). The results show that LRPPRC protein expression was increased in vivo following treatment with an antisense oligonucleotide targeting the LRPPRC uORF and comprising bicyclic nucleic acids.

TABLE 36

LRPPRC expression in vivo

| Isis No. 806740 dose (mg/kg) | Protein (% UTC) |
|---|---|
| 12.5 | 126 |
| 25 | 171 |
| 50 | 113 |
| 100 | 120 |

Example 23: Effects of Antisense Oligonucleotides Targeting the 5'-Untranslated Region of ACP1

Effects of antisense oligonucleotides designed to target the 5'-untranslated region of ACP1, which does not comprise a uORF, are shown above (see Example 19). Additional antisense oligonucleotides designed to target the 5'-untranslation region of ACP1 were tested for their effects on ACP1 protein expression in vitro. The antisense oligonucleotides target the human ACP1 mRNA (GENBANK accession number NM_004300.3, designated herein as SEQ ID NO: 78). The start and stop sites listed in the table below indicate the positions on SEQ ID NO: 78 that the antisense oligonucleotides target. HeLa cells were transfected with 25 nM of an antisense oligonucleotide shown in the table below or were not transfected as a control. Ten hours after transfection, ACP1 protein expression was analyzed by western blot using an Abcam antibody to ACP1 (catalog #ab166896). The results are shown in the tables below as percent protein expression relative to untreated control cells following normalization to the Annexin A2 loading control.

TABLE 37

ACP1 expression

| Isis No. | Sequence | Start Site | Stop Site | Protein (% mock) | SEQ ID NO. |
|---|---|---|---|---|---|
| 812658 | $G_{mo}$ $C_{mo}$ $G_{mo}$ $C_{mo}$ $A_{mo}$ $G_{mo}$ $G_{mo}$ $C_{mo}$ $G_{mo}$ $C_{mo}$ $A_{mo}$ $C_{mo}$ $U_{mo}$ $G_{mo}$ $C_{mo}$ $C_{mo}$ $A_{mo}$ $C_m$ | 27 | 44 | 127 | 80 |
| 812650 | $A_{mo}$ $G_{mo}$ $G_{mo}$ $C_{mo}$ $G_{mo}$ $C_{mo}$ $A_{mo}$ $C_{mo}$ $U_{mo}$ $G_{mo}$ $C_{mo}$ $C_{mo}$ $A_{mo}$ $C_m$ | 27 | 40 | 142 | 84 |
| (XL500) | $G_{mo}$ $C_{mo}$ $A_{mo}$ $G_{mo}$ $G_{mo}$ $C_{mo}$ $G_{mo}$ $C_{mo}$ $A_{mo}$ $C_{mo}$ $U_{mo}$ $G_{mo}$ $C_{mo}$ $C_m$ | 29 | 42 | 147 | 85 |
| 812651 | $G_{mo}$ $C_{mo}$ $G_{mo}$ $C_{mo}$ $A_{mo}$ $G_{mo}$ $G_{mo}$ $C_{mo}$ $G_{mo}$ $C_{mo}$ $A_{mo}$ $C_{mo}$ $U_{mo}$ $G_m$ | 31 | 44 | 107 | 86 |
| (XL502) | $C_{mo}$ $G_{mo}$ $G_{mo}$ $C_{mo}$ $G_{mo}$ $C_{mo}$ $A_{mo}$ $G_{mo}$ $G_{mo}$ $C_{mo}$ $G_{mo}$ $C_{mo}$ $A_{mo}$ $C_m$ | 33 | 46 | 100 | 87 |
| (XL503) | $C_{mo}$ $G_{mo}$ $C_{mo}$ $G_{mo}$ $G_{mo}$ $C_{mo}$ $G_{mo}$ $C_{mo}$ $A_{mo}$ $G_{mo}$ $G_{mo}$ $C_{mo}$ $G_{mo}$ $C_m$ | 35 | 48 | 58 | 88 |
| (XL504) | $G_{mo}$ $A_{mo}$ $C_{mo}$ $G_{mo}$ $C_{mo}$ $G_{mo}$ $G_{mo}$ $C_{mo}$ $G_{mo}$ $C_{mo}$ $A_{mo}$ $G_{mo}$ $G_{mo}$ $C_m$ | 37 | 50 | 107 | 89 |

Subscripts: "m" indicates a 2'-O-methyl modification, and "o" indicates a phosphodiester internucleoside linkage.

Example 24: Effects of Antisense Oligonucleotides Targeting ACP1 Comprising Various Modifications Antisense oligonucleotides designed to target the same or similar site of the 5'-untranslated region of ACP1 as Isis No. 812658 (see Examples 19 and 23) were designed with various modifications and tested for their effects on ACP1 protein expression in vitro. The start and stop sites listed in the table below indicate the positions on SEQ ID NO: 78 that the antisense oligonucleotides target. HeLa cells were transfected with a concentration of an antisense oligonucleotide shown in the tables below or were not transfected as a control. Ten hours after transfection, ACP1 protein expression was analyzed by western blot using an Abcam antibody to ACP1 (catalog #ab166896). The results are shown in the tables below as percent protein expression relative to untreated control cells following normalization to the Annexin A2 or TMED9 loading control.

TABLE 38

ACP1 expression

| Isis No. | Sequence | Start Site | Stop Site | Concentration (nM) | Protein (% mock) | SEQ ID NO. |
|---|---|---|---|---|---|---|
| 812675 | $G_{ms}$ $C_{ms}$ $A_{ms}$ $G_{ms}$ $G_{ms}$ $C_{ms}$ $G_{ms}$ $C_{ms}$ $A_{ms}$ $C_{ms}$ $U_{ms}$ $G_{ms}$ $C_{ms}$ $C_{ms}$ $A_{ms}$ $C_m$ | 27 | 42 | 5<br>10<br>20<br>40<br>80 | 161<br>147<br>227<br>193<br>98 | 90 |
| 812653 | $G_{mo}$ $C_{mo}$ $A_{mo}$ $G_{mo}$ $G_{mo}$ $C_{mo}$ $G_{mo}$ $C_{mo}$ $A_{mo}$ $C_{mo}$ $U_{mo}$ $G_{mo}$ $C_{mo}$ $C_{mo}$ $A_{mo}$ $C_m$ | 27 | 42 | 5<br>10<br>20<br>40<br>80 | 87<br>167<br>182<br>139<br>124 | 90 |

TABLE 39

ACP1 expression

| Isis No. | Sequence | Start Site | Stop Site | Concentration (nM) | Protein (% mock) | SEQ ID NO. |
|---|---|---|---|---|---|---|
| 813860 | $G_{ms}$ $C_{ms}$ $G_{ms}$ $C_{ms}$ $A_{ms}$ $G_{ms}$ $G_{ms}$ $C_{ms}$ $G_{ms}$ $C_{ms}$ $A_{ms}$ $C_{ms}$ $U_{ms}$ $G_{ms}$ $C_{ms}$ $^mC_{ks}$ $A_{ks}$ $^mC_k$ | 27 | 44 | 25 | 87 | 80 |
| 826061 | $G_{ms}$ $C_{ms}$ $G_{ms}$ $C_{ms}$ $A_{ms}$ $G_{ms}$ $G_{ms}$ $C_{ms}$ $G_{ms}$ $C_{ms}$ $A_{ms}$ $C_{ms}$ $U_{ms}$ $G_{ms}$ $C_{ms}$ $^mC_{ko}$ $A_{ks}$ $^mC_k$ | 27 | 44 | 25 | 109 | 80 |
| 826062 | $G_{ms}$ $C_{ms}$ $G_{ms}$ $C_{ms}$ $A_{ms}$ $G_{ms}$ $G_{ms}$ $C_{ms}$ $G_{ms}$ $C_{ms}$ $A_{ms}$ $C_{mo}$ $U_{ms}$ $G_{mo}$ $C_{ms}$ $^mC_{ko}$ $A_{ks}$ $^mC_k$ | 27 | 44 | 25 | 111 | 80 |

TABLE 39-continued

ACP1 expression

| Isis No. | Sequence | Start Site | Stop Site | Concentration (nM) | Protein (% mock) | SEQ ID NO. |
|---|---|---|---|---|---|---|
| 826063 | $G_{ms}$ $C_{mo}$ $G_{ms}$ $C_{mo}$ $A_{ms}$ $G_{ms}$ $G_{ms}$ $C_{ms}$ $G_{ms}$ $C_{ms}$ $A_{ms}$ $C_{ms}$ $U_{ms}$ $G_{ms}$ $C_{ms}$ $^{m}C_{ks}$ $A_{ks}$ $^{m}C_{k}$ | 27 | 44 | 25 | 111 | 80 |
| 826064 | $G_{ms}$ $C_{mo}$ $G_{ms}$ $C_{mo}$ $A_{ms}$ $G_{mo}$ $G_{ms}$ $C_{ms}$ $G_{ms}$ $C_{ms}$ $A_{ms}$ $C_{ms}$ $U_{ms}$ $G_{ms}$ $C_{ms}$ $^{m}C_{ks}$ $A_{ks}$ $^{m}C_{k}$ | 27 | 44 | 25 | 151 | 80 |
| 826065 | $G_{ms}$ $C_{ms}$ $G_{ms}$ $C_{ms}$ $A_{ms}$ $G_{ms}$ $G_{mo}$ $C_{ms}$ $G_{mo}$ $C_{ms}$ $A_{ms}$ $C_{ms}$ $U_{ms}$ $G_{ms}$ $C_{ms}$ $^{m}C_{ks}$ $A_{ks}$ $^{m}C_{k}$ | 27 | 44 | 25 | 158 | 80 |
| 826066 | $G_{ms}$ $C_{ms}$ $G_{ms}$ $C_{ms}$ $A_{ms}$ $G_{ms}$ $G_{ms}$ $C_{mo}$ $G_{ms}$ $C_{mo}$ $A_{ms}$ $C_{ms}$ $U_{ms}$ $G_{ms}$ $C_{ms}$ $^{m}C_{ks}$ $A_{ks}$ $^{m}C_{k}$ | 27 | 44 | 25 | 140 | 80 |
| 826069 | $G_{ms}$ $C_{ms}$ $G_{ms}$ $C_{ms}$ $A_{ms}$ $G_{ms}$ $G_{ms}$ $C_{ms}$ $G_{ms}$ $C_{ms}$ $A_{ms}$ $C_{ms}$ $U_{ms}$ $G_{ks}$ $C_{ds}$ $^{m}C_{ks}$ $A_{ds}$ $^{m}C_{k}$ | 27 | 44 | 25 | 196 | 80 |

Subscripts: "m" indicates a 2'-O-methyl modification, "o" indicates a phosphodiester internucleoside linkage, "s" indicates a phosphorothioate internucleoside linkage, "k" indicates a cEt bicyclic nucleoside, "d" indicates a 2'-deoxynucleoside. Superscript "m" preceding a "C" indicates a 5-methylcytosine.

TABLE 40

ACP1 expression

| Isis No. | Start Site | Stop Site | Concentration (nM) | Protein (% mock) | SEQ ID NO. |
|---|---|---|---|---|---|
| 813860 | 27 | 44 | 5 | 130 | 80 |
|  |  |  | 10 | 104 |  |
|  |  |  | 20 | 47 |  |
|  |  |  | 40 | 95 |  |
|  |  |  | 80 | 89 |  |
| 826065 | 27 | 44 | 5 | 143 | 80 |
|  |  |  | 10 | 137 |  |
|  |  |  | 20 | 182 |  |
|  |  |  | 40 | 153 |  |
|  |  |  | 80 | 127 |  |
| 826069 | 27 | 44 | 5 | 127 | 80 |
|  |  |  | 20 | 139 |  |
|  |  |  | 40 | 184 |  |
|  |  |  | 80 | 133 |  |

Example 25: Effects of Antisense Oligonucleotides Targeting the 5'-UTR of Mouse ACP1

Antisense oligonucleotides designed to target the 5'-untranslated region of mouse ACP1 were tested for their effects on ACP1 protein expression in vitro. The antisense oligonucleotides target the mouse ACP1 mRNA (GENBANK accession number NM_021330.4, designated herein as SEQ ID NO: 91) and were designed to target at least one stem loop structure in the 5'-UTR. The start and stop sites listed in the table below indicate the positions on SEQ ID NO: 91 that the antisense oligonucleotides target. MHT cells were transfected with a concentration of antisense oligonucleotide shown in the table below or were not transfected as a control. Ten hours after transfection, ACP1 protein expression was analyzed by western blot. The results are shown in the table below as percent protein expression relative to untreated control cells following normalization to the TCP-103 loading control. The results show that the antisense oligonucleotides targeting the 5'-untranslated region of mouse ACP1 induced translation of the target.

TABLE 41

ACP1 expression

| Isis No. | Sequence | Start Site | Stop Site | Concentration (nM) | Protein (% mock) | SEQ ID NO. |
|---|---|---|---|---|---|---|
| (XL546) | $G_{mo}$ $C_{mo}$ $A_{mo}$ $U_{mo}$ $G_{mo}$ $C_{mo}$ $G_{mo}$ $C_{mo}$ $A_{mo}$ $C_{mo}$ $U_{mo}$ $G_{mo}$ $C_{mo}$ $C_{mo}$ $A_{m}$ | 20 | 34 | 5 | 88 | 92 |
|  |  |  |  | 10 | 133 |  |
|  |  |  |  | 20 | 153 |  |
|  |  |  |  | 40 | 125 |  |
|  |  |  |  | 80 | 126 |  |
| (XL547) | $G_{ms}$ $C_{ms}$ $A_{ms}$ $U_{ms}$ $G_{ms}$ $C_{ms}$ $G_{ms}$ $C_{ms}$ $A_{ms}$ $C_{ms}$ $U_{ms}$ $G_{ms}$ $C_{ms}$ $C_{ms}$ $A_{m}$ | 20 | 34 | 5 | 161 | 92 |
|  |  |  |  | 10 | 198 |  |
|  |  |  |  | 20 | 219 |  |
|  |  |  |  | 40 | 227 |  |
|  |  |  |  | 80 | 194 |  |

See above Tables for subscripts legend.

Example 26: Effect of an Antisense Oligonucleotide Targeting the 5'-UTR Mouse ACP1 In Vivo Isis No. 827815 (see the table below) was tested for its effect on mouse ACP1 protein expression in vivo. Groups of three, male, seven week old BALB/c mice were systemically administered Isis No. 827815, at a dose listed in the table below, or saline by subcutaneous injection. Animals were sacrificed 72 hours later. Liver homogenates were prepared, and ACP1 protein expression was analyzed by western blot. The results are shown in the table below as the percent expression relative to saline treated animals following normalization to the TMED9 loading control. The results show that ACP1 protein expression was increased in vivo following treatment with an antisense oligonucleotide targeting the ACP1 5'-UTR.

TABLE 42

ACP1 expression in vivo

| Isis No. | Sequence | Start site | Stop site | Dose (mg/kg) | Protein (% UTC) | SEQ ID NO. |
|---|---|---|---|---|---|---|
| 827815 | $G_{ms}$ $C_{ms}$ $A_{ms}$ $U_{ms}$ $G_{ms}$ $C_{ms}$ $G_{ms}$ $C_{ms}$ $A_{ms}$ $C_{ms}$ $U_{ms}$ $G_{ms}$ $C_{ms}$ $C_{ms}$ $A_{ms}$ $G_{m}$ | 19 | 34 | 12.5<br>25<br>50<br>100 | 145<br>114<br>116<br>94 | 93 |

See above Tables for subscripts legend.

Example 27: Effect of Antisense Oligonucleotide Targeting the 5'-UTR of Mouse ARF1

An antisense oligonucleotide designed to target the 5'-untranslated region of mouse ADP-ribosylation factor 1 (ARF1) was tested for its effects on ARF1 protein expression in vitro. The antisense oligonucleotide targets the mouse ARF1 mRNA (GENBANK accession number NM_007476.3, designated herein as SEQ ID NO: 94), which does not comprise a uORF, and was designed to target at least one stem loop structure in the 5'-UTR. The start and stop sites listed in the table below indicate the positions on SEQ ID NO: 94 that the antisense oligonucleotide targets. MHT cells were transfected with a concentration of antisense oligonucleotide shown in the table below or were not transfected as a control. Ten hours after transfection, ARF1 protein expression was analyzed by western blot. The results are shown in the table below as percent protein expression relative to untreated control cells following normalization to the TCP-1 loading control. The results show that the antisense oligonucleotide targeting the 5'-untranslated region of mouse ARF1 induced translation of the target.

TABLE 43

ARF1 expression

| Isis No. | Sequence | Start Site | Stop Site | Concentration (nM) | Protein (% mock) | SEQ ID NO. |
|---|---|---|---|---|---|---|
| 814929 | $C_{mo}$ $G_{mo}$ $C_{mo}$ $T_{mo}$ $C_{mo}$ $C_{mo}$ $C_{mo}$ $A_{mo}$ $C_{mo}$ $A_{mo}$ $A_{mo}$ $G_{mo}$ $A_{mo}$ $T_{mo}$ $G_{mo}$ $G_{mo}$ $C_{m}$ | 44 | 60 | 5<br>10<br>20<br>40<br>80 | 112<br>179<br>215<br>181<br>122 | 95 |

See above Tables for subscripts legend.

Example 28: Effect of Antisense Oligonucleotide Targeting the 5'-UTR of Mouse USP16

An antisense oligonucleotide designed to target the 5'-untranslated region of mouse ubiquitin processing protease (USP16) was tested for its effects on USP16 protein expression in vitro. The antisense oligonucleotide targets the mouse USP16 mRNA (GENBANK accession number NM_024258.2, designated herein as SEQ ID NO: 96), and was designed to target at least one stem loop structure in the 5'-UTR. The start and stop sites listed in the table below indicate the positions on SEQ ID NO: 96 that the antisense oligonucleotide targets. MHT cells were transfected with a concentration of antisense oligonucleotide shown in the table below or were not transfected as a control. Ten hours after transfection, USP16 protein expression was analyzed by western blot. The results are shown in the table below as percent protein expression relative to untreated control cells following normalization to the β-actin (ACTB) loading control. The results show that the antisense oligonucleotide targeting the 5'-untranslated region of mouse USP16 induced translation of the target.

TABLE 44

USP16 expression

| Isis No. | Sequence | Start Site | Stop Site | Concentration (nM) | Protein (% mock) | SEQ ID NO. |
|---|---|---|---|---|---|---|
| 814928 | $G_{mo} A_{mo} G_{mo} A_{mo} G_{mo} C_{mo} G_{mo} A_{mo} C_{mo}$ $G_{mo} C_{mo} G_{mo} G_{mo} T_{mo} G_{mo} G_{mo} A_{m}$ | 21 | 37 | 5 | 124 | 97 |
| | | | | 10 | 133 | |
| | | | | 20 | 133 | |
| | | | | 40 | 116 | |
| | | | | 80 | 116 | |

See above Tables for subscripts legend.

Example 29: Effects of Antisense Oligonucleotides Targeting the 5'-UTR of Human LDLr Antisense oligonucleotides designed to target the 5'-untranslated region of human low density lipoprotein receptor (LDLr) were tested for their effects on LDLr protein expression and LDL uptake in vitro. The antisense oligonucleotides target the human LDLr mRNA (GENBANK accession number NM_000527.4, designated herein as SEQ ID NO: 98) and were designed to target at least one stem loop structure in the 5'-UTR. The start and stop sites listed in the table below indicate the positions on SEQ ID NO: 98 that the antisense oligonucleotides target. HEK293 or HeLa cells were transfected with a concentration of antisense oligonucleotide shown in the table below or were not transfected as a control. Ten hours after transfection, LDLr protein expression was analyzed by ELISA (R & D Systems, cat. #DLDLR0). The results are shown in the table below as percent protein expression relative to untreated control cells. The results show that the antisense oligonucleotides targeting the 5'-untranslated region of human LDLr induced translation of the target.

In order to test the effects of the antisense oligonucleotides in the tables below on LDL uptake, HEK 293 or HeLa cells were transfected with an antisense oligonucleotide at a concentration shown in the table below or were not transfected as a control. Approximately fourteen hours after transfection, the medium was changed to lipid-free medium, incubated at 37° C. for one hour, then 5 to 10 µg/mL of Bodipy labeled LDL was added at 4° C. for 30 to 60 minutes to all cells, including untransfected control cells. The cells were then washed with cold PBS, harvested, and lysed with RIPA buffer. The Bodipy fluorescence was measured, and the results in the table below show the percent Bodipy fluorescence relative to untransfected control cells.

TABLE 45

LDLr expression

| Isis No. | Sequence | Start Site | Stop Site | Cell type | Concentration (nM) | Protein (% UTC) | SEQ ID NO. |
|---|---|---|---|---|---|---|---|
| 814923 | $U_{mo} G_{mo} C_{mo} A_{mo} G_{mo} U_{mo} G_{mo} G_{mo}$ $G_{mo} G_{mo} U_{mo} G_{mo} A_{mo} U_{mo} U_{mo} U_{m}$ | 28 | 43 | HEK293 | 5 | 131 | 99 |
| | | | | | 10 | 146 | |
| | | | | | 20 | 169 | |
| | | | | | 40 | 188 | |
| | | | | | 80 | 238 | |

TABLE 45-continued

LDLr expression

| Isis No. | Sequence | Start Site | Stop Site | Cell type | Concentration (nM) | Protein (% UTC) | SEQ ID NO. |
|---|---|---|---|---|---|---|---|
| 814923 | $U_{mo} G_{mo} C_{mo} A_{mo} G_{mo} U_{mo} G_{mo} G_{mo}$ $G_{mo} G_{mo} U_{mo} G_{mo} A_{mo} U_{mo} U_{mo} U_{m}$ | 28 | 43 | HeLa | 5 10 20 40 80 | 124 154 113 128 106 | 99 |
| 842196? (XL512) | $U_{ms} G_{ms} C_{ms} A_{ms} G_{ms} U_{ms} G_{ms} G_{ms}$ $G_{ms} G_{ms} U_{ms} G_{ms} A_{ms} U_{ms} U_{ms} U_{m}$ | 28 | 43 | HeLa | 5 10 20 40 80 | 112 111 128 121 137 | 99 |

See above Tables for subscripts legend.

TABLE 46

LDL uptake

| Isis No. | Cell type | Bodipy-LDL incubation time (min) | Concentration (nM) | LDL uptake (% UTC) | SEQ ID NO. |
|---|---|---|---|---|---|
| 814923 | HEK293 | 60 | 40 | 152 | 99 |
| 842196 | HEK293 | 30 | 40 | 115 | 99 |
|  |  | 60 | 40 | 130 |  |
| 842196 | HeLa | 30 | 12.5 | 108 | 99 |
|  |  |  | 25 | 108 |  |
|  |  |  | 50 | 127 |  |
|  |  |  | 100 | 132 |  |

Example 30: Effects of Antisense Oligonucleotides Targeting the 5'-Untranslated Region Downstream of the CFTR uORF Start Codon on CFTR Protein Expression Antisense oligonucleotides designed to target a uORF start codon of human CFTR were tested for their effects on CFTR protein expression in vitro. These antisense oligonucleotides, described in the table below, were designed to target the CFTR mRNA (GENBANK accession number NM_000492.3, designated herein as SEQ ID NO: 81) and were uniformly modified in order to avoid inducing cleavage of the target RNA. The start and stop sites listed in the table below indicate the positions on SEQ ID NO: 81 that the antisense oligonucleotides target.

HT-29 cells were transfected with a concentration of antisense oligonucleotide listed in the table below or were mock transfected as a control. Twenty-four hours after transfection, CFTR expression was analyzed by western blot, as described in Example 20. The results are shown in the table below as percent protein expression relative to mock transfected cells following normalization to a loading control. The results show that the antisense oligonucleotides increased CFTR protein expression.

TABLE 47

CFTR expression

| Isis No. | Sequence | Start Site | Stop Site | Concentration (nM) | Protein (% mock) | SEQ ID NO. |
|---|---|---|---|---|---|---|
| 812022 | $U_{mo} G_{mo} C_{mo} U_{mo} G_{mo} U_{mo} G_{mo} A_{mo} U_{mo}$ $G_{mo} U_{mo} C_{mo} A_{mo} U_{mo} U_{mo} U_{mo} G_{mo} C_{m}$ | 9 | 26 | 50 75 100 150 | 132 117 125 112 | 100 |
| 812023 | $U_{ms} G_{ms} C_{ms} U_{ms} G_{ms} U_{ms} G_{ms} A_{ms} U_{ms}$ $G_{ms} U_{ms} C_{ms} A_{ms} U_{ms} U_{ms} U_{ms} G_{ms} C_{m}$ | 9 | 26 | 50 75 100 150 | 130 126 124 128 | 100 |

See above Tables for subscripts legend.

Example 31: Effects of Antisense Oligonucleotides Targeting the 5'-UTR of Human LDLr Antisense oligonucleotides designed to target the 5'-untranslated region of human low density lipoprotein receptor (LDLr) were tested for their effects on LDLr protein expression in vitro. The antisense oligonucleotides target the human LDLr mRNA (SEQ ID NO: 98) and were designed to target at least one stem loop structure in the 5'-UTR. The start and stop sites listed in the table below indicate the positions on SEQ ID NO: 98 that the antisense oligonucleotides target. HEK293 cells were transfected with a concentration of antisense oligonucleotide shown in the table below or were not transfected as a control. Sixteen hours after transfection, LDLr protein expression was analyzed by ELISA (R & D Systems, cat. 4 DLDLR0). The results are shown in the table below as percent protein expression relative to untreated control cells. The results show that the antisense oligonucleotides targeting the 5'-untranslated region of human LDLr induced translation of the target.

TABLE 48

LDLr expression

| Isis No. | Sequence | Start Site | Stop Site | Concentration (nM) | Protein (% UTC) | SEQ ID NO. |
|---|---|---|---|---|---|---|
| 842196 | $U_{ms}$ $G_{ms}$ $C_{ms}$ $A_{ms}$ $G_{ms}$ $U_{ms}$ $G_{ms}$ $G_{ms}$ $G_{ms}$ $G_{ms}$ $U_{ms}$ $G_{ms}$ $A_{ms}$ $U_{ms}$ $U_{ms}$ $U_{m}$ | 28 | 43 | 20 / 40 / 80 | 125 / 195 / 222 | 99 |
| 842197 | $U_{ms}$ $G_{ms}$ $C_{ms}$ $A_{ms}$ $G_{ms}$ $U_{ms}$ $G_{ms}$ $G_{ms}$ $G_{ms}$ $G_{ms}$ $U_{ms}$ $G_{ms}$ $A_{ms}$ $T_{ks}$ $T_{ks}$ $T_{k}$ | 28 | 43 | 20 / 40 / 80 | 176 / 266 / 214 | 101 |
| 842198 | $U_{ms}$ $G_{ms}$ $C_{ms}$ $A_{ms}$ $G_{mo}$ $U_{ms}$ $G_{mo}$ $G_{ms}$ $G_{mo}$ $G_{ms}$ $U_{ms}$ $G_{ms}$ $A_{ms}$ $T_{ks}$ $T_{ks}$ $T_{k}$ | 28 | 43 | 20 / 40 / 80 | 160 / 157 / 194 | 101 |
| 842200 | $U_{ms}$ $G_{ms}$ $C_{ms}$ $A_{ms}$ $G_{mo}$ $U_{ms}$ $G_{mo}$ $G_{ms}$ $G_{mo}$ $G_{ms}$ $U_{mo}$ $G_{ms}$ $A_{ms}$ $U_{ms}$ $U_{ms}$ $U_{m}$ | 28 | 43 | 20 / 40 / 80 | 131 / 175 / 170 | 99 |
| 842202 | $U_{ms}$ $G_{ms}$ $C_{ms}$ $A_{ms}$ $G_{mo}$ $U_{ms}$ $G_{mo}$ $G_{ms}$ $G_{ms}$ $G_{ms}$ $U_{ms}$ $G_{ms}$ $A_{ms}$ $U_{ms}$ $U_{ms}$ $U_{m}$ | 28 | 43 | 20 / 40 / 80 | 125 / 132 / 145 | 99 |
| 842205 | $U_{ms}$ $G_{ms}$ $C_{ms}$ $A_{ms}$ $G_{ms}$ $U_{ms}$ $G_{ms}$ $G_{ms}$ $G_{ms}$ $G_{ms}$ $U_{ms}$ $G_{ms}$ $A_{ms}$ $U_{ms}$ $U_{ms}$ $U_{ms}$ $U_{ms}$ $C_{m}$ | 26 | 43 | 20 / 40 / 80 | 123 / 136 / 107 | 102 |
| 842206 | $U_{ms}$ $G_{ms}$ $C_{ms}$ $A_{ms}$ $G_{ms}$ $U_{ms}$ $G_{ms}$ $G_{ms}$ $G_{ms}$ $G_{ms}$ $U_{ms}$ $G_{ms}$ $A_{ms}$ $U_{ms}$ $U_{ms}$ $T_{ks}$ $T_{ks}$ $^{m}C_{k}$ | 26 | 43 | 20 / 40 / 80 | 155 / 173 / 134 | 103 |
| 842207 | $U_{ms}$ $G_{ms}$ $C_{ms}$ $A_{ms}$ $G_{mo}$ $U_{ms}$ $G_{mo}$ $G_{ms}$ $G_{mo}$ $G_{ms}$ $U_{ms}$ $G_{ms}$ $A_{ms}$ $U_{ms}$ $U_{ms}$ $T_{ks}$ $T_{ks}$ $^{m}C_{k}$ | 26 | 43 | 20 / 40 / 80 | 125 / 147 / 129 | 103 |
| 842211 | $U_{ms}$ $G_{ms}$ $C_{ms}$ $A_{ms}$ $G_{mo}$ $U_{ms}$ $G_{mo}$ $G_{ms}$ $G_{ms}$ $G_{ms}$ $U_{ms}$ $G_{ms}$ $A_{ms}$ $U_{ms}$ $U_{ms}$ $U_{ms}$ $U_{ms}$ $C_{m}$ | 26 | 43 | 20 / 40 / 80 | 136 / 143 / 142 | 102 |
| 842212 | $U_{ms}$ $G_{ms}$ $C_{mo}$ $A_{ms}$ $G_{mo}$ $U_{ms}$ $G_{mo}$ $G_{ms}$ $G_{mo}$ $G_{ms}$ $U_{mo}$ $G_{ms}$ $A_{mo}$ $U_{ms}$ $U_{mo}$ $U_{ms}$ $U_{ms}$ $C_{m}$ | 26 | 43 | 20 / 40 / 80 | 103 / 101 / 120 | 102 |
| 842213 | $U_{ms}$ $G_{ms}$ $C_{ms}$ $A_{ms}$ $G_{ms}$ $U_{ms}$ $G_{ms}$ $G_{ms}$ $G_{ms}$ $G_{ms}$ $U_{ms}$ $G_{ms}$ $A_{ms}$ $T_{ks}$ $T_{ds}$ $T_{ks}$ $T_{ds}$ $^{m}C_{k}$ | 26 | 43 | 20 / 40 / 80 | 128 / 135 / 139 | 104 |
| 842214 | $U_{ms}$ $G_{ms}$ $C_{ms}$ $A_{ms}$ $G_{ms}$ $U_{ms}$ $G_{ms}$ $G_{ms}$ $G_{ms}$ $G_{ms}$ $U_{ms}$ $G_{ks}$ $A_{ds}$ $T_{ks}$ $T_{ds}$ $T_{k}$ | 28 | 43 | 20 / 40 / 80 | 134 / 152 / 139 | 101 |

See above Tables for subscripts legend.

Example 32: Time Course of LDLr Protein Expression Following Treatment with an Antisense Oligonucleotide Targeting the 5'-UTR Hep3B cells were transfected with 30 nM Isis No. 842196 (see Table 45) and Lipofectamine 2000 (Life Technologies). At various time points following transfection, the cells were harvested and LDLr protein expression was analyzed by ELISA as described in Examples 30 and 31. The results are shown in Table 49 as the percent LDLr protein expression relative to cells that did not receive antisense oligonucleotide treatment (harvested at the 0 hour time point). The results show that LDLr expression was increased over 4-fold relative to baseline expression by Isis No. 842196, at the 48 hour time point.

TABLE 49

LDLr expression
LDLr (% 0 h) following transfection
with 30 nM Isis No. 842196

| 24 h | 36 h | 48 h |
|------|------|------|
| 212  | 230  | 457  |

The invention claimed is:

1. A method of increasing the amount a target protein in a cell, comprising contacting the cell with an antisense compound comprising a modified oligonucleotide, wherein the target protein is encoded by a target transcript comprising at least one translation suppression element in the 5' untranslated region of the target transcript that is a stem-loop structure, wherein the modified oligonucleotide is complementary to a target site within the stem-loop structure; and thereby increasing expression of the target protein in the cell.

2. The method of claim 1, wherein the translation suppression element region does not contain a uORF.

3. The method of claim 1, wherein the modified oligonucleotide consists of 10 to 40 linked nucleosides.

4. The method of claim 1, wherein at least one nucleoside of the modified oligonucleotide comprises a modified sugar moiety.

5. The method of claim 1, wherein each nucleoside of the modified oligonucleotide is a modified nucleoside.

6. The method of claim 4, wherein at least one modified sugar moiety is a 2'-substituted sugar moiety.

7. The method of claim 6, wherein the 2'-substituent of at least one 2'-substituted sugar moiety is selected from: 2'-OMe, 2'-F, and 2'-MOE.

8. The method of claim 4, wherein at least one modified sugar moiety is a bicyclic sugar moiety.

9. The method of claim 8, wherein at least one bicyclic sugar moiety is LNA or cEt.

10. The method of claim 4, wherein at least one sugar moiety is a sugar surrogate.

11. The method of claim 10, wherein at least one sugar surrogate is a morpholino or a modified morpholino.

12. The method of claim 1, wherein the modified oligonucleotide comprises at least one modified internucleoside linkage.

13. The method of claim 12, wherein each internucleoside linkage of the modified oligonucleotide is either a phosphodiester internucleoside linkage or a phosphorothioate internucleoside linkage.

14. The method of claim 1, wherein the antisense compound comprises at least one conjugate group.

15. The method of claim 14, wherein the conjugate group comprises GalNAc.

16. The method of claim 1, wherein the antisense compound does not alter the amount of the target nucleic acid transcript.

17. The method of claim 1, wherein the antisense compound is single-stranded.

18. The method of claim 1, wherein the cell is in a subject.

* * * * *

SEQUENCE LISTING

<160> NUMBER OF SEQ ID NOS: 104

<210> SEQ ID NO 1
<211> LENGTH: 1862
<212> TYPE: DNA
<213> ORGANISM: Homo sapiens

<400> SEQUENCE: 1

```
cgtgcgtcat cttcccgcgc cggtgacgga agtgcggtgt tgagcgccgg cggctcgcgc        60
ccacgctggg ccgggagtcg aaatgcttcc cggtgccggg agtgagcgat gagctggctt       120
ctgttcctgg cccacagagt cgccttggcc gccttgccct gccgccgcgg ctctcgcggg       180
ttcgggatgt tctatgccgt gaggaggggc cgcaagaccg gggtctttct gacctggaat       240
gagtgcagag cacaggtgga ccggtttcct gctgccagat ttaagaagtt tgccacagag       300
gatgaggcct gggcctttgt caggaaatct gcaagcccgg aagtttcaga agggcatgaa       360
aatcaacatg gacaagaatc ggaggcgaaa gccagcaagc gactccgtga gccactggat       420
ggagatggac atgaaagcgc agagccgtat gcaaagcaca tgaagccgag cgtggagccg       480
gcgcctccag ttagcagaga cacgttttcc tacatgggag acttcgtcgt cgtctacact       540
gatggctgct gctccagtaa tgggcgtaga aggccgcgag caggaatcgg cgtttactgg       600
gggccaggcc atcctttaaa tgtaggcatt agacttcctg ggcggcagac aaaccaaaga       660
gcggaaattc atgcagcctg caaagccatt gaacaagcaa agactcaaaa catcaataaa       720
ctggttctgt atacagacag tatgtttacg ataaatggta taactaactg ggttcaaggt       780
tggaagaaaa atgggtggaa gacaagtgca gggaagagg tgatcaacaa agaggacttt       840
gtggcactgg agaggcttac ccagggggatg gacattcagt ggatgcatgt tcctggtcat       900
tcgggattta taggcaatga agaagctgac agattagcca gagaaggagc taaacaatcg       960
gaagactgag ccatgtgact ttagtccttg ggagaacttg agccagcggc tgtcttgctg      1020
cctgtactta ctggtgtgga aaatagcctg caggtaggac cattgcagtg atgggcagat      1080
gcgtctttca cacggaatca ggcacagtgg ccttctgtga catgtgttta taaaaaatgg      1140
ttaagtatat aataaattga acatctttga gattggagaa ttatgtgaga tttccacatt      1200
atgtttactg ggttcaatac tgtccttgct tgtttttattg caggcaagca aggcaaatgg      1260
cctaaaatgc tgtggcttat atttttgataa gaaatcaaaa aaccattggt taaaagatgc      1320
aactcagaag tctggaagta ttctgaaagc atccatttac cgtccagttg acaggtttga      1380
gtctcctgct tgtataggtg acttgtgccc atgggtacat taaaggaaca tgctgcccag      1440
ggcctgggcg gacagctcag tgggcaggat gtgtgctggg tctcagcccc atgtgcctgc      1500
```

| | |
|---|---|
| ttgctgggca gttagtatag ggcaaagcct gcctgcggcg accctggctg ctaggccatt | 1560 |
| ctctaggaac agctgcgact cataaagacc aagaagcata aataaacttt caaaaattta | 1620 |
| tttggctctt tcgttaaaaa ctgtgcaaat taaaaaaaaa aaaaaaaaag taagacaccg | 1680 |
| gctgggcaca gtggctcact tctgtaatcc tagcactttg ggaggccaag gcgggcagat | 1740 |
| cacttgaggt caggagtttg agaccagctt ggccaacatg acgaaaccct gtctctacta | 1800 |
| aaattacaaa aattatccag gtgtggtggc acgggcttgt agtcccagct acttgggagg | 1860 |
| ct | 1862 |

```
<210> SEQ ID NO 2
<211> LENGTH: 4638
<212> TYPE: DNA
<213> ORGANISM: Mus musculus

<400> SEQUENCE: 2
```

| | |
|---|---|
| gccaggctcg ctgagagccg gggcgctgga caagggaaca gggacactgt gaacggaaga | 60 |
| caaaaaacaa tgtatagtaa aacagaaggc ggatccaggg tatcccgcga actcggcttg | 120 |
| cctctcccgt gagccttggc ggggatctgc ctcctcctcc gctggacgcc ctcggtcctt | 180 |
| agtttgtccc actaggggcg accgggtcgt cacgtgctcc tccaggtcct ctgcaggagc | 240 |
| gtgcatccta tcctgccttg ggtacgctga gccatggcag ccctgctgag acccgcgcgt | 300 |
| tggctgctcg gggccgcggc ggccccgcgc ctcccgctgt ccctgcgcct ccctgcgggc | 360 |
| gtcccgggcc ggctgtcctc cgtcgtccgg gtcgcggctg ttggtagccg gccggctgca | 420 |
| ggagagcgtc tgagccaagc cagattgtat gccatcgttg ctgagaaaag ggatcttcaa | 480 |
| gaggagcctg ctcctgtgag aaagaacagc agtcaatttg actgggctct gatgagactg | 540 |
| gataattctg tccggagaac aggccgcatc acaaaggggc ttctgcagag agtctttgag | 600 |
| agcacgtgta gctcaggtag cccagggagc aatcaagctc tgcttctgct gcgcagctgt | 660 |
| ggctcgctcc tgcccgaact gagtctcgcc gagaggacag agtttgctca caagatctgg | 720 |
| gacaaacttc agcagttagg tgtcgtatat gatgtcagtc attacaatgc tttacttaaa | 780 |
| gtatatcttc aaaatgaata caaattttca cctactgact tcctggcaaa gatggaggga | 840 |
| gcaaacatcc aaccaaatcg agtaacatac cagaggctga tagctgccta ctgtaatgtt | 900 |
| ggggacattg aaggtgccag caagatcctt ggatttatga aaacgaaaga ccttccgatc | 960 |
| acagaggccg tgttcagtgc tctcgtcaca gggcatgcga gagctgggga tatggaaaat | 1020 |
| gcagaaaata ttctcacagt gatgaaacag gccggcattg agcctggccc agacacgtat | 1080 |
| ctggccttgt tgaatgcaca tgctgagagg ggtgacattg gccaggttag gcagattctg | 1140 |
| gagaaagtgg agaagtcaga ccattacttc atggaccgcg acttcttgca ggttattttt | 1200 |
| agcttcagta aggctggcta ccctcagtat gtctcagaaa tactggagaa gattacctat | 1260 |
| gagagacggt ctattccaga tgcaatgaac ctcattttgt ttttagccac tgagaagtta | 1320 |
| gaagacactg cgttccaggt tttattggca ttaccctgt ccaaggacga gagctccgat | 1380 |
| aactttggca gtttcttttt gcggcactgt gtgactctgg atttgccccc tgagaagctg | 1440 |
| atagactact gtcggaggct gagggacgcc aagctgcaca gctcctcact gcagttcacg | 1500 |
| ctgcactgtg ctcttcaagc caataggaca gctttggcaa aagcagtgat ggaggctttg | 1560 |
| agggaagaag ggtttcctat ccgaccgcac tatttctggc cgttgcttgc tgggcatcag | 1620 |
| aaaacaaaaa atgttcaagg aataatagat atcctcaaaa taatgaacaa agtgggagtg | 1680 |
| gatcctgatc aggaaacata tataaactat gtgtttccgt gctttgatag tgcacagtca | 1740 |

```
gttcgagctg ctttgcagga aaatgaatgt ctcctcgcaa gtagtacctt tgctcaagct   1800
gaagtgaaga atgaagcaat aaatgggaac ttacagaaca ttttgtcatt tttggaatcg   1860
aatacattgc ctttctcgtt tagttctttg agaaacagcc taatcctagg cttcaggagg   1920
tcgatgaaca tagatctttg gagcaagata acagaattgt tgtacaagga tgaacgctat   1980
tgctcaaagc ctccgggacc agcggaagct gttggctatt ttctttataa cttgattgac   2040
agcatgagtg actcagaggt acaggccaag gaggagcgtt tgagacaata cttccatcag   2100
ctgcaggaga tgaatgttaa agttcctgaa acatctaca aaggcatttg taatttgctg    2160
aatacctacc atgttcctga attgattaag gatattaagg ttctggttga cagagagaag   2220
gtagattctc aaaaaacttc tcaagttacc tcatctgatt tggaatcaac acttgagaaa   2280
ctcaaagctg aaggccaacc tgtaggatct gccctgaagc agctcctgct gctgctctgc   2340
tcagaggaga atatgcaaaa ggcccttgag gtgaaagcaa aatatgagtc agacatggtt   2400
attggtggct atgcagcatt aataaatttg tgctgtcgac atgataatgc agaagatgcg   2460
tggaacttga acaagaagt tgaccgctta gatgcttcgg ctattcttga cactgccaag    2520
tacgtagccc ttgtaaaagt actgggaaag cacagcagac tccaagatgc tattaacatt   2580
ctaaaggaga tgaaagagaa ggatgttgtt atcaaagatg caacagtctt gtccttttc    2640 cacatcctca atggtgcagc tttaagaggt gaaattgaaa cagtaaaaca gctgcatgaa   2700
gccatcgtga ctcttgggtt ggcaaagccg tccagcaaca taagcttccc gttggtcact   2760
gtgcacctgg aaaagggtga cttacctgct gctcttgaag ccagcattgc ctgccataaa   2820
aaatataaag tgttacccag gattcatgat gtcttatgta agctagtaga gaaaggcgag   2880
actgatttga tccagaaagc aatggacttt gtgagccaag aacaagggga gatgacgatg   2940
ctctacgacc tcttctttgc tttcctgcag acggggaatt acaaagaagc taagaagatc   3000
attgagactc caggcattag agctcggcct acaagactcc agtggttttg tgatcgatgc   3060
attgccagta atcaggttga agctcttgag aagttggtag agctgactga agctgtttt    3120 gagtgtgaca gagaccagat gtactacaac ttactgaagc tatacaaaat aagcagtgac   3180
tggcaaagag cggatgctgc gtggaccaaa atgcaagaag agaacattat ccctcgagag   3240
cggacactgc ggctcttagc cgagatcttg aaaaccagca accaggaagt tcctttcgac   3300
gttccggagt tgtggtttgg agatgacaga ccttccctga gtccatcctc acgctcagca   3360
ggagaggacg ttactgagaa gacgttgttg tctaactgca aactaaagaa gagtaaagat   3420
gcatataata tcttccttaa agccgaaaag caaaacgttg tatttagcag tgaaacttat   3480
agcaccttga taggcttgct gctgagtaag gacgacttca cccaagcaat gcacgtgaag   3540
gatttcgctg agaccacat caagggcttc acactgaacg atgctgccaa cagcctcctc   3600
atcataaggc aagttaggcg ggattatttg aaaggggctc tggcaactct gagagcagcc   3660
ttggatttga gcaggttcc gtcccagatc gccgtgaccc gcctcatcca ggcgttggcc   3720
ttgaagggtg atgtggaaag catagaggcc attcagagaa tggtggctgg acttgacacg   3780
attggactct caaaaatggt ttttatcaat aacatcgctt tggcccagat gaagaataat   3840
aaacttgatg ctgccataga aacattgag cacctgcttg cttccgagaa ccaagccata    3900
gaacctcagt actttggctt gtcgtatcta ttcagaaaag tgatcgaaga gcagatggaa   3960
ccagcgctag agaagttaag catcatgtct gagagaatgg cgaatcagtt tgcactttac   4020
aagcccgtca ctgatctatt cctgcagctt gtggattcag gcaaggtgga tgaggccaga   4080
```

-continued

```
gctctcttag agagatgcgg tgccattgcc gagcagagct cgcttctgtc ggtgttctgt    4140
ctgaggactt ctcagaaacc gaaaaaggca ccagttctga agactttgtt agaactgatt    4200
cctgagttac gtgataacga taaagtatat tcttgcagca tgaaaagcta tgccttagac    4260
aaagatgtgg cctcggctaa agcactgtat gagtatttga cagccaagaa cttgaagcta    4320
gatgacctgt ttctcaagcg ctatgcagct ttgctcaagg atgtcggcga accagtcccc    4380
ttccccgagc cccctgaaag ctttgcattt tatataaagc aactaaagga agcaagggaa    4440
agcccttcat gagagaagca gcgcggctgt gtgtgtgtct atgtgtgtgt gtgtctgtgt    4500
gtgtgtctgt gtgtgtgtct gtgtgtgtgt gtctatgtgt gtatatgcgc gcgcacatgc    4560
ctatgtctaa atgttatttc taaaatgtac ttgagaggaa aataaaccaa tgaaaatgta    4620
aaaaaaaaaa aaaaaaa                                                  4638

<210> SEQ ID NO 3
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 3
cauuucgacu cccggc                                                       16

<210> SEQ ID NO 4
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 4
agcauuucga cucccg                                                       16

<210> SEQ ID NO 5
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 5
gaagcauuuc gacucc                                                       16

<210> SEQ ID NO 6
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 6
gggaagcauu ucgacu                                                       16

<210> SEQ ID NO 7
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 7
ccgggaagca uuucga                                                       16
```

```
<210> SEQ ID NO 8
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 8
ucaccggcgc gggaag                                                        16

<210> SEQ ID NO 9
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 9
cucaacaccg cacuuc                                                        16

<210> SEQ ID NO 10
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 10
acucccggcc cagcgu                                                        16

<210> SEQ ID NO 11
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 11
cgacucccgg cccagc                                                        16

<210> SEQ ID NO 12
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 12
uucgacuccc ggccca                                                        16

<210> SEQ ID NO 13
<211> LENGTH: 11
<212> TYPE: RNA
<213> ORGANISM: Artificial sequence
<220> FEATURE:
<223> OTHER INFORMATION: Synthetic oligonucleotide

<400> SEQUENCE: 13
cauuucgacu c                                                             11

<210> SEQ ID NO 14
<211> LENGTH: 14
<212> TYPE: RNA
<213> ORGANISM: Artificial sequence
<220> FEATURE:
```

-continued

```
<223> OTHER INFORMATION: Synthetic oligonucleotide

<400> SEQUENCE: 14
cauuucgacu cccg                                                      14

<210> SEQ ID NO 15
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 15
cauuucgacu cccggccc                                                  18

<210> SEQ ID NO 16
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 16
cauuucgacu cccggcccag                                                20

<210> SEQ ID NO 17
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 17
cauuguuuuu ugucuucc                                                  18

<210> SEQ ID NO 18
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 18
cauuguuuuu ugucuu                                                    16

<210> SEQ ID NO 19
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 19
cauuguuuuu ugucuuccgu                                                20

<210> SEQ ID NO 20
<211> LENGTH: 3129
<212> TYPE: DNA
<213> ORGANISM: Homo sapiens

<400> SEQUENCE: 20
ggcacctccc ttaggcgcca gggacagccg agcgttacct ggtcccgggc agcggagttc    60
tttacccacc ccagttctgg ttctgacgcc ctagctcatt ccgcaaattt agggcttggg   120
tctggcttgt tcccctccgg ctcgaaccac ctcttctctg agccgagcca gctaccgggg   180
```

```
ctcctggaat tgccacccct ccctgggcac ccttgaggcc tccgtggagg gacgtcacgg      240
ggcagagcgg gacgtgagcc tgagtttgct gcaggcgtgc tctgtgtggt ggctgggttc      300
tgccaatccc cgtgcccacc gggtgggcgc ggccgggaag ctcctgcccc tccctgctgg      360
tcggcgtcac gcgtgacgtc ccgcgtgatg gctgggaggg cccggcggcg acagcggagg      420
cagagaggaa ggcggttctg agagcttcag agagcgatgg aaagcaaaat gggtgaattg      480
cctttagaca tcaacatcca ggaacctcgc tgggaccaaa gtactttcct gggcagagcc      540
cggcactttt tcactgttac tgatcctcga aatctgctgc tgtccggggc acagctggaa      600
gcttctcgga acatcgtgca gaactacagg gccggcgtgg tgaccccagg gatcaccgag      660
gaccagctgt ggagggccaa gtatgtgtat gactccgcct tccatccgga cacaggggag      720
aaggtggtcc tgattggccg catgtcagcc caggtgccca tgaacatgac catcactggc      780
tgcatgctca cattctacag gaagaccccca accgtggtgt tctggcagtg ggtgaatcag      840
tccttcaatg ccattgttaa ctactccaac cgcagtggtg acactcccat cactgtgagg      900
cagctgggga cagcctatgt gagtgccacc actggagctg tggccacggc cctgggactc      960
aaatccctca ccaagcacct gcccccttg gtcggcagat ttgtgccctt tgcagcagtg     1020
gcagctgcca actgcatcaa catccccctg atgaggcaga gagagctgca ggtgggcatc     1080
ccggtggctg atgaggcagg tcagaggctt ggctactcgg tgactgcagc caagcaggga     1140
atcttccagg tggtgatttc aagaatctgc atggcgattc ctgccatggc catcccacca     1200
ctgatcatgg acactctgga gaagaaagac ttcctgaagc gccgccctg ctgggggca     1260 cccctgcagg tgggactggt gggcttctgc ctggtatttg caacccccct gtgctgtgcc     1320
ctattccccc agaagagctc catacacata agcaacctgg aaccagagct gagagctcag     1380
atccatgagc aaaaccccag cgttgaagtg gtctactaca caaggggct ttgaggaggg     1440 tcagcctctg tcccctccct cacttccttg ggctgctgct ttagtggagt catgtcaccc     1500
ctaccacttg gctatctgcc tagcactggg caggggcctt ggtgggcaga tggcaattga     1560
gggtagcaac ctattagggt gggggaggga cctccataag gcttttcctc ccttctctgg     1620
tttcaaagat cagagcacat aacccctcct gtgcttgagt gtccatgcat atacatacat     1680
gatacacatg tgtatgtgta cattgggtcc tgaaagctag aagcaggcat gctagcctag     1740
tatgttctga catctggctt cccttctcag cctcatgtcc acctgcctgc cagccaggct     1800
acaggtgtga cttccttctc taaactgtta caccagccaa gttattttg atggcacctc      1860 atcccttcta gaaataggag gagccccagg atctcaggac agagacttat agacactagt     1920
aggacaaagc gggctgaatc cttcaggttt ctgatacta gctccccaag ctgactgggc      1980
tggcagagga gaacatgttg agacaaggga ggcagggac ttatgcatcc ctcagtgcca      2040
tcccttgtat cctggaatag ctccatttcc cctcctcctc tctaccagac aaaggagtgc     2100
ctgtgtcctg tactgccctc gctgtctccc ccaccacct acttgacagc gtgggcatct      2160
tcaggcacag ccttgggagt tcctggtgtg ctctgacatc atgacctcaa atctaaatcc     2220
tccaatccca actcccttc ccaaacaaaa agccacagag gcagagcaag cattccctt      2280 taagagcttc cactgcaccc cctcccaagg gacacagcgg taggaatggt gcttaaactc     2340
cacaggtatc agagagggtg taactaggac atcctcaagg gcagctaggc cccgaatgta     2400
caatgttaag acagggaatt ttgtgttcca ttgacttttt ttttttttt taatggagtt      2460 tcactatttt gcccaggctg gagtgcgatg gtgcgatctt ggctcactgc aacctctgcc     2520
```

```
tcctgggttc aagtgattct cttgcctcag tctcccgagt agtggaaatt acaggtgtgt    2580
gctaccacat cttgctagtt ttgtattttt agcagagatg ggggtttcac catgttggcc    2640
aggctagtct cgaactcctg acctcaggtg atccacctgc cttggcctcc caaagcactg    2700
ggattacaag catgagccac tgtgcccagc ctgttccact gcatttctt agacattcag    2760 caaaaccccc accttaacct cttttctttc ttgagggttg gtcctgtccc cacctccacc    2820
ctcccacccc ctggaagagg aagggcccgg gcatcagtgg ctagtccaaa taaaatatgg    2880
gcttggggat ggaatgggtg gtggtaagtt cacagagtgt agttagatcc caactcccat    2940
gacctctggc ttcagtggtg ggtggggcag ggcagatgaa agggcttcag tgggaacctc    3000
tgagagcatt ttcctgttcc ccctatcaac cgccccagt gataacatct gtgaagccag    3060
ccattactca ataaactgca aacttgtcta aaaaaaaaa aaaaaaaaa aaaaaaaaa    3120 aaaaaaaaa    3129

<210> SEQ ID NO 21
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 21
caucacgcgg gcaguc    16

<210> SEQ ID NO 22
<211> LENGTH: 2882
<212> TYPE: DNA
<213> ORGANISM: Mus musculus

<400> SEQUENCE: 22
gggcccttca cctctgaccc aaaatggccg cgcccagagc gtagttcttt gcttctccga    60
ggcgagctaa gattaaaatc ctacatcatg tccaagctaa gccgggccac tcggaccctc    120
aagaagcccg aggccggcgg cgtgatccgg tccatcgtgc gagcaggcca agctattcct    180
gggcctccac taggtcccat cttgggtcag cgaggtgtct ctatcaacca gttctgcaaa    240
gagttcaacg agaagacaaa ggacatcaaa gaaggcattc ccctgcctac aaaaattttt    300
ataaagcccg acaggacatt tgagctcaag attgggcagc ccactgtttc ttacttttg    360 aaggcagctg ctgggatcga aaggggggcc cggcatacag ggaaagaggt ggcaggcctg    420
gtgagtttga agcacgtata tgagattgcc tgtgtcaaag ctaaggatga tgcttttgcc    480
atgcaagatg tgcccctgtc ttctgtggtc cgttccatca ttggctctgc ccgttccctg    540
ggcattcgag tggtgaagga cctcagtgca aagaactgg aggctttcca gaaggaacga    600
gctgtgtttt tggctgctca gaaagaggca gatttggcag cccaggcaga agctgccaag    660
aagtgacccc aactttctac actctgagaa tttgaagtga gaggctgaga aaggggccca    720
cagaggaagc tgagccaaag gacttcatgg caacccgatt tctagtttcc tgacatgttt    780
ctgtacattt gctgtgccag gggatcaagc ctgaataaat atcctttgtc atcaactctc    840
agcttctctc ctgagacccc agagatgggg accaatactg cagttccca gccttcacag    900 gtgtgagctg ccctacaggt gaacgcagcc tcaaccaagc aaattatcat gcccagtgcc    960
ttggtcagcc ttgtattata tcaaaataac caaagcttgg tgctttataa agaaaaggta    1020
ttgatttggc ttctgattca tggtgctgga gtatggcaag gctcacttgc tgtatgacag    1080
catggtacag tggaaacagt cacatacata gggccatctg tgtgaggtag cctcacctgg    1140
```

```
accagtcccc gccttaaggc caacattagt gaaggttgga ctcccagacc cctccgccag    1200
accacacttt gatttattca ttttatatgt gactgttttg cctgcatata tgtgagtgca    1260
ctgtgtgcat gcttggtgtc tgtcagaaga gggtattgga tccctggag  ctggatttat    1320 gggtagttgt gaaccagtat gtggatcctg gagttgaacc tgggttctct gtaagagcaa    1380
caaacaagtg ctcttacctc ctgagccatc tctctactct atcccccttt tttgagatag    1440
gatctctgga tatccttgaa ctcacggaga tccacctgcc tctgccttcc acattgctgg    1500
gactaaagct tgcaccacca tacagggcat agccccact  tcttaaggat tccaccacct    1560
tccacactgg gaagcaagcc ttcagcccat gagcctccgg ggcacgtgtc gtaacattca    1620
ggctctgagt aggtacaagt ggagtagagc ccagggagaa atcctatgtt cagggttgaa    1680
gatgttgttt cctgatggag ctgctcctta cacaaagcct caacttctat tcccaacact    1740
tcagagcaca taagcctgtg ctcttccctc ggggatgaga aaggcacag  tcgatggggt    1800 ccacagacac taaggcttgg ctgtgttgct tgtcttttct tagtataact gttggggagt    1860
ttgtatctga gaagcaggag cctgacagag aattcagacc acagataggg ttatccttta    1920
tccaggggca gcttcaggcc tccctgctga gttgacatga ttgtttctga ggcagaatct    1980
cattatttag ccttggctgg cctgaaactg gctggctagg ctacagcctg acctctcagt    2040
gctccagtta aaggtgtgca ttaccccacc cggctcctta ctaagtttgg ttatttgctt    2100
ttttaaaact tgccatttgg ggctggagag atggctcaga ggttaagagc actagctgct    2160
cttccagagg tcctgtgttc agttcccagc aaccacatgg tagctcatca ccatatatag    2220
tgagatctgg tgccctcctc tggcttgcag gtatacatgc aggcaaaaca ctacgtagta    2280
aatctataaa acaaaacttg ctggtttttt tgtttttgtt ttgttttgtt ttgttttaat    2340
gctgttggag atgaaaccca gggcctcatt cagccagagc caggactgtg tccctctcag    2400
ctctgcctct gccaagcttg tgaatctacc ctgggtcagg gagaacagcc gaatcacagc    2460
ccagacctac ataagtgaaa ttccagtaga cacctgcctg agaagtcctt gtggacccct    2520
gacctgcctg agaagtcctt ggggacccct ggtctgcctg agaagtcctt ggggacccct    2580
ggtctgcctg agaagtcctt ggggacccct ggtctgcctg aaaagtcctt gggggcccct    2640
gacctgcctg agaagtcctt gggggcccct gacctcctgt tttcccattc tacaaaacat    2700
caagtgttct ctcagaagag aggcagaatt gacaggaaag atgaagtctg tgtttgccgt    2760
gtgttgcatg ctgggcatta ttttttgctt gttaacattc tgaacaattt agtcaaattt    2820
tcacatagta ttaatagttc aacattgttt actaatacaa ttaaaacttt tattacgtgt    2880
at                                                                   2882
```

<210> SEQ ID NO 23
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 23 cauuugggu cagaggug                                                   18

<210> SEQ ID NO 24
<211> LENGTH: 1923
<212> TYPE: DNA
<213> ORGANISM: Homo sapiens

<400> SEQUENCE: 24

```
cagaagtggc ccaggcaggc gtatgacctg ctgctgtgga ggggctgtgc cccaccgcca    60
catgtcttcc tacccatctg ctccccagag ggctgcctgc tgtgcacttg ggtcctggag   120
cccttctcca cccggataga ttcttcaccc ttggcccgcc tttgcccac cctactctgc    180
ccagaagtgc aagagcctaa gccgcctcca tggccccagg aaggattcag gggagaggcc   240
ccaaacaggg agccacgcca gccagacacc ccggccagaa tggagctgac tgaattgctc   300
ctcgtggtca tgcttctcct aactgcaagg ctaacgctgt ccagcccggc tcctcctgct   360
tgtgacctcc gagtcctcag taaactgctt cgtgactccc atgtccttca cagcagactg   420
agccagtgcc cagaggttca ccctttgcct acacctgtcc tgctgcctgc tgtggacttt   480
agcttgggag aatggaaaac ccagatggag gagaccaagg cacaggacat tctgggagca   540
gtgacccttc tgctggaggg agtgatggca gcacgggac aactgggacc cacttgcctc    600
tcatccctcc tggggcagct ttctggacag gtccgtctcc tccttggggc cctgcagagc   660
ctccttggaa cccagcttcc tccacagggc aggaccacag ctcacaagga tcccaatgcc   720
atcttcctga gcttccaaca cctgctccga ggaaaggtgc gtttcctgat gcttgtagga   780
gggtccaccc tctgcgtcag gcgggcccca cccaccacag ctgtcccag cagaacctct    840
ctagtcctca cactgaacga gctcccaaac aggacttctg gattgttgga gacaaacttc   900
actgcctcag ccagaactac tggctctggg cttctgaagt ggcagcaggg attcagagcc   960
aagattcctg gtctgctgaa ccaaacctcc aggtccctgg accaaatccc cggatacctg  1020
aacaggatac acgaactctt gaatggaact cgtggactct tcctggaccc tcacgcagg   1080
accctaggag ccccggacat ttcctcagga acatcagaca caggctccct gccacccaac  1140
ctccagcctg gatattctcc ttccccaacc catcctccta ctggacagta tacgctcttc  1200
cctcttccac ccaccttgcc caccctgtg gtccagctcc accccctgct tcctgaccct   1260
tctgctccaa cgcccacccc taccagccct cttctaaaca catcctacac ccactcccag  1320
aatctgtctc aggaagggta aggttctcag acactgccga catcagcatt gtctcgtgta  1380
cagctccctt ccctgcaggg cgcccctggg agacaactgg acaagatttc ctactttctc  1440
ctgaaaccca agccctggt aaagggata cacaggactg aaaagggaat cattttttcac   1500
tgtacattat aaaccttcag aagctatttt tttaagctat cagcaatact catcagagca  1560
gctagctctt tggtctattt tctgcagaaa tttgcaactc actgattctc tacatgctct  1620
ttttctgtga taactctgca aaggcctggg ctggcctggc agttgaacag agggagagac  1680
taaccttgag tcagaaaaca gagaaagggt aatttccttt gcttcaaatt caaggccttc  1740
caacgccccc atccccttta ctatcattct cagtgggact ctgatcccat attcttaaca  1800
gatctttact cttgagaaat gaataagctt tctctcagaa atgctgtccc tatacactag  1860
acaaaactga gcctgtataa ggaataaatg ggagcgccga aaagctccct aaaaagcaaa  1920
aaa                                                                 1923
```

<210> SEQ ID NO 25
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 25

```
cauggaggcg gcuuaggc                                                   18
```

```
<210> SEQ ID NO 26
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 26
guuuucgacu cccggc                                                      16

<210> SEQ ID NO 27
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 27
caaaucgacu cccggc                                                      16

<210> SEQ ID NO 28
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 28
cauuaggacu cccggc                                                      16

<210> SEQ ID NO 29
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 29 cauuccucu cccggc                                                       16

<210> SEQ ID NO 30
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 30
cauuucgaga cccggc                                                      16

<210> SEQ ID NO 31
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 31
cauuucgacu ggcggc                                                      16

<210> SEQ ID NO 32
<211> LENGTH: 16
<212> TYPE: RNA
<213> ORGANISM: Artificial sequence
<220> FEATURE:
```

<223> OTHER INFORMATION: Synthetic oligonucleotide

<400> SEQUENCE: 32
cauuucgacu ccgcgc                                                       16

<210> SEQ ID NO 33
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 33
cauuucgacu cccgcg                                                       16

<210> SEQ ID NO 34
<211> LENGTH: 12
<212> TYPE: RNA
<213> ORGANISM: Artificial sequence
<220> FEATURE:
<223> OTHER INFORMATION: Synthetic oligonucleotide

<400> SEQUENCE: 34
cauuucgacu cc                                                           12

<210> SEQ ID NO 35
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 35
cauuucgacu cccg                                                         14

<210> SEQ ID NO 36
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 36
catttcgact cc                                                           12

<210> SEQ ID NO 37
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 37
catttcgact cccg                                                         14

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
catttcgact cccggc                                                       16

-continued

```
<210> SEQ ID NO 39
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 39
catttcgact cccggccc                                                18

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
catttcgact cccggcccag                                              20

<210> SEQ ID NO 41
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: bases at these positions are RNA
<220> FEATURE:
<221> NAME/KEY: misc_feature
<222> LOCATION: (17)..(18)
<223> OTHER INFORMATION: bases at these positions are RNA

<400> SEQUENCE: 41
cauuguuuuu ugucutcc                                                18

<210> SEQ ID NO 42
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: bases at these positions are RNA
<220> FEATURE:
<221> NAME/KEY: misc_feature
<222> LOCATION: (17)..(18)
<223> OTHER INFORMATION: bases at these positions are RNA

<400> SEQUENCE: 42
cauuguuuuu ugucttcc                                                18

<210> SEQ ID NO 43
<211> LENGTH: 2419
<212> TYPE: DNA
<213> ORGANISM: Mus musculus

<400> SEQUENCE: 43
gggtcctgtc agcagcgcca caaagtcttc gagaagagaa gatggcctga gcactgtcaa    60
gccttgccgc gggactcaaa cttcatcagg cccacctcca ccccagccta cctgtgtggc   120
catcagcacg ggtccgctcc ccaacgccgg gttcccctcg atcactgtaa ctgcgatgct   180
ctggatccct tggatactcg aagaccaggc cagcgggctg tggatctaga ttgctgcgct   240
```

```
ctgcatccgg ggacagagtc cttggcccac ctctctccca cccgactctg ccgaaagaag    300
cacagaagct caagccgcct ccatggcccc aggaaagatt caggggagag cccccataca    360
gggagccact tcagttagac accctggcca gaatggagct gactgatttg ctcctggcgg    420
ccatgcttct tgcagtggca agactaactc tgtccagccc cgtagctcct gcctgtgacc    480
ccagactcct aaataaactg ctgcgtgact cccacctcct tcacagccga ctgagtcagt    540
gtcccgacgt cgaccctttg tctatccctg ttctgctgcc tgctgtggac tttagcctgg    600
gagaatggaa aacccagacg aacagagca aggcacagga cattctaggg gcagtgtccc    660
ttctactgga gggagtgatg gcagcacgag gacagttgga accctcctgc ctctcatccc    720
tcctgggaca gctttctggg caggttcgcc tcctcttggg ggccctgcag ggcctcctag    780
gaacccagct tcctctacag ggcaggacca cagctcacaa ggaccccaat gccctcttct    840
tgagcttgca acaactgctt cggggaaagg tgcgcttcct gcttctggta aaggtcccca    900
ccctctgtgt cagacggacc ctgccaacca cagctgtccc aagcagtact tctcaactcc    960
tcacactaaa caagttccca acaggactt ctggattgtt ggagacgaac ttcagtgtca   1020
cagccagaac tgctggccct ggacttctga gcaggcttca gggattcaga gtcaagatta   1080
ctcctggtca gctaaatcaa acctccaggt ccccagtcca aatctctgga tacctgaaca   1140
ggacacacgg acctgtgaat ggaactcatg ggctctttgc tggaacctca cttcagaccc   1200
tggaagcctc agacatctcg cccggagctt tcaacaaagg ctccctggca ttcaacctcc   1260
agggtggact tcctccttct ccaagccttg ctcctgatgg acacacaccc ttccctcctt   1320
cacctgcctt gcccaccacc catggatctc caccccagct ccaccccctg tttcctgacc   1380
cttccaccac catgcctaac tctaccgccc ctcatccagt cacaatgtac cctcatccca   1440
ggaatttgtc tcaggaaaca tagcgcgggc actggcccag tgagcgtctg cagcttctct   1500 cgggggacaag cttccccagg aaggctgaga ggcagctgca tctgctccag atgttctgct   1560
ttcacctaaa aggccctggg gaagggatac acagcactgg agattgtaaa atttttaggag   1620 ctatttttttt taacctatc agcaatattc atcagagcag ctagcgatct ttggtctatt   1680
ttcggtataa atttgaaaat cactaattct ctatatgtgc tttcatacat taagtctgca   1740
aatgcctagg caggtcttgc cttttaaccc aggtagatgc tacaccatat cagaaaacaa   1800
aagggaactt tcctttgctt caagtttaag ccttcccgcg cctccaacac cccacaatg    1860 ccctccttcc cttcactgta attctcagtg agactgtatg gtcctcgaga tatactgctc    1920
ttgataaaga attaacaggc tatcacttag aaagactgtc cctacttaag agacaaaact   1980
gaacctgtaa gagaataact gggagcaccc aaaagccaat aaaaatcagg gaccaatgtt   2040
cttcactggg gcaacagagc tcctggaccc tgcctcccaa gaaagctaac aggaagcctg   2100
ggagctccac accccaggta aggctgtgca gctggctcag taaagagcag acttggatgt   2160
ggcagctgag caaagagcat cagcagctca gcagggctc agccaggcct gggctcctgc   2220
ttccctcctg tggaggtcag gcggaagtgc aggaagtggc aagaggcagg ctcctcggct   2280
cacacagcag gacaagcaca gagcgcttga aggctcttta taatttccac aaatgcacct   2340
aaaaagcagc cctgtgtggc cactccaaac tttattggaa ccctcccaaa tgaaggcaga   2400
cttataggac tttccaacc                                                2419
```

<210> SEQ ID NO 44
<211> LENGTH: 17
<212> TYPE: RNA
<213> ORGANISM: Artificial sequence

```
<220> FEATURE:
<223> OTHER INFORMATION: Synthetic oligonucleotide

<400> SEQUENCE: 44
cauggaggcg gcuugag                                                      17

<210> SEQ ID NO 45
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 45
gccgggaguc gaaaug                                                       16

<210> SEQ ID NO 46
<211> LENGTH: 23
<212> TYPE: DNA
<213> ORGANISM: Artificial sequence
<220> FEATURE:
<223> OTHER INFORMATION: Primer

<400> SEQUENCE: 46
cttgcaatga tgtcgtaatt tgc                                               23

<210> SEQ ID NO 47
<211> LENGTH: 23
<212> TYPE: DNA
<213> ORGANISM: Artificial sequence
<220> FEATURE:
<223> OTHER INFORMATION: Primer

<400> SEQUENCE: 47
tcgtcaacct tctgtaccag ctt                                               23

<210> SEQ ID NO 48
<211> LENGTH: 29
<212> TYPE: DNA
<213> ORGANISM: Artificial sequence
<220> FEATURE:
<223> OTHER INFORMATION: Probe

<400> SEQUENCE: 48
ttactctgtt ctcagcgaca gttgcctgc                                         29

<210> SEQ ID NO 49
<211> LENGTH: 21
<212> TYPE: DNA
<213> ORGANISM: Artificial sequence
<220> FEATURE:
<223> OTHER INFORMATION: Primer

<400> SEQUENCE: 49
gcttggcttc ttctggactc a                                                 21

<210> SEQ ID NO 50
<211> LENGTH: 18
<212> TYPE: DNA
<213> ORGANISM: Artificial sequence
<220> FEATURE:
<223> OTHER INFORMATION: Primer

<400> SEQUENCE: 50
tcgcgagctt caccatga                                                     18
```

```
<210> SEQ ID NO 51
<211> LENGTH: 24
<212> TYPE: DNA
<213> ORGANISM: Artificial sequence
<220> FEATURE:
<223> OTHER INFORMATION: Probe

<400> SEQUENCE: 51
cgccacttgt ccgcttcaca ctcc                                              24

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
cagcaggcaa ctgtcgctga                                                   20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
gtcatcgtca tcctcatcat                                                   20

<210> SEQ ID NO 54
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 54
aagaugacgc acgucu                                                       16

<210> SEQ ID NO 55
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 55
ggaagaugac gcacgu                                                       16

<210> SEQ ID NO 56
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 56
cgggaagaug acgcac                                                       16

<210> SEQ ID NO 57
<211> LENGTH: 16
<212> TYPE: RNA
<213> ORGANISM: Artificial sequence
<220> FEATURE:
<223> OTHER INFORMATION: Synthetic oligonucleotide
```

-continued

<400> SEQUENCE: 57
cgcgggaaga ugacgc                                                         16

<210> SEQ ID NO 58
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 58
caccggcgcg ggaaga                                                         16

<210> SEQ ID NO 59
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 59
gucaccggcg cgggaa                                                         16

<210> SEQ ID NO 60
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 60
ccgucaccgg cgcggg                                                         16

<210> SEQ ID NO 61
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 61
uuccgucacc ggcgcg                                                         16

<210> SEQ ID NO 62
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 62
acuuccguca ccggcg                                                         16

<210> SEQ ID NO 63
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 63
gcacuuccgu caccgg                                                         16

<210> SEQ ID NO 64

```
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 64
ccgcacuucc gucacc                                                        16

<210> SEQ ID NO 65
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 65
caccgcacuu ccguca                                                        16

<210> SEQ ID NO 66
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 66
aacaccgcac uuccgu                                                        16

<210> SEQ ID NO 67
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 67
ucaacaccgc acuucc                                                        16

<210> SEQ ID NO 68
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 68
gcucaacacc gcacuu                                                        16

<210> SEQ ID NO 69
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 69
gcgcucaaca ccgcac                                                        16

<210> SEQ ID NO 70
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 70
```
cggcgcucaa caccgc                                           16

<210> SEQ ID NO 71
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 71
gccggcgcuc aacacc                                           16

<210> SEQ ID NO 72
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 72
ccgccggcgc ucaaca                                           16

<210> SEQ ID NO 73
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 73
ggcgcgggaa gaugac                                           16

<210> SEQ ID NO 74
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 74
cgagccgccg gcgcuc                                           16

<210> SEQ ID NO 75
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 75
ggcgcgagcc gccggc                                           16

<210> SEQ ID NO 76
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 76
cgugggcgcg agccgc                                           16

<210> SEQ ID NO 77
<211> LENGTH: 16
<212> TYPE: RNA

```
<213> ORGANISM: Artificial sequence
<220> FEATURE:
<223> OTHER INFORMATION: Synthetic oligonucleotide

<400> SEQUENCE: 77
ccagcguggg cgcgag                                                    16

<210> SEQ ID NO 78
<211> LENGTH: 1568
<212> TYPE: DNA
<213> ORGANISM: Homo sapiens

<400> SEQUENCE: 78
actgcgcagg cgcgcgggc aagagggtgg cagtgcgcct gcgccgcgtc ggcgtgcgga      60
acgccgcggt gtctcggcgc ctctgcgcgc gggaagatgg cggaacaggc taccaagtcc    120
gtgctgtttg tgtgtctggg taacatttgt cgatcaccca ttgcagaagc agttttcagg    180
aaacttgtaa ccgatcaaaa catctcagag aattggaggg tagacagcgc ggcaacttcc    240
gggtatgaga tagggaaccc ccctgactac cgagggcaga gctgcatgaa gaggcacggc    300
attcccatga gccacgttgc ccggcagatt accaaagaag attttgccac atttgattat    360
atactatgta tggatgaaag caatctgaga gatttgaata gaaaaagtaa tcaagttaaa    420
acctgcaaag ctaaaattga actacttggg agctatgatc cacaaaaaca acttattatt    480
gaagatccct attatgggaa tgactctgac tttgagacgg tgtaccagca gtgtgtcagg    540
tgctgcagag cgttcttgga aaggcccac tgaggcaggt tcgtgccctg ctgcggccag     600
cctgactaga ccccacccctg aggtcctgca tttctcagtc ggtgtgtaat cacgttccag   660
ggcccaaagc ccagctcttt gttcagttga cttactgttt cttaccttaa aaagtaattg    720
tagatggaaa tcagttgtgt ttggcaggag aatcaataaa aatctttgat tcagacagct    780
tatggggtat tttaagcatt cttagactag ttgaacatct cactttgccc cagttacaaa    840
aatagtagaa caagcaacat aaaacaatga aggaaaacct cacttgaagg cccaggtcaa    900
catctaagcc tgttgagact tagataatcg agtctacctc ttcagtaggt ttgtgtggat    960
ggcctggagg gcaggtgccc tctgctcccc agtgctacct ctctcttccc tagggccttt   1020
tgtggattga cagtagtccc ctccgtagga gctcacagtc tagattagaa gtgttttaat   1080
ttctacacac ccatagtgca cacttgtata ttgaaaagat agggaagaga gaaacattta   1140
tggaatcagt cgttggcacc ttcaatactt catgattttt gtcgagttta cttcatgagg   1200
aggtcagccc attggctccc atctgaacca ctttgcctct gaaacttaat tacatccaga   1260
aagaaggaca cttgtatgct agtctatggt cagttgagga atatgactgt ttttatatgc   1320
acatgtaacc caaatgtcca atataaattg gcttattttt taaaataatt ttaaaagttg   1380
ggaaaagtgt tattatttgg catgcttaaa tattgaataa gtattcttca tcagcattta   1440
ataaatgtat aggcagatgt aaggtaattt ctgtgtattt tgagataatg tcaaaatcat   1500
gaatatttca aaataaactg gggagttata aaaatacaac tagagatata aaaaaaaaa   1560 aaaaaaaa                                                          1568

<210> SEQ ID NO 79
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 79
```

-continued

| | |
|---|---|
| cgacgcggcg caggcg | 16 |

<210> SEQ ID NO 80
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 80

| | |
|---|---|
| gcgcaggcgc acugccac | 18 |

<210> SEQ ID NO 81
<211> LENGTH: 6132
<212> TYPE: DNA
<213> ORGANISM: Homo sapiens

<400> SEQUENCE: 81

| | |
|---|---|
| aattggaagc aaatgacatc acagcaggtc agagaaaaag ggttgagcgg caggcaccca | 60 |
| gagtagtagg tctttggcat taggagcttg agcccagacg gccctagcag ggaccccagc | 120 |
| gcccgagaga ccatgcagag gtcgcctctg gaaaaggcca gcgttgtctc caaacttttt | 180 |
| ttcagctgga ccagaccaat tttgaggaaa ggatacagac agcgcctgga attgtcagac | 240 |
| atataccaaa tcccttctgt tgattctgct gacaatctat ctgaaaaatt ggaaagagaa | 300 |
| tgggatagag agctggcttc aaagaaaaat cctaaactca ttaatgccct tcggcgatgt | 360 |
| tttttctgga gatttatgtt ctatggaatc tttttatatt tagggaagt caccaaagca | 420 |
| gtacagcctc tcttactggg aagaatcata gcttcctatg acccggataa caaggaggaa | 480 |
| cgctctatcg cgatttatct aggcataggc ttatgccttc tctttattgt gaggacactg | 540 |
| ctcctacacc cagccatttt tggccttcat cacattggaa tgcagatgag aatagctatg | 600 |
| tttagtttga tttataagaa gactttaaag ctgtcaagcc gtgttctaga taaataagt | 660 |
| attggacaac ttgttagtct cctttccaac aacctgaaca aatttgatga aggacttgca | 720 |
| ttggcacatt tcgtgtggat cgctccttg caagtggcac tcctcatggg gctaatctgg | 780 |
| gagttgttac aggcgtctgc cttctgtgga cttggtttcc tgatagtcct tgcccttttt | 840 |
| caggctgggc tagggagaat gatgatgaag tacagagatc agagagctgg gaagatcagt | 900 |
| gaaagacttg tgattacctc agaaatgatt gaaaatatcc aatctgttaa ggcatactgc | 960 |
| tgggaagaag caatggaaaa aatgattgaa aacttaagac aaacagaact gaaactgact | 1020 |
| cggaaggcag cctatgtgag atacttcaat agctcagcct tcttcttctc agggttcttt | 1080 |
| gtggtgtttt tatctgtgct tcccctatgca ctaatcaaag gaatcatcct ccggaaaata | 1140 |
| ttcaccacca tctcattctg cattgttctg cgcatggcgg tcactcggca atttcctgg | 1200 |
| gctgtacaaa catggtatga ctctcttgga gcaataaaca aaatacagga tttcttacaa | 1260 |
| aagcaagaat ataagacatt ggaatataac ttaacgacta cagaagtagt gatggagaat | 1320 |
| gtaacagcct tctgggagga gggatttggg gaattatttg agaaagcaaa acaaaacaat | 1380 |
| aacaatagaa aaacttctaa tggtgatgac agcctcttct tcagtaattt ctcacttctt | 1440 |
| ggtactcctg tcctgaaaga tattaatttc aagatagaaa gaggacagtt gttggcggtt | 1500 |
| gctggatcca ctggagcagg caagacttca cttctaatgg tgattatggg agaactggag | 1560 |
| ccttcagagg gtaaaattaa gcacagtgga agaatttcat tctgttctca gtttcctgg | 1620 |
| attatgcctg gcaccattaa agaaaatatc atctttggtg tttcctatga tgaatataga | 1680 |

```
tacagaagcg tcatcaaagc atgccaacta gaagaggaca tctccaagtt tgcagagaaa      1740
gacaatatag ttcttggaga aggtggaatc acactgagtg gaggtcaacg agcaagaatt      1800
tctttagcaa gagcagtata caaagatgct gatttgtatt tattagactc tccttttgga      1860
tacctagatg ttttaacaga aaaagaaata tttgaaagct gtgtctgtaa actgatggct      1920
aacaaaacta ggattttggt cacttctaaa atggaacatt taaagaaagc tgacaaaata      1980
ttaattttgc atgaaggtag cagctatttt tatgggacat tttcagaact ccaaaatcta      2040
cagccagact ttagctcaaa actcatggga tgtgattctt cgaccaatt tagtgcagaa       2100 agaagaaatt caatcctaac tgagaccttacaccgtttct cattagaagg agatgctcct      2160
gtctcctgga cagaaacaaa aaacaatct tttaaacaga ctggagagtt tggggaaaaa       2220
aggaagaatt ctattctcaa tccaatcaac tctatacgaa aattttccat tgtgcaaaag     2280
actcccttac aaatgaatgg catcgaagag gattctgatg agcctttaga gagaaggctg     2340
tccttagtac cagattctga gcagggagag gcgatactgc ctcgcatcag cgtgatcagc     2400
actggcccca cgcttcaggc acgaaggagg cagtctgtcc tgaacctgat gacacactca     2460
gttaaccaag gtcagaacat tcaccgaaag acaacagcat ccacacgaaa agtgtcactg     2520
gcccctcagg caaacttgac tgaactggat atatattcaa gaaggttatc tcaagaaact     2580
ggcttggaaa taagtgaaga aattaacgaa gaagacttaa aggagtgctt ttttgatgat     2640
atggagagca taccagcagt gactacatgg aacacatacc ttcgatatat tactgtccac     2700
aagagcttaa ttttttgtgct aatttggtgc ttagtaattt ttctggcaga ggtggctgct    2760
tctttggttg tgctgtggct ccttggaaac actcctcttc aagacaaagg gaatagtact    2820
catagtagaa ataacagcta tgcagtgatt atcaccagca ccagttcgta ttatgtgttt     2880
tacatttacg tgggagtagc cgacactttg cttgctatgg gattcttcag aggtctacca    2940
ctggtgcata ctctaatcac agtgtcgaaa attttacacc acaaaatgtt acattctgtt    3000
cttcaagcac ctatgtcaac cctcaacacg ttgaaagcag gtgggattct taatagattc    3060
tccaaagata tagcaatttt ggatgacctt ctgcctctta ccatatttga cttcatccag    3120
ttgttattaa ttgtgattgg agctatagca gttgtcgcag ttttacaacc ctacatcttt    3180
gttgcaacag tgccagtgat agtggctttt attatgttga gagcatattt cctccaaacc    3240
tcacagcaac tcaaacaact ggaatctgaa ggcaggagtc aattttcac tcatcttgtt     3300 acaagcttaa aaggactatg gacacttcgt gccttcggac ggcagcctta ctttgaaact    3360
ctgttccaca aagctctgaa tttacatact gccaactggt tcttgtacct gtcaacactg    3420
cgctggttcc aaatgagaat agaaatgatt tttgtcatct tcttcattgc tgttaccttc    3480
atttccattt taacaacagg agaaggagaa ggaagagttg gtattatcct gactttagcc    3540
atgaatatca tgagtacatt gcagtgggct gtaaactcca gcatagatgt ggatagcttg    3600
atgcgatctg tgagccgagt ctttaagttc attgacatgc caacagaagg taaacctacc    3660
aagtcaacca aaccatacaa gaatggccaa ctctcgaaag ttatgattat tgagaattca    3720
cacgtgaaga agatgacat ctggccctca gggggccaaa tgactgtcaa agatctcaca     3780
gcaaaataca cagaaggtgg aaatgccata ttagagaaca tttccttctc aataagtcct    3840
ggccagaggg tgggcctctt gggaagaact ggatcaggga agagtacttt gttatcagct    3900
tttttgagac tactgaacac tgaaggagaa atccagatcg atggtgtgtc ttgggattca    3960
ataactttgc aacagtggag gaaagccttt ggagtgatac cacagaaagt atttattttt    4020
tctggaacat ttagaaaaaa cttggatccc tatgaacagt ggagtgatca agaaatatgg    4080
```

-continued

```
aaagttgcag atgaggttgg gctcagatct gtgatagaac agtttcctgg gaagcttgac    4140
tttgtccttg tggatggggg ctgtgtccta agccatggcc acaagcagtt gatgtgcttg    4200
gctagatctg ttctcagtaa ggcgaagatc ttgctgcttg atgaacccag tgctcatttg    4260
gatccagtaa cataccaaat aattagaaga actctaaaac aagcatttgc tgattgcaca    4320
gtaattctct gtgaacacag gatagaagca atgctggaat gccaacaatt tttggtcata    4380
gaagagaaca aagtgcggca gtacgattcc atccagaaac tgctgaacga gaggagcctc    4440
ttccggcaag ccatcagccc ctccgacagg gtgaagctct tccccaccg gaactcaagc    4500 aagtgcaagt ctaagcccca gattgctgct ctgaaagagg agacagaaga agaggtgcaa    4560
gatacaaggc tttagagagc agcataaatg ttgacatggg acatttgctc atggaattgg    4620
agctcgtggg acagtcacct catggaattg gagctcgtgg aacagttacc tctgcctcag    4680
aaaacaagga tgaattaagt ttttttttaa aaagaaaca tttggtaagg ggaattgagg    4740
acactgatat gggtcttgat aaatggcttc ctggcaatag tcaaattgtg tgaaaggtac    4800
ttcaaatcct tgaagattta ccacttgtgt tttgcaagcc agattttcct gaaaacccctt    4860 gccatgtgct agtaattgga aaggcagctc taaatgtcaa tcagcctagt tgatcagctt    4920
attgtctagt gaaactcgtt aatttgtagt gttggagaag aactgaaatc atacttctta    4980
gggttatgat taagtaatga taactggaaa cttcagcggt ttatataagc ttgtattcct    5040
ttttctctcc tctccccatg atgtttagaa acacaactat attgtttgct aagcattcca    5100
actatctcat ttccaagcaa gtattagaat accacaggaa ccacaagact gcacatcaaa    5160
atatgcccca ttcaacatct agtgagcagt caggaaagag aacttccaga tcctggaaat    5220
cagggttagt attgtccagg tctaccaaaa atctcaatat ttcagataat cacaatacat    5280
cccttacctg ggaaagggct gttataatct ttcacagggg acaggatggt tcccttgatg    5340
aagaagttga tatgcctttt cccaactcca gaaagtgaca agctcacaga cctttgaact    5400
agagtttagc tggaaaagta tgttagtgca aattgtcaca ggacagccct tctttccaca    5460
gaagctccag gtagagggtg tgtaagtaga taggccatgg gcactgtggg tagacacaca    5520
tgaagtccaa gcatttagat gtataggttg atggtggtat gttttcaggc tagatgtatg    5580
tacttcatgc tgtctacact aagagagaat gagagacaca ctgaagaagc accaatcatg    5640
aattagtttt tatatgcttct gttttataat tttgtgaagc aaaattttttt ctctaggaaa    5700 tatttatttt aataatgttt caaacatata taacaatgct gtattttaaa agaatgatta    5760
tgaattacat ttgtataaaa taattttttat atttgaaata ttgacttttt atggcactag    5820
tatttctatg aaatattatg ttaaaactgg gacaggggag aacctagggt gatattaacc    5880
aggggccatg aatcaccttt tggtctggag ggaagccttg gggctgatgc agttgttgcc    5940
cacagctgta tgattcccag ccagcacagc ctcttagatg cagttctgaa gaagatggta    6000
ccaccagtct gactgtttcc atcaagggta cactgccttc tcaactccaa actgactctt    6060
aagaagactg cattatattt attactgtaa gaaaatatca cttgtcaata aatccatac    6120 atttgtgtga aa                                                         6132
```

<210> SEQ ID NO 82
<211> LENGTH: 18
<212> TYPE: RNA
<213> ORGANISM: Artificial sequence
<220> FEATURE:
<223> OTHER INFORMATION: Synthetic oligonucleotide

```
-continued

<400> SEQUENCE: 82
uucucugacc ugcuguga                                           18

<210> SEQ ID NO 83
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 83
ccaaagaccu acuacucu                                           18

<210> SEQ ID NO 84
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 84
aggcgcacug ccac                                               14

<210> SEQ ID NO 85
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 85
gcaggcgcac ugcc                                               14

<210> SEQ ID NO 86
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 86
gcgcaggcgc acug                                               14

<210> SEQ ID NO 87
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 87
cggcgcaggc gcac                                               14

<210> SEQ ID NO 88
<211> LENGTH: 14
<212> TYPE: RNA
<213> ORGANISM: Artificial sequence
<220> FEATURE:
<223> OTHER INFORMATION: Synthetic oligonucleotide

<400> SEQUENCE: 88
cgcggcgcag gcgc                                               14

<210> SEQ ID NO 89
<211> LENGTH: 14
```

```
<212> TYPE: RNA
<213> ORGANISM: Artificial sequence
<220> FEATURE:
<223> OTHER INFORMATION: Synthetic oligonucleotide

<400> SEQUENCE: 89
gacgcggcgc aggc                                                        14

<210> SEQ ID NO 90
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 90
gcaggcgcac ugccac                                                      16

<210> SEQ ID NO 91
<211> LENGTH: 3107
<212> TYPE: DNA
<213> ORGANISM: Mus musculus

<400> SEQUENCE: 91
atgtccacgg tcagaaccct ggcagtgcgc atgcgcctcg tcccgacgcg gtttctgggc      60
gccagggtct gcaccgaaac atggcagagg ttgggtccaa gtcagtgctg ttcgtgtgtc     120
tcggtaacat ttgccggtca cccattgcag aagcagtatt caggaaactg gtaactgatg     180
aaaaggtttc agataattgg aggatagaca gtgcggctac atccacctat gaagtgggga     240
accctcctga ctatcgaggg cagaactgca tgagaaaaca tggcatccac atgcagcaca     300
ttgcacggca gattacaaaa gaagactttg ccacattcga ttatatacta tgtatggatg     360
aaagcaatct gagagatctc aatagaaaaa gtaatcaagt taaaaactgc aaagctaaaa     420
ttgagctact tgggagctat gatccacaga aacagctcat cattgaagat ccctattatg     480
gcaatgactc tgacttcgag gtggtgtacc agcaatgcct taggtgctgc aaggccttcc     540
tggagaagac ttactagctg gtcctaagcc ccaccattga gcagctcact catcagtgct     600
gtgcccaagg gtggtggcag tccttagccc catacccac ctctctttc agctgactta      660 ctgtatatct ttaaaataat tgtaggtggg aattaggcat atgttcagaa ggataaaagc     720
atttgagtca gacagtttga ggtgtggcta agcattctta gactaactaa acctctgacc     780
ttgcggtgat tacaaaacag tggaacaagc aaatatggaa caaagaaaa caaaaacaaa      840 aacaaaaacc cagaaagtaa gagtgaccta gaaggtccat atcagcctct gagctcggca     900
agcctgggtc gtctggtcta agtggagtgt gtgcatgacc cgcacccagt gtgccgtttg     960
cttgccgtgt actctcttct ctaggctctc gttgtgacaa tagctccatt cacggcagcc    1020
ttccagttaa cactggcagt ttaagctcag acacactgag ggtgttgagg gatttgagag    1080
aggagacgct ggatgtgctg atgggcctgg gactccagca ggccgtcctg gctggacag     1140 tgacaccctg tctaaaaggg gaacaaaaat aacaacggat gggagcagca gatggataaa    1200
gttaccatct tcagtcttac ttggtttttg tctactttcc tgagctttgt tcttgtttga    1260
gccactttgc tttaaaaaaa aagtaagtgt gcttaaatac tggtatgtgt ttgtaagtgt    1320
tctctcatgg gcaatttaca agttataggg caagcaagag taattttgt gtattttcag     1380 aaaagagacc tcaaatttat atgaatgtat gtcagaaagg aacatgaatt caactgggaa    1440
gttatcaaat acaactgaga tacaaatcca gtgtctgcct gcttcttact gacaagtgaa    1500
```

-continued

| | |
|---|---|
| caagatacct aaatgttgcc tccatgtgcc tttttatttg cttgagtgtg aagtttgggc | 1560 |
| tctcagcctc tgtgttagaa agtaaagtga tgagatggat acacacaatg ctgtgttgga | 1620 |
| tggcgatggg tgtctaattg agagactcca ggcactatcc ttatccttgg gccttcttca | 1680 |
| tgtagctggt gctccctacc cgcttcccag ctgaaaaggt ggtaactgtc tgtcttagcc | 1740 |
| tgtcttagct caggtcacta ctggtgagct ccagtcacgc agaacttgta gttagaagag | 1800 |
| ccatcctgac gtctgaaagg aaggaagccc aggggcctag gaatatgcag tctcttcttg | 1860 |
| gccagggctc ctctctcgaa ggaggaaagc ttacacctga ctcttccaga agaaagcagc | 1920 |
| tatcccagca ccctctcaca gaaaggccat gatgtcccag caaaggcaga cacttcagct | 1980 |
| gccttttttgg gctcctgtgg ggttttggtc agagtcttca caaaattaaa accgaggaag | 2040 |
| ggagaggaca ggtagtcagc cacaaggagg aaatggatta agtcaaagct ctccacccta | 2100 |
| cttcagtgct tgcttcagaa tctcagattt ctctttcagg tcataagatc ctattgtttt | 2160 |
| cttgaaattt tacctgtgta tcttacacgc agatccttgg aatgtcaggt tctgctttgt | 2220 |
| tctacggctg tctcaaacag cacagtgtgt ttataagggc tcatgaacag agaaattaac | 2280 |
| ttttttacatt caatcaaatt acatttgttt aaaatacagc cattaaattt taaaactgtt | 2340 |
| ctcagggtgc ttcttggttt gacattctct tacaatcagg tagagatggt agatgtggag | 2400 |
| tattgatggc taaatgagac caagcgatca ggagtttatg ttattcagta cttagtcaca | 2460 |
| tctacacaca cacacacgca cacgtgtata tatatagtga acaatgtgta tgtatgttta | 2520 |
| tatatacata tattctgagc cttgacattg ttatttaaga gtcattctga agactgttca | 2580 |
| ttattccaaa cacttcattt atttccttgt atttattcac agtatttaca tattgtacaa | 2640 |
| tacctggaat gtacttttac atttacagag acaagtggg actggccttg gcatagccac | 2700 |
| agatacatat gccactgttt tcaacacaac tgaggttttt ttggttttca ttaaaatttt | 2760 |
| tcatgcagtt ccaaactata ctttgggatt ttaattgtag aatacaaaat gtcaaatcat | 2820 |
| actatatgct ctatgaaaat acagtttaat gttctgccta tgtttctaaa gaatattcc | 2880 |
| ttgtggttcc acctaatctt aaaaagaaaa tacctcattt tacagaacaa tacatcaaat | 2940 |
| gtggaatgtt gtctgttttt acaatcataa gagtggcaaa tctcactgac agatacactg | 3000 |
| attcactgaa tgcatatttg taaactgtca gcaacataga aaatgcaaag gaattatgga | 3060 |
| agagtgcaaa aataaatctc tgtccacagg aagtgggcat gaagatg | 3107 |

<210> SEQ ID NO 92
<211> LENGTH: 15
<212> TYPE: RNA
<213> ORGANISM: Artificial sequence
<220> FEATURE:
<223> OTHER INFORMATION: Synthetic oligonucleotide

<400> SEQUENCE: 92
gcaugcgcac ugcca                                                    15

<210> SEQ ID NO 93
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 93
gcaugcgcac ugccag                                                   16

<210> SEQ ID NO 94
<211> LENGTH: 1799
<212> TYPE: DNA
<213> ORGANISM: Mus musculus

<400> SEQUENCE: 94

| | | | | | | |
|---|---|---|---|---|---|---|
| ggcgtgcccc | gcggcaggcg | ctgacgtggc | tgccgtcagc | gccgccatct | tgtgggagcg | 60 |
| aaaccaacgc | ctggctggga | gcagccgccg | cggaggtctt | tggccagtat | cgattccacc | 120 |
| tgtccacaaa | catggggaat | atctttgcaa | acctcttcaa | gggcctttt | ggcaaaaaag | 180 |
| aaatgcgcat | tctcatggtg | ggcctggatg | ctgcaggaa | gacaacaatt | ctatacaaac | 240 |
| ttaagctggg | cgaaattgtg | accaccattc | ccaccattgg | tttcaatgtg | gagactgttg | 300 |
| aatacaagaa | tatcagcttc | accgtgtggg | atgtgggcgg | ccaggacaag | atccggccgc | 360 |
| tgtggcgcca | ctacttccag | aacacccaag | gcttgatctt | cgtagtggac | agcaatgaca | 420 |
| gagagcgtgt | gaacgaggcc | cgtgaagagc | tcatgaggat | gctagctgaa | gatgagctcc | 480 |
| gagatgctgt | tctcttggtg | tttgccaaca | gcaggacct | ccccaatgcc | atgaatgcgg | 540 |
| ccgaaatcac | agacaagctg | gggctgcact | ctctacgcca | caggaactgg | tacattcagg | 600 |
| ccacctgtgc | caccagcggg | gacgggctct | atgaaggact | agattggctg | tctaatcagc | 660 |
| tccggaacca | gaagtgaacc | agacccctcc | ctccccctca | cttcctcttc | tccgccctca | 720 |
| gctttcctct | catgtggcaa | acgtgcgact | ctgtggtcct | gagtgccaga | agctgtctcc | 780 |
| atgggttggt | cacagtgtgc | atcgcaccgt | gctgtacatg | tgcagacgca | gcctgcagcc | 840 |
| aggttttat | ttaatgtaaa | tagttctgt | ttccactgag | gcagtttctg | gtactccctat | 900 |
| gcaatattac | ttagcttttt | tattgtaaaa | agagaatcaa | ctcaactgtc | agtactgaga | 960 |
| agggatttgg | gtgtagggc | acctggcctc | cgggagccat | tgggctgtag | actggtgtcg | 1020 |
| gtatccattt | ggtggttggt | ttttaaccca | aactcagtgc | atttttaaa | aatagttaaa | 1080 |
| aatacaggac | aagaacactt | gaacacacag | aacggagact | atgccagtg | taggttttgc | 1140 |
| agttaatggc | ctgaatgcta | gatatcagat | cacctgtttc | gctgtgggaa | caggagagaa | 1200 |
| ggtgatgaac | aaaccaccat | ccgctgcatg | gtcacagtag | agccccgtg | actcgcctgt | 1260 |
| cttttgggtca | cctgcattcc | atagcattgt | gcttgtactt | gtgctcacac | ggttacctag | 1320 |
| ggtaggctgg | gagccattgt | ggggtgcagg | gcctggcttg | tacttggtgt | gtgcaaggcc | 1380 |
| caatggcagc | ctgcataccc | agcctactct | tgggcccact | tggacgcgct | ggcaggaggc | 1440 |
| ctgggtctca | ccagcaggag | tgcgtgcaag | gtgggagggt | cggtccatta | cagacccaca | 1500 |
| tcctggagca | ccccatctc | catgtgtgaa | gtagcttcct | ccctcagcct | gcaagggtcc | 1560 |
| gatttgccat | cgaaagacga | cctctacttt | tttcttttgt | attttgataa | acactgaaga | 1620 |
| agctggagct | gttaaattta | tcttggggaa | atctcagaac | tggtttattt | ggtgtcgtgg | 1680 |
| aacctcttac | cgctttcaat | acacaattag | taatcaactg | ttttgtatac | ttgttttcag | 1740 |
| ttttcatttc | gacaagcact | gtaattatag | ctgttagaat | aaagtctctt | aactatttg | 1799 |

<210> SEQ ID NO 95
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 95
cgctcccaca agatggc    17

<210> SEQ ID NO 96
<211> LENGTH: 2926
<212> TYPE: DNA
<213> ORGANISM: Mus musculus

<400> SEQUENCE: 96

| | | | | | | |
|---|---|---|---|---|---|---|
| tctccgggag | ggtggctggt | tccaccgcgt | cgctctctct | gcgtcacctg | gaggaagcgg | 60 |
| agctggcggc | cggctcnggg | cccgtcgcgg | gaggcagtta | tgggcgccgt | cgccccggat | 120 |
| tgtaactttg | tgtcagcgtg | cagtccataa | agtgccagca | tggggaagaa | acggaccaag | 180 |
| gggagaagtg | ctccagacac | ggtggcctca | gagtctgcag | aaccagtgtg | cagacacctt | 240 |
| agaaaagggt | tggaacaagg | taatttgaaa | aaagctttag | taaatgtgga | gtggaatatc | 300 |
| tgccaagact | gtaagactga | caataaagtg | aaagataaac | ctgaggagga | agcagaagac | 360 |
| ccttcggttt | ggctctgtct | taaatgtggc | catcagggct | gtggcagaga | ttctcaggag | 420 |
| cagcatgcct | tgaagcacta | cacgacaccg | agatccgagc | ctcactacct | ggtgctcagt | 480 |
| ctggacaact | ggagcgtctg | gtgctacaag | tgtgacgagg | aagtcaagta | ctgtagctca | 540 |
| aaccgattgg | gccaagtggt | tgattatgtt | agaaaacaag | ctggcgtaag | aacttcaaaa | 600 |
| ccagcagaga | aaaataatgg | acacattgag | ctcgaaaata | aaaaattgga | gaaagagagt | 660 |
| aaaaatgaac | aagagagaga | gaaatcggaa | aacctggcta | agaaaactat | tcccatggac | 720 |
| tctgcttccc | agataactgt | gaaaggactc | agtaatttgg | ggaatacttg | tttcttcaat | 780 |
| gcagttatgc | agaacttgtc | acaaacgcca | gtgcttagag | aactactaaa | agaagtgaag | 840 |
| atgtctggaa | cgattgtaaa | aatagagcca | cctgatctgg | cactaacaga | acctttagaa | 900 |
| gtaaacctcg | agcctccagg | tcctcttact | ttagccatga | gccagtttct | cagtgagatg | 960 |
| caagagaaca | aaaagcgagt | tgtgacacct | aaagagctct | tttctcaggt | ctgtaaaaaa | 1020 |
| gcaacacgtt | ttaaagggta | ccagcaacaa | gacagccagg | agctgcttcg | ctacctactg | 1080 |
| gatgggatga | gagcggaaga | acaccaaaga | gtgagtaaag | gaattcttaa | agcatttggt | 1140 |
| aattctactg | aaaaattgga | tgaagaagta | aaaaataaag | ttaaagatta | tgaaaagaaa | 1200 |
| aaggcaatcc | cgagttttgt | ggaccgcatc | tttggtggcg | agctgactag | tacgatcatg | 1260 |
| tgtgatgaat | gcaggactgt | ctccttagtg | catgaatcgt | tccttgattt | gtctcttcca | 1320 |
| gttttagatg | atcagagtgg | taagaaaagt | ataaatgata | aaaatgtgaa | aatgacaatg | 1380 |
| gaggaagaag | ataaagacag | tgaggaagag | aaagatgaca | gctacatgaa | atcaaggagc | 1440 |
| gatcttccgt | cagggacaag | caagcaccta | cagaaaaagg | caagaagca | ggccaaaaag | 1500 |
| caggccaaga | ccaacgaag | gcaacaaaaa | attcagaaa | gatttcttca | cttcaatgag | 1560 |
| ctctgcgcca | ctgactacac | ggaagacaat | gaacgtgaag | ctgacacagc | acttgcggga | 1620 |
| gaagtggaag | tggataccga | ctccacccat | ggttctcaag | aggaggccac | acagatagag | 1680 |
| ctgtctgtta | accagaagga | tttggatggc | aagagagca | tgatagaaag | gacacctgat | 1740 |
| gtgcaggaaa | gcccagagga | cctaggagtg | aaaagtgcta | caccgagag | tgatctgggg | 1800 |
| attgtgacgc | ctgctcctga | atgtcctagg | gatttcaatg | gtgccttcct | ggaagaaagg | 1860 |
| accagtggag | aactagacat | tatcaatggt | ttaaaaaacc | ttaatttgaa | tgctgctgtt | 1920 |
| gatcctgatg | aaataaatat | agagattccg | aatgacagtc | attctgcacc | caaggtatat | 1980 |
| gaggtcatga | acgaggaccc | agaaactgct | ttctgtaccc | tcgcgaaccg | agaagcgttt | 2040 |
| agtactgatg | agtgttccat | tcaacattgc | ttatatcagt | tcacccggaa | tgagaaactt | 2100 |
| caagatgcca | ataaactgct | ttgtgaagtg | tgttcaagac | ggcagtgtaa | tggaccaaag | 2160 |

```
gcaaatataa aaggtgacag gagacatgtt tacaccaatg ccaagaagca gatgctggtc    2220
tccctcgcgc ctcctgtcct cactctgcat ttaaagcgat tccagcaggc tggttttaac    2280
ctgcgcaaag ttaacaaaca cataaagttt ccagaaatct tagatttggc tcctttttgt    2340
acccttaaat gtaagaatgt tgctgaagaa agtacacgag tgctgtattc cttatatgga    2400
gttgttgaac acagtggtac tatgaggtca gggcattaca ctgcctatgc gaaggagaga    2460
actgcaagct gtcacctctc caatcttgtt cttcacggtg acattccaca agattgtgaa    2520
atggaatcaa ccaaagggca gtggtttcac atcagcgata cacatgtgca agctgtgcct    2580
ataactaaag tactgaactc acaagcgtat ctcctatttt atgagagaat actgtgataa    2640
caaaaagtgc tttctctgga aatacaccta tggcttttat actggctatt ataacaataa    2700
aaagttaaac tataaattat gttcacctaa gtaaatgaca gaaaaaaaat catgtttatt    2760
tatttaaata caggcaaaat aatttacagc ggttttgtat tagcatactg gttttttattc    2820 cttctagttt caactttagg aaggatttga ataactaagt tctgtgctta ctctgactgg    2880
gtggtagtgc ttgacacatc aataaactga tattcccaaa aaaaaa                   2926
```

<210> SEQ ID NO 97
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 97

```
gagagcgacg cggtgga                                                     17
```

<210> SEQ ID NO 98
<211> LENGTH: 5292
<212> TYPE: DNA
<213> ORGANISM: Homo sapiens

<400> SEQUENCE: 98

```
ctcttgcagt gaggtgaaga catttgaaaa tcaccccact gcaaactcct ccccctgcta      60
gaaacctcac attgaaatgc tgtaaatgac gtgggccccg agtgcaatcg cgggaagcca     120
gggtttccag ctaggacaca gcaggtcgtg atccgggtcg ggacactgcc tggcagaggc     180
tgcgagcatg gggccctggg gctggaaatt gcgctggacc gtcgccttgc tcctcgccgc     240
ggcggggact gcagtgggcg acagatgcga agaaacgag ttccagtgcc aagacgggaa     300
atgcatctcc tacaagtggg tctgcgatgg cagcgctgag tgccaggatg gctctgatga     360
gtcccaggag acgtgcttgt ctgtcacctg caaatccggg acttcagct gtggggccg      420 tgtcaaccgc tgcattcctc agttctggag gtgcgatggc caagtggact cgacaacgg      480 ctcagacgag caaggctgtc ccccaagac gtgctcccag gacgagtttt gctgccacga     540
tgggaagtgc atctctcggc agttcgtctg tgactcagac cggactgct tggacggctc     600 agacgaggcc tcctgcccgg tgctcacctg tggtcccgcc agcttccagt gcaacagctc     660
cacctgcatc ccccagctgt gggcctgcga caacgacccc gactgcgaag atggctcgga     720
tgagtggccg cagcgctgta ggggtcttta cgtgttccaa gggacagta gcccctgctc     780 ggccttcgag ttccactgcc taagtggcga gtgcatccac tccagctggc gctgtgatgg     840 tggcccccgac tgcaaggaca aatctgacga ggaaaactgc gctgtggcca cctgtcgccc     900
tgacgaattc cagtgctctg atggaaactg catccatggc agccggcagt gtgaccggga     960
```

```
atatgactgc aaggacatga gcgatgaagt tggctgcgtt aatgtgacac tctgcgaggg    1020
acccaacaag ttcaagtgtc acagcggcga atgcatcacc ctggacaaag tctgcaacat    1080
ggctagagac tgccgggact ggtcagatga acccatcaaa gagtgcggga ccaacgaatg    1140
cttggacaac aacggcggct gttcccacgt ctgcaatgac cttaagatcg ctacgagtg     1200 cctgtgcccc gacggcttcc agctggtggc ccagcgaaga tgcgaagata tcgatgagtg    1260
tcaggatccc gacacctgca gccagctctg cgtgaacctg gagggtggct acaagtgcca    1320
gtgtgaggaa ggcttccagc tggaccccca cacgaaggcc tgcaaggctg tgggctccat    1380
cgcctacctc ttcttcacca accggcacga ggtcaggaag atgacgctgg accgagcga    1440 gtacaccagc ctcatcccca acctgaggaa cgtggtcgct ctggacacgg aggtggccag    1500
caatagaatc tactggtctg acctgtccca gagaatgatc tgcagcaccc agcttgacag    1560
agcccacggc gtctcttcct atgacaccgt catcagcaga gacatccagg cccccgacgg    1620
gctggctgtg gactggatcc acagcaacat ctactggacc gactctgtcc tgggcactgt    1680
ctctgttgcg gataccaagg gcgtgaagag gaaaacgtta ttcagggaga acggctccaa    1740
gccaagggcc atcgtggtgg atcctgttca tggcttcatg tactggactg actggggaac    1800
tcccgccaag atcaagaaag ggggcctgaa tggtgtggac atctactcgc tggtgactga    1860
aaacattcag tggcccaatg gcatcaccct agatctcctc agtggccgcc tctactgggt    1920
tgactccaaa cttcactcca tctcaagcat cgatgtcaac gggggcaacc ggaagaccat    1980
cttggaggat gaaaagaggc tgcccaccc cttctccttg gccgtctttg aggacaaagt    2040
attttggaca gatatcatca cgaagccat tttcagtgcc aaccgcctca caggttccga    2100
tgtcaacttg ttggctgaaa acctactgtc cccagaggat atggttctct ccacaacct    2160 cacccagcca agaggagtga actggtgtga aggaccacc ctgagcaatg gcggctgcca    2220
gtatctgtgc ctccctgccc cgcagatcaa ccccactcg cccaagttta cctgcgcctg    2280 cccggacgg atgctgctgg caggggacat gaggagctgc ctcacagagg ctgaggctgc    2340
agtggccacc caggagacat ccaccgtcag gctaaaggtc agctccacag ccgtaaggac    2400
acagcacaca accacccgac ctgttcccga cacctcccgg ctgcctgggg ccaccccgg    2460 gctcaccacg gtggagatag tgacaatgtc tcaccaagct ctgggcgacg ttgctggcag    2520
aggaaatgag aagaagccca gtagcgtgag ggctctgtcc attgtcctcc ccatcgtgct    2580
cctcgtcttc ctttgcctgg ggtcttcct tctatggaag aactggcggc ttaagaacat    2640
caacagcatc aactttgaca ccccgtcta tcagaagacc acagaggatg aggtccacat    2700
ttgccacaac caggacggct acagctaccc ctcgagacag atggtcagtc tggaggatga    2760
cgtggcgtga acatctgcct ggagtcccgt ccctgcccag aacccttcct gagacctcgc    2820
cggccttgtt ttattcaaag acagagaaga ccaaagcatt gcctgccaga gctttgtttt    2880
atatatttat tcatctggga ggcagaacag gcttcggaca gtgccatgc aatggcttgg    2940 gttgggattt tggtttcttc ctttcctcgt gaaggataag agaaacaggc ccgggggac    3000 caggatgaca cctccatttc tctccaggaa gttttgagtt tctctccacc gtgacacaat    3060
cctcaaacat ggaagatgaa agggagggg atgtcaggcc cagagaagca agtggctttc    3120
aacacacaac agcagatggc accaacggga ccccctggcc ctgcctcatc caccaatctc    3180
taagccaaac ccctaaactc aggagtcaac gtgtttacct cttctatgca agccttgcta    3240
gacagccagg ttagccttg ccctgtcacc cccgaatcat gaccccacca gtgtctttcg    3300
aggtgggttt gtaccttcct taagccagga aagggattca tggcgtcgga aatgatctgg    3360
```

```
ctgaatccgt ggtggcaccg agaccaaact cattcaccaa atgatgccac ttcccagagg    3420
cagagcctga gtcactggtc acccttaata tttattaagt gcctgagaca cccggttacc    3480
ttggccgtga ggacacgtgg cctgcaccca ggtgtggctg tcaggacacc agcctggtgc    3540
ccatcctccc gaccccctacc cacttccatt cccgtggtct ccttgcactt tctcagttca    3600
gagttgtaca ctgtgtacat ttggcatttg tgttattatt ttgcactgtt ttctgtcgtg    3660
tgtgttggga tgggatccca ggccagggaa agcccgtgtc aatgaatgcc ggggacagag    3720
aggggcaggt tgaccgggac ttcaaagccg tgatcgtgaa tatcgagaac tgccattgtc    3780
gtctttatgt ccgcccacct agtgcttcca cttctatgca aatgcctcca agccattcac    3840
ttccccaatc ttgtcgttga tgggtatgtg tttaaaacat gcacggtgag gccgggcgca    3900
gtggctcacg cctgtaatcc cagcactttg ggaggccgag gcgggtggat catgaggtca    3960
ggagatcgag accatcctgg ctaacacgtg aaacccgtc tctactaaaa atacaaaaaa    4020
ttagccgggc gtggtggcgg gcacctgtag tcccagctac tcgggaggct gaggcaggag    4080
aatggtgtga acccgggaag cggagcttgc agtgagccga gattgcgcca ctgcagtccg    4140
cagtctggcc tggcgacag agcgagactc cgtctcaaaa aaaaaaaaca aaaaaaaacc    4200
atgcatggtg catcagcagc ccatggcctc tggccaggca tggcgaggct gaggtgggag    4260
gatggtttga gctcaggcat ttgaggctgt cgtgagctat gattatgcca ctgctttcca    4320
gcctgggcaa catagtaaga ccccatctct taaaaaatga atttggccag acacaggtgc    4380
ctcacgcctg taatcccagc actttgggag gctgagctgg atcacttgag ttcaggagtt    4440
ggagaccagg cctgagcaac aaagcgagat cccatctcta caaaaccaa aaagttaaaa    4500 atcagctggg tacggtggca cgtgcctgtg atcccagcta cttgggaggc tgaggcagga    4560
ggatcgcctg agcccaggag gtggaggttg cagtgagcca tgatcgagcc actgcactcc    4620
agcctgggca acagatgaag accctatttc agaaatacaa ctataaaaaa ataaataaat    4680
cctccagtct ggatcgtttg acgggacttc aggttctttc tgaaatcgcc gtgttactgt    4740
tgcactgatg tccggagaga cagtgacagc ctccgtcaga ctcccgcgtg aagatgtcac    4800
aagggattgg caattgtccc cagggacaaa acactgtgtc cccccagtg cagggaaccg    4860 tgataagcct ttctggtttc ggagcacgta aatgcgtccc tgtacagata gtggggattt    4920
tttgttatgt ttgcactttg tatattggtt gaaactgtta tcacttatat atatatat     4980 acacacatat atataaaatc tatttatttt tgcaaaccct ggttgctgta tttgttcagt    5040
gactattctc ggggccctgt gtaggggtt attgcctctg aaatgcctct tctttatgta    5100
caaagattat ttgcacgaac tggactgtgt gcaacgcttt ttgggagaat gatgtccccg    5160
ttgtatgtat gagtggcttc tgggagatgg gtgtcacttt ttaaaccact gtatagaagg    5220
tttttgtagc ctgaatgtct tactgtgatc aattaaattt cttaaatgaa ccaatttgtc    5280
taaaaaaaaa aa                                                       5292
```

<210> SEQ ID NO 99
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 99
ugcagugggg ugauuu                                                   16

```
<210> SEQ ID NO 100
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 100
ugcugugaug ucauuugc                                                    18

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: bases at these positions are RNA

<400> SEQUENCE: 101 ugcaguggggg ugattt                                                     16

<210> SEQ ID NO 102
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 102
ugcagugggg ugauuuuc                                                    18

<210> SEQ ID NO 103
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: bases at these positions are RNA
<220> FEATURE:
<221> NAME/KEY: misc_feature
<222> LOCATION: (18)..(18)
<223> OTHER INFORMATION: bases at these positions are RNA

<400> SEQUENCE: 103
ugcagugggg ugauuttc                                                    18

<210> SEQ ID NO 104
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(13)
<223> OTHER INFORMATION: bases at these positions are RNA
<220> FEATURE:
<221> NAME/KEY: misc_feature
```

```
<222> LOCATION: (18)..(18)
<223> OTHER INFORMATION: bases at these positions are RNA

<400> SEQUENCE: 104
ugcagugggg ugattttc                                                   18
```